(12) United States Patent
McKenna et al.

(10) Patent No.: US 7,820,165 B2
(45) Date of Patent: Oct. 26, 2010

(54) COMPOSITIONS AND METHODS OF PRODUCING HYBRID ANTIGEN BINDING MOLECULES AND USES THEREOF

(75) Inventors: Sean D. McKenna, Duxbury, MA (US); Robert K. Campbell, Wrentham, MA (US); Xuliang Jiang, Braintree, MA (US); Giampiero De Luca, Conches (CH); Meijia Yang, Scituate, MA (US); Christie Ann Kelton, Hopkinton, MA (US); Stephen J. Arkinstall, Belmont, MA (US); Chaomei He, Wellesley, MA (US); Rene Lynn Schweickhardt, Medfield, MA (US)

(73) Assignee: Merck Serono, S.A., Coinsins, Vaud (CH)

( * ) Notice: Subject to any disclaimer, the term of this patent is extended or adjusted under 35 U.S.C. 154(b) by 0 days.

(21) Appl. No.: 12/085,155

(22) PCT Filed: Nov. 21, 2006

(86) PCT No.: PCT/US2006/045056

§ 371 (c)(1),
(2), (4) Date: May 15, 2008

(87) PCT Pub. No.: WO2007/062037

PCT Pub. Date: May 31, 2007

(65) Prior Publication Data

US 2009/0130712 A1    May 21, 2009

Related U.S. Application Data

(60) Provisional application No. 60/738,647, filed on Nov. 21, 2005.

(51) Int. Cl.
*C07K 16/46* (2006.01)
*C07K 14/59* (2006.01)
*C07K 16/28* (2006.01)

(52) U.S. Cl. .............. 424/134.1; 424/185.1; 424/192.1; 530/350

(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,889,803 A | 12/1989 | Revel et al. |
| 4,965,188 A | 10/1990 | Mullis et al. |
| 5,225,539 A | 7/1993 | Winter et al. |
| 5,453,491 A | 9/1995 | Takatsu et al. |
| 5,530,101 A | 6/1996 | Queen et al. |
| 5,585,089 A | 12/1996 | Queen et al. |
| 5,589,369 A | 12/1996 | Seidman et al. |
| 5,591,669 A | 1/1997 | Krimpenfort et al. |
| 5,599,905 A | 2/1997 | Mosley et al. |
| 5,639,605 A | 6/1997 | Kitamura et al. |
| 5,648,273 A | 7/1997 | Bettaro et al. |
| 5,658,570 A | 8/1997 | Newman et al. |
| 5,686,292 A | 11/1997 | Schwall et al. |
| 5,693,761 A | 12/1997 | Queen et al. |
| 5,693,762 A | 12/1997 | Queen et al. |
| 5,693,780 A | 12/1997 | Newman et al. |
| 5,756,096 A | 5/1998 | Newman et al. |
| 5,811,524 A | 9/1998 | Brams et al. |
| 5,892,019 A | 4/1999 | Schlom et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,194,177 B1 | 2/2001 | Campbell et al. |
| 6,696,245 B2 | 2/2004 | Winter et al. |

FOREIGN PATENT DOCUMENTS

| | | |
|---|---|---|
| EP | 0 125 023 B1 | 11/1984 |
| EP | 0 417 014 A2 | 3/1991 |
| EP | 0 455 460 A2 | 11/1991 |
| EP | 0 522 530 A2 | 1/1993 |
| EP | 0 368 684 B1 | 3/1994 |
| EP | 0 240 975 B1 | 8/1994 |
| EP | 0 417 563 B1 | 7/2000 |
| EP | 1541689 A2 * | 6/2005 |
| WO | WO 90/07861 A1 | 7/1990 |
| WO | WO 02/053596 A2 | 7/2002 |
| WO | WO 2007/047829 A2 | 4/2007 |

OTHER PUBLICATIONS

Cary Queen, et al., Proc. Natl. Acad. Sci. USA, 86, pp. 10029-10033 (1989).
C. Stahli, et al., Methods in Enzymology, 92, pp. 242-253 (1983).
Theo N. Kirkland, et al., J. Immunol., 137(11), pp. 3614-3619 (1986).
Harlow and Lane, Antibodies: A Laboratory Manual, Cold Spring Harbor Press (1988).

(Continued)

*Primary Examiner*—Phuong Huynh
(74) *Attorney, Agent, or Firm*—Pascal A. Stein; EMD Serono, Inc.

(57) ABSTRACT

This disclosure relates to hybrid antigen binding molecules including at least two polypeptide chains, with at least one polypeptide chain comprises an antigen binding moiety linked to an amino acid sequence of a subunit of a heterodimeric proteinaceous hormone. Also disclosed are methods of making and using such hybrid antigen binding molecules for diagnosis and/or therapy.

4 Claims, 52 Drawing Sheets

OTHER PUBLICATIONS

Guillemette A. Morel, et al., Molecular Immunology, 25(1), pp. 7-15 (1988).
Ramsey C. Cheung, et al., Virology, 176, pp. 546-552 (1990).
G. Moldenhauer, et al., Scand. J. Immunol., 32, pp. 77-82 (1990).
W. Paul. ed., Fundamental Immunology, 2nd ed. Raven Press, N.Y., Chapter 7, 1989.
Kabat, Sequences of Polypeptides of Immuological Interest, National Institutes of Health, Bethesda, MD (1987 and 1991).
Cyrus Chothia, et al., J. Mol. Biol., 196, 901-917 (1987).
Cyrus Chothia, et al., Nature, 342(6252), pp. 877-883 (1989).
Cyrus Chothia, J. Mol. Biol., 186, pp. 651-663 (1985).
G. Kohler, et al., Nature, 256(5517), pp. 495-497 (1975).
Goding, Monoclonal Antibodies: Principles and Practice, pp. 59-103 (Academic Press) 1986.
Zoltan A. Nagy, et al., Nature Medicine, 8(8), pp. 801-807 (2002).
Michael A. Huie, et al., PNAS, 98(5), pp. 2682-2687 (2001).
Bin Liu, et al., J. Mol. Biol., 315, pp. 1063-1073 (2002).
James D. Marks, et al., Bio/Technology, 10, pp. 779-783 (1992).
Jozef Hanes, et al., Nat. Biotechnol., 18, pp. 1287-1292 (2000).
David S. Wilson, et al., PNAS, 98(7), pp. 3750-3755 (2001).
Robert A. Irving, et al., J. Immunol. Methods, 248, pp. 31-45 (2001).
Eric T. Boder, et al., PNAS, 97(20), pp. 10701-10705, (2000).
Patrick S. Daugherty, et al., J. Immunol. Methods, 243, pp. 211-227 (2000).
Roland Newman, et al., Biotechnology, 10, pp. 1455-1460 (1992).
Current Protocols in Immunology, Colligan, et al., Eds., Green Publishing Associates and Wiley Interscience, John Wiley and Sons, New York (1991.
Itai Benhar and Ira Pastan, Protein Engineering, 7(11), pp. 1509-1515 (1994).
F. Ruberti, et al., J. Immunol. Methods, 173, pp. 33 (1994).
James W. Larrick, et al., Biochem. Biophys. Res. Commun., 160(3), 1250-1256 (1989).
Rosaria Orlandi, PNAS, 86, pp. 3833-3837 (1989).
Danielle Sblattero, et al., Immunotechnology, 3, pp. 271-278 (1998).
Anke Krebber, et al., J. Immunol. Methods, 201, pp. 35-55 (1997).
Steffan N. Ho, et al., Gene, 77, pp. 51-59 (1989).
Robert M. Horton, et. al., Methods in Enzymology, 217, pp. 270-279 (1993).
William D. Huse, et al., Science, 246, pp. 1275-1281 (1989).
Eric T. Boder, et al., Nature Biotechnology, 15, pp. 553-557 (1997).
Joseph A. Francisco, et al., PNAS, 90, pp. 10444-10448 (1994).
George Georgiou, et al., Nature Biotechnology, 15, pp. 29-34 (1997).
Hennie R. Hoogenboom, et al., Immunotechnology, 4, pp. 1-20 (1998).
Greg Winter, et al., Annu. Rev. Immunol., 12, 433-455 (1994).
Andrew D. Griffiths, et al., Curr. Opin. Biotechnol., 9, pp. 102-108 (1998).
Jozef Hanes, et al., PNAS, 95, pp. 14130-14135 (1998).
J. Hanes, et al., Curr. Top. Microbiol. Immunol., 243, pp. 107-122 (1999).
Mingyue He, et al., Nucleic Acids Research, 25(24), pp. 5132-5134 (1997).
Hennie R. Hoogenboom, et al., J. Mol. Biol., 227, pp. 381-388 (1992).
Andrew D. Griffiths, et al., The EMBO Journal, 13(14), pp. 3245-3260 (1994).
John De Kruif, et al., J. Mol. Biol., 248, pp. 97-105 (1995).
Carlos F. Barbas, et al., PNAS, 89, pp. 4457-4461 (1992).
Julia Thompson, et al., J. Mol. Biol., 256, pp. 77-88 (1996).
Urpo Lamminmaki, et al., J. Mol. Biol., 291, pp. 589-602 (1999).
R. Craig Caldwell, et al., PCR Methods and Applications, 2, pp. 28-33 (1992).
R. Craig Caldwell, et al., PCR Methods and Applications, 3, S136-S140 (1994).
John Devereaux, et al., Nucleic Acids Research, 12(1), pp. 387-395 (1984).
Tatiana A. Tatusova, et al., FEMS Microbiology Letters, 174, pp. 247-250 (1999).
Current Protocols in Molecular Biology, John Wiley & Sons, N.Y., 6.3.1-6.3.6 (1989).
Francis J. Morgan, et al., J. Biol. Chem., 250(13), pp. 5247-5258 (1975).
John C. Fiddes, et al., Nature, 281, pp. 351-356 (1979).
Paul C. Watkins, et al., DNA, 6(3), 205-212 (1987).
Alan Munro, Nature, 312, pp. 597 (1984).
Michael S. Neuberger, et al., Nature, 312, pp. 604-608 (1984).
J. Sharon, et al., Nature, 309, pp. 364-367 (1984).
Sherie L. Morrison, et al., PNAS, 84, pp. 6851-6855 (1984).
Sherie L. Morrison, Science, 229, pp. 1202-1207 (1985).
Gabrielle L. Boulianne, et al., Nature, 312, pp. 643-646 (1984).
Fang Chen, et al., Molecular Endocrinology, 6(6), pp. 914-919 (1992).
Jakyoung Yoo, et al., J. Biol. Chem., 268(18), pp. 13034-13042 (1993).
Sheri A. Kostelny, et al., Journal of Immunology, 148(5), pp. 1547-1553 (1992).
John De Kruif, et al., Journal of Biological Chemistry, 271(13), 7630-7634 (1996).

* cited by examiner

FIG. 1

DNA sequence of the EGFR VH region clone. (SEQ ID NO:33)
AGATCTGCCATGGCTGTCTTGGCGCTGCTCTTCTGCCTGGTGACATTCCCAAGCTGTGT
CCTATCCCAGGTGCAGCTGAAGCAGTCAGGACCTGGCCTAGTGCAGCCCTCACAGAGC
CTGTCCATCACCTGCACAGTCTCTGGTTTCTCATTAACTAACTATGGTGTACACTGGGTT
CGCCAGTCTCCAGGAAAGGGTCTGGAGTGGCTGGGAGTGATATGGAGTGGTGGAAAC
ACAGACTATAATACACCTTTCACATCCAGACTGAGCATCAACAAGGACAATTCCAAGA
GCCAAGTTTTCTTTAAAATGAACAGTCTGCAATCTAATGACACAGCCATATATTACTGT
GCCAGAGCCCTCACCTACTATGATTACGAGTTTGCTTACTGGGGCCAAGGGACTCTGGT
CACTGTCTCTGCAGCGGCCGC

FIG. 2

DNA sequence of the EGFR VL region clone. (SEQ ID NO:34)
TGAGGGCCCCTGCTCAGTTCCTTGTATTTTTGCTTTTCTGGATTCCAGCCTCCAGAAGTG
ACATCTTGCTGACTCAGTCTCCAGTCATCCTGTCTGTGAGTCCAGGAGAAAGAGTCAGT
TTCTCCTGCAGGGCCAGTCAGAGTATTGGCACAAACATACACTGGTATCAGCAAAGAA
CAAATGGTTCTCCAAGGCTTCTCATAAAGTATGCTTCTGAGTCTATCTCTGGGATCCCT
TCCAGGTTTAGTGGCAGTGGATCAGGGACAGATTTTACTCTTAGCATCAACAGTGTGG
AGTCTGAAGATATTGCAGATTATTACTGTCAACAAAATAATAACTGGCCAACCACGTT
CGGTGCTGGGACCAAGCTGGAGCTGAAAGCGGCCGC

FIG. 3 pENTR1a/alpha(1-87) (SEQ ID NO:35)

```
            SalI                          NcoI
         ~~~~~~~                        ~~~~~~~
                                              M   A   T   G   S   R   T
TTAAAGGAAC CAATTCAGTC GACTGGATCT TGAACCACCA TGGCTACAGG CTCCCGGACG
AATTTCCTTG GTTAAGTCAG CTGACCTAGA ACTTGGTGGT ACCGATGTCC GAGGGCCTGC

BamHI        NotI
                                                      ~~~~~~~       ~~~
  S   L   L   L   A   F   G   L   L   C   L   P   W   L   Q   E   G   S   A   A
TCCCTGCTCC TGGCTTTTGG CCTGCTCTGC CTGCCCTGGC TTCAAGAGGG ATCCGCCGCG
AGGGACGAGG ACCGAAAACC GGACGAGACG GACGGGACCG AAGTTCTCCC TAGGCGGCGC
NotI
~~~~~
  A   A   P   D   V   Q   D   C   P   E   C   T   L   Q   E   N   P   F   F   S
GCCGCGCCCG ATGTGCAGGA TTGCCCAGAA TGCACGCTAC AGGAAAACCC ATTCTTCTCC
CGGCGCGGGC TACACGTCCT AACGGGTCTT ACGTGCGATG TCCTTTTGGG TAAGAAGAGG

Q   P   G   A   P   I   L   Q   C   M   G   C   C   F   S   R   A   Y   P   T
CAGCCGGGTG CCCCAATACT TCAGTGCATG GGCTGCTGCT TCTCTAGAGC ATATCCCACT
GTCGGCCCAC GGGGTTATGA AGTCACGTAC CCGACGACGA AGAGATCTCG TATAGGGTGA

P   L   R   S   K   K   T   M   L   V   Q   K   N   V   T   S   E   S   T   C
CCACTAAGGT CCAAGAAGAC GATGTTGGTC CAAAAGAACG TCACCTCAGA GTCCACTTGC
GGTGATTCCA GGTTCTTCTG CTACAACCAG GTTTTCTTGC AGTGGAGTCT CAGGTGAACG

C   V   A   K   S   Y   N   R   V   T   V   M   G   G   F   K   V   E   N   H
TGTGTAGCTA AATCATATAA CAGGGTCACA GTAATGGGGG GTTTCAAAGT GGAGAACCAC
ACACATCGAT TTAGTATATT GTCCCAGTGT CATTACCCCC CAAAGTTTCA CCTCTTGGTG

XhoI
                                 ~~~~~~~
            PstI           EcoRV
           ~~~~~~         ~~~~~~
  T   A   C   H   C   S   T   C
ACGGCGTGCC ACTGCAGTAC TTGTTAGCTC GAGATATCTA G
TGCCGCACGG TGACGTCATG AACAATCGAG CTCTATAGAT C
```

FIG. 4 pENTR1a/beta (SEQ ID NO:36)

```
          SalI                          NcoI
       ~~~~~~~                       ~~~~~~~
                                         M   A   T   G   S   R   T
TTAAAGGAAC CAATTCAGTC GACTGGATCT TGAACCACCA TGGCTACAGG CTCCCGGACG
AATTTCCTTG GTTAAGTCAG CTGACCTAGA ACTTGGTGGT ACCGATGTCC GAGGGCCTGC

BamHI      NotI
                                                  ~~~~~~~    ~~~
  S   L   L   L   A   F   G   L   L   C   L   P   W   L   Q   E   G   S   A   A
TCCCTGCTCC TGGCTTTTGG CCTGCTCTGC CTGCCCTGGC TTCAAGAGGG ATCCGCCGCG
AGGGACGAGG ACCGAAAACC GGACGAGACG GACGGGACCG AAGTTCTCCC TAGGCGGCGC

NotI
~~~~~
  A   A   S   K   E   P   L   R   P   R   C   P   I   N   A   T   L   A   V
GCCGCGTCCA AGGAGCCGCT TCGGCCACGG TGCCGCCCCA TCAATGCCAC CCTGGCTGTG
CGGCGCAGGT TCCTCGGCGA AGCCGGTGCC ACGGCGGGGT AGTTACGGTG GGACCGACAC

E   K   E   G   C   P   V   C   I   T   V   N   T   T   I   C   A   G   Y   C
GAGAAGGAGG GCTGCCCCGT GTGCATCACC GTCAACACCA CCATCTGTGC CGGCTACTGC
CTCTTCCTCC CGACGGGGCA CACGTAGTGG CAGTTGTGGT GGTAGACACG GCCGATGACG

PstI
                      ~~~~~~~
  P   T   M   T   R   V   L   Q   G   V   L   P   A   L   P   Q   V   V   C   N
CCCACCATGA CCCGCGTGCT GCAGGGGGTC CTGCCGGCCC TGCCTCAGGT GGTGTGCAAC
GGGTGGTACT GGGCGCACGA CGTCCCCCAG GACGGCCGGG ACGGAGTCCA CCACACGTTG

Y   R   D   V   R   F   E   S   I   R   L   P   G   C   P   R   G   V   N   P
TACCGCGATG TGCGCTTCGA GTCCATCCGG CTCCCTGGCT GCCCGCGCGG CGTGAACCCC
ATGGCGCTAC ACGCGAAGCT CAGGTAGGCC GAGGGACCGA CGGGCGCGCC GCACTTGGGG

PvuII
               ~~~~~~
  V   V   S   Y   A   V   A   L   S   C   Q   C   A   L   C   R   R   S   T   T
GTGGTCTCCT ACGCCGTGGC TCTCAGCTGT CAATGTGCAC TCTGCCGCCG CAGCACCACT
CACCAGAGGA TGCGGCACCG AGAGTCGACA GTTACACGTG AGACGGCGGC GTCGTGGTGA

D   C   G   G   P   K   D   H   P   L   T   C   D   D   P   R   F   Q   D   S
GACTGCGGGG GTCCAAGGA CCACCCCTTG ACCTGTGATG ACCCCCGCTT CCAGGACTCC
CTGACGCCCC CAGGGTTCCT GGTGGGGAAC TGGACACTAC TGGGGGCGAA GGTCCTGAGG

XmaI
                                                           ~~~~~~~
                                                              SmaI
                                                           ~~~~~~~
  S   S   S   K   A   P   P   P   S   L   P   S   P   S   R   L   P   G   P   S
TCTTCCTCAA AGGCCCCTCC CCCCAGCCTT CCAAGCCCAT CCCGACTCCC GGGGCCCTCG
AGAAGGAGTT TCCGGGGAGG GGGGTCGGAA GGTTCGGGTA GGGCTGAGGG CCCCGGGAGC

XhoI
               ~~~~~~~
                 EcoRV
               ~~~~~~~
  D   T   P   I   L   P   Q
GACACCCCGA TCCTCCCACA ATAGCTCGAG ATATCTAG
CTGTGGGGCT AGGAGGGTGT TATCGAGCTC TATAGATC
```

FIG. 5A.

EGFR VH hCGbeta nucleotide sequence (SEQ ID NO:37)

ATGGCTACAGGCTCCCGGACGTCCCTGCTCCTGGCTTTTGGCCTGCTCTGCCTGCCCTGGCTTCAA
GAGGGATCTGCCCAGGTGCAGCTGAAGCAGTCAGGACCTGGCCTAGTGCAGCCCTCACAGAGCCTG
TCCATCACCTGCACAGTCTCTGGTTTCTCATTAACTAACTATGGTGTACACTGGGTTCGCCAGTCT
CCAGGAAAGGGTCTGGAGTGGCTGGGAGTGATATGGAGTGGTGGAAACACAGACTATAATACACCT
TTCACATCCAGACTGAGCATCAACAAGGACAATTCCAAGAGCCAAGTTTTCTTTAAAATGAACAGT
CTGCAATCTAATGACACAGCCATATATTACTGTGCCAGAGCCCTCACCTACTATGATTACGAGTTT
GCTTACTGGGGCCAAGGGACTCTGGTCACTGTCTCTGCAGCGGCCGCGTCCAAGGAGCCGCTTCGG
CCACGGTGCCGCCCCATCAATGCCACCCTGGCTGTGGAGAAGGAGGGCTGCCCCGTGTGCATCACC
GTCAACACCACCATCTGTGCCGGCTACTGCCCCACCATGACCCGCGTGCTGCAGGGGGTCCTGCCG
GCCCTGCCTCAGGTGGTGTGCAACTACCGCGATGTGCGCTTCGAGTCCATCCGGCTCCCTGGCTGC
CCGCGCGGCGTGAACCCCGTGGTCTCCTACGCCGTGGCTCTCAGCTGTCAATGTGCACTCTGCCGC
CGCAGCACCACTGACTGCGGGGGTCCCAAGGACCACCCCTTGACCTGTGATGACCCCCGCTTCCAG
GACTCCTCTTCCTCAAAGGCCCCTCCCCCAGCCTTCCAAGCCCATCCCGACTCCCGGGGCCCTCG
GACACCCCGATCCTCCCACAATAG

FIG. 5B

EGFR VH hCGbeta amino acid sequence (SEQ ID NO:38)
MATGSRTSLLLAFGLLCLPWLQEGSAQVQLKQSGPGLVQPSQSLSITCTVSGFSLTNYGVHWVRQS
PGKGLEWLGVIWSGGNTDYNTPFTSRLSINKDNSKSQVFFKMNSLQSNDTAIYYCARALTYYDYEF
AYWGQGTLVTVSAAAASKEPLRPRCRPINATLAVEKEGCPVCITVNTTICAGYCPTMTRVLQGVLP
ALPQVVCNYRDVRFESIRLPGCPRGVNPVVSYAVALSCQCALCRRSTTDCGGPKDHPLTCDDPRFQ
DSSSSKAPPPSLPSPSRLPGPSDTPILPQ

FIG. 6A.

EGFR VL alpha(1-87) DNA sequence (SEQ ID NO:39)

ATGGCTACAGGCTCCCGGACGTCCCTGCTCCTGGCTTTTGGCCTGCTCTGCCTGCCCTGGCTTCAA
GAGGGATCTGCCGACATCTTGCTGACTCAGTCTCCAGTCATCCTGTCTGTGAGTCCAGGAGAAAGA
GTCAGTTTCTCCTGCAGGGCCAGTCAGAGTATTGGCACAAACATACACTGGTATCAGCAAAGAACA
AATGGTTCTCCAAGGCTTCTCATAAAGTATGCTTCTGAGTCTATCTCTGGGATCCCTTCCAGGTTT
AGTGGCAGTGGATCAGGGACAGATTTTACTCTTAGCATCAACAGTGTGGAGTCTGAAGATATTGCA
GATTATTACTGTCAACAAAATAATAACTGGCCAACCACGTTCGGTGCTGGGACCAAGCTGGAGCTG
AAAGCGGCCGCGCCCGATGTGCAGGATTGCCCAGAATGCACGCTACAGGAAAACCCATTCTTCTCC
CAGCCGGGTGCCCCAATACTTCAGTGCATGGGCTGCTGCTTCTCTAGAGCATATCCCACTCCACTA
AGGTCCAAGAAGACGATGTTGGTCCAAAAGAACGTCACCTCAGAGTCCACTTGCTGTGTAGCTAAA
TCATATAACAGGGTCACAGTAATGGGGGGTTTCAAAGTGGAGAACCACACGGCGTGCCACTGCAGT
ACTTGTTAG

FIG. 6B

EGFR VL alpha(1-87) amino acid sequence (SEQ ID NO:40)

MATGSRTSLLLAFGLLCLPWLQEGSADILLTQSPVILSVSPGERVSFSCRASQSIGTNIHWYQQRT
NGSPRLLIKYASESISGIPSRFSGSGSGTDFTLSINSVESEDIADYYCQQNNNWPTTFGAGTKLEL
KAAAPDVQDCPECTLQENPFFSQPGAPILQCMGCCFSRAYPTPLRSKKTMLVQKNVTSESTCCVAK
SYNRVTVMGGFKVENHTACHCSTC

FIG. 7A.

EGFR scFv alpha(1-87) DNA sequence (SEQ ID NO:41)

ATGGCTACAGGCTCCCGGACGTCCCTGCTCCTGGCTTTTGGCCTGCTCTGCCTGCCCTGGCTTCAA
GAGGGATCTGCCCAGGTGCAGCTGAAGCAGTCAGGACCTGGCCTAGTGCAGCCCTCACAGAGCCTG
TCCATCACCTGCACAGTCTCTGGTTTCTCATTAACTAACTATGGTGTACACTGGGTTCGCCAGTCT
CCAGGAAAGGGTCTGGAGTGGCTGGGAGTGATATGGAGTGGTGGAAACACAGACTATAATACACCT
TTCACATCCAGACTGAGCATCAACAAGGACAATTCCAAGAGCCAAGTTTTCTTTAAAATGAACAGT
CTGCAATCTAATGACACAGCCATATATTACTGTGCCAGAGCCCTCACCTACTATGATTACGAGTTT
GCTTACTGGGGCCAAGGGACTCTGGTCACTGTCTCTGCAGGTGGCGGTGGCTCGGGCGGTGGTGGG
TCGGGTGGCGGCGGATCTGACATCTTGCTGACTCAGTCTCCAGTCATCCTGTCTGTGAGTCCAGGA
GAAAGAGTCAGTTTCTCCTGCAGGGCCAGTCAGAGTATTGGCACAAACATACACTGGTATCAGCAA
AGAACAAATGGTTCTCCAAGGCTTCTCATAAAGTATGCTTCTGAGTCTATCTCTGGGATCCCTTCC
AGGTTTAGTGGCAGTGGATCAGGGACAGATTTTACTCTTAGCATCAACAGTGTGGAGTCTGAAGAT
ATTGCAGATTATTACTGTCAACAAAATAATAACTGGCCAACCACGTTCGGTGCTGGGACCAAGCTG
GAGCTGAAAGCGGCCGCGCCCGATGTGCAGGATTGCCCAGAATGCACGCTACAGGAAAACCCATTC
TTCTCCCAGCCGGGTGCCCCAATACTTCAGTGCATGGGCTGCTGCTTCTCTAGAGCATATCCCACT
CCACTAAGGTCCAAGAAGACGATGTTGGTCCAAAAGAACGTCACCTCAGAGTCCACTTGCTGTGTA
GCTAAATCATATAACAGGGTCACAGTAATGGGGGGTTTCAAAGTGGAGAACCACACGGCGTGCCAC
TGCAGTACTTGTTAG

FIG. 7B

EGFR scFv alpha(1-87) amino acid sequence (SEQ ID NO:42)

QVQLKQSGPGLVQPSQSLSITCTVSGFSLTNYGVHWVRQSPGKGLEWLGVIWSGGNTDYNTPFTSR
LSINKDNSKSQVFFKMNSLQSNDTAIYYCARALTYYDYEFAYWGQGTLVTVSAGGGGSGGGGSGGG
GSDILLTQSPVILSVSPGERVSFSCRASQSIGTNIHWYQQRTNGSPRLLIKYASESISGIPSRFSG
SGSGTDFTLSINSVESEDIADYYCQQNNNWPTTFGAGTKLELKAAAPDVQDCPECTLQENPFFSQP
GAPILQCMGCCFSRAYPTPLRSKKTMLVQKNVTSESTCCVAKSYNRVTVMGGFKVENHTACHCSTC

FIG. 8A.

EGFR scFV hCGβ DNA sequence (SEQ ID NO:43)

ATGGCTACAGGCTCCCGGACGTCCCTGCTCCTGGCTTTTGGCCTGCTCTGCCTGCCCTGGCTTCAA
GAGGGATCTGCCCAGGTGCAGCTGAAGCAGTCAGGACCTGGCCTAGTGCAGCCCTCACAGAGCCTG
TCCATCACCTGCACAGTCTCTGGTTTCTCATTAACTAACTATGGTGTACACTGGGTTCGCCAGTCT
CCAGGAAAGGGTCTGGAGTGGCTGGGAGTGATATGGAGTGGTGGAAACACAGACTATAATACACCT
TTCACATCCAGACTGAGCATCAACAAGGACAATTCCAAGAGCCAAGTTTTCTTTAAAATGAACAGT
CTGCAATCTAATGACACAGCCATATATTACTGTGCCAGAGCCCTCACCTACTATGATTACGAGTTT
GCTTACTGGGGCCAAGGGACTCTGGTCACTGTCTCTGCAGGTGGCGGTGGCTCGGGCGGTGGTGGG
TCGGGTGGCGGCGGATCTGACATCTTGCTGACTCAGTCTCCAGTCATCCTGTCTGTGAGTCCAGGA
GAAAGAGTCAGTTTCTCCTGCAGGGCCAGTCAGAGTATTGGCACAAACATACACTGGTATCAGCAA
AGAACAAATGGTTCTCCAAGGCTTCTCATAAAGTATGCTTCTGAGTCTATCTCTGGGATCCCTTCC
AGGTTTAGTGGCAGTGGATCAGGGACAGATTTTACTCTTAGCATCAACAGTGTGGAGTCTGAAGAT
ATTGCAGATTATTACTGTCAACAAAATAATAACTGGCCAACCACGTTCGGTGCTGGGACCAAGCTG
GAGCTGAAAGCGGCCGCGTCCAAGGAGCCGCTTCGGCCACGGTGCCGCCCCATCAATGCCACCCTG
GCTGTGGAGAAGGAGGGCTGCCCCGTGTGCATCACCGTCAACACCACCATCTGTGCCGGCTACTGC
CCCACCATGACCCGCGTGCTGCAGGGGGTCCTGCCGGCCCTGCCTCAGGTGGTGTGCAACTACCGC
GATGTGCGCTTCGAGTCCATCCGGCTCCCTGGCTGCCCGCGCGGCGTGAACCCCGTGGTCTCCTAC
GCCGTGGCTCTCAGCTGTCAATGTGCACTCTGCCGCCGCAGCACCACTGACTGCGGGGGTCCCAAG
GACCACCCCTTGACCTGTGATGACCCCCGCTTCCAGGACTCCTCTTCCTCAAAGGCCCCTCCCCCC
AGCCTTCCAAGCCCATCCCGACTCCCGGGGCCCTCGGACACCCCGATCCTCCCACAATAG

FIG. 8B.

EGFR scFv hCGβ amino acid sequence (SEQ ID NO:44)

MATGSRTSLLLAFGLLCLPWLQEGSAQVQLKQSGPGLVQPSQSLSITCTVSGFSLTNYGVHWVRQS
PGKGLEWLGVIWSGGNTDYNTPFTSRLSINKDNSKSQVFFKMNSLQSNDTAIYYCARALTYYDYEF
AYWGQGTLVTVSAGGGSGGGGSGGGGSDILLTQSPVILSVSPGERVSFSCRASQSIGTNIHWYQQ
RTNGSPRLLIKYASESISGIPSRFSGSGSGTDFTLSINSVESEDIADYYCQQNNNWPTTFGAGTKL
ELKAAASKEPLRPRCRPINATLAVEKEGCPVCITVNTTICAGYCPTMTRVLQGVLPALPQVVCNYR
DVRFESIRLPGCPRGVNPVVSYAVALSCQCALCRRSTTDCGGPKDHPLTCDDPRFQDSSSSKAPPP
SLPSPSRLPGPSDTPILPQ

FIG. 9

Codon optimized DNA sequence of the VEGF VH region (SEQ ID NO:45)
AGATCTGCCGAGGTCCAGCTGGTCGAGTCAGGAGGCGGACTTGTCCAGCCCGGTGGCTCCTTGAGA
CTGAGCTGTGCCGCAAGCGGCTATACATTTACAAATTATGGAATGAATTGGGTGCGGCAGGCACCT
GGGAAGGGACTGGAGTGGGTGGGCTGGATCAATACATACACTGGCGAGCCTACATACGCCGCGGAT
TTCAAGCGGAGATTCACATTCTCTCTTGACACAAGTAAGTCCACAGCTTATTTGCAAATGAACTCA
TTGAGAGCCGAGGACACAGCTGTGTACTATTGTGCCAAGTACCCCCACTATTATGGATCAAGCCAC
TGGTATTTTGATGTTTGGGGACAGGGTACGCTGGTGACCGTGTCATCAGCGGCCGC

FIG. 10

Codon optimized DNA sequence of the VEGF VL region (SEQ ID NO:46)
AGATCTGCCGATATCCA

FIG. 11

The DNA sequence of VEGF scFv(VHVL)hng (SEQ ID NO:47)
AGATCTGCCGAGGTCCAGCTGGTCGAGTCAGGAGGCGGACTTGTCCAGCCCGGTGGCTCCTTGAGA
CTGAGCTGTGCCGCAAGCGGCTATACATTTACAAATTATGGAATGAATTGGGTGCGGCAGGCACCT
GGGAAGGGACTGGAGTGGGTGGGCTGGATCAATACATACACTGGCGAGCCTACATACGCCGCGGAT
TTCAAGCGGAGATTCACATTCTCTCTTGACACAAGTAAGTCCACAGCTTATTTGCAAATGAACTCA
TTGAGAGCCGAGGACACAGCTGTGTACTATTGTGCCAAGTACCCCCACTATTATGGATCAAGCCAC
TGGTATTTTGATGTTTGGGGACAGGGTACGCTGGTGACCGTGTCATCAGGTGGCGGTGGCTCGGGC
GGTGGTGGGTCGGGTGGCGGCGGATCTGATATCCAAATGACCCAGTCCCCTTCATCACTGTCCGCA
TCTGTAGGGGATCGAGTTACAATCACTTGTTCTGCCTCCCAGGATATTTCCAATTACCTCAACTGG
TATCAGCAAAAGCCCGGGAAGGCCCCAAAGGTGCTGATCTACTTTACCAGTTCCCTGCATTCTGGC
GTGCCAAGTAGATTCAGCGGTAGTGGTTCTGGTACAGACTTTACTTTGACCATCTCATCTCTGCAG
CCTGAAGATTTCGCCACATATTACTGTCAGCAGTACTCAACCGTCCCCTGGACGTTTGGACAGGGA
ACCAAGGTGGAAATCAAGCGCGACAAAACTCACACATGCCCACCGTGCCCAGCACCTGAACTCCTG
GGGGGAGCGGCCGC

FIG. 12

The DNA sequence of VEGF scFv(VLVH)hng (SEQ ID NO:48)
AGATCTGCCGATATCCAAATGACCCAGTCCCCTTCATCACTGTCCGCATCTGTAGGGGATCGAGTT
ACAATCACTTGTTCTGCCTCCCAGGATATTTCCAATTACCTCAACTGGTATCAGCAAAAGCCCGGG
AAGGCCCCAAAGGTGCTGATCTACTTTACCAGTTCCCTGCATTCTGGCGTGCCAAGTAGATTCAGC
GGTAGTGGTTCTGGTACAGACTTTACTTTGACCATCTCATCTCTGCAGCCTGAAGATTTCGCCACA
TATTACTGTCAGCAGTACTCAACCGTCCCCTGGACGTTTGGACAGGGAACCAAGGTGGAAATCAAG
CGCGGTGGCGGTGGCTCGGGCGGTGGTGGGTCGGGTGGCGGCGGATCTGAGGTCCAGCTGGTCGAG
TCAGGAGGCGGACTTGTCCAGCCCGGTGGCTCCTTGAGACTGAGCTGTGCCGCAAGCGGCTATACA
TTTACAAATTATGGAATGAATTGGGTGCGGCAGGCACCTGGGAAGGGACTGGAGTGGGTGGGCTGG
ATCAATACATACACTGGCGAGCCTACATACGCCGCGGATTTCAAGCGGAGATTCACATTCTCTCTT
GACACAAGTAAGTCCACAGCTTATTTGCAAATGAACTCATTGAGAGCCGAGGACACAGCTGTGTAC
TATTGTGCCAAGTACCCCCACTATTATGGATCAAGCCACTGGTATTTTGATGTTTGGGGACAGGGT
ACGCTGGTGACCGTGTCATCAGACAAAACTCACACATGCCCACCGTGCCCAGCACCTGAACTCCTG
GGGGGAGCGGCCGC

FIG. 13

DNA sequence of IGF-1R VH. (SEQ ID NO:49)
AGATCTGCCCAGGTGCAGCTTCAGGAGTCGGGCCCAGGACTGGTGAAGCCTTCGGAGACCCTGTCC
CTCACCTGCACTGTCTCTGGTTACTCCATCACCGGTGGTTATTTATGGAACTGGATACGGCAGCCC
CCAGGGAAGGGACTGGAGTGGATCGGGTATATCAGCTACGACGGTACCAATAACTACAAACCCTCC
CTCAAGGATCGAGTCACCATATCACGTGACACGTCCAAGAACCAGTTCTCCCTGAAGCTGAGCTCT
GTGACCGCTGCGGACACTGCAGTGTATTACTGTGCGAGATACGGTAGGGTCTTCTTTGACTACTGG
GGCCAGGGAACCCTGGTCACCGTCTCCTCAGCGGCCGC

FIG. 14

DNA sequence of IGF-1R VL. (SEQ ID NO:50)
AGATCTGCCGATATTGTGATGACTCAGTCTCCACTCTCCCTGCCCGTCACCCCTGGAGAGCCGGCC
TCCATCTCCTGCAGGTCTAGTCAGAGCATTGTACATAGTAATGGAAACACCTATTTGCAATGGTAC
CTGCAGAAGCCAGGGCAGTCTCCACAGCTCCTGATCTATAAAGTTTCTAATCGGCTTTATGGGGTC
CCTGACAGGTTCAGTGGCAGTGGATCAGGCACAGATTTTACACTGAAAATCAGCAGAGTGGAGGCT
GAGGATGTTGGGGTTTATTACTGCTTTCAAGGTTCACATGTTCCGTGGACGTTCGGCCAAGGGACC
AAGGTGGAAATCAAAGCGGCCGC

FIG. 15A

The DNA sequence of IGF-1R VHalpha(1-87) (SEQ ID NO:51)
ATGGCTACAGGCTCCCGGACGTCCCTGCTCCTGGCTTTTGGCCTGCTCTGCCTGCCCTGGCTTCAA
GAGGGATCTGCCCAGGTGCAGCTTCAGGAGTCGGGCCCAGGACTGGTGAAGCCTTCGGAGACCCTG
TCCCTCACCTGCACTGTCTCTGGTTACTCCATCACCGGTGGTTATTTATGGAACTGGATACGGCAG
CCCCCAGGGAAGGGACTGGAGTGGATCGGGTATATCAGCTACGACGGTACCAATAACTACAAACCC
TCCCTCAAGGATCGAGTCACCATATCACGTGACACGTCCAAGAACCAGTTCTCCCTGAAGCTGAGC
TCTGTGACCGCTGCGGACACTGCAGTGTATTACTGTGCGAGATACGGTAGGGTCTTCTTTGACTAC
TGGGGCCAGGGAACCCTGGTCACCGTCTCCTCAGCGGCCGCGCCCGATGTGCAGGATTGCCCAGAA
TGCACGCTACAGGAAAACCCATTCTTCTCCCAGCCGGGTGCCCCAATACTTCAGTGCATGGGCTGC
TGCTTCTCTAGAGCATATCCCACTCCACTAAGGTCCAAGAAGACGATGTTGGTCCAAAAGAACGTC
ACCTCAGAGTCCACTTGCTGTGTAGCTAAATCATATAACAGGGTCACAGTAATGGGGGGTTTCAAA
GTGGAGAACCACACGGCGTGCCACTGCAGTACTTGTTAG

FIG. 15B

The amino acid sequence of IGF-1R VHalpha(1-87) (SEQ ID NO:52)
MATGSRTSLLLAFGLLCLPWLQEGSAQVQLQESGPGLVKPSETLSLTCTVSGYSITGGYLWNWIRQ
PPGKGLEWIGYISYDGTNNYKPSLKDRVTISRDTSKNQFSLKLSSVTAADTAVYYCARYGRVFFDY
WGQGTLVTVSSAAAPDVQDCPECTLQENPFFSQPGAPILQCMGCCFSRAYPTPLRSKKTMLVQKNV
TSESTCCVAKSYNRVTVMGGFKVENHTACHCSTC

FIG. 16A

The DNA sequence of IGF-1R VhhCGbeta (SEQ ID NO:53)
ATGGCTACAGGCTCCCGGACGTCCCTGCTCCTGGCTTTTGGCCTGCTCTGCCTGCCCTGGCTTCAA
GAGGGATCTGCCCAGGTGCAGCTTCAGGAGTCGGGCCCAGGACTGGTGAAGCCTTCGGAGACCCTG
TCCCTCACCTGCACTGTCTCTGGTTACTCCATCACCGGTGGTTATTTATGGAACTGGATACGGCAG
CCCCCAGGGAAGGGACTGGAGTGGATCGGGTATATCAGCTACGACGGTACCAATAACTACAAACCC
TCCCTCAAGGATCGAGTCACCATATCACGTGACACGTCCAAGAACCAGTTCTCCCTGAAGCTGAGC
TCTGTGACCGCTGCGGACACTGCAGTGTATTACTGTGCGAGATACGGTAGGGTCTTCTTTGACTAC
TGGGGCCAGGGAACCCTGGTCACCGTCTCCTCAGCGGCCGCGTCCAAGGAGCCGCTTCGGCCACGG
TGCCGCCCCATCAATGCCACCCTGGCTGTGGAGAAGGAGGGCTGCCCCGTGTGCATCACCGTCAAC
ACCACCATCTGTGCCGGCTACTGCCCCACCATGACCCGCGTGCTGCAGGGGGTCCTGCCGGCCCTG
CCTCAGGTGGTGTGCAACTACCGCGATGTGCGCTTCGAGTCCATCCGGCTCCCTGGCTGCCCGCGC
GGCGTGAACCCCGTGGTCTCCTACGCCGTGGCTCTCAGCTGTCAATGTGCACTCTGCCGCCGCAGC
ACCACTGACTGCGGGGGTCCCAAGGACCACCCCTTGACCTGTGATGACCCCGCTTCCAGGACTCC
TCTTCCTCAAAGGCCCCTCCCCCCAGCCTTCCAAGCCCATCCCGACTCCCGGGGCCCTCGGACACC
CCGATCCTCCCACAATAG

FIG. 16B

The amino acid sequence of IGF-1R VhhCGbeta (SEQ ID NO:54)
MATGSRTSLLLAFGLLCLPWLQEGSAQVQLQESGPGLVKPSETLSLTCTVSGYSITGGYLWNWIRQ
PPGKGLEWIGYISYDGTNNYKPSLKDRVTISRDTSKNQFSLKLSSVTAADTAVYYCARYGRVFFDY
WGQGTLVTVSSAAASKEPLRPRCRPINATLAVEKEGCPVCITVNTTICAGYCPTMTRVLQGVLPAL
PQVVCNYRDVRFESIRLPGCPRGVNPVVSYAVALSCQCALCRRSTTDCGGPKDHPLTCDDPRFQDS
SSSKAPPPSLPSPSRLPGPSDTPILPQ

FIG. 17A

The DNA sequence of IGF-1R VLalpha(1-87) (SEQ ID NO:55)
ATGGCTACAGGCTCCCGGACGTCCCTGCTCCTGGCTTTTGGCCTGCTCTGCCTGCCCTGGCTTCAA
GAGGGATCTGCCGATATTGTGATGACTCAGTCTCCACTCTCCCTGCCCGTCACCCCTGGAGAGCCG
GCCTCCATCTCCTGCAGGTCTAGTCAGAGCATTGTACATAGTAATGGAAACACCTATTTGCAATGG
TACCTGCAGAAGCCAGGGCAGTCTCCACAGCTCCTGATCTATAAAGTTTCTAATCGGCTTTATGGG
GTCCCTGACAGGTTCAGTGGCAGTGGATCAGGCACAGATTTTACACTGAAAATCAGCAGAGTGGAG
GCTGAGGATGTTGGGGTTTATTACTGCTTTCAAGGTTCACATGTTCCGTGGACGTTCGGCCAAGGG
ACCAAGGTGGAAATCAAAGCGGCCGCGCCCGATGTGCAGGATTGCCCAGAATGCACGCTACAGGAA
AACCCATTCTTCTCCCAGCCGGGTGCCCCAATACTTCAGTGCATGGGCTGCTGCTTCTCTAGAGCA
TATCCCACTCCACTAAGGTCCAAGAAGACGATGTTGGTCCAAAAGAACGTCACCTCAGAGTCCACT
TGCTGTGTAGCTAAATCATATAACAGGGTCACAGTAATGGGGGGTTTCAAAGTGGAGAACCACACG
GCGTGCCACTGCAGTACTTGTTAG

FIG. 17B

The amino acid sequence of IGF-1R VLalpha(1-87) (SEQ ID NO:56)
MATGSRTSLLLAFGLLCLPWLQEGSADIVMTQSPLSLPVTPGEPASISCRSSQSIVHSNGNTYLQW
YLQKPGQSPQLLIYKVSNRLYGVPDRFSGSGSGTDFTLKISRVEAEDVGVYYCFQGSHVPWTFGQG
TKVEIKAAAPDVQDCPECTLQENPFFSQPGAPILQCMGCCFSRAYPTPLRSKKTMLVQKNVTSEST
CCVAKSYNRVTVMGGFKVENHTACHCSTC

FIG. 18A

The DNA sequence of IGF-1R VlhCGbeta (SEQ ID NO:57)
ATGGCTACAGGCTCCCGGACGTCCCTGCTCCTGGCTTTTGGCCTGCTCTGCCTGCCCTGGCTTCAA
GAGGGATCTGCCGATATTGTGATGACTCAGTCTCCACTCTCCCTGCCCGTCACCCCTGGAGAGCCG
GCCTCCATCTCCTGCAGGTCTAGTCAGAGCATTGTACATAGTAATGGAAACACCTATTTGCAATGG
TACCTGCAGAAGCCAGGGCAGTCTCCACAGCTCCTGATCTATAAAGTTTCTAATCGGCTTTATGGG
GTCCCTGACAGGTTCAGTGGCAGTGGATCAGGCACAGATTTTACACTGAAAATCAGCAGAGTGGAG
GCTGAGGATGTTGGGGTTTATTACTGCTTTCAAGGTTCACATGTTCCGTGGACGTTCGGCCAAGGG
ACCAAGGTGGAAATCAAAGCGGCCGCGTCCAAGGAGCCGCTTCGGCCACGGTGCCGCCCCATCAAT
GCCACCCTGGCTGTGGAGAAGGAGGGCTGCCCCGTGTGCATCACCGTCAACACCACCATCTGTGCC
GGCTACTGCCCCACCATGACCCGCGTGCTGCAGGGGGTCCTGCCGGCCCTGCCTCAGGTGGTGTGC
AACTACCGCGATGTGCGCTTCGAGTCCATCCGGCTCCCTGGCTGCCCGCGCGGCGTGAACCCCGTG
GTCTCCTACGCCGTGGCTCTCAGCTGTCAATGTGCACTCTGCCGCCGCAGCACCACTGACTGCGGG
GGTCCCAAGGACCACCCCTTGACCTGTGATGACCCCGCTTCCAGGACTCCTCTTCCTCAAAGGCC
CCTCCCCCCAGCCTTCCAAGCCCATCCCGACTCCCGGGGCCCTCGGACACCCCGATCCTCCCACAA
TAG

FIG. 18B

The amino acid sequence of IGF-1R VlhCGbeta (SEQ ID NO:58)

MATGSRTSLLLAFGLLCLPWLQEGSADIVMTQSPLSLPVTPGEPASISCRSSQSIVHSNGNTYLQW
YLQKPGQSPQLLIYKVSNRLYGVPDRFSGSGSGTDFTLKISRVEAEDVGVYYCFQGSHVPWTFGQG
TKVEIKAAASKEPLRPRCRPINATLAVEKEGCPVCITVNTTICAGYCPTMTRVLQGVLPALPQVVC
NYRDVRFESIRLPGCPRGVNPVVSYAVALSCQCALCRRSTTDCGGPKDHPLTCDDPRFQDSSSSKA
PPPSLPSPSRLPGPSDTPILPQ

FIG. 19A

The DNA sequence of IGF-1R scFv alpha(1-87) (SEQ ID NO:59)
ATGGCTACAGGCTCCCGGACGTCCCTGCTCCTGGCTTTTGGCCTGCTCTGCCTGCCCTGGCTTCAA
GAGGGATCTGCCCAGGTGCAGCTTCAGGAGTCGGGCCCAGGACTGGTGAAGCCTTCGGAGACCCTG
TCCCTCACCTGCACTGTCTCTGGTTACTCCATCACCGGTGGTTATTTATGGAACTGGATACGGCAG
CCCCCAGGGAAGGGACTGGAGTGGATCGGGTATATCAGCTACGACGGTACCAATAACTACAAACCC
TCCCTCAAGGATCGAGTCACCATATCACGTGACACGTCCAAGAACCAGTTCTCCCTGAAGCTGAGC
TCTGTGACCGCTGCGGACACTGCAGTGTATTACTGTGCGAGATACGGTAGGGTCTTCTTTGACTAC
TGGGGCCAGGGAACCCTGGTCACCGTCTCCTCAGGTGGCGGTGGCTCGGGCGGTGGTGGGTCGGGT
GGCGGCGGATCTGATATTGTGATGACTCAGTCTCCACTCTCCCTGCCCGTCACCCCTGGAGAGCCG
GCCTCCATCTCCTGCAGGTCTAGTCAGAGCATTGTACATAGTAATGGAAACACCTATTTGCAATGG
TACCTGCAGAAGCCAGGGCAGTCTCCACAGCTCCTGATCTATAAAGTTTCTAATCGGCTTTATGGG
GTCCCTGACAGGTTCAGTGGCAGTGGATCAGGCACAGATTTTACACTGAAAATCAGCAGAGTGGAG
GCTGAGGATGTTGGGGTTTATTACTGCTTTCAAGGTTCACATGTTCCGTGGACGTTCGGCCAAGGG
ACCAAGGTGGAAATCAAAGCGGCCGCGCCCGATGTGCAGGATTGCCCAGAATGCACGCTACAGGAA
AACCCATTCTTCTCCCAGCCGGGTGCCCCAATACTTCAGTGCATGGGCTGCTGCTTCTCTAGAGCA
TATCCCACTCCACTAAGGTCCAAGAAGACGATGTTGGTCCAAAAGAACGTCACCTCAGAGTCCACT
TGCTGTGTAGCTAAATCATATAACAGGGTCACAGTAATGGGGGGTTTCAAAGTGGAGAACCACACG
GCGTGCCACTGCAGTACTTGTTAG

FIG. 19B

The amino acid sequence of IGF-1R scFv alpha(1-87) (SEQ ID NO:60)
MATGSRTSLLLAFGLLCLPWLQEGSAQVQLQESGPGLVKPSETLSLTCTVSGYSITGGYLWNWIRQ
PPGKGLEWIGYISYDGTNNYKPSLKDRVTISRDTSKNQFSLKLSSVTAADTAVYYCARYGRVFFDY
WGQGTLVTVSSGGGGSGGGGSGGGGSDIVMTQSPLSLPVTPGEPASISCRSSQSIVHSNGNTYLQW
YLQKPGQSPQLLIYKVSNRLYGVPDRFSGSGSGTDFTLKISRVEAEDVGVYYCFQGSHVPWTFGQG
TKVEIKAAAPDVQDCPECTLQENPFFSQPGAPILQCMGCCFSRAYPTPLRSKKTMLVQKNVTSEST
CCVAKSYNRVTVMGGFKVENHTACHCSTC

FIG. 20A

The DNA sequence of IGF-1R scFv hCG beta (SEQ ID NO:61)
ATGGCTACAGGCTCCCGGACGTCCCTGCTCCTGGCTTTTGGCCTGCTCTGCCTGCCCTGGCTTCAA
GAGGGATCTGCCCAGGTGCAGCTTCAGGAGTCGGGCCCAGGACTGGTGAAGCCTTCGGAGACCCTG
TCCCTCACCTGCACTGTCTCTGGTTACTCCATCACCGGTGGTTATTTATGGAACTGGATACGGCAG
CCCCCAGGGAAGGGACTGGAGTGGATCGGGTATATCAGCTACGACGGTACCAATAACTACAAACCC
TCCCTCAAGGATCGAGTCACCATATCACGTGACACGTCCAAGAACCAGTTCTCCCTGAAGCTGAGC
TCTGTGACCGCTGCGGACACTGCAGTGTATTACTGTGCAGATACGGTAGGGTCTTCTTTGACTAC
TGGGGCCAGGGAACCCTGGTCACCGTCTCCTCAGGTGGCGGTGGCTCGGGCGGTGGTGGGTCGGGT
GGCGGCGGATCTGATATTGTGATGACTCAGTCTCCACTCTCCCTGCCCGTCACCCCTGGAGAGCCG
GCCTCCATCTCCTGCAGGTCTAGTCAGAGCATTGTACATAGTAATGGAAACACCTATTTGCAATGG
TACCTGCAGAAGCCAGGGCAGTCTCCACAGCTCCTGATCTATAAAGTTTCTAATCGGCTTTATGGG
GTCCCTGACAGGTTCAGTGGCAGTGGATCAGGCACAGATTTTACACTGAAAATCAGCAGAGTGGAG
GCTGAGGATGTTGGGGTTTATTACTGCTTTCAAGGTTCACATGTTCCGTGGACGTTCGGCCAAGGG
ACCAAGGTGGAAATCAAAGCGGCCGCGTCCAAGGAGCCGCTTCGGCCACGGTGCCGCCCCATCAAT
GCCACCCTGGCTGTGGAGAAGGAGGGCTGCCCCGTGTGCATCACCGTCAACACCACCATCTGTGCC
GGCTACTGCCCCACCATGACCCGCGTGCTGCAGGGGGTCCTGCCGGCCCTGCCTCAGGTGGTGTGC
AACTACCGCGATGTGCGCTTCGAGTCCATCCGGCTCCCTGGCTGCCCGCGCGGCGTGAACCCCGTG
GTCTCCTACGCCGTGGCTCTCAGCTGTCAATGTGCACTCTGCCGCCGCAGCACCACTGACTGCGGG
GGTCCCAAGGACCACCCCTTGACCTGTGATGACCCCCGCTTCCAGGACTCCTCTTCCTCAAAGGCC
CCTCCCCCCAGCCTTCCAAGCCCATCCCGACTCCCGGGGCCCTCGGACACCCCGATCCTCCCACAA
TAG

FIG. 20B

The amino acid sequence of IGF-1R scFv hCG beta (SEQ ID NO:62)
MATGSRTSLLLAFGLLCLPWLQEGSAQVQLQESGPGLVKPSETLSLTCTVSGYSITGGYLWNWIRQ
PPGKGLEWIGYISYDGTNNYKPSLKDRVTISRDTSKNQFSLKLSSVTAADTAVYYCARYGRVFFDY
WGQGTLVTVSSGGGGSGGGGSGGGGSDIVMTQSPLSLPVTPGEPASISCRSSQSIVHSNGNTYLQW
YLQKPGQSPQLLIYKVSNRLYGVPDRFSGSGSGTDFTLKISRVEAEDVGVYYCFQGSHVPWTFGQG
TKVEIKAAASKEPLRPRCRPINATLAVEKEGCPVCITVNTTICAGYCPTMTRVLQGVLPALPQVVC
NYRDVRFESIRLPGCPRGVNPVVSYAVALSCQCALCRRSTTDCGGPKDHPLTCDDPRFQDSSSSKA
PPPSLPSPSRLPGPSDTPILPQ

FIG. 21

Displacement of Alexa fluor 488-labeled EGF from the surface of A431 cells by 10X concentrated conditioned culture supernatants containing EGFR V region-hCG fusion proteins.

Displacement of Alexa fluor 488-labeled EGF from the surface of A431 cells by serially diluted 10X concentrated conditioned culture supernatants containing EGFR V region-hCG fusion proteins.

FIG. 23A

DNA sequence of alpha(1-87)scFv EGFR (SEQ ID NO:63)
ATGGCTACAGGCTCCCGGACGTCCCTGCTCCTGGCTTTTGGCCTGCTCTGCCTGCCCTGGCTTCAA
GAGGGCAGTGCCGCTCCTGATGTGCAGGATTGCCCAGAATGCACGCTACAGGAAAACCCATTCTTC
TCCCAGCCGGGTGCCCCAATACTTCAGTGCATGGGCTGCTGCTTCTCTAGAGCATATCCCACTCCA
CTAAGGTCCAAGAAGACGATGTTGGTCCAAAAGAACGTCACCTCAGAGTCCACTTGCTGTGTAGCT
AAATCATATAACAGGGTCACAGTAATGGGGGGTTTCAAAGTGGAGAACCACACGGCGTGCCACTGC
AGTACTTGTCAGGTGCAGCTGAAGCAGTCAGGACCTGGCCTAGTGCAGCCCTCACAGAGCCTGTCC
ATCACCTGCACAGTCTCTGGTTTCTCATTAACTAACTATGGTGTACACTGGGTTCGCCAGTCTCCA
GGAAAGGGTCTGGAGTGGCTGGGAGTGATATGGAGTGGTGGAAACACAGACTATAATACACCTTTC
ACATCCAGACTGAGCATCAACAAGGACAATTCCAAGAGCCAAGTTTTCTTTAAAATGAACAGTCTG
CAATCTAATGACACAGCCATATATTACTGTGCCAGAGCCCTCACCTACTATGATTACGAGTTTGCT
TACTGGGGCCAAGGGACTCTGGTCACTGTCTCTGCAGGTGGCGGTGGCTCGGGCGGTGGTGGGTCG
GGTGGCGGCGGATCTGACATCTTGCTGACTCAGTCTCCAGTCATCCTGTCTGTGAGTCCAGGAGAA
AGAGTCAGTTTCTCCTGCAGGGCCAGTCAGAGTATTGGCACAAACATACACTGGTATCAGCAAAGA
ACAAATGGTTCTCCAAGGCTTCTCATAAAGTATGCTTCTGAGTCTATCTCTGGGATCCCTTCCAGG
TTTAGTGGCAGTGGATCAGGGACAGATTTTACTCTTAGCATCAACAGTGTGGAGTCTGAAGATATT
GCAGATTATTACTGTCAACAAAATAATAACTGGCCAACCACGTTCGGTGCTGGGACCAAGCTGGAG
CTGAAATGACTCGAG

FIG. 23B

Amino acid sequence of alpha(1-87)scFv EGFR (SEQ ID NO:64)
MATGSRTSLLLAFGLLCLPWLQEGSAAPDVQDCPECTLQENPFFSQPGAPILQCMGCCFSRAYPTP
LRSKKTMLVQKNVTSESTCCVAKSYNRVTVMGGFKVENHTACHCSTCQVQLKQSGPGLVQPSQSLS
ITCTVSGFSLTNYGVHWVRQSPGKGLEWLGVIWSGGNTDYNTPFTSRLSINKDNSKSQVFFKMNSL
QSNDTAIYYCARALTYYDYEFAYWGQGTLVTVSAGGGGSGGGGSGGGGSDILLTQSPVILSSPGER
VSFSCRASQSIGTNIHWYQQRTNGSPRLLIKYASESISGIPSRFSGSGSGTDFTLSINSVESEDIA
DYYCQQNNNWPTTFGAGTKLELK

FIG. 24A

DNA sequence of alpha(1-87)GFSASPAFFscFv EGFR (SEQ ID NO:65)
ATGGCTACAGGCTCCCGGACGTCCCTGCTCCTGGCTTTTGGCCTGCTCTGCCTGCCCTGGCTTCAA
GAGGGCAGTGCCGCTCCTGATGTGCAGGATTGCCCAGAATGCACGCTACAGGAAAACCCATTCTTC
TCCCAGCCGGGTGCCCCAATACTTCAGTGCATGGGCTGCTGCTTCTCTAGAGCATATCCCACTCCA
CTAAGGTCCAAGAAGACGATGTTGGTCCAAAAGAACGTCACCTCAGAGTCCACTTGCTGTGTAGCT
AAATCATATAACAGGGTCACAGTAATGGGGGGTTTCAAAGTGGAGAACCACACGGCGTGCCACTGC
AGTACTTGTGGTTTTAGCGCTTCTCCAGCATTCTTCCAGGTGCAGCTGAAGCAGTCAGGACCTGGC
CTAGTGCAGCCCTCACAGAGCCTGTCCATCACCTGCACAGTCTCTGGTTTCTCATTAACTAACTAT
GGTGTACACTGGGTTCGCCAGTCTCCAGGAAAGGGTCTGGAGTGGCTGGGAGTGATATGGAGTGGT
GGAAACACAGACTATAATACACCTTTCACATCCAGACTGAGCATCAACAAGGACAATTCCAAGAGC
CAAGTTTTCTTTAAAATGAACAGTCTGCAATCTAATGACACAGCCATATATTACTGTGCCAGAGCC
CTCACCTACTATGATTACGAGTTTGCTTACTGGGGCCAAGGGACTCTGGTCACTGTCTCTGCAGGT
GGCGGTGGCTCGGGCGGTGGTGGGTCGGGTGGCGGCGGATCTGACATCTTGCTGACTCAGTCTCCA
GTCATCCTGTCTGTGAGTCCAGGAGAAAGAGTCAGTTTCTCCTGCAGGGCCAGTCAGAGTATTGGC
ACAAACATACACTGGTATCAGCAAAGAACAAATGGTTCTCCAAGGCTTCTCATAAAGTATGCTTCT
GAGTCTATCTCTGGGATCCCTTCCAGGTTTAGTGGCAGTGGATCAGGGACAGATTTTACTCTTAGC
ATCAACAGTGTGGAGTCTGAAGATATTGCAGATTATTACTGTCAACAAAATAATAACTGGCCAACC
ACGTTCGGTGCTGGGACCAAGCTGGAGCTGAAATGAGTCGAC

FIG. 24B

Amino acid sequence of alpha(1-87)GFSASPAFFscFv EGFR (SEQ ID NO:66)
MATGSRTSLLLAFGLLCLPWLQEGSAAPDVQDCPECTLQENPFFSQPGAPILQCMGCCFSRAYPTP
LRSKKTMLVQKNVTSESTCCVAKSYNRVTVMGGFKVENHTACHCSTCGFSASPAFFQVQLKQSGPG
LVQPSQSLSITCTVSGFSLTNYGVHWVRQSPGKGLEWLGVIWSGGNTDYNTPFTSRLSINKDNSKS
QVFFKMNSLQSNDTAIYYCARALTYYDYEFAYWGQGTLVTVSAGGGGSGGGGSGGGGSDILLTQSP
VILSVSPGERVSFSCRASQSIGTNIHWYQQRTNGSPRLLIKYASESISGIPSRFSGSGSGTDFTLS
INSVESEDIADYYCQQNNNWPTTFGAGTKLELK

FIG. 25A

DNA sequence of alpha(1-87)-EGFR VH (SEQ ID NO:67)
ATGGCTACAGGCTCCCGGACGTCCCTGCTCCTGGCTTTTGGCCTGCTCTGCCTGCCCTGGCTTCAA
GAGGGCAGTGCCGCTCCTGATGTGCAGGATTGCCCAGAATGCACGCTACAGGAAAACCCATTCTTC
TCCCAGCCGGGTGCCCCAATACTTCAGTGCATGGGCTGCTGCTTCTCTAGAGCATATCCCACTCCA
CTAAGGTCCAAGAAGACGATGTTGGTCCAAAAGAACGTCACCTCAGAGTCCACTTGCTGTGTAGCT
AAATCATATAACAGGGTCACAGTAATGGGGGGTTTCAAAGTGGAGAACCACACGGCGTGCCACTGC
AGTACTTGTCAGGTGCAGCTGAAGCAGTCAGGACCTGGCCTAGTGCAGCCCTCACAGAGCCTGTCC
ATCACCTGCACAGTCTCTGGTTTCTCATTAACTAACTATGGTGTACACTGGGTTCGCCAGTCTCCA
GGAAAGGGTCTGGAGTGGCTGGGAGTGATATGGAGTGGTGGAAACACAGACTATAATACACCTTTC
ACATCCAGACTGAGCATCAACAAGGACAATTCCAAGAGCCAAGTTTTCTTTAAAATGAACAGTCTG
CAATCTAATGACACAGCCATATATTACTGTGCCAGAGCCCTCACCTACTATGATTACGAGTTTGCT
TACTGGGGCCAAGGGACTCTGGTCACTGTCTCTGCATGAGTCGAC

FIG. 25B

Amino acid sequence of alpha(1-87)-EGFR VH (SEQ ID NO:68)
MATGSRTSLLLAFGLLCLPWLQEGSAAPDVQDCPECTLQENPFFSQPGAPILQCMGCCFSRAYPTP
LRSKKTMLVQKNVTSESTCCVAKSYNRVTVMGGFKVENHTACHCSTCQVQLKQSGPGLVQPSQSLS
ITCTVSGFSLTNYGVHWVRQSPGKGLEWLGVIWSGGNTDYNTPFTSRLSINKDNSKSQVFFKMNSL
QSNDTAIYYCARALTYYDYEFAYWGQGTLVTVSA

FIG. 26A

DNA sequence of hCGbeta EGFR scFv (SEQ ID NO:69)
ATGGCTACAGGCTCCCGGACGTCCCTGCTCCTGGCTTTTGGCCTGCTCTGCCTGCCCTGGCTTCAA
GAGGGATCCGCCTCCAAGGAGCCGCTTCGGCCACGGTGCCGCCCCATCAATGCCACCCTGGCTGTG
GAGAAGGAGGGCTGCCCCGTGTGCATCACCGTCAACACCACCATCTGTGCCGGCTACTGCCCCACC
ATGACCCGCGTGCTGCAGGGGGTCCTGCCGGCCCTGCCTCAGGTGGTGTGCAACTACCGCGATGTG
CGCTTCGAGTCCATCCGGCTCCCTGGCTGCCCGCGCGGCGTGAACCCCGTGGTCTCCTACGCCGTG
GCTCTCAGCTGTCAATGTGCACTCTGCCGCCGCAGCACCACTGACTGCGGGGGTCCCAAGGACCAC
CCCTTGACCTGTGATGACCCCGCTTCCAGGACTCCTCTTCCTCAAAGGCCCCTCCCCCCAGCCTT
CCAAGCCCATCCCGACTCCCGGGGCCCTCGGACACCCCGATCCTCCCACAACAGGTGCAGCTGAAG
CAGTCAGGACCTGGCCTAGTGCAGCCCTCACAGAGCCTGTCCATCACCTGCACAGTCTCTGGTTTC
TCATTAACTAACTATGGTGTACACTGGGTTCGCCAGTCTCCAGGAAAGGGTCTGGAGTGGCTGGGA
GTGATATGGAGTGGTGGAAACACAGACTATAATACACCTTTCACATCCAGACTGAGCATCAACAAG
GACAATTCCAAGAGCCAAGTTTTCTTTAAAATGAACAGTCTGCAATCTAATGACACAGCCATATAT
TACTGTGCCAGAGCCCTCACCTACTATGATTACGAGTTTGCTTACTGGGGCCAAGGGACTCTGGTC
ACTGTCTCTGCAGGTGGCGGTGGCTCGGGCGGTGGTGGGTCGGGTGGCGGCGGATCTGACATCTTG
CTGACTCAGTCTCCAGTCATCCTGTCTGTGAGTCCAGGAGAAAGAGTCAGTTTCTCCTGCAGGGCC
AGTCAGAGTATTGGCACAAACATACACTGGTATCAGCAAAGAACAAATGGTTCTCCAAGGCTTCTC
ATAAAGTATGCTTCTGAGTCTATCTCTGGGATCCCTTCCAGGTTTAGTGGCAGTGGATCAGGGACA
GATTTTACTCTTAGCATCAACAGTGTGGAGTCTGAAGATATTGCAGATTATTACTGTCAACAAAAT
AATAACTGGCCAACCACGTTCGGTGCTGGGACCAAGCTGGAGCTGAAATGA

FIG. 26B

Amino acid sequence of hCGbeta EGFR scFv (SEQ ID NO:70)
MATGSRTSLLLAFGLLCLPWLQEGSASKEPLRPRCRPINATLAVEKEGCPVCITVNTTICAGYCPT
MTRVLQGVLPALPQVVCNYRDVRFESIRLPGCPRGVNPVVSYAVALSCQCALCRRSTTDCGGPKDH
PLTCDDPRFQDSSSSKAPPPSLPSPSRLPGPSDTPILPQQVQLKQSGPGLVQPSQSLSITCTVSGF
SLTNYGVHWVRQSPGKGLEWLGVIWSGGNTDYNTPFTSRLSINKDNSKSQVFFKMNSLQSNDTAIY
YCARALTYYDYEFAYWGQGTLVTVSAGGGSGGGGSGGGGSDILLTQSPVILSVSPGERVSFSCRA
SQSIGTNIHWYQQRTNGSPRLLIKYASESISGIPSRFSGSGSGTDFTLSINSVESEDIADYYCQQN
NNWPTTFGAGTKLELK

FIG. 27A

DNA sequence of hCGbeta EGFR VL (SEQ ID NO:71)
ATGGCTACAGGCTCCCGGACGTCCCTGCTCCTGGCTTTTGGCCTGCTCTGCCTGCCCTGGCTTCAA
GAGGGATCCGCCTCCAAGGAGCCGCTTCGGCCACGGTGCCGCCCCATCAATGCCACCCTGGCTGTG
GAGAAGGAGGGCTGCCCCGTGTGCATCACCGTCAACACCACCATCTGTGCCGGCTACTGCCCCACC
ATGACCCGCGTGCTGCAGGGGGTCCTGCCGGCCCTGCCTCAGGTGGTGTGCAACTACCGCGATGTG
CGCTTCGAGTCCATCCGGCTCCCTGGCTGCCCGCGCGGCGTGAACCCCGTGGTCTCCTACGCCGTG
GCTCTCAGCTGTCAATGTGCACTCTGCCGCCGCAGCACCACTGACTGCGGGGGTCCCAAGGACCAC
CCCTTGACCTGTGATGACCCCGCTTCCAGGACTCCTCTTCCTCAAAGGCCCCTCCCCCCAGCCTT
CCAAGCCCATCCCGACTCCCGGGGCCCTCGGACACCCCGATCCTCCCACAAGACATCTTGCTGACT
CAGTCTCCAGTCATCCTGTCTGTGAGTCCAGGAGAAAGAGTCAGTTTCTCCTGCAGGGCCAGTCAG
AGTATTGGCACAAACATACACTGGTATCAGCAAAGAACAAATGGTTCTCCAAGGCTTCTCATAAAG
TATGCTTCTGAGTCTATCTCTGGGATCCCTTCCAGGTTTAGTGGCAGTGGATCAGGGACAGATTTT
ACTCTTAGCATCAACAGTGTGGAGTCTGAAGATATTGCAGATTATTACTGTCAACAAAATAATAAC
TGGCCAACCACGTTCGGTGCTGGGACCAAGCTGGAGCTGAAATGA

FIG. 27B

Amino acid sequence of hCGbeta EGFR VL (SEQ ID NO:72)
MATGSRTSLLLAFGLLCLPWLQEGSASKEPLRPRCRPINATLAVEKEGCPVCITVNTTICAGYCPT
MTRVLQGVLPALPQVVCNYRDVRFESIRLPGCPRGVNPVVSYAVALSCQCALCRRSTTDCGGPKDH
PLTCDDPRFQDSSSSKAPPPSLPSPSRLPGPSDTPILPQDILLTQSPVILSVSPGERVSFSCRASQ
SIGTNIHWYQQRTNGSPRLLIKYASESISGIPSRFSGSGSGTDFTLSINSVESEDIADYYCQQNNN
WPTTFGAGTKLELK

FIG. 28

Amino acid sequence of Fab12scFvHL-alpha(1-87)(GGGGS)4-EGFRscFv
MATGSRTSLLLAFGLLCLPWLQEGSAEVQLVESGGGLVQPGGSLRLSCAASGYTFTNYGM
NWVRQAPGKGLEWVGWINTYTGEPTYAADFKRRFTFSLDTSKSTAYLQMNSLRAEDTAV
YYCAKYPHYYGSSHWYFDVWGQGTLVTVSSGGGGSGGGGSGGGGSDIQMTQSPSSLSAS
VGDRVTITCSASQDISNYLNWYQQKPGKAPKVLIYFTSSLHSGVPSRFSGSGSGTDFTLTISS
LQPEDFATYYCQQYSTVPWTFGQGTKVEIKRAPDVQDCPECTLQENPFFSQPGAPILQCMG
CCFSRAYPTPLRSKKTMLVQKNVTSESTCCVAKSYNRVTVMGGFKVENHTACHCSTCGG
GGSGGGGSGGGGSGGGGSQVQLKQSGPGLVQPSQSLSITCTVSGFSLTNYGVHWVRQSPG
KGLEWLGVIWSGGNTDYNTPFTSRLSINKDNSKSQVFFKMNSLQSNDTAIYYCARALTYY
DYEFAYWGQGTLVTVSAGGGGSGGGGSGGGGSDILLTQSPVILSVSPGERVSFSCRASQSI
GTNIHWYQQRTNGSPRLLIKYASESISGIPSRFSGSGSGTDFTLSINSVESEDIADYYCQQNN
NWPTTFGAGTKLELK*

FIG. 29

Amino acid sequence of Fab12scFvHL-hCGbeta-225scFv

MATGSRTSLLLAFGLLCLPWLQEGSAEVQLVESGGGLVQPGGSLRLSCAASGYTFTNYGM
NWVRQAPGKGLEWVGWINTYTGEPTYAADFKRRFTFSLDTSKSTAYLQMNSLRAEDTAV
YYCAKYPHYYGSSHWYFDVWGQGTLVTVSSGGGGSGGGGSGGGGSDIQMTQSPSSLSAS
VGDRVTITCSASQDISNYLNWYQQKPGKAPKVLIYFTSSLHSGVPSRFSGSGSGTDFTLTISS
LQPEDFATYYCQQYSTVPWTFGQGTKVEIKRSKEPLRPRCRPINATLAVEKEGCPVCITVNT
TICAGYCPTMTRVLQGVLPALPQVVCNYRDVRFESIRLPGCPRGVNPVVSYAVALSCQCAL
CRRSTTDCGGPKDHPLTCDDPRFQDSSSSKAPPPSLPSPSRLPGPSDTPILPQQVQLKQSGPG
LVQPSQSLSITCTVSGFSLTNYGVHWVRQSPGKGLEWLGVIWSGGNTDYNTPFTSRLSINK
DNSKSQVFFKMNSLQSNDTAIYYCARALTYYDYEFAYWGQGTLVTVSAGGGGSGGGGSG
GGGSDILLTQSPVILSVSPGERVSFSCRASQSIGTNIHWYQQRTNGSPRLLIKYASESISGIPSR
FSGSGSGTDFTLSINSVESEDIADYYCQQNNNWPTTFGAGTKLELK

FIG. 30

Amino acid sequence of VEGF(2)scFvHL-AA-alpha(1-87)-(GS)4-225scFvHL
MATGSRTSLLLAFGLLCLPWLQEGSAEVQLVQSGAEVKKPGASVKVSCKASGDTFTTYVI
HWMRQAPGQGLEWIGYINPYNDGTKYNEKFKGRVTITSDKSTSTAYMELSSLRSEDTAVY
YCARIYYDYDGDYWGQGTLVTVSSGGGGSGGGGSGGGGSDIQMTQSPSSLSASVGDRVTI
TCITSNDIDDDMNWYQQKPGKAPKLLISEGNTLRPGVPSRFSGSGYGTDFTLTISSLQPEDV
ATYYCFQSDNLPYTFGQGTKVEIKAAAPDVQDCPECTLQENPFFSQPGAPILQCMGCCFSR
AYPTPLRSKKTMLVQKNVTSESTCCVAKSYNRVTVMGGFKVENHTACHCSTCGGGGSGG
GGSGGGGSGGGGSQVQLKQSGPGLVQPSQSLSITCTVSGFSLTNYGVHWVRQSPGKGLEW
LGVIWSGGNTDYNTPFTSRLSINKDNSKSQVFFKMNSLQSNDTAIYYCARALTYYDYEFAY
WGQGTLVTVSAGGGGSGGGGSGGGGSDILLTQSPVILSVSPGERVSFSCRASQSIGTNIHW
YQQRTNGSPRLLIKYASESISGIPSRFSGSGSGTDFTLSINSVESEDIADYYCQQNNNWPTTF
GAGTKLELK

FIG. 31

Amino acid sequence of VEGF(2)scFvHL-AAA-hCGbeta-EGFRscfvHL
MATGSRTSLLLAFGLLCLPWLQEGSAEVQLVQSGAEVKKPGASVKVSCKASGDTFTTYVI
HWMRQAPGQGLEWIGYINPYNDGTKYNEKFKGRVTITSDKSTSTAYMELSSLRSEDTAVY
YCARIYYDYDGDYWGQGTLVTVSSGGGGSGGGGSGGGGSDIQMTQSPSSLSASVGDRVTI
TCITSNDIDDDMNWYQQKPGKAPKLLISEGNTLRPGVPSRFSGSGYGTDFTLTISSLQPEDV
ATYYCFQSDNLPYTFGQGTKVEIKAAASKEPLRPRCRPINATLAVEKEGCPVCITVNTTICA
GYCPTMTRVLQGVLPALPQVVCNYRDVRFESIRLPGCPRGVNPVVSYAVALSCQCALCRR
STTDCGGPKDHPLTCDDPRFQDSSSSKAPPPSLPSPSRLPGPSDTPILPQQVQLKQSGPGLVQ
PSQSLSITCTVSGFSLTNYGVHWVRQSPGKGLEWLGVIWSGGNTDYNTPFTSRLSINKDNS
KSQVFFKMNSLQSNDTAIYYCARALTYYDYEFAYWGQGTLVTVSAGGGGSGGGGSGGGG
SDILLTQSPVILSVSPGERVSFSCRASQSIGTNIHWYQQRTNGSPRLLIKYASESISGIPSRFSG
SGSGTDFTLSINSVESEDIADYYCQQNNNWPTTFGAGTKLELK

FIG. 32

Amino acid sequence of VEGF(2)scFvLH-AA-alpha(1-87)-(GS)4-225scFvHL
MATGSRTSLLLAFGLLCLPWLQEGSADIQMTQSPSSLSASVGDRVTITCITSNDIDDDMNW
YQQKPGKAPKLLISEGNTLRPGVPSRFSGSGYGTDFTLTISSLQPEDVATYYCFQSDNLPYT
FGQGTKVEIKGGGGSGGGGSGGGGSEVQLVQSGAEVKKPGASVKVSCKASGDTFTTYVIH
WMRQAPGQGLEWIGYINPYNDGTKYNEKFKGRVTITSDKSTSTAYMELSSLRSEDTAVYY
CARIYYDYDGDYWGQGTLVTVSSAAAPDVQDCPECTLQENPFFSQPGAPILQCMGCCFSR
AYPTPLRSKKTMLVQKNVTSESTCCVAKSYNRVTVMGGFKVENHTACHCSTCGGGGSGG
GGSGGGGSGGGGSQVQLKQSGPGLVQPSQSLSITCTVSGFSLTNYGVHWVRQSPGKGLEW
LGVIWSGGNTDYNTPFTSRLSINKDNSKSQVFFKMNSLQSNDTAIYYCARALTYYDYEFAY
WGQGTLVTVSAGGGGSGGGGSGGGGSDILLTQSPVILSVSPGERVSFSCRASQSIGTNIHW
YQQRTNGSPRLLIKYASESISGIPSRFSGSGSGTDFTLSINSVESEDIADYYCQQNNNWPTTF
GAGTKLELK

FIG. 33

Amino acid sequence of VEGF(2)scFvLH-AAA-hCGbeta-EGFRscFvHL
MATGSRTSLLLAFGLLCLPWLQEGSADIQMTQSPSSLSASVGDRVTITCITSNDIDDDMNW
YQQKPGKAPKLLISEGNTLRPGVPSRFSGSGYGTDFTLTISSLQPEDVATYYCFQSDNLPYT
FGQGTKVEIKGGGGSGGGGSGGGGSEVQLVQSGAEVKKPGASVKVSCKASGDTFTTYVIH
WMRQAPGQGLEWIGYINPYNDGTKYNEKFKGRVTITSDKSTSTAYMELSSLRSEDTAVYY
CARIYYDYDGDYWGQGTLVTVSSAAASKEPLRPRCRPINATLAVEKEGCPVCITVNTTICA
GYCPTMTRVLQGVLPALPQVVCNYRDV

FIG. 34

Amino acid sequence of V2(LH)-AA-alpha1-87-TOM(LH)
MATGSRTSLLLAFGLLCLPWLQEGSADIQMTQSPSSLSASVGDRVTITCITSNDIDDDMNW
YQQKPGKAPKLLISEGNTLRPGVPSRFSGSGYGTDFTLTISSLQPEDVATYYCFQSDNLPYT
FGQGTKVEIKGGGGSGGGGSGGGGSEVQLVQSGAEVKKPGASVKVSCKASGDTFTTYVIH
WMRQAPGQGLEWIGYINPYNDGTKYNEKFKGRVTITSDKSTSTAYMELSSLRSEDTAVYY
CARIYYDYDGDYWGQGTLVTVSSAAAPDVQDCPECTLQENPFFSQPGAPILQCMGCCFSR
AYPTPLRSKKTMLVQKNVTSESTCCVAKSYNRVTVMGGFKVENHTACHCSTCGGGGSGG
GGSGGGGSGGGGSLEADILMTQSPSSMSVSLGDTVSITCHSSQDINSNIGWLQQRPGKSFKG
LIYHGTNLDDEVPSRFSGSGSGADYSLTISSLESEDFADYYCVQYAQFPWTFGGGTKLEIKR
GGGGSGGGGSGGGGSDVQLQESGPSLVKPSQSLSLTCTVTGYSITSDFAWNWIRQFPGNKL
EWMGYISYSGNTRYNPSLKSRISITRDTSKNQFFLQLNSVTIEDTATYYCVTAGRGFPYWG
QGTLVTVSA

FIG. 35

Amino acid sequence of V2 (LH)-hCGbeta-TOM (LH)
MATGSRTSLLLAFGLLCLPWLQEGSADIQMTQSPSSLSASVGDRVTITCITSNDIDDDMNW
YQQKPGKAPKLLISEGNTLRPGVPSRFSGSGYGTDFTLTISSLQPEDVATYYCFQSDNLPYT
FGQGTKVEIKGGGGSGGGGSGGGGSEVQLVQSGAEVKKPGASVKVSCKASGDTFTTYVIH
WMRQAPGQGLEWIGYINPYNDGTKYNEKFKGRVTITSDKSTSTAYMELSSLRSEDTAVYY
CARIYYDYDGDYWGQGTLVTVSSAAASKEPLRPRCRPINATLAVEKEGCPVCITVNTTICA
GYCPTMTRVLQGVLPALPQVVCNYRDVRFESIRLPGCPRGVNPVVSYAVALSCQCALCRR
STTDCGGPKDHPLTCDDPRFQDSSSSKAPPPSLPSPSRLPGPSDTPILPQLEADILMTQSPSSM
SVSLGDTVSITCHSSQDINSNIGWLQQRPGKSFKGLIYHGTNLDDEVPSRFSGSGSGADYSL
TISSLESEDFADYYCVQYAQFPWTFGGGTKLEIKRGGGGSGGGGSGGGGSDVQLQESGPSL
VKPSQSLSLTCTVTGYSITSDFAWNWIRQFPGNKLEWMGYISYSGNTRYNPSLKSRISITRD
TSKNQFFLQLNSVTIEDTATYYCVTAGRGFPYWGQGTLVTVSA

FIG. 36

Amino acid sequence of Tom-alpha-V2(LH)

MATGSRTSLLLAFGLLCLPWLQEGSADILMTQSPSSMSVSLGDTVSITCHSSQDINSNIGWL
QQRPGKSFKGLIYHGTNLDDEVPSRFSGSGSGADYSLTISSLESEDFADYYCVQYAQFPWTF
GGGTKLEIKRGGGGSGGGGSGGGGSDVQLQESGPSLVKPSQSLSLTCTVTGYSITSDFAWN
WIRQFPGNKLEWMGYISYSGNTRYNPSLKSRISITRDTSKNQFFLQLNSVTIEDTATYYCVT
AGRGFPYWGQGTLVTVSAAAAPDVQDCPECTLQENPFFSQPGAPILQCMGCCFSRAYPTPL
RSKKTMLVQKNVTSESTCCVAKSYNRVTVMGGFKVENHTACHCSTCGGGGSGGGGSGG
GGSGGGGSLDDIQMTQSPSSLSASVGDRVTITCITSNDIDDDMNWYQQKPGKAPKLLISEG
NTLRPGVPSRFSGSGYGTDFTLTISSLQPEDVATYYCFQSDNLPYTFGQGTKVEIKGGGGSG
GGGSGGGGSEVQLVQSGAEVKKPGASVKVSCKASGDTFTTYVIHWMRQAPGQGLEWIGY
INPYNDGTKYNEKFKGRVTITSDKSTSTAYMELSSLRSEDTAVYYCARIYYDYDGDYWGQ
GTLVTVSS

FIG. 37

Amino acid sequence Tom hCGbeta V2(LH)
MATGSRTSLLLAFGLLCLPWLQEGSAGSADILMTQSPSSMSVSLGDTVSITCHSSQDINSNI
GWLQQRPGKSFKGLIYHGTNLDDEVPSRFSGSGSGADYSLTISSLESEDFADYYCVQYAQF
PWTFGGGTKLEIKRGGGGSGGGGSGGGGSDVQLQESGPSLVKPSQSLSLTCTVTGYSITSD
FAWNWIRQFPGNKLEWMGYISYSGNTRYNPSLKSRISITRDTSKNQFFLQLNSVTIEDTATY
YCVTAGRGFPYWGQGTLVTVSAAAASKEPLRPRCRPINATLAVEKEGCPVCITVNTTICAG
YCPTMTRVLQGVLPALPQVVCNYRDVRFESIRLPGCPRGVNPVVSYAVALSCQCALCRRS
TTDCGGPKDHPLTCDDPRFQDSSSSKAPPPSLPSPSRLPGPSDTPILPQLDDIQMTQSPSSLSA
SVGDRVTITCITSNDIDDDMNWYQQKPGKAPKLLISEGNTLRPGVPSRFSGSGYGTDFTLTI
SSLQPEDVATYYCFQSDNLPYTFGQGTKVEIKGGGGSGGGGSGGGGSEVQLVQSGAEVKK
PGASVKVSCKASGDTFTTYVIHWMRQAPGQGLEWIGYINPYNDGTKYNEKFKGRVTITSD
KSTSTAYMELSSLRSEDTAVYYCARIYYDYDGDYWGQGTLVTVSS

FIG. 38

The amino acid sequence of huEGFR alpha(1-87)
MATGSRTSLLLAFGLLCLPWLQEGSAEVQLVQSGAEVKKPGASVKVSCKASGFSLTNYGV
HWMRQAPGQGLEWIGVIWSGGNTDYNTPFTSRVTITSDKSTSTAYMELSSLRSEDTAVYY
CARALTYYDYEFAYWGQGTLVTVSSGGGGSGGGGSGGGGSDIQMTQSPSSLSASVGDRV
TITCRASQSIGTNIHWYQQKPGKAPKLLIKYASESISGVPSRFSGSGYGTDFTLTISSLQPEDV
ATYYCQQNNNWPTTFGQGTKVEIKAAAPDVQDCPECTLQENPFFSQPGAPILQCMGCCFS
RAYPTPLRSKKTMLVQKNVTSESTCCVAKSYNRVTVMGGFKVENHTACHCSTC

FIG. 39

The amino acid sequence of huEGFR hCGbeta
MATGSRTSLLLAFGLLCLPWLQEGSAEVQLVQSGAEVKKPGASVKVSCKASGFSLTNYGV
HWMRQAPGQGLEWIGVIWSGGNTDYNTPFTSRVTITSDKSTSTAYMELSSLRSEDTAVYY
CARALTYYDYEFAYWGQGTLVTVSSGGGGSGGGGSGGGGSDIQMTQSPSSLSASVGDRV
TITCRASQSIGTNIHWYQQKPGKAPKLLIKYASESISGVPSRFSGSGYGTDFTLTISSLQPEDV
ATYYCQQNNNWPTTFGQGTKVEIKAAASKEPLRPRCRPINATLAVEKEGCPVCITVNTTIC
AGYCPTMTRVLQGVLPALPQVVCNYRDVRFESIRLPGCPRGVNPVVSYAVALSCQCALCR
RSTTDCGGPKDHPLTCDDPRFQDSSSSKAPPPSLPSPSRLPGPSDTPILPQ

FIG. 40

Amino acid sequence of huEGFR-alpha(1-87)-V2(LH)
MATGSRTSLLLAFGLLCLPWLQEGSAEVQLVQSGAEVKKPGASVKVSCKASGFSLTNYGV
HWMRQAPGQGLEWIGVIWSGGNTDYNTPFTSRVTITSDKSTSTAYMELSSLRSEDTAVYY
CARALTYYDYEFAYWGQGTLVTVSSGGGGSGGGGSGGGGSDIQMTQSPSSLSASVGDRV
TITCRASQSIGTNIHWYQQKPGKAPKLLIKYASESISGVPSRFSGSGYGTDFTLTISSLQPEDV
ATYYCQQNNNWPTTFGQGTKVEIKAAAPDVQDCPECTLQENPFFSQPGAPILQCMGCCFS
RAYPTPLRSKKTMLVQKNVTSESTCCVAKSYNRVTVMGGFKVENHTACHCSTCGGGGSG
GGGSGGGGSGGGGSLDDIQMTQSPSSLSASVGDRVTITCITSNDIDDDMNWYQQKPGKAP
KLLISEGNTLRPGVPSRFSGSGYGTDFTLTISSLQPEDVATYYCFQSDNLPYTFGQGTKVEIK
GGGGSGGGGSGGGGSEVQLVQSGAEVKKPGASVKVSCKASGDTFTTYVIHWMRQAPGQ
GLEWIGYINPYNDGTKYNEKFKGRVTITSDKSTSTAYMELSSLRSEDTAVYYCARIYYDYD
GDYWGQGTLVTVSS

FIG. 41

Amino acid sequence of huEGFR-hCGbeta-V2(LH)
MATGSRTSLLLAFGLLCLPWLQEGSAEVQLVQSGAEVKKPGASVKVSCKASGFSLTNYGV
HWMRQAPGQGLEWIGVIWSGGNTDYNTPFTSRVTITSDKSTSTAYMELSSLRSEDTAVYY
CARALTYYDYEFAYWGQGTLVTVSSGGGGSGGGGSGGGGSDIQMTQSPSSLSASVGDRV
TITCRASQSIGTNIHWYQQKPGKAPKLLIKYASESISGVPSRFSGSGYGTDFTLTISSLQPEDV
ATYYCQQNNNWPTTFGQGTKVEIKAAASKEPLRPRCRPINATLAVEKEGCPVCITVNTTIC
AGYCPTMTRVLQGVLPALPQVVCNYRDVRFESIRLPGCPRGVNPVVSYAVALSCQCALCR
RSTTDCGGPKDHPLTCDDPRFQDSSSSKAPPPSLPSPSRLPGPSDTPILPQLDDIQMTQSPSSL
SASVGDRVTITCITSNDIDDDMNWYQQKPGKAPKLLISEGNTLRPGVPSRFSGSGYGTDFTL
TISSLQPEDVATYYCFQSDNLPYTFGQGTKVEIKGGGGSGGGGSGGGGSEVQLVQSGAEV
KKPGASVKVSCKASGDTFTTYVIHWMRQAPGQGLEWIGYINPYNDGTKYNEKFKGRVTIT
SDKSTSTAYMELSSLRSEDTAVYYCARIYYDYDGDYWGQGTLVTVSS

FIG. 42

Amino acid sequence of A12(LH)alpha(1-87)
MATGSRTSLLLAFGLLCLPWLQEGSASSELTQDPAVSVALGQTVRITCQGDSLRSYYATW
YQQKPGQAPILVIYGENKRPSGIPDRFSGSSSGNTASLTITGAQAEDEADYYCKSRDGSGQH
LVFGGGTKLTVLGGGGSGGGGSGGGGSEVQLVQSGAEVKKPGSSVKVSCKASGGTFSSY
AISWVRQAPGQGLEWMGGIIPIFGTANYAQKFQGRVTITADKSTSTAYMELSSLRSEDTAV
YYCARAPLRFLEWSTQDHYYYYMDVWGKGTTVTVSSAAAPDVQDCPECTLQENPFFSQ
PGAPILQCMGCCFSRAYPTPLRSKKTMLVQKNVTSESTCCVAKSYNRVTVMGGFKVENHT
ACHCSTC

FIG. 43

Amino acid sequence of A12(LH)hCGbeta

MATGSRTSLLLAFGLLCLPWLQEGSASSELTQDPAVSVALGQTVRITCQGDSLRSYYATW
YQQKPGQAPILVIYGENKRPSGIPDRFSGSSSGNTASLTITGAQAEDEADYYCKSRDGSGQH
LVFGGGTKLTVLGGGGSGGGGSGGGGSEVQLVQSGAEVKKPGSSVKVSCKASGGTFSSY
AISWVRQAPGQGLEWMGGIIPIFGTANYAQKFQGRVTITADKSTSTAYMELSSLRSEDTAV
YYCARAPLRFLEWSTQDHYYYYYMDVWGKGTTVTVSSAAASKEPLRPRCRPINATLAVE
KEGCPVCITVNTTICAGYCPTMTRVLQGVLPALPQVVCNYRDVRFESIRLPGCPRGVNPVV
SYAVALSCQCALCRRSTTDCGGPKDHPLTCDDPRFQDSSSSKAPPPSLPSPSRLPGPSDTPIL
PQ

FIG. 44

Amino acid sequence of EM164(LH)scFv-alpha(1-87)
MATGSRTSLLLAFGLLCLPWLQ

FIG. 45

Amino acid sequence of EM164(LH)scFv-hCGbeta

MATGSRTSLLLAFGLLCLPWLQEGSADVVMTQTPLSLPVSLGDPASISCRSSQSIVHSNVNT
YLEWYLQKPGQSPRLLIYKVSNRFSGVPDRFSGSGAGTDFTLRISRVEAEDLGIYYCFQGSH
VPPTFGGGTKLEIKRGGGGSGGGGSGGGGSQVQLVQSGAEVVKPGASVKLSCKASGYTFT
SYWMHWVKQRPGQGLEWIGEINPSNGRTNYNQKFQGKATLTVDKSSSTAYMQLSSLTSE
DSAVYYFARGRPDYYGSSKWYFDVWGQGTTVTVSSAAASKEPLRPRCRPINATLAVEKEG
CPVCITVNTTICAGYCPTMTRVLQGVLPALPQVVCNYRDVRFESIRLPGCPRGVNPVVSYA
VALSCQCALCRRSTTDCGGPKDHPLTCDDPRFQDSSSSKAPPPSLPSPSRLPGPSDTPILPQ

FIG. 46

Amino acid sequence of 19D12(LH)scFv alpha(1-87)
MATGSRTSLLLAFGLLCLPWLQEGSAEIVLTQVPDFQSVTPKEKVTITCRASQSIGSSLHWY
QQKPDQSPKLLIKYASQSLSGVPSRFSGSGSGTDFTLTINSLEAEDAAAYYCHQSSRLPHTF
GGGTKVEIKRTGGGGSGGGGSGGGGSEVQLVQSGGGLVHPGGSLRLSCAASGFTFSSFAM
HWVRQAPGKGLEWISVIDTRGATYYADSVKGRFTISRDNAKNSLYLQMNSLRAEDMAVY
YCARLGNFYYGMDVWGQGTTVTVSSAAAPDVQDCPECTLQENPFFSQPGAPILQCMGCCF
SRAYPTPLRSKKTMLVQKNVTSESTCCVAKSYNRVTVMGGFKVENHTACHCSTC

FIG. 47

Amino acid sequence of 19D12(LH)scFv-hCGbeta
MATGSRTSLLLAFGLLCLPWLQEGSAEIVLTQVPDFQSVTPKEKVTITCRASQSIGSSLHWY
QQKPDQSPKLLIKYASQSLSGVPSRFSGSGSGTDFTLTINSLEAEDAAAYYCHQSSRLPHTF
GGGTKVEIKRTGGGGSGGGGSGGGGSEVQLVQSGGGLVHPGGSLRLSCAASGFTFSSFAM
HWVRQAPGKGLEWISVIDTRGATYYADSVKGRFTISRDNAKNSLYLQMNSLRAEDMAVY
YCARLGNFYYGMDVWGQGTTVTVSSAAASKEPLRPRCRPINATLAVEKEGCPVCITVNTTI
CAGYCPTMTRVLQGVLPALPQVVCNYRDVRFESIRLPGCPRGVNPVVSYAVALSCQCALC
RRSTTDCGGPKDHPLTCDDPRFQDSSSSKAPPPSLPSPSRLPGPSDTPILPQ

FIG. 48

Amino acid sequence of the EGFR scFv VH-E105C/VL-H34C mutant
QVQLKQSGPGLVQPSQSLSITCTVSGFSLTNYGVHWVRQSPGKGLEWLGVIWSGGNTDYN
TPFTSRLSINKDNSKSQVFFKMNSLQSNDTAIYYCARALTYYDYCFAYWGQGTLVTVSAG
GGGSGGGGSGGGGSDILLTQSPVILSVSPGERVSFSCRASQSIGTNICWYQQRTNGSPRLLIK
YASESISGIPSRFSGSGSGTDFTLSINSVESEDIADYYCQQNNNWPTTFGAGTKLELK

FIG. 49

Amino acid sequence of the EGFR scFv VH-W109C/VL-S43C mutant
QVQLKQSGPGLVQPSQSLSITCTVSGFSLTNYGVHWVRQSPGKGLEWLGVIWSGGNTDYN
TPFTSRLSINKDNSKSQVFFKMNSLQSNDTAIYYCARALTYYDYEFAYCGQGTLVTVSAGG
GGSGGGGSGGGGSDILLTQSPVILSVSPGERVSFSCRASQSIGTNIHWYQQRTNGCPRLLIKY
ASESISGIPSRFSGSGSGTDFTLSINSVESEDIADYYCQQNNNWPTTFGAGTKLELK

FIG. 50

Amino acid sequence of the EGFR scFv VH-A107C/VL-L46C mutant
QVQLKQSGPGLVQPSQSLSITCTVSGFSLTNYGVHWVRQSPGKGLEWLGVIWSGGNTDYN
TPFTSRLSINKDNSKSQVFFKMNSLQSNDTAIYYCARALTYYDYEFCYWGQGTLVTVSAG
GGGSGGGGSGGGGSDILLTQSPVILSVSPGERVSFSCRASQSIGTNIHWYQQRTNGSPRCLIK
YASESISGIPSRFSGSGSGTDFTLSINSVESEDIADYYCQQNNNWPTTFGAGTKLELK

FIG. 51

Amino acid sequence of the EGFR scFv VH-L45C/VL-F98C mutant
QVQLKQSGPGLVQPSQSLSITCTVSGFSLTNYGVHWVRQSPGKGCEWLGVIWSGGNTDYN
TPFTSRLSINKDNSKSQVFFKMNSLQSNDTAIYYCARALTYYDYEFAYWGQGTLVTVSAG
GGGSGGGGSGGGGSDILLTQSPVILSVSPGERVSFSCRASQSIGTNIHWYQQRTNGSPRLLIK
YASESISGIPSRFSGSGSGTDFTLSINSVESEDIADYYCQQNNNWPTTCGAGTKLELK

FIG. 52

Amino acid sequence of the EGFR scFv VH-G112C/VL-S43C mutant
QVQLKQSGPGLVQPSQSLSITCTVSGFSLTNYGVHWVRQSPGKGLEWLGVIWSGGNTDYN
TPFTSRLSINKDNSKSQVFFKMNSLQSNDTAIYYCARALTYYDYEFAYWGQCTLVTVSAG
GGGSGGGGSGGGGSDILLTQSPVILSVSPGERVSFSCRASQSIGTNIHWYQQRTNGCPRLLIK
YASESISGIPSRFSGSGSGTDFTLSINSVESEDIADYYCQQNNNWPTTFGAGTKLELK

US 7,820,165 B2

COMPOSITIONS AND METHODS OF PRODUCING HYBRID ANTIGEN BINDING MOLECULES AND USES THEREOF

The present application is filed under 35 U.S.C. §371 as a U.S. National Phase of PCT application number PCT/US/2006/045056 which was filed Nov. 21, 2006, which claims benefit to U.S. Provisional Application No. 60/738,647 filed Nov. 21, 2005, which are hereby incorporated by reference in their entirety.

BACKGROUND

The binding of ligands to molecules on the surface of cells often results in the transduction of intracellular signals. Frequently, such binding initiates a complicated cascade of second messengers, the end result of which is either stimulatory or inhibitory to the cell. Ligand binding can modulate cellular homeostasis by altering, for example, the activation state, growth, or differentiation of cells, usually by modulating gene transcription.

Antibodies to many cellular receptors, other cell-associated molecules, and ligands, such as cytokines and other growth factors have been developed. Some of these antibodies stimulate signal transduction, while others block or inhibit the signals transduced by the binding of cognate ligands. Still other antibodies bind to specific populations of cells and, therefore, are useful in targeting or identifying such cells in vivo. e.g., for visualization using a detectable label or for killing by a cytotoxic drug.

The development of such antibodies for diagnostic or therapeutic use has often been hampered, however, by problems with half-life, effective dose at the target site, toxicity and the like. The development of antigen binding molecules and method of generating such antigen binding molecules having improved properties would be of great benefit in the development of diagnostics and therapeutics.

SUMMARY

This invention is based, at least in part, on the discovery that non-immunoglobulin polypeptides such as heterodimeric proteinaceous hormones, can be fused to one or more antigen binding moieties, including but not limited to complementarity-determining regions (CDRs), variable heavy (VH) and light chains (VL), engineered antigen binding moieties, e.g., single chain antibodies (ScFv) and/or fragments thereof, to produce hybrid antigen binding molecules having superior properties relative to their non-hybrid counterparts.

The subject hybrid antigen binding molecules employ the α and β chains of a heterodimeric hormone or a portion thereof as a scaffold to which an antigen binding moiety is linked. An example of a heterodimeric proteinaceous hormone is the human chorionic hybrid proteins employing hCG found in U.S. Pat. No. 6,194,177, to Campbell et al., the entire content of which is incorporated by reference herein.

In general, this invention relates to hybrid proteins comprising α and β polypeptide chains of a heterodimeric hormone or a portion thereof, wherein at least one polypeptide chain further comprises at least one antigen binding moiety. The hybrid proteins of the invention have an antagonist activity and are useful in the treatment of the various diseases where a particular antagonist activity is desirable.

For example, in a specific embodiment, a hybrid protein comprises two polypeptide chains, with at least one chain further comprising one or more antigen binding moieties binding specifically to the epidermal growth factor receptor (EGFR), wherein the hybrid protein has EGFR antagonist activity.

In another embodiment, a hybrid protein comprises two polypeptide chains, with at least one chain further comprising one or more antigen binding moieties binding specifically to the insulin-like growth factor-1 receptor (IGF-1R), wherein the hybrid protein has IGF-1R antagonist activity.

In another embodiment, a hybrid protein comprises two polypeptide chains, with at least one chain further comprising one or more antigen binding moieties binding specifically to vascular endothelial cell growth factor (VEGF), wherein the hybrid protein has VEGF antagonist activity.

In some embodiments, the hybrid protein comprises one polypeptide chain comprising a first antigen binding moiety linked to a subunit of a heterodimeric proteinaceous hormone or a fragment thereof, and a second polypeptide chain comprising a second antigen binding moiety linked to another subunit of a heterodimeric proteinaceous hormone or a fragment thereof. For example, in some embodiments described herein, the first antigen binding moiety specifically binds to one of the following of the non-limiting group of targets comprising EGFR, IGF-1R and VEGF, and a second antigen binding moiety specifically binds to one of the following of the non-limiting group of targets comprising EGFR, IGF-1R and VEGF, wherein the first and the second antigen binding moieties may bind the same or different targets.

The antigen binding moieties may be linked to either the amino or carboxy terminus or both termini of the heterodimeric proteinaceous hormone.

The hybrid proteins of the present invention may comprise one, two, three or four antigen binding moieties, each with binding specificity for the same or different targets.

The antigen binding moieties of the present invention may be linked to the heterodimeric proteinaceous hormone via a peptide linker. In one embodiment the peptide linker is a cleavable linker. In one embodiment the cleavable linker is cleavable enzymatically. In another embodiment the linker is an IgG hinge region or fragment thereof.

In some embodiments the antigen binding moiety comprises at least one, two, or three or more CDRs. The CDRs comprising the antigen binding moieties of the present invention may be linked to the heterodimeric proteinaceous hormone either directly or through a peptide linker. Each CDR comprising an antigen binding moiety may be linked directly to each other or linked to each other via a peptide linker.

In some embodiments the antigen binding moiety comprises one or more VH domains optionally associated with a VL domain. In some embodiments the hybrid proteins of the present invention may comprise a VH region linked to the amino terminus of one polypeptide chain of a heterodimeric proteinaceous hormone and a VL domain linked to the amino terminus of the other polypeptide chain of the heterodimeric proteinaceous hormone. In other embodiments the VH and VL domains are linked to the carboxy termini of the heterodimeric proteinaceous hormone chains. In other embodiments the VH and VL domains are linked to both termini, with one VH domain linked to the amino terminus and one VH domain linked to the carboxy terminus of one chain of a heterodimeric proteinaceous hormone and a VL domain linked to the amino terminus and another VL domain link to the carboxy terminus of the other polypeptide chain of the heterodimeric proteinaceous hormone. In other embodiments the VH domain may be linked directly or through a peptide linker with the VL domain. In other embodiments an ScFv antibody may be linked to either the amino terminus, carboxy terminus or to both termini of one or both chains of a heterodimeric proteinaceous hormone.

In some embodiments, hybrid proteins having antagonist activity described herein comprise at least two polypeptide chains, with each chain comprising: (a) an amino acid sequence of an antigen binding moiety; and (b) an amino acid sequence of a subunit of a heterodimeric proteinaceous hormone or a fragment thereof, wherein the antigen binding moiety binds to a specific target and wherein the subunit of the heterodimeric proteinaceous hormone or a fragment thereof is capable of dimerizing with another subunit of the hormone or a fragment thereof. In some embodiments, hybrid proteins comprise the amino acid sequence of the antigen binding moiety and the amino acid sequence of a subunit of the heterodimeric proteinaceous hormone joined by a linker peptide. Examples of the specific targets of the antigen binding moieties for use in this invention include but are not limited to EGFR, IGF-1R and VEGF. Examples of proteinaceous heterodimeric hormones for use in this invention, include but are not limited to FSH, inhibin, TSH, hCG, and LH.

In some embodiments, one of the subunits of the heterodimeric proteinaceous hormone in the hybrid protein comprises one or more alterations which reduce or eliminate the biological activity of the hormone, while preserving the ability of the altered subunit to dimerize with another subunit of the hormone. In some embodiments, an altered subunit is an alpha subunit of hCG which comprises a deletion of amino acids 88-92, thereby rendering the hCG biologically inactive; however, preserving the ability of the alpha subunit to dimerize with the beta subunit of hCG. In another embodiment an altered subunit is an alpha subunit which comprises a mutation of a cysteine residue at amino acid position 26 substituted to alanine. In another embodiment an altered subunit is an alpha subunit comprising a deletion of amino acids 88-92 and a mutation of a cysteine residue at amino acid position 26 to alanine. In another embodiment an altered subunit is a beta subunit comprising a deletion of amino acids 104-145. The hybrid proteins of the invention may comprise: a) an altered alpha subunit and an unaltered beta subunit; b) an altered alpha subunit and an altered beta subunit; c) an unaltered alpha subunit and an altered beta subunit; or d) an unaltered alpha subunit and an unaltered beta subunit.

The invention also comprises nucleic acid molecules encoding fusion proteins and the fusion proteins encoded by such nucleic acid molecules. In some embodiments, an isolated nucleic acid molecule encoding a fusion protein comprises (a) a first nucleotide sequence encoding an antigen binding moiety, and (b) a second nucleotide sequence encoding a subunit of a heterodimeric proteinaceous hormone or a fragment thereof, wherein the subunit or fragment thereof is capable of forming a heterodimer with another subunit of the heterodimeric hormone and wherein the nucleic acid molecule is a DNA molecule. The first and the second nucleotide sequences may either be directly linked to each other, or they may be linked via a nucleotide sequence which encodes a peptide linker which is located between the first and the second nucleotide sequences.

In some embodiments, a fusion protein comprises (a) a first amino acid sequence of an antigen binding moiety; and (b) a second amino acid sequence of a subunit of a heterodimeric proteinaceous hormone or a fragment thereof, wherein the subunit or fragment thereof is capable of forming a heterodimer with another subunit of the hormone. Examples of the specific targets of the antigen binding moieties for use in this invention include but are not limited to EGFR, IGF-1R and VEGF. Examples of proteinaceous heterodimeric hormones for use in this invention, include but are not limited to FSH, inhibin, TSH, hCG, and LH.

Fusion proteins of the invention include, but are not limited to, fusion proteins comprising: (a) An antigen binding moiety that specifically binds to the EGFR, linked to a subunit of a heterodimeric proteinaceous hormone or a fragment thereof; (b) an antigen binding moiety that specifically binds to the IGF-1R, linked to a subunit of a heterodimeric proteinaceous hormone or a fragment thereof; and (c) an antigen binding moiety that specifically binds to VEGF, linked to a subunit of a heterodimeric proteinaceous hormone or a fragment thereof.

In some embodiments, the fusion proteins of the invention include a linker peptide located between the antigen binding moiety and the subunit of a heterodimeric proteinaceous hormone. The linker peptide can be enzymatically cleavable, for example, to include a thrombin cleavage site. Non limiting examples of the amino acid sequences of such linkers are: AA, AAA, GADK (SEQ ID NO: 1), GFASPAFF (SEQ ID NO: 98), DETYVPKEFNAE (SEQ ID NO: 2), DKTHTCP-PCPAPELLGGAA (SEQ ID NO: 99), DKTHTCPPCPA-PELLGGAAA (SEQ ID NO: 100), DKTHTSPPSPA-PELLGGAA (SEQ ID NO: 101), DKTHTSPPSPAPELLGGAAA (SEQ ID NO: 102), GGGS (SEQ ID NO: 103), (GGGS)$_2$ (SEQ ID NO: 104), GGGGS (SEQ ID NO: 105), (GGGGS)$_2$ (SEQ ID NO: 106), (GGGGS)$_4$ (SEQ ID NO: 107), GGGGC (SEQ ID NO: 108).

Fusion proteins can also be secreted.

In some embodiments, hybrid proteins having antagonist activity comprise: (a) a first fusion protein comprising an amino acid sequence of an antigen binding moiety linked to an amino acid sequence of a subunit of a heterodimeric proteinaceous hormone or a fragment thereof; and (b) a second fusion protein comprising an amino acid sequence of an antigen binding moiety linked to an amino acid sequence of another subunit of the heterodimeric proteinaceous hormone or a fragment thereof, wherein the antigen binding moiety is able to specifically bind a target and wherein the subunits of the heterodimeric proteinaceous hormone are capable of dimerizing with each other.

Examples of the specific targets of the antigen binding moieties for use in this invention include but are not limited to EGFR, IGF-1R and VEGF. Examples of proteinaceous heterodimeric hormones for use in this invention, include but are not limited to FSH, inhibin, TSH, hCG, and LH.

The invention further comprises expression vectors which comprise nucleic acid molecules which encode the fusion proteins or hybrid proteins described herein. The invention further comprises host cells comprising one or more expression vectors described herein. Host cells can either be co-transfected with two expression vectors, each comprising a nucleotide sequence encoding a polypeptide chain or a fusion protein which form a hybrid protein, or host cells can be transfected sequentially with the two expression vectors. Alternatively, host cells can be transfected with one expression vector which comprises a nucleotide sequence encoding two fusion proteins or polypeptide chains forming a hybrid protein.

The invention further comprises methods of treating disorders where antagonism of a cytokine activity is desirable. The methods of the invention include for example, disorders which can be treated by antagonism of one or more targets including, but not limited to, EGFR, IGF-1R and VEGF.

Examples of disorders which can be treated by antagonism of EGFR include but are not limited to cancer and other cell proliferative disorders.

Examples of disorders which can be treated by antagonism of IGF-1R include but are not limited to cancer and other cell proliferative disorders as well as gigantism and acromegaly.

Examples of disorders which can be treated by antagonism of VEGF include but are not limited to cancer and other cell proliferative disorders as well as disorders characterized by aberrant or uncontrolled angiogenesis, e.g. diabetic retinopathy.

The invention comprises pharmaceutical compositions comprising an effective amount of one or more hybrid proteins described herein in combination with a pharmaceutically acceptable carrier.

The invention comprises methods of making the hybrid proteins described herein. For example, in some embodiments, a method of making a hybrid protein comprises (a) transfecting a cell with two vectors, wherein each vector comprises a nucleic acid molecule encoding a fusion protein comprising an amino acid sequence of an antigen binding moiety or fragment thereof linked to a subunit of a heterodimeric proteinaceous hormone or a fragment thereof, and (b) culturing the cell under suitable conditions, thereby to produce the hybrid protein. Such a method may further comprise the step of testing the hybrid protein for antagonist activity.

BRIEF DESCRIPTION OF THE DRAWINGS

FIG. 1 depicts the nucleotide sequence synthesized de novo which encodes the variable heavy chain of an antibody that selectively binds EGFR (EGFR antibody).

FIG. 2 depicts the nucleotide sequence synthesized de novo which encodes the variable light chain of an antibody that selectively binds EGFR (EGFR antibody).

FIG. 3 depicts a portion of the pENTR1a vector (INVITROGEN) comprising a nucleotide construct encoding an hGH signal peptide linked to amino acids 1-87 of the alpha subunit of hCG. The amino acid sequence of the hGH signal peptide linked to amino acids 1-87 of the alpha subunit of hCG is also depicted.

FIG. 4 depicts portion of a pENTR1a vector (INVITROGEN) comprising a nucleotide construct encoding an hGH signal peptide linked to the beta subunit of hCG. The amino acid sequence of the hGH signal peptide linked to the beta subunit of hCG is also depicted.

FIG. 5A depicts the nucleotide sequence encoding a VH region from a molecule molecule that selectively binds EGFR linked to the beta subunit of hCG via an alanine linker.

FIG. 5B depicts the amino acid sequence encoded by construct depicted in FIG. 5A.

FIG. 6A depicts the nucleotide sequence encoding a VL region from a molecule that selectively binds EGFR linked to alpha (1-87) subunit of hCG via an alanine linker.

FIG. 6B depicts the amino acid sequence encoded by the construct depicted in FIG. 6A.

FIG. 7A depicts the nucleic acid sequence of a construct encoding an ScFv molecule comprising variable regions from the EGFR antibody linked to the alpha (1-87) subunit of hCG.

FIG. 7B depicts the amino acid sequence encoded by the construct depicted in FIG. 7A.

FIG. 8A depicts the nucleic acid sequence of a construct encoding an ScFv molecule comprising variable regions from the EGFR antibody linked to the beta subunit of hCG. FIG. 8B depicts the amino acid sequence encoded by the construct depicted in FIG. 8A.

FIG. 9 depicts the nucleotide sequence synthesized de novo which encodes the variable heavy chain of an antibody that selectively binds VEGF.

FIG. 10 depicts the nucleotide sequence synthesized de novo which encodes the variable light chain of an antibody that selectively binds VEGF.

FIG. 11 depicts the nucleotide sequence synthesized de novo which encodes an ScFv molecule (VH-VL) that selectively binds VEGF and comprises an IgG1 hinge region (hng) at the 3' end.

FIG. 12 depicts the nucleotide sequence synthesized de novo which encodes an ScFv molecule (VL-VH) that selectively binds VEGF and comprises an IgG1 hinge region (hng) at the 3' end.

FIG. 13 depicts the nucleotide sequence synthesized de novo which encodes the VH portion of an antibody that selectively binds IGF-1R.

FIG. 14 depicts the nucleotide sequence synthesized de novo which encodes the VL portion of an antibody that selectively binds IGF-1R.

FIG. 15A depicts the nucleic acid sequence encoding IGF-1RVHalpha(1-87).

FIG. 15B depicts the amino acid sequence encoded by the nucleic acid sequence of FIG. 15A.

FIG. 16A depicts the nucleic acid sequence encoding IGF-1RVHhCGbeta.

FIG. 16B depicts the amino acid sequence encoded by the nucleic acid sequence of FIG. 16A.

FIG. 17A depicts the nucleic acid sequence encoding IGF-1RVLalpha (1-87).

FIG. 17B depicts the amino acid sequence encoded by the nucleic acid sequence of FIG. 17A.

FIG. 18A depicts the nucleic acid sequence encoding IGF-1RVLhCGbeta.

FIG. 18B depicts the amino acid sequence encoded by the nucleic acid sequence of FIG. 18A.

FIG. 19A depicts the nucleic acid sequence encoding IGF-1RScFv hCGalpha (1-87).

FIG. 19B depicts the amino acid sequence encoded by the nucleic acid sequence depicted in FIG. 19A.

FIG. 20A depicts the nucleic acid sequence encoding IGF-1RScFv hCGbeta and

FIG. 20B depicts the amino acid sequence encoded by the nucleic acid sequence depicted in FIG. 20B.

FIG. 21 depicts a bar graph summarizing the results of an experiment where alexa fluor 488-labeled EGF was displaced from the surface of A431 cells by 10× concentrated conditioned culture supernatants derived from cells transfected with the various EGFR variable region hybrid antigen binding molecule constructs. A commercially available EGFR antibody, M225, was used as control.

FIG. 23A depicts the nucleic acid sequence encoding hCGalpha (1-87)-ScFvEGFR and FIG. 23B depicts the amino acid sequence encoded by the nucleic acid sequence of FIG. 23A.

FIG. 24A depicts the nucleic acid sequence encoding hCGalpha (1-87)GFASPAFF-ScFvEGFR and FIG. 24B depicts the amino acid sequence encoded by the nucleic acid molecule of FIG. 24B.

FIG. 25A depicts the nucleic acid sequence encoding alpha (1-87)-EGFRVH and FIG. 25B depicts the amino acid sequence encoded by the molecule of FIG. 25A.

FIG. 26A depicts the nucleic acid sequence encoding hCG-beta-ScFvEGFR and FIG. 26B depicts the amino acid sequence encoded by the molecule of FIG. 26A.

FIG. 27A depicts the nucleic acid sequence encoding hCG-beta-EGFRVL and FIG. 27B depicts the amino acid sequence encoded by the molecule of FIG. 27B.

FIG. 28 depicts the amino acid sequence of hCG alpha chain (1-87) comprising a VEGF-specific antigen binding moiety, an EGFR-specific antigen binding moiety and a linker.

FIG. 29 depicts the amino acid sequence of hCG beta chain comprising a VEGF-specific antigen binding moiety and an EGFR-specific antigen binding moiety.

FIG. 30 depicts the amino acid sequence of hCG alpha chain (1-87) comprising a VEGF-specific antigen binding moiety, an EGFR-specific antigen binding moiety and a linker.

FIG. 31 depicts the amino acid sequence of hCG beta chain comprising a VEGF-specific antigen binding moiety, an EGFR-specific antigen binding moiety and a linker.

FIG. 32 depicts the amino acid sequence of hCG alpha chain (1-87) comprising a VEGF-specific antigen binding moiety, an EGFR-specific antigen binding moiety and a linker.

FIG. 33 depicts the amino acid sequence of hCG beta chain comprising a VEGF-specific antigen binding moiety, an EGFR-specific antigen binding moiety and a linker.

FIG. 34 depicts the amino acid sequence of hCG alpha chain (1-87) comprising a VEGF-specific antigen binding moiety, an EGFR-specific antigen binding moiety and a linker.

FIG. 35 depicts the amino acid sequence of hCG beta chain comprising a VEGF-specific antigen binding moiety and an EGFR-specific antigen binding moiety.

FIG. 36 depicts the amino acid sequence of hCG alpha chain (1-87) comprising a VEGF-specific antigen binding moiety and an EGFR-specific antigen binding moiety.

FIG. 37 depicts the amino acid sequence of hCG beta chain comprising a VEGF-specific antigen binding moiety and an EGFR-specific antigen binding moiety.

FIG. 38 depicts the amino acid sequence of hCG alpha chain (1-87) comprising a humanized EGFR-specific antigen binding moiety.

FIG. 39 depicts the amino acid sequence of hCG beta chain comprising a humanized EGFR-specific antigen binding moiety.

FIG. 40 depicts the amino acid sequence of hCG alpha chain (1-87) comprising a humanized EGFR-specific antigen binding moiety and a VEGF-specific antigen binding moiety.

FIG. 41 depicts the amino acid sequence of hCG beta chain comprising a humanized EGFR-specific antigen binding moiety and a VEGF-specific antigen binding moiety.

FIG. 42 depicts the amino acid sequence of hCG alpha chain (1-87) comprising an IGF-1R-specific antigen binding moiety.

FIG. 43 depicts the amino acid sequence of hCG beta chain comprising an IGF-1R-specific antigen binding moiety.

Figure 44:
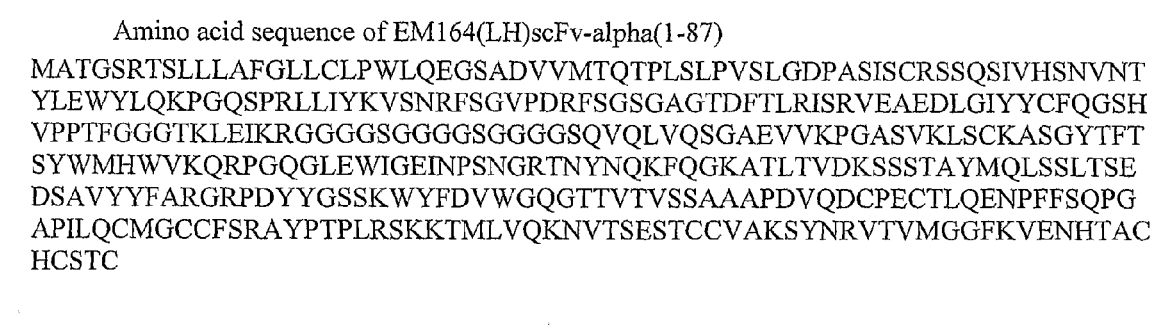

FIG. 44 depicts the amino acid sequence of hCG alpha chain (1-87) comprising an IGF-1R-specific antigen binding moiety.

Figure 45:
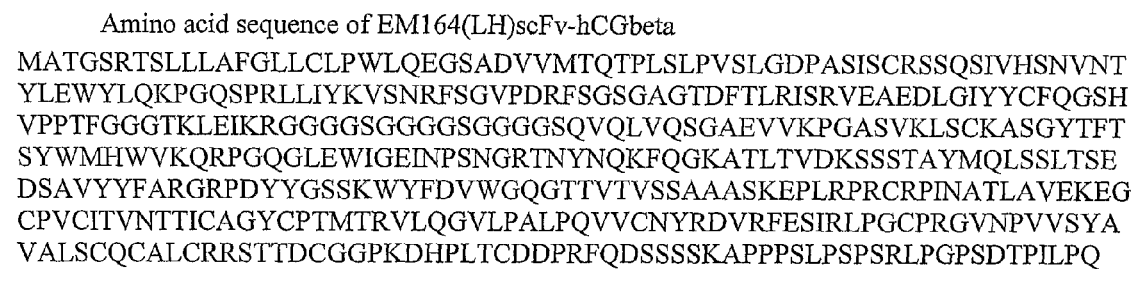

FIG. 45 depicts the amino acid sequence of hCG beta chain comprising an IGF-1R-specific antigen binding moiety.

FIG. 46 depicts the amino acid sequence of hCG alpha chain (1-87) comprising an IGF-1R-specific antigen binding moiety.

FIG. 47 depicts the amino acid sequence of hCG beta chain comprising an IGF-1R-specific antigen binding moiety.

FIG. 48 depicts the amino acid sequence of an hCG mutant comprising an EGFR-specific antigen binding moiety.

FIG. 49 depicts the amino acid sequence of an hCG mutant comprising an EGFR-specific antigen binding moiety.

FIG. 50 depicts the amino acid sequence of an hCG mutant comprising an EGFR-specific antigen binding moiety.

FIG. 51 depicts the amino acid sequence of an hCG mutant comprising an EGFR-specific antigen binding moiety.

FIG. 52 depicts the amino acid sequence of an hCG mutant comprising an EGFR-specific antigen binding moiety.

DETAILED DESCRIPTION

Figure 22:
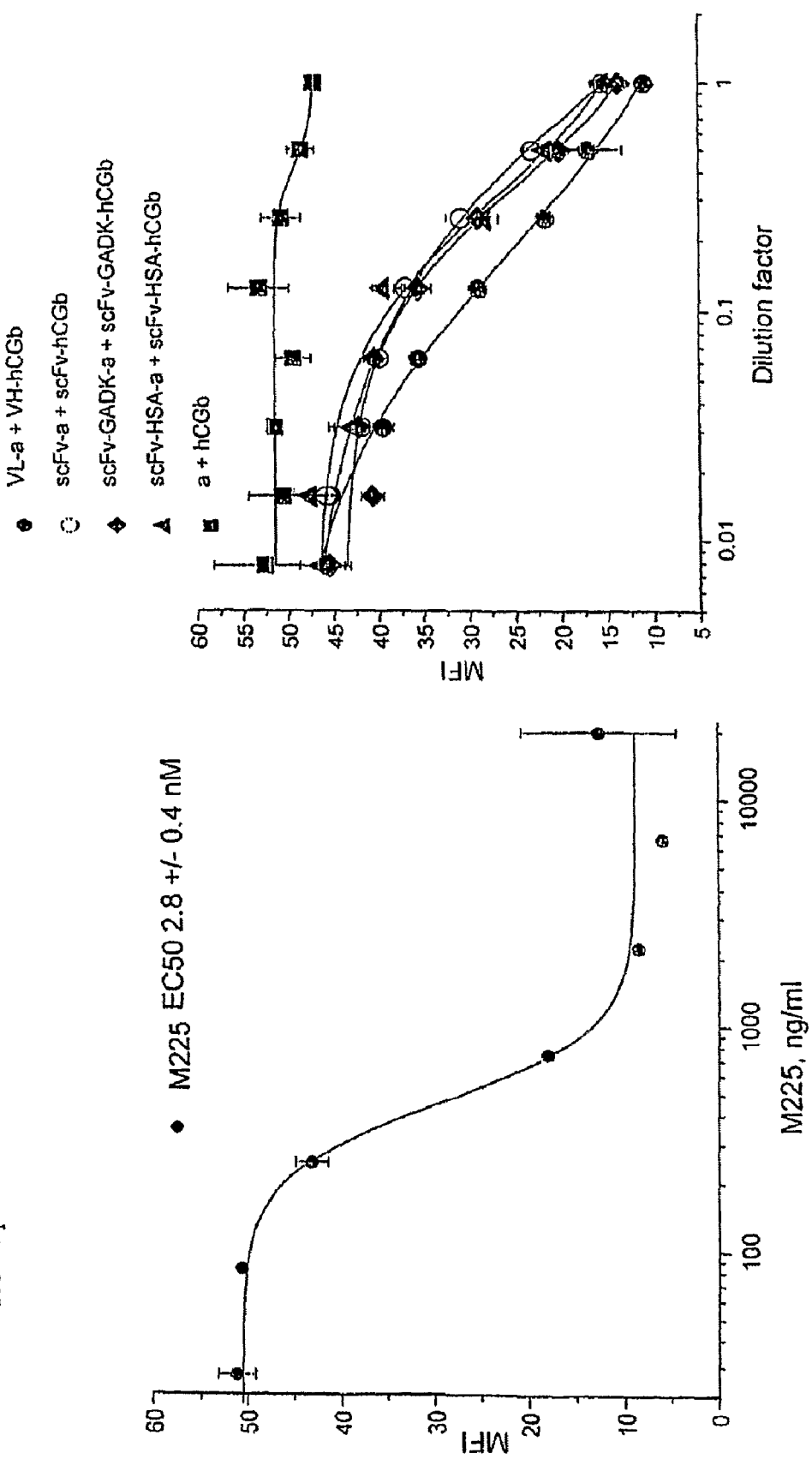
FIG. 22 depicts a graph summarizing the results of an experiment where alexa-fluor 488 labeled EGF was displaced from the surface of A431 cells by serially diluted 10× concentrated culture supernatants derived from cells transfected with the various EGFR variable region hybrid antigen binding molecule constructs.

The invention is based, at least in part, on the discovery that non-immunoglobulin polypeptides such as heterodimeric proteinaceous hormones can be used to make hybrid antigen binding molecules having improved therapeutic properties.

One exemplary heterodimeric proteinaceous hormone is hCG. Given hCG's prominent role as a marker of pregnancy, many reagents have been developed to quantitate levels of the protein and to study the protein in vitro and in vivo. hCG has been studied extensively using mutagenesis and it has been reported that several alterations can be made in one or both subunits of hCG which reduce or eliminate the biological activity of the hormone while preserving its ability to form heterodimers. Additionally, small insertions, for example, of up to 30 amino acids, have been shown to be tolerated at the amino- and carboxyl-termini of the α subunit. Further, fusion of the α subunit to the carboxyl terminus of the β subunit also has little effect on heterodimer formation. Therefore, hCG and similar heterodimeric proteinaceous hormones are attractive candidates as scaffolds for generating therapeutic hybrid proteins, such as the hybrid antigen binding molecules described herein.

The hybrid antigen binding molecules of the invention show greater efficacy when used in the diagnosis or treatment of diseases or disorders when compared to their non-hybrid counterparts. For example, owing to the longer half-life of such hybrid molecules, a lower dose may be administered to a patient compared to the non-hybrid antigen binding molecule, thereby reducing side effects. Another advantage presented by the hybrid antigen binding molecules of the invention is their ease of production.

I. Definitions

In order that the present disclosure is more readily understood, certain terms are first defined. Additional definitions are set forth throughout the disclosure.

The terms "immunoglobulin" and "antibody," as used interchangeably herein, refer to antigen-binding polypeptides having a basic four-polypeptide chain structure which has the ability to specifically bind an antigen, consisting of two heavy and two light chains, the chains being stabilized, for example, by interchain disulfide bonds. Both heavy and light chains are folded into domains. The term "domain" refers to a globular region of a polypeptide, e.g., a heavy or light chain polypeptide, comprising peptide loops (e.g., comprising 3 to 4 peptide loops) stabilized, for example, by β-pleated sheet and/or intrachain disulfide bond. Antibodies comprise both "constant" and "variable" regions. "Constant" regions on the light chain are referred to as "light chain constant regions" or "CL" while "constant" regions on the heavy chain are referred to as "heavy chain constant regions" or "CH" "Variable" regions on the light chain are referred to as "light chain variable regions" or "VL" regions and "variable" domains on the heavy chain are referred to as "heavy chain variable regions"

or "VH" regions. The term "antibody," as used herein, includes monoclonal antibodies (including full length monoclonal antibodies), polyclonal antibodies, multispecific antibodies (e.g., bispecifc antibodies), chimeric antibodies, CDR-grafted antibodies, humanized antibodies, human antibodies. Examples of antibodies include, for example, chimeric antibodies, CDR-grafted antibodies, humanized antibodies, fully human antibodies, antibodies produced in transgenic organisms, synthetic antibodies, engineered antibodies, single chain antibodies, antibodies with modified Fc regions, and camelid like antibodies.

The term "region" refers to a part or portion of a polypeptide, e.g., comprising a constant or variable region, as well as more discrete parts or portions of said regions. For example, light and heavy chain variable regions comprise three "complementarity determining regions" or "CDRs" and non-CDR "framework regions" or "FRs."

A "monoclonal antibody," as used herein, is a population of antibody molecules that contains only one species of an antigen binding site capable of immunoreacting with a particular epitope of a particular antigen.

A "polyclonal antibody" is a mixture of heterogeneous antibodies. Generally, polyclonal antibodies recognize more than one epitope of an antigen.

The term "humanized antibody" refers to an antibody comprising at least one chain comprising variable region framework residues substantially from a human antibody chain (referred to as the acceptor immunoglobulin or antibody) and at least one complementarity determining region substantially from a non-human-antibody, (referred to as the donor immunoglobulin or antibody). See, e.g., Queen et al., *Proc. Natl. Acad. Sci. USA* 86:10029-10033 (1989), U.S. Pat. Nos. 5,530,101, 5,585,089, 5,693,761, 5,693,762, Selick et al., WO 90/07861, and Winter, U.S. Pat. No. 5,225,539 (incorporated by reference in their entirety for all purposes). The constant region(s), if present, are also substantially or entirely from a human immunoglobulin.

The term "an antigen-binding moiety" or "an antigen-binding portion", as used herein, refers to an amino acid sequence capable of specifically binding to an antigen. In a preferred embodiment, an antigen binding moiety is encoded, at least in part, by an a nucleotide sequence encoding an antibody variable region or at least one CDR thereof. In one embodiment, an antigen binding moiety is an antigen binding portion of an antibody comprising enough of an antibody variable region to confer antigen binding. Antigen binding portions may be produced by recombinant DNA techniques or by enzymatic or chemical cleavage of intact antibodies. Antigen binding portions of antibodies include fragments of antibodies and engineered molecules comprising at least one antigen binding site, for example, an antibody light chain (VL), an antibody heavy chain (VH), an engineered antibody, e.g., a single chain antibody (ScFv), and one or more CDRs. The term "antigen-binding portion" generally refers to a polypeptide fragment of an immunoglobulin or antibody that binds an antigen or competes with intact antibody (i.e., with the intact antibody from which they were derived) for antigen binding e.g., specific binding).

"Engineered antigen binding moieties," or "engineered antibodies" as used herein, refer to artificially generated forms of antibodies which comprise an antigen binding portion of an antibody. Examples of engineered antigen binding moieties include, but are not limited to, for example, multi-specific antibodies, ScFv molecules (single chain antibodies), ScFv dimers (diabodies), ScFv trimers (triabodies), ScFv tetramers (tetrabodies), minibodies which include two ScFv modules joined by two C domains, Fab dimers, Fab trimers and domain antibodies (dAbs). Such molecules are well known in the art and so are the methods for making such molecules.

The "hybrid antigen binding molecules" of the invention comprise at least two polypeptide chains of a heterodimeric proteinaceous hormone or fragment thereof, wherein at least one of the polypeptide chain comprises at least one antigen binding moiety and the polypeptide chains form a heterodimer. The term "hybrid antigen binding molecules," as used herein are capable of dimerizing to form a heterodimer. In one embodiment, two polypeptide chains dimerize using non-covalent interactions between the two polypeptide chains, such as, for example, between α and β subunits of a heterodimeric proteinaceous hormone such as, hCG. The hybrid antigen binding molecules of the invention comprise at least one antigen binding site.

An "antigen" is a moiety to which an antibody specifically binds.

The terms "epitope" and "antigenic determinant" refer to a site on an antigen to which an antigen binding molecule (e.g., an antibody) specifically binds. Epitopes can be formed both from contiguous amino acids or noncontiguous amino acids juxtaposed by tertiary folding of a polypeptide. Epitopes formed from contiguous amino acids are typically retained on exposure to denaturing solvents whereas epitopes formed by tertiary folding are typically lost on treatment with denaturing solvents. An epitope typically comprises at least 3, 4, 5, 6, 7, 8, 9, 10, 11, 12, 13, 14 or 15 amino acids in a unique spatial conformation.

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen, such as, for example, VEGF, EGFR or IGF-1R. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

The term "bind," as used herein, refers to the recognition or adherence of a first binding molecule to a second molecule. Such binding is "substantially specific" or "selective" where the first molecule does not substantially bind to a different molecule in the sample (e.g., Protein A "binds" to the constant region of Human IgG1 but not to Chicken IgG). Specific or selective binding can be determined according to any art-recognized means for determining such binding. Preferably, specific binding is determined according to Scatchard analysis and/or competitive binding assays. Preferably, the level of binding to other molecules is not significantly above background levels.

Preferably, antigen binding molecules that exhibit substantially "specific binding" or "selective binding" have appreciable affinity for antigen or a preferred epitope and, preferably, do not exhibit significant crossreactivity. "Appreciable affinity" includes, e.g., binding with an affinity of at least $10^6$, $10^7$, $10^8$, $10^9$ $M^{-1}$, or $10^{10}$ $M^{-1}$. Affinities greater than $10^7$ $M^{-1}$, preferably greater than $10^8$ $M^{-1}$ are more preferred. Values intermediate of those set forth herein are also intended to be within the scope of the present invention and a preferred binding affinity can be indicated as a range of affinities, for example, $10^6$ to $10^{10}$ $M^{-1}$, preferably $10^7$ to $10^{10}$ $M^{-1}$, more preferably $10^8$ to $10^{10}$ $M^{-1}$.

The antigen binding molecules of the invention may comprise one antigen binding moiety or multiple antigen binding moieties. For example, while naturally occurring antibodies are bivalent, the hybrid antigen binding molecules of the invention may be monovalent, bivalent, trivalent, tetravalent, etc. These antigen binding moieties may have the same or different specificity. For example, naturally occurring antibodies comprise two identical binding sites and, therefore, are monospecific. A "multispecific" antibody (e.g., a "bispecific" or "bifunctional antibody") is an artificial antibody comprising multiple binding sites that recognize more than one antigen.

As used herein, the term "fusion protein" refers to a molecule which comprises two or more polypeptides linked in frame to each other. The two or more polypeptides may either be linked via a peptide linker or they can be linked directly.

As used herein, "peptide linker" refers to one or more amino acids used to link an antigen binding moiety and a subunit of a heterodimeric proteinaceous hormone together. In one embodiment, the peptide linker comprises a series of about 2 to 15 amino acids, for example, in certain embodiments, glycine and/or serine. In another embodiment, a linker peptide of the invention comprises the sequence Ser Cys Ala Gly Ala Gly (SEQ ID NO: 109). Other exemplary linker sequences comprise or consist of two or more alanine residues. Other peptide linkers suitable for use in the claimed invention are known in the art. Non limiting examples of the amino acid sequences of such linkers are: AA, AAA, GADK (SEQ ID NO: 1), GFASPAFF (SEQ ID NO: 98), DETYVPKEFNAE (SEQ ID NO: 2), DKTHTCPPCPAPELLGGAA (SEQ ID NO: 99), DKTHTCPPCPAPELLGGAAA (SEQ ID NO: 100), DKTHTSPPSPAPELLGGAA (SEQ ID NO: 101), DKTHTSPPSPAPELLGGAAA (SEQ ID NO: 102), GGGS (SEQ ID NO: 103), (GGGS)$_2$ (SEQ ID NO: 104), GGGGS (SEQ ID NO: 105), (GGGGS)$_2$ (SEQ ID NO: 106), (GGGGS)$_4$ (SEQ ID NO: 107), GGGGC (SEQ ID NO: 108).

The term "cell-associated molecule," as used herein, refers to a molecule expressed on the surface of a cell. Exemplary types of cell-associated molecules include, but are not limited to, for example, cell surface antigens (e.g., cell surface receptors and cancer cell-specific antigens). Specific examples, of cell-associated molecules include, but are not limited to, the epidermal growth factor receptor (EGFR) and insulin-like growth factor-1 receptor (IGF-1R).

The term "soluble molecule" includes molecules found in soluble form in the circulation, e.g., molecules that are not cell associated, but rather are secreted by cells. Examples of soluble molecules include growth factors.

As used herein, the terms "heterodimer" or "heterodimer formation" refer to the stable association of two or more different polypeptides either through covalent or non-covalent interaction. An example of a covalent interaction is disulphide bonding. For example, the hybrid binding molecules described herein comprise two polypeptide chains, the first comprising an alpha chain of a heterodimeric hormone and the second comprising a beta chain of a heterodimeric hormone.

The terms "effective dose" and "effective dosage" are defined as an amount sufficient to achieve or at least partially achieve the desired effect. The terms "therapeutically effective dose" and "therapeutically effective amount" refer to an amount sufficient to cure or at least partially arrest the disease and its complications in a patient already suffering from the disease. Amounts effective for this use will depend upon the severity of the infection and the general state of the patient's own immune system. The therapeutically effective amount will vary depending upon the subject and disease condition being treated, the weight and age of the subject, the severity of the disease condition, the manner of administration and the like, which can be readily determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of a hybrid antigen binding molecule of the invention.

The term "patient" includes human and other mammalian subjects that receive either prophylactic or therapeutic treatment.

As used herein, the terms "treat," "treating," and "treatment" refer to a reduction (partial or complete) in at least one symptom associated with a disease or disorder based on antagonism of the activity of a stimulatory or inhibitory receptor. For example, antagonism of VEGF, EGFR or IGF-1R can be used for treating diseases associated with proliferation of cells, such as, for example, cancer.

As used herein, the term "pharmaceutically acceptable carrier" includes compounds that are compatible with the other ingredients in a pharmaceutical formulation and not injurious to a subject when administered in a therapeutically effective amount.

As used herein, the term "pharmaceutically acceptable salt" refers to salts that are physiologically tolerated by a subject. Such salts are typically prepared from an inorganic and/or organic acid. Examples of suitable inorganic acids include, but are not limited to, hydrochloric, hydrobromic, hydroiodic, nitric, sulfuric, and phosphoric acid. Organic acids may be aliphatic, aromatic, carboxylic, and/or sulfonic acids. Suitable organic acids include, but are not limited to, formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

The term "agonist," as used herein, refers to a compound that binds to a receptor of a cell and triggers a response by the cell. An agonist often mimics the action of a naturally occurring ligand for the receptor. An agonist generally produces an action which is the opposite of an antagonist.

The term "antagonist" as used herein, refers to a compound that competes either with a naturally occurring ligand for binding to its receptor and which does not transduce a signal via the receptor or results in a lower level of signaling than the naturally occurring ligand, or it binds a ligand and prevents the ligand from binding to its receptor.

A ligand may either be a natural ligand to which a receptor binds, or a molecule which is a functional analog of the natural ligand. The functional analog may be a ligand with structural modifications, or may be a wholly unrelated molecule which has a molecular shape which interacts with the appropriate ligand binding determinants.

The term "agonist activity," as used herein, refers to an activity of a compound which transmits a signal via a receptor which mimics binding of a cognate ligand to its receptor.

The term "antagonist activity," as used herein, refers to an activity of a compound which acts as an antagonist of a receptor or a ligand that binds a receptor. In one embodiment, a hybrid antigen binding molecule of the invention comprising at least one antigen binding moiety linked to at least one polypeptide chain of a heterodimeric proteinaceous hormone scaffold has antagonist activity. Such antagonist activity includes antagonism of the function of an activating or an inhibiting receptor. Preferably, such hybrid antigen binding molecules have one or more of a VEGF antagonist activity, an EGFR antagonist activity and an IGF-1R antagonist activity.

The term "VEGF antagonist activity," as used herein, refers to the ability of a molecule, for example, a VEGF hybrid antigen binding molecule described herein, to interfere with the normal functioning of VEGF, as determined by one or more assays that would be well-known to one of ordinary skill in the art. For example, in one embodiment, a hybrid antigen binding molecule having VEGF antagonist activity inhibits endothelial cell growth. In other embodiments, a hybrid antigen binding molecule having VEGF antagonist activity inhibits growth of tumor cells. In yet other embodiments a hybrid antigen binding molecule having VEGF antagonist activity inhibits angiogenesis.

The term "EGFR antagonist activity," as used herein, refers to the ability of a molecule, for example, an EGFR hybrid antigen binding molecule described herein, to interfere with the normal functioning of EGFR, as determined by one or more proliferative assays known in the art. For example, in one embodiment, a hybrid antigen binding molecule having EGFR antagonist activity inhibits tumor growth The term "IGF-1R antagonist activity," as used herein, refers to the ability of a molecule for example, an IGF-1R hybrid antigen binding molecule described herein, to interfere with the normal functioning of IGF-1R, as determined by one or more proliferative assays des known in the art. For example, in one embodiment, a hybrid antigen binding molecule having IGF-1R antagonist activity inhibits tumor growth. In another embodiment, a hybrid antigen binding molecule having IGF-1R antagonist activity reduces aberrant cell growth as seen in acromegaly and gigantism.

II. Antigen Binding Moieties

The hybrid antigen binding molecules of the invention comprise at least one antigen binding moiety, e.g., the antigen binding portion of antibodies, e.g., one or more CDRs, VH and VL, or engineered antigen binding moieties, e.g., ScFv and/or fragments thereof.

A. Antigen Binding Portions of Antibodies

In one embodiment, the antigen binding moiety is an antigen binding portion of an antibody. An antigen-binding portion of an antibody is contained within the variable region of an antibody and is the portion of the antibody that confers antigen specificity to the antibody, e.g., one or more CDRs, or VH and/or VL either alone or in association with each other.

In general, the basic antibody structural unit is known to comprise a tetramer of subunits. Each tetramer is composed of two identical polypeptide dimers, each pair having one "light" (about 25 kDa) and one "heavy" chain (about 50-70 kDa). The amino-terminal portion of each chain comprises a variable region of about 100 to 110 or more amino acids primarily responsible for antigen recognition. The carboxy-terminal portion of each chain defines a constant region primarily responsible for effector function.

Light chains are classified as either kappa or lambda and are about 230 residues in length. Heavy chains are classified as gamma ($\gamma$), mu ($\mu$), alpha ($\alpha$), delta ($\delta$), or epsilon ($\epsilon$), are about 450-600 residues in length, and define the antibody's isotype as IgG, IgM, IgA, IgD and IgE, respectively. Both heavy and light chains are folded into domains. Intact light chains have, for example, two domains ($V_L$ and $C_L$) and intact heavy chains have, for example, four or five domains ($V_H$, $C_H1$, $C_H2$, and $C_H3$).

Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y. (1989), Ch. 7, incorporated by reference in its entirety for all purposes).

The variable regions of each light/heavy chain pair form the antibody-binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. Naturally-occurring chains or recombinantly produced chains can be expressed with a leader sequence which is removed during cellular processing to produce a mature chain. Mature chains can also be recombinantly produced having a non-naturally occurring leader sequence, for example, to enhance secretion or alter the processing of a particular chain of interest.

The CDRs of the two mature chains of each pair are aligned by the framework regions. From N-terminal to C-terminal, both light and heavy chains comprise the domains FR1, CDR1, FR2, CDR2, FR3, CDR3 and FR4. "FR4" also is referred to in the art as the D/J region of the variable heavy chain and the J region of the variable light chain. The assignment of amino acids to each domain is in accordance with the definitions of Kabat, *Sequences of Polypeptides of Immunological Interest* (National Institutes of Health, Bethesda, Md., 1987 and 1991). An alternative structural definition has been proposed by Chothia et al., *J. Mol. Biol.* 196:901 (1987); *Nature* 342:878 (1989); and *J. Mol. Biol.* 186:651 (1989).

Antibodies may be produced by a cell and purified or synthesized de novo.

In one embodiment, a hybrid antigen binding molecule of the invention comprises an antigen binding moiety of a human antibody. In another embodiment, an antigen binding molecule of the invention comprises an antigen binding moiety from a non-human antibody. In one embodiment, the non-human antibody is modified to reduce its immunogenicity, e.g., by making a chimeric antibody, a humanized antibody, or a deimmunized antibody using techniques well known in the art.

B. Engineered Antigen Binding Moieties

In one embodiment, the antigen binding moieties of the invention are engineered binding moieties. As used herein, the term "engineered binding moieties" includes synthetic forms of antibodies which are altered such that they are not naturally occurring. E.g., minibodies; multispecific forms of antibodies (e.g., bispecific, trispecific, etc.) altered to bind to two or more different antigens or to different epitopes on a single antigen). In addition, the term "engineered binding moieties" includes multivalent forms of antibodies (e.g., trivalent, tetravalent, etc., antibodies that bind to three or more copies of the same antigen). Exemplary engineered binding moieties include scFv molecules; diabodies; heavy chain molecules joined to scFv molecules and the like. Other engineered forms include, for example, disulfide-linked scFv, tandem scFv, dsFs-dsFv', scFv-CL, scFv-CL/CH1, scFv-CH3-scFv-Fc, Fab-scFv, Fab-ScFv$_2$, F(ab')2-scFv, IgG-scFv and dAb. Domain antibodies (□abs) are the smallest known antigen binding fragments of antibodies. □abs can be derived from either the variable light or the variable heavy chain of an immunoglobulin. Methods for the construction of such antibody molecules are well known in the art. See, for example, Antibody Engineering (Kontermann and Dubel, Springer lab manual, 2001) and U.S. Pat. No. 6,696,245, incorporated by reference herein.

Methods of making such engineered molecules are known in the art. For example, ScFv molecules are known in the art and are described, e.g., in U.S. Pat. No. 5,892,019. In scFv fragments, the variable domain of the heavy chain is bound covalently to the variable domain of the light chain via a short peptide linker which can be introduced, for example, by recombinant DNA technology. The scFv fragments can be purified and detected using standard techniques, for example, by adding short marker sequences either at the N-terminus or at the C-terminus.

In one embodiment, the term "engineered binding moieties" according to the present invention, include immunoglobulins, antibodies, or immunoreactive fragments or recombinants thereof, in which at least a fraction of one or more of the constant region domains has been deleted or otherwise altered so as to provide desired biochemical characteristics.

Diabodies can be generated by using a very short linker between the variable domain of the heavy chain and the variable domain of the light chain, to prevent the $V_H$ and $V_L$ domains of a chain joining together. This can lead to the formation of dimeric molecules, in which the $V_H$ and $V_L$ domains of two different chains form a double-headed molecule. By using two different, noncoupled antibody specificities (e.g. A and B), which are expressed in the order $V_{HA}$-$V_{LB}$ and $V_{HB}$-$V_{LA}$ in the same cell, bispecific diabodies can be formed. These dimeric diabody molecules can also be produced via a monomeric molecule, if the two $V_H$-$V_L$ fragments are bound covalently with an additional peptide linker (single-chain diabody, scDb). These dimeric bispecific antibodies thus possess two valences for each specificity. Bispecific diabodies or antibodies can be generated to increase both the valence as well as the stability and therefore the therapeutic potential.

C. Specificity of Antigen Binding Moieties

Antigen binding moieties that bind cell-associated or soluble molecules (or the nucleic acid molecules that encode them) can be used for generating hybrid antigen binding molecules that have several advantages compared to their non-hybrid counterparts. Such binding moieties may bind to one or more of the cell-associated or soluble molecules described in the instant application. These binding moieties may comprise or be derived from antibodies that are known in the art or that are novel.

Novel antibodies may be made using techniques well known in the art. Using art recognized protocols, for example, antibodies may be raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (Mabs). Preferably, the lymphocytes are obtained from the spleen.

In this well known process (Kohler et al., *Nature*, 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, DNA encoding a desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be modified as described herein) may be used to clone constant and variable region sequences for the manufacture antibodies as described in Newman et al, U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; *Nagy et al.* 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal antibodies.

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the Vh and Vl genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or modified to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Variable and constant region domains can be obtained from any source and be incorporated into a modified antibody of the invention. To clone antibodies, mRNA can be isolated from hybridoma, spleen, or lymph cells, reverse transcribed into DNA, and antibody genes amplified by PCR. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250); or based on known variable region framework amino acid sequences from the Kabat (Kabat et al. 1991. Sequences of Proteins of Immunological Interest. Bethesda, Md.:JS Dep. Health Hum. Serv. 5$^{th}$ ed.) or the V-base databases (e.g., Orlandi et al. 1989. Proc. Natl. Acad. Sci. USA 86:3833; Sblattero et al. 1998. Immunotechnology 3:271; or Krebber et al. 1997. J. Immunol. Methods 201:35). Variable and constant domains can be cloned, e.g., using the polymerase chain reaction and primers which are selected to amplify the domain of interest. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270).

Alternatively, V domains can be obtained from libraries of V gene sequences from an animal of choice. Libraries expressing random combinations of domains, e.g., VH and VL domains, can be screened with a desired antigen to identify elements which have desired binding characteristics. Methods of such screening are well known in the art. For example, antibody gene repertoires can be cloned into a λ bacteriophage expression vector (Huse, W D et al. 1989. Science 2476:1275). In addition, cells (Boder and Wittrup. 1997. Nat. Biotechnol. 15:553; Daugtherty, P. et al. 2000. J. Immunol. Methods. 243:211; Francisco et al. 1994. Proc. Natl. Acad. Sci. USA 90:10444; Georgiou et al. 1997. Nature Biotechnology 15:29) or viruses (e.g., Hoogenboom, HR. 1998 Immunotechnology 4:1 Winter et al. 1994. Annu. Rev. Immunol. 12:433; Griffiths, A D. 1998. Curr. Opin. Biotechnol. 9:102) expressing antibodies on their surface can be screened. Ribosomal display can also be used to screen antibody libraries (Hanes J., et al. 1998. Proc. Natl. Acad. Sci. USA 95:14130; Hanes, J. and Pluckthun. 1999. Curr. Top. Microbiol. Immunol. 243:107; He, M. and Taussig. 1997. Nucleic Acids Research 25:5132).

Preferred libraries for screening are human V gene libraries. VL and VH domains from a non-human source may also be used. In one embodiment, such non-human V domains can be altered to reduce their immunogenicity using art recognized techniques.

Libraries can be naïve, from immunized subjects, or semi-synthetic (Hoogenboom, H. R. and Winter. 1992. J. Mol. Biol. 227:381; Griffiths, A D, et al. EMBO J. 13:3245; de Kruif, J. et al. 1995. J. Mol. Biol. 248:97; Barbas, C. F., et al. 1992. Proc. Natl. Acad. Sci. USA 89:4457). In addition, the sequences of many antibody V and C domains are known and such domains can be synthesized using methods well known in the art.

In one embodiment, mutations can be made to immunoglobulin domains to create a library of nucleic acid molecules having greater heterogeneity (Thompson, J., et al. 1996. J. Mol. Biol. 256:77; Lamminmaki, U. Et al. 1999. J. Mol. Biol. 291:589; Caldwell, R. C. and Joyce G F. 1992. PCR Methods Appl. 2:28; Caldwell R C and Joyce G F. 1994. PCR Methods Appl. 3:S136. Standard screening procedures can be used to select high affinity variants. In another embodiment, changes to VH and VL sequences can be made to increase antibody avidity, e.g., using information obtained from crystal structures using techniques known in the art.

In another embodiment, one or more antibodies for use in making an antigen binding moiety of the invention is known in the art. Exemplary art recognized antibodies (or portions thereof) suitable for use in the subject hybrid antigen binding molecules include, e.g., OKT3 (anti-CD3; Johnson & Johnson); Rituxan (anti-CD20; Genentech); Zenpax (anti-CD25; Hoffman La Roche); Simulect (anti-CD25; Novartis); Remicade (anti-TNFa; Centocor); Herceptin (anti-HER2; Genentech); Mylotarg (anti-CD33; Wyeth); Campath-1H (anti-CD52; Genzyme); Humira (anti-TNFa; Abbott); Xolair (anti-IgE; Genentech) Raptiva (anti-CD11a; Genentech); Tysabri (anti-a4-integrin; Biogen Idec); AMG-162 (anti-RANKL; Amgen); Humax CD4 (anti-CD4; Genmab); Mepolizumab (anti-IL5; GlaxoSmithKline); Lymphocide (anti-CD22; Immunomedics); Cimzia (anti-TNFa; UCB); Segard (anti-TNFa; Abbott); Removab (bispecific anti-CD3/Epcam; Trion); Rencarex (anti-carbonic anhudrase IX; Wilex) and Pexelizumab (anti-C5; Alexion).

In one embodiment, A nucleic acid molecule that is homologous to one encoding an antibody known in the art or portion thereof may be used to encode an antigen binding moiety of the invention. A "homolog," in reference to a gene refers to a nucleotide sequence that is substantially identical over at least part of the gene or to its complementary strand or a part thereof, provided that the nucleotide sequence encodes a protein that has substantially the same activity/function as the protein encoded by the gene which it is a homologous. Homologs of antibody genes can be identified by percent identity between amino acid or nucleotide sequences for putative homologs and the sequences for the genes or proteins encoded by them. Percent identity may be determined, for example, by visual inspection or by using various computer programs known in the art or as described herein. For example, percent identity of two nucleotide sequences can be determined by comparing sequence information using the GAP computer program described by Devereux et al. (1984) Nucl. Acids. Res., 12:387 and available from the University of Wisconsin Genetics Computer Group (UWGCG). Percent identity can also be determined by aligning two nucleotide sequences using the Basic Local Alignment Search Tool (BLAST™) program (as described by Tatusova et al. (1999) FEMS Microbiol. Lett., 174:247). For example, for nucleotide sequence alignments using the BLAST™ program, the default settings are as follows: reward for match is 2, penalty for mismatch is −2, open gap and extension gap penalties are 5 and 2 respectively, gap times dropoff is 50, expect is 10, word size is 11, and filter is OFF.

In another embodiment, antigen binding molecules having amino acid identity to known antibody molecules or portions thereof may be used in the hybrid proteins described herein. To determine the percent identity of two amino acid sequences, the sequences are aligned for optimal comparison purposes (e.g., gaps can be introduced in the amino acid sequence of one protein for optimal alignment with the amino acid sequence of another protein). The amino acid residues at corresponding amino acid positions are then compared. When a position in one sequence is occupied by the same amino acid residue as the corresponding position in the other, then the molecules are identical at that position. The percent identity between the two sequences is a function of the number of identical positions shared by the sequences (i.e., % identity=# of identical positions/total # of positions multiplied by 100).

In some embodiments, nucleic acid and amino acid sequences of molecules described herein comprise a nucleotide sequence or amino acid sequence which hybridizes to or is at least about 50%, 60%, 70%, 80%, 90%, 95%, 96%, 97%, 98%, 99% or more identical to a nucleic acid or amino acid sequence described herein.

In another embodiment, nucleic acid molecules appropriate for use in the fusion proteins of the invention comprise a nucleotide sequence which hybridizes under stringent conditions to the complement of a nucleic acid molecule encoding the antibody molecule or portion thereof (e.g., a CDR, a variable region, or other portion). As used herein, the term "hybridizes under stringent conditions" is intended to describe conditions for hybridization and washing under which nucleotide sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In one embodiment, an antigen binding moiety binds to EGFR. In one embodiment, hybrid proteins described herein compete with EGF for binding to its receptor. EGF, like all growth factors, binds to specific high-affinity, low-capacity receptors on the surface of responsive cells. Intrinsic to the EGF receptor is tyrosine kinase activity, which is activated in response to EGF binding. The kinase domain of the EGF receptor phosphorylates the EGF receptor itself (autophosphorylation) as well as other proteins, in signal transduction cascades, that associate with the receptor following activation. EGF has proliferative effects on cells of both mesodermal and ectodermal origin, particularly keratinocytes and fibroblasts. EGF exhibits negative growth effects on certain carcinomas as well as hair follicle cells. Growth-related responses to EGF include the induction of nuclear proto-oncogene expression, such as Fos, Jun and Myc. EGF also has the effect of decreasing gastric acid secretion.

Exemplary anti-EGFR antibodies include Erbitux (Imclone Systems) and Panitumumab (Abgenix). Other antigen binding moieties that are specific for EGFR may also be used.

In one embodiment, an antigen binding moiety binds to VEGF. In yet other embodiments, hybrid proteins described herein prevent VEGF from binding to its receptor. VEGF is a homodimeric glycoprotein of relative molecular mass 45,000, and it that specifically acts on endothelial cells. VEGF has been reported as being a major regulator of tumor angiogenesis in vivo.

Exemplary VEGF antibodies that can be used in the hybrid antigen binding molecules of this invention include, for example, AVASTIN® (bevacizumab; Genentech) and Lucentis (Genentech). In one embodiment, a hybrid antigen binding molecule includes an antigen binding portion of a VEGF-binding antibody such as, for example, AVASTIN®, which can be used for treatment of various types of cancers including for example, colorectal cancer. In one embodiment, owing to the longer half-life and greater efficacy of the hybrid antigen binding molecules described herein, AVASTIN® may be used for treatment of colorectal cancer without the need for combining it with use of chemotherapeutic agents. Other antigen binding moieties that are specific for VEGF may also be used.

In another embodiment, an antigen binding moiety of the invention binds to IGF-1R. In other embodiments, hybrid proteins described herein compete with IGF for binding to its receptor. IGF (originally called somatomedin C) is a growth factor structurally related to insulin. IGF is the primary protein involved in responses of cells to growth hormone (GH). IGF is produced in response to GH and then induces subsequent cellular activities, particularly on bone growth. IGF has been reported to have both autocrine and paracrine activities in addition to the initially observed endocrine activities on bone. The IGF receptor, like the insulin receptor, has intrinsic tyrosine kinase activity. Owing to their structural similarities, IGF can bind to the insulin receptor but does so at a much lower affinity than does insulin itself.

Exemplary anti IGFR antibodies include those described in WO 02/053596. Other antigen binding moieties that are specific for IGF-1R may also be used.

III. Exemplary Heterodimeric Proteinaceous Hormones

Examples of heterodimeric proteinaceous hormones include FSH, inhibin, TSH, hCG, and LH.

The sequences of these and other hormones are readily available to those of skill in the art. For example, an exemplary nucleotide and amino acid sequence of the alpha and beta subunits of hCG can be found in the GenBank database at Accession number J00117; gi: 180436 and Accession number CAA23777; gi:31869, respectively. Also, see, for example, Morgan et al., J. Biol. Chem., 250(13):5247-58 (1975) and Fiddes et al., Nature, 281(5730): 351-6 (1979).

In one embodiment, amino acids 20-161 of the alpha subunit of hCG and amino acids 20-161 of the beta subunit of hCG can be included in a hybrid antigen binding molecule described herein.

Heterodimeric hormones hCG, TSH, FSH and LH share the same alpha subunit, which heterodimerizes with the respective beta subunit. An exemplary nucleotide and amino acid sequence of the beta subunit of human FSH can be found in the GenBank database (Accession number NM_000510; gi:66528900). In one embodiment, human FSH coding region was derived from the DdeI-Sau3A1 subfragment of the 15B genomic clone described by Watkins, P. C. et al., DNA 6:205-212 (1987). In one embodiment, amino acids 1-111 of FSH (excluding signal sequence) may be incorporated into a hybrid antigen binding molecule described herein. An exemplary nucleotide and amino acid sequence of the beta subunit of human TSH can be found in the GenBank database (Accession number NM_000549; gi:42490754). An exemplary nucleotide and amino acid sequence of the beta subunit of human LH can be found in the GenBank database (Accession number X00264; gi:34351).

An exemplary nucleotide and amino acid sequence of the alpha chain of human inhibin can be found in the GenBank database (Accession number M13981; gi: 186410), and the nucleotide and amino acid sequence of the beta chain of human inhibin can be found in the GenBank database (Accession number M31669; gi:186419).

In one embodiment, one or more of the subunits of the heterodimeric proteinaceous hormone in the hybrid antigen binding molecule comprises one or more alterations to the naturally occurring sequence which reduce or eliminate the biological activity of the hormone, while preserving the ability of the altered subunit to dimerize with another subunit of the hormone to form a heterodimer.

For example, it has been reported that removal of just five residues at the extreme carboxyl-terminus of a subunit of hCG can effectively eliminate its biological activity while preserving its capability to form heterodimers. In one embodiment, an altered subunit is an alpha subunit of hCG which comprises a deletion of amino acids 88-92 (del 88-92), thereby rendering the hCG biologically inactive; however, preserving the ability of the alpha subunit to dimerize with the beta subunit of hCG, thereby to generate a hybrid antigen binding molecule. In another embodiment, an altered subunit is an alpha subunit which comprises a substitution of a cysteine residue at amino acid position 26 with an alanine (C26A). In another embodiment an altered subunit is an alpha subunit comprising a deletion of amino acids 88-92 (del 88-92) and substitution of a cysteine residue at amino acid position 26 with an alanine (C26A). In another embodiment, an altered subunit is a beta subunit comprising a deletion of amino acids 104-145 (del 101-145). The hybrid antigen binding molecules of the invention may comprise: a) an altered alpha subunit and an unaltered beta subunit; b) an altered alpha subunit and an altered beta subunit; c) an unaltered alpha subunit and an altered beta subunit; or d) an unaltered alpha subunit and an unaltered beta subunit.

It will be understood by one of ordinary skill in the art that homologs of the above-described heterodimeric proteinaceous hormones may be substituted (see the discussion of homologs with respect to antibodies and portions thereof, supra.)

IV. Exemplary Cell-Associated and Soluble Molecules

A. Cell-Associated Molecules

In one embodiment, the hybrid antigen binding molecules can be used for binding to a cell-associated molecule. Exemplary cell-associated molecules which can be detected or measured using hybrid antigen-binding molecules include, but are not limited to, cell surface antigens (e.g., cell surface receptors) and cancer cell-specific antigens. Exemplary cell-associated molecules are described below in more detail.

1. Receptors

In one embodiment, an antigen binding molecule of the invention binds to a receptor, e.g., a cytokine receptor. Exemplary receptors include those for (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-α, β, or γ.

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

In another embodiment, an antigen binding molecule of the invention binds to a receptor which is an adhesion molecule. Adhesion molecules are membrane-bound proteins that allow cells to interact with one another. Leukocyte homing receptors are expressed on leukocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

In another embodiment, an antigen binding molecule of the invention binds to a chemokine receptor. Chemokines are chemotactic proteins which stimulate the migration of leucocytes towards a site of infection, can also be incorporated into a fusion protein of the invention. Exemplary chemokine receptors include those for Macrophage inflammatory proteins (MIP-1-α and MIP-1-β), neutrophil chemotactic factor, and RANTES (regulated on activation normally T-cell expressed and secreted).

In another embodiment, an antigen binding molecule of the invention binds to a growth factor receptor. Exemplary growth factor receptors include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as $p75^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)).

2. Cancer Cell-Specific Antigens

In one embodiment, a hybrid antigen-binding molecule of the invention binds a cancer cell-specific antigen. Cancer cell-specific antigens are those which are preferentially expressed or exclusively expressed on cancer cells. Such antigens can be targeted, for example, for the detection or treatment of cancer or for monitoring patients following cancer treatment. In one embodiment, the presence of a cancer cell-specific antigen is detected using a hybrid antigen binding molecule of the invention to indicate the presence of the cancer. In yet other embodiments, it is the lack of the expression of an antigen on a cell, as demonstrated using a hybrid antigen binding molecule of the invention, which is indicative of the presence of the cancer. Expression of cancer cell-specific antigens can be used to monitor patients following cancer therapy.

For example, in one embodiment, a hybrid antigen binding molecule that specifically binds to the Carcinoembryonic antigen (CEA), found in the majority of breast cancers, is used for detection of breast cancer in patients. Such a hybrid antigen binding molecule can be linked, for example, to a label such as a radioactive label and used for diagnosis of breast cancer and/or monitoring patients subsequent to treatment.

Other exemplary antigens found on cancer cells include those recognized by the antibodies Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath® (Millennium Pharmaceuticals, Cambridge) MB1, BH3, B4, B72.3 (Cytogen Corp.), CC49 (National Cancer Institute) and 5E10 (University of Iowa). Other antibody binding sites that can be incorporated into the subject binding molecules include: Orthoclone OKT3 (CD3), ReoPro (GpIIb/gIIa), Zenapax (C25), Remicade (TNF-a), Simulect (CD25), Synagis (RSV), Mylotarg (CD33), and Campath (CD52).

B. Soluble Molecules

In one embodiment, the hybrid antigen binding molecules can also be used for binding to soluble molecules. Exemplary soluble molecules which can be bound using hybrid antigen-binding molecules include, but are not limited to, cytokines and other growth factors. Exemplary cell-associated molecules are described below in more detail.

1. Cytokines

Cytokines are a large, diverse group of bioactive proteins and peptides generally having relatively low molecular weights which regulate a large number of cellular activities. For example, cytokines regulate immunoglobulin production by B lymphocytes and the biosynthetic activities of various cell types. Cytokines are generally produced in response to activation or stimulation of the cell producing the cytokine, presumably through a cell-surface receptor. While many of the better characterized cytokines are produced by the cells of the immune system, cytokines are generally produced by a wide variety of cell types. The largest group of cytokines stimulates immune cell proliferation and differentiation. This group includes Interleukin 1 (IL-1), which activates T cells; IL-2, which stimulates proliferation of antigen-activated T and B cells; IL-4, IL-5, and IL-6, which stimulate proliferation and differentiation of B cells; Interferon gamma (IFNg), which activates macrophages; and IL-3, IL-7 and Granulocyte Monocyte Colony-Stimulating Factor (GM-CSF), which stimulate hematopoiesis.

Other groups of cytokines include interferons and chemokines. Interferons IFNα and IFNβ inhibit virus replication in infected cells, while IFNγ also stimulates antigen-presenting cell MHC expression. Chemokines attract leukocytes to infection sites. Representative chemokines, are C—C chemokines (RANTES, MCP-1, MIP-1a, and MIP-1b), C—X—C chemokines (IL-8), C chemokines (Lymphotactin), and CXXXC chemokines (Fractalkine). Some cytokines are predominantly inhibitory. For example, IL-10 and IL-13 inhibit inflammatory cytokine production by macrophages.

Cytokines have been implicated in a wide variety of immune and inflammatory responses and have pleiotropic effects on the proliferation, differentiation, and functional activation of lymphocytes.

2. Growth Factors

Growth factors are proteins that bind to receptors on the cell surface, with the primary result of activating cellular proliferation and/or differentiation. Many growth factors are quite versatile, stimulating cellular division in numerous different cell types; while others are specific to a particular cell-type. Exemplary growth factors include platelet derived growth factor (PDGF), epidermal growth factor (EGF), fibroblast growth factors (FGFs), transforming growth factors (TGFs), insulin-like growth factor (IGF), erythropoietin (EPO) and vascular endothelial growth factor (VEGF).

V. Fusion Proteins

In one embodiment, a fusion protein comprises a polypeptide chain comprising an antigen binding moiety that selectively binds to an antigen linked to a chain of a heterodimeric proteinaceous hormone. The subject fusion proteins can be made using methods known in the art. For example, the fusion proteins of the invention may be constructed as described in U.S. Pat. No. 6,194,177 and U.S. Provisional Patent Application No. 60/728,184, both of which are incorporated by reference herein in their entirety. Additionally, the subject fusion proteins can be made employing methods used to make chimeric antibodies in which a variable domain from an antibody of one species is substituted for the variable domain of another species. See, for example, EP 0 125 023; Munro, Nature 312:597 (1984); Neuberger et al., Nature 312:604-608 (1984); Sharon et al., Nature 309:364-367 (1984); Morrison et al., Proc. Natl. Acad. Sci. USA 81:6851-6855 (1984); Morrison et al., Science 229:1202-1207 (1985); and Boulianne et al., Nature 312:643-646 (1984). In general, a nucleic acid molecule encoding the variable (e.g., heavy or light) chain of an antibody or an antigen-binding fragment thereof is cloned, for example, by PCR and ligated, in frame, with a nucleic acid molecule encoding a heterodimeric hormone α or β chain. The nucleic acid molecule encoding the fusion protein is subsequently transfected into a host cell for expression. The sequence of the final construct can be confirmed by sequencing.

In one embodiment, when preparing the fusion proteins of the present invention, a nucleic acid molecule encoding the antigen-binding fragment of an antibody will be fused in frame C-terminally to nucleic acid molecule encoding the hormone. N-terminal fusions are also possible in which antigen binding portion of the antibody is fused to the N-terminus of the hormone. The precise site at which the fusion is made is not critical; particular sites are well known and may be selected in order to optimize the biological activity, secretion, or binding characteristics of the molecule. Methods for making fusion proteins are well known in the art.

In one embodiment, the signal sequence of the proteinaceous hormone is excluded prior to incorporation of the hormone amino acid sequence into a hybrid antigen binding molecule of the invention. A heterologous signal sequence such as, for example, that derived from hGH may be included, however, such sequences may also be omitted and replaced with the signal sequence for a different polypeptide if secretion of the hybrid antigen binding molecule is desired.

In other embodiments, introns can be excluded from either one or both the antibody or antigen-binding fragment moiety and the hormone moiety prior to incorporation into a construct for making a fusion protein.

In one embodiment, the amino acid sequence of an antigen binding moiety linked to a subunit of a heterodimeric proteinaceous hormone via a peptide linker. Exemplary peptide linkers are well known in the art and may comprise, e.g., two or more alanine residues, or several Gly and several Ser residues, e.g., such as GlyGlyGlySerSerGlyGlyGlySerGly (SEQ ID NO: 110). In one embodiment, a peptide linker for use in a fusion protein of the invention acts as a flexible hinge. Non limiting examples of peptide linkers include AA, AAA, GADK (SEQ ID NO: 1), GFASPAFF (SEQ ID NO: 98), DETYVPKEFNAE (SEQ ID NO: 2), DKTHTCPPCPA-PELLGGAA (SEQ ID NO: 99), DKTHTCPPCPAPELLG-GAAA (SEQ ID NO: 100), DKTHTSPPSPAPELLGGAA (SEQ ID NO: 101), DKTHTSPPSPAPELLGGAAA (SEQ ID NO: 102), GGGS (SEQ ID NO: 103), (GGGS)$_2$ (SEQ ID NO: 104), GGGGS (SEQ ID NO: 105), (GGGGS)$_2$ (SEQ ID NO: 106), (GGGGS)$_4$ (SEQ ID NO: 107), GGGGC (SEQ ID NO: 108).

In another embodiment, a peptide linker for use in a fusion protein of the invention is cleavable in vivo (e.g., by an enzyme). Examples of cleavable linkers comprise linkers comprising a thrombin cleavage site. In another embodiment the linker is degradable by natural factors found in the circulation.

The site at which the antibody moiety is linked to the hormone moiety may vary and the optimal site for a specific outcome can be readily determined by one of ordinary skill in the art. In an exemplary embodiment, an antibody moiety may be linked via a peptide linker to alpha and beta subunits of hCG starting at residues Ala1 in the alpha subunit or Ser1 in the beta subunit, respectively.

VI. Hybrid Antigen Binding Molecules

The fusion proteins of the invention are assembled as multimers, particularly as heterodimers. The heterodimeric hybrid antigen binding molecules described herein typically comprise two polypeptide chains of a heterodimeric proteinaceous hormone receptor, with at least one chain comprising an antigen binding moiety. In the subject constructs, the two subunits of the heterodimeric proteinaceous hormone are capable of dimerizing to form the hybrid antigen binding molecule.

In one embodiment, hybrid antigen binding molecules of the invention are formed by non-covalent linkage between at least two polypeptide chains which form the hybrid antigen binding molecule. One or more covalent bonds can also be added between the two subunits of a heterodimeric proteinaceous hormone to enhance the stability of the resulting hybrid antigen binding molecule. This can be achieved by, for example, adding one or more non-native interchain disulfide bonds. One skilled in the art can easily identify appropriate sites for such cross-links, for example, based on the known structures of heterodimeric hormones. For example, cysteine residues can be incorporated into an hCG molecule at Lys45 in the α subunit and Glu21 in the β subunit, thereby replacing a salt bridge (non-covalent bond) with a disulfide bond (covalent bond). Methods for insertion of cysteine residues are well known in the art. Other forms of modifications include PEGylation and other types of chemical modifications of the hybrid polypeptides.

In one embodiment, modifications can be made, such as chemical or protease cleavage of the polypeptide backbone, or chemical or enzymatic modification of certain amino acid side chains, to reduce the activity of or inactivate one or more molecules which form part of the hybrid antigen binding molecules. Such modifications can also be accomplished through the use of hybrid DNA techniques, for example, by altering the coding sequence for one or more molecules which form a part of a hybrid antigen binding molecule, thereby resulting in reducing the activity of or inactivating a molecule which forms a part of the hybrid antigen binding molecule. Alternatively, such a modification can render hybrid antigen binding molecule more amenable to subsequent chemical or enzymatic modification.

Hybrid antigen binding molecules of the invention can either be monofunctional, bifunctional or multifunctional, depending on whether the dimeric proteinaceous hormone is functional, and on the specificity of the antigen binding moiety(ies) employed. For example, in one embodiment, more than one antigen binding moieties are included, each imparting a different function to the molecule, e.g., by binding to different antigens.

VII. Exemplary Configurations of Antigen Binding Molecules

A. Positioning of One Antigen Binding Moiety

In one embodiment, an antigen binding moiety is linked to the N-terminus of a subunit of a subunit of a heterodimeric proteinaceous hormone. In another embodiment, an antigen binding moiety is linked to the C-terminus of a subunit of a heterodimeric proteinaceous hormone.

For example, in one embodiment, an antigen binding moiety chosen from one or more CDRs, VH and/or VL and an ScFv fragment of an antibody, for example, an antibody that selectively binds VEGF, EGFR or IGF-1R, which is linked to an alpha subunit and/or beta subunit (at the N or the C terminus) of a heterodimeric proteinaceous hormone, e.g., hCG.

B. Positioning of More than One Antigen Binding Moiety

In one embodiment, a hybrid antigen binding molecule of the invention comprises more than one antigen binding moiety. In one embodiment, an antigen binding molecule of the invention comprises at least two antigen binding moieties. In other embodiments, an antigen binding molecule of the invention comprises at least three, four, or more antigen binding moieties.

In one embodiment, the antigen binding moieties are present on one of the polypeptide chains, e.g., the alpha or beta chain or portion thereof.

In another embodiment, antigen moieties are present at both the N and the C terminus of the alpha or the beta chain or portion thereof.

In another embodiment, the antigen binding moieties are present on two of the polypeptide chains, i.e., on both the alpha and beta chains.

In other embodiments, an antigen binding moiety is present at the N-terminus on both the alpha and the beta chains. In yet other embodiments, the antigen binding moiety is present at the N-terminus of one chain, e.g., the alpha or the beta chain, and the C-terminus of the other chain, e.g., the alpha or the beta chain.

In one embodiment, an antigen binding moiety is present at the N-terminus and the C-terminus of both the alpha and the beta chains. Also encompassed by this invention are hybrid molecules that contain one or more antigen binding moieties only on one of the alpha and beta chains, which dimerizes with the other chain which is not linked to an antigen binding moiety.

In one embodiment, the antigen binding moieties have the same specificity. In another embodiment, the antigen biding moieties have different specificity, e.g., specificity for different epitopes on the same antigen or specificity for different antigens, i.e., the resulting hybrid constructs are multispecific (are specific for two or more antigens or two or more epitopes on the same antigen). Various strategies are available for producing multispecific recombinant antibodies, antibody fragments, or engineered multispecific antibodies. For example, two different binding sites may be present in one polypeptide chain of a hybrid antigen binding molecule (e.g., two antigen binding moieties attached to an alpha chain) or one different antigen binding moiety may be attached to an alpha chain and a beta chain).

C. Preferred Hybrid Antigen Binding Molecules

In preferred hybrid antigen binding molecules of the invention, an antigen binding moiety is chosen from an antibody that selectively binds VEGF, EGFR or IGF-1R.

1. Hybrid EGFR Binding Molecules

For example, in some hybrid antigen binding molecules described herein, a variable light chain domain of an antibody that selectively binds EGFR (EGFR antibody) is linked via an alanine linker containing two alanines to an alpha subunit of hCG (i.e., alpha (1-87)), which dimerizes with the beta subunit of hCG linked to the variable heavy chain domain of the EGFR antibody via an alanine linker containing three alanines.

In another embodiment, an ScFv fragment of the EGFR antibody is linked to the alpha subunit (1-87) of hCG via an alanine linker containing two alanines which dimerizes with the beta subunit of hCG linked via an alanine linker containing three alanines to another ScFv molecule.

In other hybrid antigen binding molecules described herein, an ScFv chain of the EGFR antibody is linked to the alpha (1-87) subunit of hCG via a linker (GADK-AA (SEQ ID NO: 111)) and via GADK-AAA (SEQ ID NO: 112) to the beta subunit of hCG, wherein the alpha and the beta subunits dimerize to form the hybrid molecule.

In yet other embodiments, the light chain variable domain of the EGFR antibody is linked to the alpha (1-87) subunit of hCG which heterodimerizes with the beta subunit of the hCG.

In yet other embodiments, a hybrid EGFR-binding molecule includes a heavy chain variable domain of the EGFR antibody linked to the beta subunit of hCG which heterodimerizes with the alpha (1-87) subunit of hCG.

In yet other embodiments, a hybrid EGFR-binding molecule includes an ScFv fragment of the EGFR antibody linked to the beta subunit of hCG which heterodimerizes with the alpha (1-97) subunit of the hCG. Additionally, bispecific hybrid molecules are described herein that include an EGFR binding moiety of an antibody linked to one subunit of hCG (e.g., alpha or beta) and an antigen binding moiety that binds a different antigen (e.g., IGF-1R or VEGF) linked to the beta subunit of hCG.

The above molecules may or may not contain a linker as set forth above with said linker selected from AA, AAA, GADK (SEQ ID NO: 1), GFASPAFF (SEQ ID NO: 98), DETYVP- KEFNAE (SEQ ID NO: 2), DKTHTCPPCPAPELLGGAA (SEQ ID NO: 99), DKTHTCPPCPAPELLGGAAA (SEQ ID NO: 100), DKTHTSPPSPAPELLGGAA (SEQ ID NO: 101), DKTHTSPPSPAPELLGGAAA (SEQ ID NO: 102), GGGS (SEQ ID NO: 103), (GGGS)$_2$ (SEQ ID NO: 104), GGGGS (SEQ ID NO: 105), (GGGGS)$_2$ (SEQ ID NO: 106), (GGGGS)$_4$ (SEQ ID NO: 107), GGGGC (SEQ ID NO: 108).

Such molecules are more fully described in the examples set forth below.

2. Hybrid IGF-1R Binding Molecules

In other embodiments, hybrid IGF-1R binding molecules are described herein which include a variable heavy chain of an antibody that selectively binds IGF-1R (e.g., IGF-1R antibody) linked to beta subunit of hCG and the variable light chain of the IGF-1R antibody linked to the alpha subunit of hCG, where the alpha and the beta subunits dimerize to form the hybrid antigen binding molecule that binds IGF-1R.

Other exemplary hybrid IGF-1R binding molecules described herein include, for example, molecules including: (1) variable heavy chain of the IGF-1R antibody linked to the alpha subunit of hCG and the variable light chain of IGF-1R antibody linked to the beta subunit of hCG; (2) an ScFv fragment of the IGF-1R antibody linked to both the alpha and the beta subunits of hCG, either with or without a linker; (3) variable heavy chain of the IGF-1R antibody linked to the beta subunit of hCG and the variable heavy chain of the EGFR antibody linked to the alpha subunit of hCG; (4) variable light chain of the IGF-1R antibody linked to the beta subunit of hCG and the variable light chain of the EGFR antibody linked to the alpha subunit of hCG; (5) an ScFv fragment of the IGF-1R antibody linked to the alpha subunit of hCG and an ScFv fragment of the EGFR antibody linked to the beta subunit of hCG; and (6) an ScFv fragment of the IGF-1R antibody linked to the beta subunit of hCG and an ScFv fragment of the EGFR antibody linked to the alpha subunit of hCG. These molecules may or may not include a linker with said linker is selected from AA, AAA, GADK (SEQ ID NO: 1), GFASPAFF (SEQ ID NO: 98), DETYVPKEFNAE (SEQ ID NO: 2), DKTHTCPPCPAPELLGGAA (SEQ ID NO: 99), DKTHTCPPCPAPELLGGAAA (SEQ ID NO: 100), DKTHTSPPSPAPELLGGAA (SEQ ID NO: 101), DKTHTSPPSPAPELLGGAAA (SEQ ID NO: 102), GGGS (SEQ ID NO: 103), (GGGS)$_2$ (SEQ ID NO: 104), GGGGS (SEQ ID NO: 105), (GGGGS)$_2$ (SEQ ID NO: 106), (GGGGS)$_4$ (SEQ ID NO: 107), GGGGC (SEQ ID NO: 108).

3. Hybrid VEGF Binding Molecules

In other embodiments, hybrid VEGF binding molecules are described herein which include a variable heavy chain of an antibody that selectively binds VEGF (e.g., VEGF antibody) linked to beta subunit of hCG and the variable light chain of the VEGF antibody linked to the alpha subunit of hCG, where the alpha and the beta subunits dimerize to form the hybrid antigen binding molecule that binds VEGF.

Other exemplary hybrid VEGF binding molecules described herein include, for example, molecules including: (1) variable heavy chain of the VEGF antibody linked to the alpha subunit of hCG and the variable light chain of VEGF antibody linked to the beta subunit of hCG; (2) an ScFv fragment of the VEGF antibody linked to both the alpha and the beta subunits of hCG, either with or without a linker; (3) variable heavy chain of the VEGF antibody linked to the beta subunit of hCG and the variable heavy chain of the EGFR antibody linked to the alpha subunit of hCG; (4) variable light chain of the VEGF antibody linked to the beta subunit of hCG and the variable light chain of the EGFR antibody linked to the alpha subunit of hCG; (5) an ScFv fragment of the VEGF antibody linked to the alpha subunit of hCG and an ScFv fragment of the EGFR antibody linked to the beta subunit of hCG; and (6) an ScFv fragment of the VEGF antibody linked to the beta subunit of hCG and an ScFv fragment of the EGFR antibody linked to the alpha subunit of hCG. These molecules may or may not include a linker with said linker is selected from AA, AAA, GADK (SEQ ID NO: 1), GFASPAFF (SEQ ID NO: 98), DETYVPKEFNAE (SEQ ID NO: 2), DKTHTCPPCPAPELLGGAA (SEQ ID NO: 99), DKTHTCPPCPAPELLGGAAA (SEQ ID NO: 100), DKTHTSPPSPAPELLGGAA (SEQ ID NO: 101), DKTHTSPPSPAPELLGGAAA (SEQ ID NO: 102), GGGS (SEQ ID NO: 103), (GGGS)$_2$ (SEQ ID NO: 104), GGGGS (SEQ ID NO: 105), (GGGGS)$_2$ (SEQ ID NO: 106), (GGGGS)$_4$ (SEQ ID NO: 107), GGGGC (SEQ ID NO: 108).

VIII. Expression of Fusion Proteins and Hybrid Antigen Binding Molecules

The invention also includes isolated nucleic acid molecules which encode, for example, a polypeptide chain of a hybrid antigen binding molecule. Two isolated nucleic acid molecules, each comprising a nucleotide sequence encoding an antigen binding fragment linked to a nucleotide sequence encoding a subunit of a heterodimeric proteinaceous hormone can either be co-expressed or they may be expressed separately. In another embodiment, such a nucleic acid molecule may be caused to be expressed in a subject, e.g., in a nucleic acid based therapy.

In order to express the fusion or hybrid antigen binding molecules of the invention, DNA molecules obtained by any of the methods described herein or those that are known in the art, can be inserted into appropriate expression vectors by techniques well known in the art. For example, a double stranded cDNA can be cloned into a suitable vector by homopolymeric tailing or by restriction enzyme linking involving the use of synthetic DNA linkers or by blunt-ended ligation. DNA ligases are usually used to ligate the DNA molecules and undesirable joining can be avoided by treatment with alkaline phosphatase.

Therefore, the invention includes vectors (e.g., recombinant plasmids and bacteriophages) that include nucleic acid molecules (e.g., genes or recombinant nucleic acid molecules comprising genes) as described herein. The term "recombinant vector" includes a vector (e.g., plasmid, phage, phasmid, virus, cosmid, fosmid, or other purified nucleic acid vector) that has been altered, modified or engineered such that it contains greater, fewer or different nucleic acid sequences than those included in the native or natural nucleic acid molecule from which the recombinant vector was derived. For example, in one embodiment, a recombinant vector includes a nucleic acid sequence encoding an antigen binding moiety-operably linked to regulatory sequences, for example, promoter sequences, terminator sequences and/or artificial ribosome binding sites (RBSs), as defined herein. Additionally, a "recombinant vector" includes a nucleic acid molecule encoding a subunit of a heterodimeric proteinaceous hormone or a fragment thereof operably linked to regulatory sequences known in the art and those described herein. Further, a "recombinant vector" includes a vector which comprises a nucleic acid molecule encoding an antigen binding moietylinked to a nucleic acid molecule encoding a subunit of a heterodimeric proteinaceous hormone or a fragment thereof, operably linked to regulatory sequences. Recombinant vectors which allow for expression of the genes or nucleic acids included in them are referred to as "expression vectors."

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples include, but are not limited to, the TK promoter of the Herpes virus, the SV40 early promoter, the yeast gal 4 gene promoter, etc. Transcriptional initiation regulatory signals may be selected which allow for repression or activation, so that expression of the genes can be modulated.

In one embodiment, one or more DNA molecules comprising a nucleotide sequence encoding one or more polypeptide chains of a hybrid antigen binding molecule are operably linked to one or more regulatory sequences, which are capable of integrating the desired DNA molecule into a host cell. Cells which have been stably transformed by the introduced DNA can be selected, for example, by introducing one or more markers which allow for selection of host cells which contain the expression vector. A selectable marker gene can either be linked directly to a nucleic acid sequence to be expressed, or be introduced into the same cell by co-transfection. Additional elements may also be needed for optimal synthesis of polypeptides and antibodies described herein. It would be apparent to one of ordinary skill in the art which additional elements to use, if necessary.

Factors of importance in selecting a particular plasmid or viral vector include, but are not limited to, the ease with which recipient cells that contain the vector are recognized and selected from those recipient cells which do not contain the vector; the number of copies of the vector which are desired in a particular host; and whether it is desirable to be able to "shuttle" the vector between host cells of different species.

Once the vector(s) is constructed to include a DNA sequence for expression, it may be introduced into an appropriate host cell by one or more of a variety of suitable methods that are known in the art, including but not limited to, for example, transformation, transfection, conjugation, protoplast fusion, electroporation, calcium phosphate-precipitation, direct microinjection, etc.

Host cells may either be prokaryotic or eukaryotic. Examples of eukaryotic host cells include, for example, mammalian cells, such as human, monkey, mouse, and Chinese hamster ovary (CHO) cells. Such cells facilitate post-translational modifications of polypeptides, including, for example, correct folding or glycosylation. Additionally, yeast cells can also be used to express hybrid polypeptides of the invention. Like most mammalian cells, yeast cells also enable post-translational modifications of polypeptides, including, for example, glycosylation. A number of recombinant DNA strategies exist which utilize strong promoter sequences and high copy number plasmids that can be utilized for production of polypeptides in yeast. Yeast transcription and translation machinery can recognize leader sequences on cloned mammalian gene products, thereby enabling the secretion of peptides bearing leader sequences (i.e., pre-peptides). One method of high-yield production of the hybrid antigen binding molecules of the invention is through the use of dihydrofolate reductase (DHFR) amplification in DHFR-deficient CHO cells, by the use of successively increasing levels of methotrexate as described in U.S. Pat. No. 4,889,803.

After the introduction of one or more vector(s), host cells are usually grown in a selective medium, which selects for the growth of vector-containing cells. Purification of the recombinant antibodies can be carried out by any of the methods known in the art, for example, any conventional procedures involving extraction, precipitation, chromatography and electrophoresis. A further purification procedure that may be used for purifying antibodies is affinity chromatography using a known antigen. Generally, crude preparations containing a recombinant antibody are passed through a column on which a suitable antigen is immobilized. The antibody usually binds to the column via the specific antigen while the impurities pass through. After washing the column, the antibody is eluted from the gel by changing pH or ionic strength, for example.

IX. Testing Hybrid Antigen Binding Molecules for Activity

The ability of the subject antigen binding molecules to bind to the target antigen, agonize receptor activity, or antagonize, receptor activity can be tested using methods known in the art.

Binding can be measured, e.g., using a binding assay. In other embodiment, a competitive binding assay can be used. For example, in one embodiment, binding can be detected by contacting cells expressing a target molecule with a labeled ligand for the target (for example, radio-active label) and increasing concentrations of an unlabeled hybrid antigen binding molecule, which competes for binding to the same target are added. The cells are subsequently washed and labeled ligand is measured. A decrease in the amount of the labeled ligand in the presence of the unlabeled hybrid antigen binding molecule is indicative of competition for binding by the hybrid antigen binding molecule.

Agonism or antagonism of biological activity of a receptor can be measured, for example, by assaying a cellular responses such as, for example, cell proliferation. In one embodiment, an agonist is identified by its ability to mimic the cellular response of the cognate ligand. In another embodiment, a cognate ligand and a potential antagonist are contacted with a cell and the cellular response is measured. A decreased cellular response in the presence of the hybrid antigen binding molecule relative to the response elicited by the ligand alone indicates that the hybrid antigen binding molecule has antagonist activity. Also, a change in second messenger production from a receptor can also be measured as an indicia of agonist or antagonist activity.

X. Pharmaceutical Compositions

The invention also pertains to pharmaceutical compositions comprising one or more hybrid antigen binding molecules described herein and a pharmaceutically acceptable diluent or carrier. Such pharmaceutical compositions may be included in a kit or container. Such kit or container may be packaged with instructions pertaining to the extended in vivo half-life or the in vitro shelf life of the hybrid antigen binding molecules. Such compositions may be used in methods of treating, preventing, or ameliorating a disease or a disease symptom in a patient, preferably a mammal and most preferably a human, by administering the pharmaceutical composition to the patient.

In general, a therapeutically effective amount of a pharmaceutical composition of the invention would be from about 0.0001 mg/Kg to 0.001 mg/Kg; 0.001 mg/kg to about 10 mg/kg body weight or from about 0.02 mg/kg to about 5 mg/kg body weight. In one embodiment, a therapeutically effective amount of a hybrid antigen binding molecule is from about 0.001 mg to about 0.01 mg, about 0.01 mg to about 100 mg, or from about 100 mg to about 1000 mg, for example.

In one embodiment, a therapeutically effective amount of a hybrid antigen binding molecule described herein is lower than the amount of the corresponding non-hybrid antigen binding molecule.

The optimal pharmaceutical formulations for a hybrid antigen binding molecule can be determined by one or ordinary skilled in the art depending upon the route of administration and desired dosage. (See, for example, Remington's Pharmaceutical Sciences, 18th Ed. (1990), Mack Publishing Co., Easton, Pa., the entire disclosure of which is hereby incorporated by reference).

Hybrid antigen binding molecules of the invention for use in the methods or compositions described herein can be formulated for the most effective route of administration, including for example, oral, transdermal, sublingual, buccal, parenteral, rectal, intranasal, intrabronchial or intrapulmonary administration.

Hybrid antigen binding molecules of the invention and described herein can either by administered alone or in combination of other therapeutic agents known to be useful in the treatment of the disease being treated. For example, in one embodiment, hybrid antigen binding molecules described herein are used in conjunction with chemotherapeutic agents.

XI. Methods of Treatment or Diagnosis

Hybrid antigen binding molecules described herein can be used, for example, in diagnostic and/or treatment methods, for example, diagnosis and/or treatment of cancer or other proliferative disorders.

In one embodiment, hybrid antigen binding molecules described herein are used for detection of antigens specifically or preferentially expressed on cells, e.g., cancer cell-specific antigens. For example, hybrid antigen binding molecules can be labeled with a detectible moiety, such as a radionuclide. Examples of radionuclides include $^{123}$Iodine, $^{125}$Iodine, $^{131}$Iodine, $^{105}$Rhodium, $^{67}$Gallium, $^{153}$Sm, $^{177}$Lu, $^{186}$Re, $^{188}$Re, $^{166}$Ho, $^{67}$Cu, $^{90}$Y, $^{111}$Indium, $^{18}$Fluorine, or $^{99m}$Technetium (Tc99m). In one embodiment, such radionuclides can be conjugated to a hybrid antigen binding molecule, either directly or indirectly, where the hybrid antigen binding molecule specifically binds to an antigen expressed exclusively or preferentially on cancer cells. Such hybrid antigen binding molecules can be used, for example, either for the detection of cells that express a cancer cell-specific antigen (e.g., in diagnostic methods); or such molecules can be used for cytotoxic killing of such cells (e.g., in treatment methods).

Spectroscopic probes can also be conjugated to hybrid antigen binding molecules of the invention, which are used in imaging techniques for detection of cells to which the hybrid antigen molecule binds, for example. Examples of spectroscopic probes include, but are not limited to, fluorophores (e.g., Fluorescein), chromophores (e.g., luminal, luciferase, luciferin, and aequorin), magnetic probes and contrast reagents (e.g., MRI contrast reagents). Other examples of spectroscopic probes include, but are not limited to, phosphorescent probes and PET labels.

In one embodiment, hybrid antigen binding molecules of the invention are used for agonism or antagonism of a receptor function.

In one embodiment, the invention comprises methods of treating disorders associated with proliferation of cells, for example, cancer. Exemplary hybrid antigen binding molecules of the invention antagonize at least one biological activity of a molecule selected from the group consisting of VEGF, EGFR and IGF-1R.

In one embodiment, a hybrid antigen binding molecule, comprises an optional functional moiety. Preferred agents for conjugation to the subject hybrid antigen binding molecules are cytotoxic drugs. Additionally, cytotoxic moieties can be conjugated to hybrid antigen binding molecules which of the invention. A cytotoxic moiety is generally an agent that is detrimental to the growth and proliferation of cells and may act to reduce, inhibit or destroy a cell or malignancy. Exemplary cytotoxins include, but are not limited to, certain radionuclides, biotoxins, enzymatically active toxins, cytostatic or cytotoxic therapeutic agents, prodrugs, immunologically active ligands and biological response modifiers such as cytokines.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the maytansinoid family of drugs. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, caminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

Among other cytotoxins, it will be appreciated that polypeptides can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the binding molecule-toxin construct.

Other biological response modifiers that may be associated with the polypeptides of the invention of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed polypeptides are radiosensitizing drugs that may be effectively directed to tumor or immunoreactive cells. Such drugs enhance the sensitivity to ionizing radiation, thereby increasing the efficacy of radiotherapy. An conjugate internalized by the tumor cell would deliver the radiosensitizer nearer the nucleus where radiosensitization would be maximal. The unbound radiosensitizer linked polypeptides of the invention would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting molecule. A potentially attractive variation of this approach would be the attachment of a therapeutic radioisotope to the radiosensitized immunoconjugate, thereby providing the convenience of administering to the patient a single drug.

The subject optional functional moieties may be conjugated to either an antigen binding moiety or one or more chains of a heterodimeric proteinaceous hormone receptor using techniques known in the art.

In one embodiment, a hybrid antigen binding molecule of the invention comprises two polypeptide chains, with each polypeptide chain comprising an amino acid sequence of an antibody that selectively binds VEGF or a VEGF-binding fragment thereof linked to an amino acid sequence of a subunit of a heterodimeric proteinaceous hormone chosen from the group including but not limited to hCG, FSH, LH, TSH, inhibin, or a fragment thereof, wherein the hybrid polypeptide has VEGF antagonist activity.

In one embodiment, the disorder that would benefit from VEGF antagonism comprises but is not limited to cancer or precancerous condition. In one embodiment, the cancer is colorectal cancer. In other embodiments, the disorder involves other unwanted proliferation of blood vessels, e.g., as occurs in diabetic retinopathy.

In one embodiment, a hybrid antigen binding molecule used in a method for treating cancer comprises two polypeptide chains, with one chain comprising an amino acid sequence for a variable heavy chain or a variable light chain of an antigen binding moiety that selectively binds EGFR linked to the alpha subunit of hCG and the second chain comprising an amino acid sequence of a variable heavy chain or a variable light chain of an antigen binding moiety that selectively binds EGFR linked to beta subunit of hCG wherein the hybrid polypeptide has EGFR antagonist activity.

In another embodiment, a hybrid antigen binding molecule used in a method for treating cancer comprises two polypeptide chains, with one chain comprising an amino acid sequence for a variable heavy chain linked to an amino acid sequence for variable light chain of an antigen binding moiety that selectively binds EGFR linked to the alpha subunit of hCG and the second chain comprising an amino acid sequence of a variable heavy chain linked to an amino acid sequence for variable light chain of an antigen binding moiety that selectively binds EGFR linked to beta subunit of hCG wherein the hybrid polypeptide has EGFR antagonist activity.

In another embodiment, a hybrid antigen binding molecule used in a method for treating cancer comprises two polypeptide chains, with one chain comprising an amino acid sequence for an ScFv that selectively binds EGFR linked to the alpha subunit of hCG and the second chain comprising an amino acid sequence for an ScFv that selectively binds EGFR linked to beta subunit of hCG wherein the hybrid polypeptide has EGFR antagonist activity.

In one embodiment, a hybrid antigen binding molecule used in a method for treating cancer comprises two polypeptide chains, with one chain comprising an amino acid sequence for a variable heavy chain or a variable light chain of an antigen binding moiety that selectively binds IGF-1R linked to the alpha subunit of hCG and the second chain comprising an amino acid sequence of a variable heavy chain or a variable light chain of an antibody that selectively binds IGF-1R linked to beta subunit of hCG wherein the hybrid polypeptide has IGF-1R antagonist activity.

In another embodiment, a hybrid antigen binding molecule used in a method for treating cancer comprises two polypeptide chains, with one chain comprising an amino acid sequence for a variable heavy chain linked to an amino acid sequence for variable light chain of an antigen binding moiety that selectively binds IGF-1R linked to the alpha subunit of hCG and the second chain comprising an amino acid sequence of a variable heavy chain linked to an amino acid sequence for variable light chain of an antigen binding moiety that selectively binds IGF-1R linked to beta subunit of hCG wherein the hybrid polypeptide has IGF-1R antagonist activity.

In another embodiment, a hybrid antigen binding molecule used in a method for treating cancer comprises two polypeptide chains, with one chain comprising an amino acid sequence for an ScFv that selectively binds IGF-1R linked to the alpha subunit of hCG and the second chain comprising an amino acid sequence for an ScFv that selectively binds IGF-1R linked to beta subunit of hCG wherein the hybrid polypeptide has IGF-1R antagonist activity.

In one embodiment, a hybrid antigen binding molecule used in a method for treating cancer or any condition associated with aberrant angiogenesis, e.g. dibetic retinopathy, comprises two polypeptide chains, with one chain comprising an amino acid sequence for a variable heavy chain or a variable light chain of an antigen binding moiety that selectively binds VEGF linked to the alpha subunit of hCG and the second chain comprising an amino acid sequence of a variable heavy chain or a variable light chain of an antibody that selectively binds VEGF linked to beta subunit of hCG wherein the hybrid polypeptide has VEGF antagonist activity.

In another embodiment, a hybrid antigen binding molecule used in a method for treating cancer or any condition associated with aberrant angiogenesis, e.g. diabetic retinopathy, comprises two polypeptide chains, with one chain comprising an amino acid sequence for a variable heavy chain linked to an amino acid sequence for a variable light chain of an antigen binding moiety that selectively binds VEGF linked to the alpha subunit of hCG and the second chain comprising an amino acid sequence of a variable heavy chain linked to an amino acid sequence for variable light chain of an antigen binding moiety that selectively binds VEGF linked to beta subunit of hCG wherein the hybrid polypeptide has VEGF antagonist activity.

In another embodiment, a hybrid antigen binding molecule used in a method for treating cancer or any condition associated with aberrant angiogenesis, e.g. diabetic retinopathy, comprises two polypeptide chains, with one chain comprising an amino acid sequence for an ScFv that selectively binds VEGF linked to the alpha subunit of hCG and the second chain comprising an amino acid sequence for an ScFv that selectively binds VEGF linked to beta subunit of hCG wherein the hybrid polypeptide has VEGF antagonist activity.

In other embodiments of the present invention a hybrid antigen molecule used in a method for treating cancer may comprise one or more EGFR binding moieties and one or more IGF-1R binding moieties.

In other embodiments of the present invention a hybrid antigen binding molecule used in a method for treating cancer may comprise one or more EGFR binding moieties and one or more VEGF binding moieties.

In yet other embodiments of the present invention a hybrid antigen binding molecule used in a method for treating cancer may comprise one or more IGF-1R binding moieties and one or more VEGF binding moieties.

This invention is further illustrated by the following examples which should not be construed as limiting. The contents of all references, patents and published patent applications cited throughout this application are incorporated herein by reference.

EXAMPLES

Example 1

Construction of EGFR Hybrid Antigen Binding Molecules

The nucleotide sequences of the VH and VL regions corresponding to those of an anti-EGFR antibody, i.e., 225 antibody (ATCC HB8505) were synthesized de novo and are provided as clones in pUC18minusMCS (BLUE HERON BIOTECHNOLOGY, Bothell, Wash.). The DNA sequences of the synthesized VH and VL fragments are shown in FIGS. 1 and 2, respectively.

The VH and VL region clones were used as templates in a PCR reaction to synthesize fragments that could be used for generating the following fusion molecules: EGFR VH-AAA-hCGβ; EGFR-VL AA alpha(1-87), EGFR ScFv-AA-alpha (1-87), and EGFR ScFv-AAA-hCGβ. The alanines (AAA and AA) are linkers between the V region and hCG subunit domains, introduced by a NotI cloning site. It is contemplated that the linkers could be eliminated entirely, or that alternative linkers of different sizes and structures could also be introduced between the domains. The use of different linkers is illustrated in this example. The first is a short flexible linker segment, GADK (SEQ ID NO: 1), and the second is a long linker with an extended structure found in human serum albumin, DETYVPKEFNAE (SEQ ID NO:2), subsequently abbreviated HSA. Primers used to synthesize PCR fragments for fusion constructs are shown below.

VH Region-Fragment 1 (VH-NotI):

5'-AGATCTGCCCAGGTGCAGCTGAAGCAGTC-3' (SEQ ID NO: 3)
and

5'-GCGGCCGCTGCAGAGACAGTGACCAGAGTC-3' (SEQ ID NO: 4)

VH Fragment 2 (VH-Linker):

(SEQ ID NO: 3)
5'-AGATCTGCCCAGGTGCAGCTGAAGCAGTC-3'
and (SEQ ID NO: 5)
5'-CAGCAAGATGTCAGATCCGCCGCCACCCGACCCACCAC

CGCCCGAGCCACCGCCACCTGCAGAGACAGTGACCAGAGT

CCCTTGG-3'

VL Region Fragment 1 (VL-NotI):

(SEQ ID NO: 6)
5'-AGATCTGCCGACATCTTGCTGACTCAGTCTC-3'
and (SEQ ID NO: 7)
5'-GCGGCCGCTTTCAGCTCCAGCTTGGTCCCAG-3'

VL Region Fragment 2 (Linker-VL):

(SEQ ID NO: 8)
5'-GCGGATCTGACATCTTGCTGACTCAGTCTCC-3'
and (SEQ ID NO: 7)
5'-GCGGCCGCTTTCAGCTCCAGCTTGGTCCCAG-3'

VL Region Fragment 3 (Linker-VL-GADK-NotI):

(SEQ ID NO: 8)
5'-GCGGATCTGACATCTTGCTGACTCAGTCTCC-3'
and (SEQ ID NO: 9)
5'-GCGGCCGCTTTATCGGCGCCTTTCAGCTCCAGCTTGGTCCCAG-3'

VL Region Fragment 4 (Linker-VL-HSA-NotI):

(SEQ ID NO: 8)
5'-GCGGATCTGACATCTTGCTGACTCAGTCTCC-3'
and (SEQ ID NO: 10)
5'-GCGGCCGCTTCAGCATTAAACTCTTTGGGAACGTATGTTT

CATCTTTCAGCTCCAGCTTGGTCCCAG-3'

The VH and VL region PCR fragments were gel purified by size fractionation on agarose gels and purification on Wizard PCR columns (PROMEGA). ScFv fusions were designed with the VH region at the N-terminus followed by the (Gly$_4$Ser)$_3$ linker and the VL region. The VL-(Gly$_4$Ser)$_3$-VH configuration could also be used, and the linker between the V regions could also be varied in size and sequence. The ScFv fusions used in this example were created in the following second step PCR reactions:

EGFR ScFv-NotI:
Primers:

```
5'-AGATCTGCCCAGGTGCAGCTGAAGCAGTC-3'    (SEQ ID NO: 11)
and
5'-GCGGCCGCTTTCAGCTCCAGCTTGGTCCCAG-3'   (SEQ ID NO: 12)
```

Template: VH Fragment 2 and VL Fragment 2
EGFR ScFv GADK-NotI
Primers:

```
5'-AGATCTGCCCAGGTGCAGCTGAAGCAGTC-3'    (SEQ ID NO: 11)
and
5'-GCGGCCGCTTTATCGGCGCCTTTCAGCTCCAGCTTGGTCCCAG-3'   (SEQ ID NO: 13)
```

Template: VH Fragment 2 and VL Fragment 3
EGFR ScFv-HSA-NotI
Primers:

```
5'-AGATCTGCCCAGGTGCAGCTGAAGCAGTC-3'    (SEQ ID NO: 11)
and
5'-GCGGCCGCTTCAGCATTAAACTCTTTGGGAACGTATGTTTCAT   (SEQ ID NO: 14)
CTTTCAGCTCCAGCTTGGTCCCAG-3'
```

Template: VH Fragment 2 and VL Fragment 4

VH fragment 1, VL fragment 1, and the ScFv fusions were cloned into pCR4Blunt-TOPO and subjected to DNA sequence analysis. Correct clones were identified and inserts were excised by double digestion with BglII and NotI. Fusions to the alpha and beta subunit of hCG were made by cloning the purified fragments into pENTR1a vectors (IN-VITROGEN) double digested with BamHI and NotI, and having the insertions between the ATTL sites shown in FIGS. 3 and 4. The alpha subunit used in this example has a 5 amino acid C-terminal deletion to reduce the bioactivity of the hCG scaffold. The hGH signal peptide is also encoded in the pENTR1a insertions and is used to direct secretion of the fusion proteins.

The DNA and amino acid sequences of the EGFR VH and VL regions fused to the hCG beta and alpha(1-87), respectively, and the EGFR ScFv constructs containing the alanine linker are shown in FIGS. 5A thorough 8B. ScFv-hCG subunit fusions with the GADK and HSA linkers were similarly prepared

Example 2

Construction of VEGF Hybrid Antigen Binding Molecules

Figure 10:
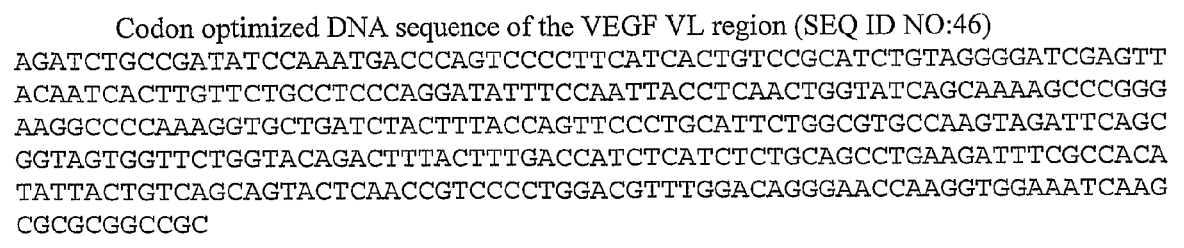

The amino acid sequences for VEGF VH and VEGF VL were subjected to codon optimization analysis (BLUE HERON BIOTECHNOLOGY) and the resulting DNA sequences were synthesized de novo. The VEGF VH DNA sequence is shown in FIG. 9 and the VEGF VL DNA sequence is shown in FIG. 10.

The codon optimized VH and VL regions were assembled to encode ScFv molecules with the following compositions: VH-(Gly$_4$Ser)$_3$-VL and VL-(Gly$_4$Ser)$_3$-VH. These were also synthesized de novo (BLUE HERON). A portion of the IgG1 hinge region (hng) was added to the 3' end to use as a linker. It is contemplated that the linkers could be eliminated entirely, or that alternative linkers of different sizes and structures could also be introduced between the domains. The DNA sequences of the VH-VL and VL-VH VEGF ScFv molecules are shown in FIGS. 11 and 12, respectively.

The de novo synthesized DNA fragments were received as clones in pUCminusMCS (BLUE HERON BIOTECHNOLOGY). Fusions to the hGH signal peptide and the alpha(1-87) and hCGbeta subunits were made by excising the inserts with BglII and NotI and cloning them into pENTR1a vectors (IN-VITROGEN) double digested with BamHI and NotI, and having the insertions between the ATTL sites shown in FIGS. 3 and 4. The alpha subunit used in this example has a 5 amino acid C-terminal deletion to reduce the bioactivity of the hCG scaffold.

Additional constructs, with or without linkers between the V-region and hCG subunit domains are made by a 2-step PCR using the de novo synthesized DNA clones as templates.

Example 3

Construction of IGF-1R Hybrid Antigen Binding Molecules

The amino acid sequences for IGF-1R VH and IGF-1R VL (WO03059951) were synthesized de novo (BLUE HERON BIOTECHNOLOGY). The DNA sequences for IGF-1R VH and VL are shown in FIGS. 13 and 14.

The de novo synthesized DNA fragments were received as clones in pUCminusMCS (BLUE HERON BIOTECHNOLOGY). Fusions to the hGH signal peptide and the alpha(1-87) and hCGbeta subunits were made by excising the inserts with BglII and NotI and cloning them into pENTR1a vectors (IN-VITROGEN) double digested with BamHI and NotI, and having the insertions between the ATTL sites shown in FIGS. 3 and 4. The alpha subunit used in this example has a 5 amino acid C-terminal deletion to reduce the bioactivity of the hCG scaffold. The NotI cloning site introduces three alanines and two alanines, respectively, between the V region domains and the hCG beta and alpha(1-87) subunits. The DNA and amino acid sequences of the IGF-1R VH region and IGF-1R VL region fusions with the alpha(1-87) and hCGbeta subunits are shown in FIGS. 15A to 18B.

The IGF-1R clones in pUCminusMCS were used as the templates for 2-step PCR to construct ScFv fragments having the composition VH-(Gly$_4$Ser)$_3$-VL. Three ScFv constructs were tested in this example. One had a NotI cloning site at the C-terminus, leading to the insertion of three and two alanine linkers between the V contemplated that the linkers could be eliminated entirely, or that alternative linkers of different sizes and structures could also be introduced between the domains. Examples of other linkers are illustrated by the other two ScFv molecules synthesized. The second ScFv contained a short flexible linker segment, GADK (SEQ ID NO:1) in addition to the NotI site. The third ScFv contained a long linker with an extended structure found in human serum albumin, DETYVPKEFNAE (SEQ ID NO:2), abbreviated HSA, in addition to the alanines encoded in the NotI site. Primers used to synthesize step 1 PCR fragments for fusion constructs are listed below.

VH Fragment
Primers:

(SEQ ID NO: 15)
5'-AGATCTGCCCAGGTGCAGCTTCAG-3'
and (SEQ ID NO: 16)
5'-CCACCACCGCCCGAGCCACCGCCACCTGAGGAGACGGT
GACCAGGGT-3'

Template: Plasmid Encoding IGF-1R VH
VL Fragment 1 (NotI):
Primers:

(SEQ ID NO: 17)
5'-TGGCTCGGGCGGTGGTGGGTCGGGTGGCGGCGGATCT
GATATTGTGATGACTCAGTCTCCACTC-3' and
and (SEQ ID NO: 18)
5'-GCGGCCGCTTTGATTTCCACCTTGGTCCCTTGGC-3'

Template: Plasmid Encoding IGF-1R VL
VL Fragment 2 (GADK-NotI):
Primers:

(SEQ ID NO: 17)
5'-TGGCTCGGGCGGTGGTGGGTCGGGTGGCGGCGGATCT
GATATTGTGATGACTCAGTCTCCACTC-3'
and (SEQ ID NO: 19)
5'-GCGGCCGCTTTATCGGCGCCTTTGATTTCCACCTTGGTCC
CTTGGC-3'

Template: Plasmid Encoding IGF-1R VL2
VL Fragment 3 (HSA-NotI):
Primers:

(SEQ ID NO: 17)
5'-TGGCTCGGGCGGTGGTGGGTCGGGTGGCGGCGGATCT
GATATTGTGATGACTCAGTCTCCACTC-3'
and (SEQ ID NO: 20)
5'-GCGGCCGCTTCAGCATTAAACTCTTTGGGAACGTATG
TTTCATCTTTGATTTCCACCTTGGTCCCTTGGC-3'

Template: Plasmid Encoding IGF-1R VL2

Primers and templates used to synthesize ScFv fragments in step 2 PCR are listed below:
IGF-1R ScFv-NotI
Primers:

(SEQ ID NO: 21)
5'-AGATCTGCCCAGGTGCAGCTTCAG-3'
and (SEQ ID NO: 22)
5'-GCGGCCGCTTTGATTTCCACCTTGGTCCCTTGGC-3'

Template: VH Fragment and VL Fragment 1
IGF-1R ScFv-GADK-NotI
Primers:

(SEQ ID NO: 21)
5'-AGATCTGCCCAGGTGCAGCTTCAG-3'
and (SEQ ID NO: 23)
5'-GCGGCCGCTTTATCGGCGCCTTTGATTTCCACCTTGGTCCC
TTGGC-3'

Template: VH Fragment and VL Fragment 2
IGF-1R ScFv-HSA-NotI
Primers:

(SEQ ID NO: 21)
5'-AGATCTGCCCAGGTGCAGCTTCAG-3'
and (SEQ ID NO: 24)
5'-GCGGCCGCTTCAGCATTAAACTCTTTGGGAACGTATGTTTCA
TCTTTGATTTCCACCTTGGTCCCTTGGC-3'

Template: VH Fragment and VL Fragment 3

The PCR fragments encoding ScFv fusions were cloned into pCR4Blunt-TOPO (INVITROGEN) and subjected to DNA sequence analysis. Correct clones were identified and inserts were excised by double digestion with BglII and NotI. Fusions to the hGH signal peptide and the alpha and beta subunits of hCG were made by cloning the purified fragments into pENTR1a/alpha(1-87) and pENTR1a/beta vectors (FIGS. 3 and 4) double digested with BamHI and NotI. The DNA and amino acid sequences of the IGF-1R ScFv-NotI-alpha(1-87) and IGF-1R ScFv-NotI-hCGbeta constructs are shown in FIGS. 19 and 20.

Example 4

Confirmation of Production of EGFR Hybrid Antigen Binding Molecules Using ELISA

The EGFR V region-hCG fusion proteins were cloned by LR reactions (INVITROGEN) into a Gateway-modified vector expression vector, pEAK12d. Transient transfections were done in 293-EBNA cells (INVITROGEN) to assess polypeptide production, dimerization, and in vitro activity. Lipofectamine-2000 reagent (INVITROGEN) was used to do the transfections. The protocols supplied by the manufacturer were used for cell culture and cell transfections. Conditioned medium was harvested 2-5 days following addition of Opti-MEM medium (INVITROGEN). The production of EGFR hybrid antigen binding molecules was measured using an ELISA specific for intact hCG (DSL). A TBP hCG fusion protein was used as the standard for the assay, except for sample 11 [α(1-87)+hCGβ] which was assayed using hCG as a standard. The results are shown in Table 1 below.

TABLE 1

Detection of EGFR hybrid antigen binding molecules in
supernatants from transfected 293-EBNA cells by ELISA

| transfection # | Constructs transfected | Hybrid antigen binding molecule production (ng/ml) |
|---|---|---|
| 1 | VL-AA-hCGα(1-87) + VH-AAA-hCGβ | 3400 |
| 2 | ScFv-AA-hCGα(1-87) + ScFv-AAA-hCGβ | 140 |
| 3 | ScFv-GADK-AA-hCGα(1-87) + ScFv-GADK-AAA-hCGβ | 140 |
| 4 | ScFv-HSA-AA-hCGα(1-87) + ScFv-HSA-AAA-hCGβ | 104 |
| 5 | VL-AA-hCGα(1-87) + hCGγ | 1900 |
| 6 | VH-AAA-hCGβ + α (1-87) | 25 |
| 7 | ScFv-AAA-hCGβ + α (1-87) | 411 |
| 8 | ScFv-GADK-AAA-hCGβ + α (1-87) | 500 |
| 9 | ScFv-HSA-AAA-hCGβ + α (1-87) | 500 |
| 10 | ScFv-AA-α + hCGβ | 584 |
| 11 | α(1-87) + hCGβ | 6800 |
| 12 | Mock | Negative |
| 13 | GFP | Negative |

As summarized in Table 1, hybrid antigen binding molecules were detectable in all samples, with the exception of the controls, mock and GFP, and the possible exception of VH-AAA-hCGβ+α(1-87).

Example 5

Confirmation of Production of IGF-1R Hybrid Antigen Binding Molecules Using ELISA The IGF-1R V region-hCG fusion proteins were cloned by LR reactions (INVITROGEN) into a Gateway-modified vector expression vector, pEAK12d. Transient transfections were done in 293-EBNA cells (INVITROGEN) to assess polypeptide production, dimerization, and in vitro activity. Lipofectamine2000 reagent (INVITROGEN) was used to do the transfections. The protocols supplied by the manufacturer were used for cell culture and cell transfections. Conditioned medium was harvested 2-5 days following addition of Opti-MEM medium (INVITROGEN). The production of hybrid antigen binding molecules was measured using an ELISA specific for intact hCG (DSL). Transfections 6 and 7 comprised a VLα(1-87) fusion derived from the EGFR-specific antibody 225, in combination with the IGF-1R VHβ and VLβ, respectively, as controls that should not bind to either the IGF-1R or the EGFR. IGF-1R hybrid antigen binding molecules produced in transfections 8 and 9 contain one ScFv fusion specific for the IGF-1R and one specific for the EGFR, and therefore should bind to both receptors.

TABLE 2

Detection of IGF-1R hybrid antigen binding molecules in
supernatants from transfected 293-EBNA cells by ELISA

| TF# | Constructs | Heterodimer (ng/ml) |
|---|---|---|
| 1 | IGF-1R β + h7C10 α | 630 |
| 2 | IGF-1R α + h7C10 β | 113 |
| 3 | IGF-1R β + h7C10 α | 96 |
| 4 | IGF-1R scFv-β + h7C10 scFv-α | 98 |
| 5 | IGF-1R scFv-β + h7C10 scFv-α | 245 |
| 6 | IGF-1R β + 225 α | 43 |
| 7 | IGF-1R β + 225 α | 26 |
| 8 | IGF-1R scFv-α + 225 scFv-β | 10 |
| 9 | IGF-1R scFv-β + 225 scFv-α | 46 |
| 10 | α(1-β) | 512 |
| 11 | GFP | 0 |
| 12 | Mock | 0 |

As summarized in Table 2, IGF-1R antibodies were detectable in all the transfections.

Example 6

EGFR Hybrid Antigen Binding Molecules are Capable of Displacing Alexa Fluor 488-Labeled EGF from the Surface of A431 Cells The activity of the EGFR V-region hCG subunit fusion proteins produced by 293-EBNA cells was assessed in a competitive binding assay. The culture supernatants were concentrated approximately 10 fold using Centriprep YM-10 columns (MILLIPORE). Alexa fluor 488-labeled EGF complex (MOLECULAR PROBES) was mixed with purified anti-EGFR M225 antibody (CALBIOCHEM CAT. NO. GR13) or the concentrated culture supernatants. Between 20,000-40,000 A431 cells (ATCC CRL-1555) were added to each sample and incubated for 1 h at RT. The final concentration of the EGF complex was 100 ng/ml. Mean fluorescence intensity (MFI) was measured using the Guava Easycyte. The results of a representative assay are shown in FIGS. 21 and 22

As depicted in FIG. 21, The results show that the monovalent VH-AAA-hCGβ+VL-AA-α(1-87) heterodimer and heterodimers of the ScFv molecules fused to both subunits (bivalent constructs, transfections 2-4) were good competitors of EGF binding, as were the various dilutions of the M225 antibody control. The culture supernatants containing monovalent ScFv molecules (transfections 7-10) also displaced EGF from the surface of A431 cells, but were not quite as effective. Culture supernatants containing VH-AAA-hCGβ+α(1-87), VL-AA-α(1-87)+hCGβ, the hCG scaffold alone(sample #11), and culture supernatant from mock transfected cells, showed no EGF displacement activity.

The competitive binding activity of 2-fold serial dilutions of the concentrated culture supernatants from transfections 1-4 and 11, was compared to dilutions of the purified M225 antibody, as shown in FIG. 22 The results are consistent with those shown in FIG. 21, indicating that the EGFR VH/VL-hCG antibodies and EGFR ScFv-hCG antibodies are correctly folded and secreted to form molecules that are able to displace EGF by binding to the EGFR.

Example 7

Fusion of EGFR Variable Regions to the C-Termini of the hCG Alpha(1-87) and hCG Beta Subunits The EGFR V-regions may also be fused to the C-termini of the hCG subunits, or both the N-termini and C-termini. In this example, fusions to the C-termini with the following compositions: hCG subunit-(+/−linker)-VH-linker-VL; hCG subunit-(+/−linker)-VH; and hCG subunit-(+/−linker)-VL are described. This configuration is not limiting; other composition with or without linkers are envisioned, such as hCG subunit-(+/−linker)-VL-linker-VH.

PCR fragments for cloning or for building the fusion proteins may be synthesized with the following primers and templates:

EGFR VL Fragment 1 (Fusion to hCG Beta):
5'-CGATCCTCCCACAAGACATCTTGCT-GACTCAGTCTCCAGTC-3' (SEQ ID NO:25) and
EGFR VLsal or EGFRVLxho
Template: plasmid encoding VL region EGFR scFv Fragment 1 (Fusion to Alpha(1-87) without Linker):
5'-GCGTGCCACTGCAGTACTTGTCAGGTG-CAGCTGAAGCAGTCAG-3' (SEQ ID NO:26) and
EGFRVLsal or EGFRVLxho
Template: Plasmid encoding EGFR ScFv (VH-linker-VL)

EGFR ScFv Fragment 2 (Fusion to Alpha(1-87) with GFSASPAFF Linker):
5'-GGTTTTAGCGCTTCTCCAGCATTCTTC-CAGGTGCAGCTGAAGCAGTCAG-3' (SEQ ID NO:27) and
EGFR VLsal or EGFR VLxho
Template: Plasmid encoding EGFR ScFv (VH-linker-VL)

EGFR ScFv Fragment 3 (Fusion to hCGbeta):
5'-ACACCCCGATCCTCCCACAACAGGTG-CAGCTGAAGCAGTCAG-3' (SEQ ID NO:28) and
EGFR VLsal or EGFR VLxho Alpha(1-87) Fragment 1 (without Linker):
Primers: hGHsp(−int)+
5'-CTGACTGCTTCAGCTGCACCTGACAAG-TACTGCAGTGGCACGC-3' (SEQ ID NO:29)
Template: Plasmid encoding alpha(1-87) with the hGH signal peptide Alpha(1-87) Fragment 2 (with Linker):
Primers: hGHsp(−int)+
5'-CTGACTGCTTCAGCTGCACCTGGAA-GAATGCTGGAGAAGCGCTAAAACC-3' (SEQ ID NO:30).
Template: Plasmid encoding alpha(1-87) with the hGH signal peptide HCGbeta Fragment 1 (VL Fusion):
hGHsp(−int) and
5'-CTGAGTCAGCAAGATGTCTTGTGGGAG-GATCGGGGTGTCCGA-3' (SEQ ID NO:31)
Template: plasmid encoding hCGbeta with hGH signal peptide HCGbeta Fragment 2 (ScFv Fusion):
hGHsp(−int) and
5'-CTGACTGCTTCAGCTGCACCTGTTGTGG-GAGGATCGGGGTGT-3' (SEQ ID NO:32)
Template: plasmid encoding hCGbeta with hGH signal peptide For the alpha(1-87)-EGFR ScFv construct, second step PCR can be done as follows:
Primers: hGH(+int)sp and 225VLsal or 225V1xho
Templates: Alpha(1-87) fragment 1 (without linker) and EGFR ScFv fragment 1 (fusion to alpha(1-87) without linker)

For the alpha(1-87)-GFSASPAFF EGFR ScFv construct, second step PCR can be done as follows:
Primers: hGH(+int)sp and EGFR VLsal or EGFR V1xho
Templates: Alpha(1-87) fragment 2 (with linker) and EGFR ScFv fragment 2 (fusion to alpha(1-87) with linker)

For the alpha(1-87)-EGFR VH construct, PCR can be done as follows:
Primers: hGH(+int)sp and VHstop
Template: Alpha(1-87) EGFR ScFv For the hCGbeta-EGFR ScFv construct, second step PCR can be done as follows:
Primers: hGH(+int)sp and EGFR VLsal or EGFR V1xho
Templates: EGFR ScFv fragment 3 (fusion to hCGbeta) and HCGbeta fragment 2 (ScFv fusion)

For the hCGbeta-EGFR VL construct, second step PCR can be done as follows:
Primers: hGH(+int)sp and EGFR VLsal or EGFR V1xho
Templates: HCGbeta fragment 1 (VL fusion) and EGFR VL fragment 1 (fusion to hCG beta)

PCR fragments were cloned into pENTR/D-TOPO (INVITROGEN) using the protocol supplied by the manufacturer. DNA sequence analysis was used to identify correctly assembled constructs. The regions encoding the fusion proteins were transferred to Gateway modified mammalian cell expression vectors as described in Example 1.

Example 8

Tetravalent Hybrid Molecules

The following are non limiting embodiments of the present invention comprising either an alpha or beta chain of hCG and a VEGF-specific antigen binding moiety and an EGFR-specific antigen binding moiety:

Fab12scFvHL-alpha(1-87)(GGGS)$_4$-EGFRscFV (FIG. 28).

Figure 29:
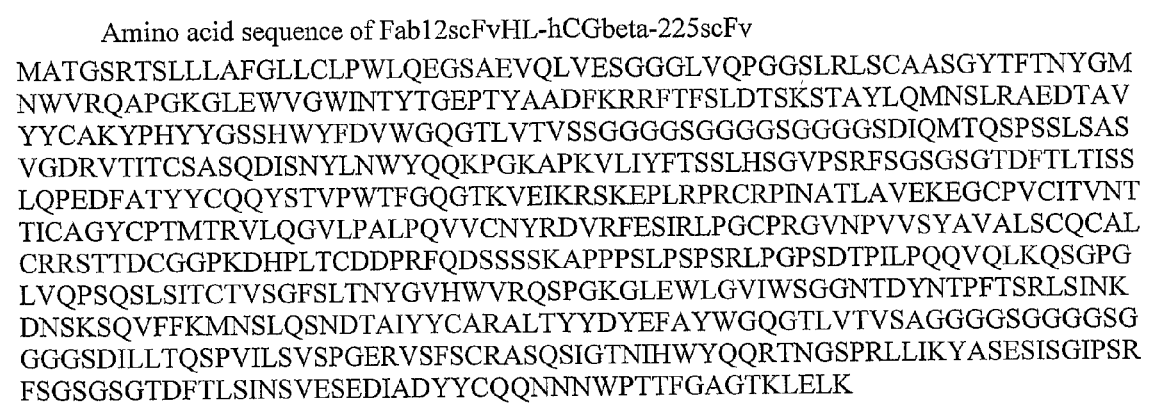

Fab12scFvHL-hCGbeta-EGFRscFV (FIG. 29)

VEGF(2)scFvHL-AA-alpha(1-87)-(GGGS)$_4$-225scFvHL (FIG. 30)

VEGF(2)scFvHL-AAA-hCGbeta-EGFRscFvHL (FIG. 31)

VEGF(2)scFvLH-AA-alpha(1-87)-(GGGS)$_4$-225scFvHL (FIG. 32)

VEGF(2)scFvLH-AAA-hCGbeta-EGFRscFvHL (FIG. 33)

V2LH-AA-alpha(1-87)-TOM-LH (FIG. 34)

V2-LH-hCGbeta-TOM LH (FIG. 35)

TOM-alpha-V2-LH (FIG. 36)

TOM hCGbeta-V2-LH (FIG. 37)

In one non limiting example, hybrid molecules of the present invention may be formed by co-expressing constructs encoding the polypeptides as depicted in the above figures, either on the same vector or on different vectors, one of the above modified alpha chains with one of the above modified beta chains. The resultant hybrid molecules are able to bind both VEGF and EGFR.

TABLE 3

Detection of Bispecific Hybrid antigen binding molecules in Supernatants of transfected 293-EBNA cells by ELISA

| TF | Constructs | Heterodimer formation (ng/ml) |
|---|---|---|
| 1 | V2(HL)scFv-AA-α-(G$_4$S)$_4$ – EGFRscFv + V2(HL)scFv-AAA-CGβ – EGFRscFv | 45 |
| 2 | V2(LH)scFv-AA-α-(G$_4$S)$_4$ – EGFRscFv + V2(LH)scFv-AAA-CGβ – EGFRscFv | 96 |
| 3 | V2(HL) scFv-AA-α + EGFRscFv – CGβ – EGFRscFv | 24 |
| 4 | V2(LH) scFv-AA-α + EGFRscFv-AAA-CGβ – EGFRscFv | 40 |
| 5 | EGFRscFv-AA-α + V2(HL) scFv-AAA-CGβ – EGFRscFv | 63 |
| 6 | EGFR scFv-AA-α + V2(LH)-AAA-CGβ – EGFRscFv | 138 |
| 7 | V1(HL) scFv-hng-AA-α-(G$_4$S)$_4$ – EGFRscFv + V1(HL) scFv-hng-AAA-CGβ – EGFRscFv | 7 |
| 8 | EGFR scFv-AA-α + V1(HL)-AAA-CGβ – EGFRscFv | 19 |
| 9 | V2(HL)scFv-AA-α + V2(HL scFv)-AAA-CGβ | 723 |
| 9 | V2(HL) scFv-AA-α + V2(HL) scFv-AAA-CGβ | 912 |
| 10 | V1(HL) scFv-α + V1(HL) scFv-CGβ | 12 |
| 11 | V1(HL) scFv-hng-AA-α- + V1(HL) scFv-hng-AAA-CGβ | 26 |
| 12 | GFP | 0 |
| 13 | MOCK | 0 |

Example 9

Humanized EGFR-Specific Hybrid Molecules

A humanized version of an EGFR-specific antigen binding moiety was prepared by grafting the CDR of said antigen binding moiety to the variable region framework of a human antibody. The resulting humanized EGFR-specific antigen binding moiety (huEGFR) was fused to either the alpha(1-87) or beta chain of hCG. The amino acid sequence of huEGFR-alpha(1-87) is shown in FIG. 38, and the amino acid sequence of huEGFR-hCG beta is shown in FIG. 39. When both chains are co-expressed the resultant hybrid molecule was highly expressed and stable.

Example 10

Tetravalent Hybrid Molecules Comprising huEGFR

The following are non limiting embodiments of the present invention comprising either an alpha or beta chain of hCG and a VEGF-specific antigen binding moiety and an EGFR-specific antigen binding moiety:

huEGFR-alpha(1-87)-V2LH (FIG. 40)
huEGFR-hCGbeta-V2-LH (FIG. 41)

In one non limiting example, hybrid molecules of the present invention may be formed by co-expressing constructs encoding the polypeptides as depicted in the above figures, either on the same vector or on different vectors, one of the above modified alpha chains with one of the above modified beta chains. The resultant hybrid molecules are able to bind both VEGF and EGFR.

TABLE 4

Detection of hybrid antigen binding molecules in Supernatants of transfected 293-EBNA cells by ELISA at 31° C. and 37° C.

| | | hCG (ng/ml) | |
|---|---|---|---|
| TF# | Constructs | 31° C. | 37° C. |
| 1 | EGFRscFv-alpha + EGFRscFv-hCGbeta | 843 | 37 |
| 2 | V2(LH)scFv-alpha + V2(LH)scFv-hCGbeta | 2269 | 3961 |
| 3 | huEGFRscFv-alpha + huEGFRscFv-hCGbeta | 4557 | 16332 |
| 4 | alpha-LD-V2(LH)scFv + hCGbeta-LD-V2(LH)scFv | 922 | 2394 |
| 5 | Tom-scFv-alpha-LD-V2(LH)scFv + Tom-scFv-hCGbeta-LD-V2(LH)scFv | 47 | 120 |
| 6 | V2(LH)scFv-alpha-LEA-Tom-scFv + V2(LH)scFv-hCGbeta-LEA-Tom-scFv | 82 | 196 |
| 7 | E-alpha-LD-V2LH + E-hCGbeta-LD-V2LH | 60 | 8 |
| 8 | huE-alpha-LD-V2LH + huE-hCGbeta-LD-V2LH | 83 | 590 |
| 9 | MOCK | Not done | 0 |

Example 11

Hybrid Molecules Comprising IGF-1R-Specific Antigen Binding Moieties

The following are non limiting embodiments of the present invention comprising either an alpha or beta chain of hCG and a IGF-1R-specific antigen binding moiety:

A12(LH)alpha(1-87) (FIG. 42)
A12(LH)hCGbeta (FIG. 43)
EM164(LH)scFv-alpha(1-87) (FIG. 44)
EM164(LH)scFv-hCGbeta (FIG. 45)
19D12(LH)scFv alpha (1-87) (FIG. 46)
19D12(LH)scFv-hCG beta (FIG. 47)

In one non limiting example, hybrid molecules of the present invention may be formed by co-expressing constructs encoding the polypeptides as depicted in the above figures, either on the same vector or on different vectors, one of the above modified alpha chains with one of the above modified beta chains. The resultant hybrid molecules are able to bind IGF-1R

TABLE 5

Detection of IGF-1R hybrid antigen binding molecules in supernatants from transfected 293-EBNA cells by ELISA in two different growth media and temperatures

| | | Incubation | hCG dimer (ng/ml, no mass correction) | |
|---|---|---|---|---|
| TF# | Constructs Transfected | Temp (° C.) | Optimem | 293 growth medium |
| 1 | EGFR-Alpha + EGFR-Beta | 31 | 680 | — |
| 7 | A12-Alpha + A12-Beta | 31 | 1004 | 1465 |
| 8 | A12-Alpha + A12-Beta | 37 | 1350 | 1978 |
| 9 | EM164-Alpha + EM164-beta | 31 | 847 | 1513 |
| 10 | EM164-Alpha + EM164-beta | 37 | 319 | 462 |
| 11 | 19D12-Alpha + 19D12-Beta | 31 | 1449 | 1930 |
| 12 | 19D12-Alpha + 19D12-Beta | 37 | 1089 | 1063 |
| 13 | Mock | | 0 | — |

Example 11

Stabilizing Mutations

Stabilization of antigen binding moieties such as scFv's can be achieved by introducing a disulfide bond between the VH and VL region as exemplified below for EGFR-specific scFv:

EGFR scFv VH-E105C/VL-H34C mutant (FIG. 48)
EGFR scFv VH-W109C/VL-S43C mutant (FIG. 49)
EGFR scFv VH-A107C/VL-L46C mutant (FIG. 50)
EGFR scFv VH-L45C/VL-F98C mutant (FIG. 51)
EGFR scFv VH-G112C/VL-S43C mutant (FIG. 52)

Example 12

In Vivo Efficacy of an EGFR-Specific Hybrid Antigen Binding Molecule

An EGFR-specific hybrid antigen binding molecule of the present invention (EGFR-SHARC) was tested for its in vivo efficacy against tumor cells in an A431, human epidermoid carcinoma xenograft tumor model. Briefly, A431 cells were grown to confluency with 10% RPMI and harvested by trypsinization. Cells were checked for viability by trypan blue exclusion, washed and resuspended in PBS. Athymic nude mice were injected with $5 \times 10^6$ A431 cells per mouse, i.p. and treated with either Erbitux at varying doses, PBS, or EGFR-SHARC. Twice weekly tumor size was measured using a digital caliper and the tumor volume was determined. At day 15 of the study the mice were euthanized, the tumors excised and weighed. EGFR-SHARC completed inhibited tumor growth of A431 cells compared to the negative control of PBS alone. 5 groups of 15 athymic mice each, were treated as follows:

TABLE 6

In vivo efficacy of EGFR-SHARC

| Group | # Mice | Tumor Cells | Treatment | Result at day 15 |
|---|---|---|---|---|
| 1 | 15 | $5 \times 10^6$ A431 cells/mouse | 0.5 ml PBS, i.p. daily for 14 days | No tumor inhibition |
| 2 | 15 | $5 \times 10^6$ A431 cells/mouse | 0.5 mg EGFR-SHARC/0.5 ml PBS, i.p. daily for 14 days | >95% tumor inhibition |
| 3 | 15 | $5 \times 10^6$ A431 cells/mouse | 0.1 mg Erbitux/0.5 ml PBS, i.p. twice weekly for 14 days | >95% tumor inhibition |
| 4 | 15 | $5 \times 10^6$ A431 cells/mouse | 0.25 mg Erbitux/0.5 ml PBS, i.p. twice weekly for 14 days | >95% tumor inhibition |
| 5 | 15 | $5 \times 10^6$ A431 cells/mouse | 0.5 mg Erbitux/0.5 ml PBS, i.p. twice weekly for 14 days | >95% tumor inhibition |

The specification is most thoroughly understood in light of the teachings of the references cited within the specification which are hereby incorporated by reference. The embodiments within the specification provide an illustration of embodiments in this disclosure and should not be construed to limit its scope. The skilled artisan readily recognizes that many other embodiments are of the invention. All publications and patents cited and sequences identified by accession or database reference numbers in this disclosure are incorporated by reference in their entirety. The citation of any references herein is not an admission that such references are prior art to the present disclosure.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-EGFR fusion protein comprising the humanized EGFR-specific antigen binding moiety of SEQ ID NO.: 83 linked to a fusion partner.

2. The anti-EGFR fusion protein of claim 1 comprising the amino acid sequence of SEQ ID NO:84.

3. The anti-EGFR fusion protein of claim 1 comprising the amino acid sequence of SEQ ID NO:85.

4. An anti-EGFR binding protein comprising the amino acid sequence of SEQ ID NO:83 or a EGFR-specific antigen binding moiety thereof.

* * * * *

```
                              SEQUENCE LISTING

<160> NUMBER OF SEQ ID NOS: 112

<210> SEQ ID NO 1
<211> LENGTH: 4
<212> TYPE: PRT
<213> ORGANISM: Artificial
<220> FEATURE:
<223> OTHER INFORMATION: Linker

<400> SEQUENCE: 1

Gly Ala Asp Lys
1

<210> SEQ ID NO 2
<211> LENGTH: 12
<212> TYPE: PRT
<213> ORGANISM: Artificial
<220> FEATURE:
<223> OTHER INFORMATION: Linker

<400> SEQUENCE: 2

Asp Glu Thr Tyr Val Pro Lys Glu Phe Asn Ala Glu
1               5                   10

<210> SEQ ID NO 3
<211> LENGTH: 29
<212> TYPE: DNA
<213> ORGANISM: Artificial
<220> FEATURE:
<223> OTHER INFORMATION: PCR Primer

<400> SEQUENCE: 3
agatctgccc aggtgcagct gaagcagtc                                     29

<210> SEQ ID NO 4
<211> LENGTH: 30
<212> TYPE: DNA
<213> ORGANISM: Artificial
<220> FEATURE:
<223> OTHER INFORMATION: PCR Primer

<400> SEQUENCE: 4
gcggccgctg cagagacagt gaccagagtc                                    30

<210> SEQ ID NO 5
<211> LENGTH: 85
<212> TYPE: DNA
<213> ORGANISM: Artificial
<220> FEATURE:
<223> OTHER INFORMATION: PCR Primer

<400> SEQUENCE: 5
cagcaagatg tcagatccgc cgccacccga cccaccaccg cccgagccac cgccacctgc   60
```

-continued agagacagtg accagagtcc cttgg                                         85

<210> SEQ ID NO 6
<211> LENGTH: 31
<212> TYPE: DNA
<213> ORGANISM: Artificial
<220> FEATURE:
<223> OTHER INFORMATION: PCR Primer

<400> SEQUENCE: 6
agatctgccg acatcttgct gactcagtct c                                  31

<210> SEQ ID NO 7
<211> LENGTH: 31
<212> TYPE: DNA
<213> ORGANISM: Artificial
<220> FEATURE:
<223> OTHER INFORMATION: PCR PRimer

<400> SEQUENCE: 7
gcggccgctt tcagctccag cttggtccca g                                  31

<210> SEQ ID NO 8
<211> LENGTH: 31
<212> TYPE: DNA
<213> ORGANISM: Artificial
<220> FEATURE:
<223> OTHER INFORMATION: PCR Primer

<400> SEQUENCE: 8
gcggatctga catcttgctg actcagtctc c                                  31

<210> SEQ ID NO 9
<211> LENGTH: 43
<212> TYPE: DNA
<213> ORGANISM: Artificial
<220> FEATURE:
<223> OTHER INFORMATION: PCR Primer

<400> SEQUENCE: 9
gcggccgctt tatcggcgcc tttcagctcc agcttggtcc cag                     43

<210> SEQ ID NO 10
<211> LENGTH: 67
<212> TYPE: DNA
<213> ORGANISM: Artificial
<220> FEATURE:
<223> OTHER INFORMATION: PCR Primer

<400> SEQUENCE: 10
gcggccgctt cagcattaaa ctctttggga acgtatgttt catctttcag ctccagcttg   60
gtcccag                                                             67

<210> SEQ ID NO 11
<211> LENGTH: 29
<212> TYPE: DNA
<213> ORGANISM: Artificial
<220> FEATURE:
<223> OTHER INFORMATION: PCR Primer

<400> SEQUENCE: 11
agatctgccc aggtgcagct gaagcagtc                                     29

<210> SEQ ID NO 12

<211> LENGTH: 31
<212> TYPE: DNA
<213> ORGANISM: Artificial
<220> FEATURE:
<223> OTHER INFORMATION: PCR Primer

<400> SEQUENCE: 12
gcggccgctt tcagctccag cttggtccca g                          31

<210> SEQ ID NO 13
<211> LENGTH: 43
<212> TYPE: DNA
<213> ORGANISM: Artificial
<220> FEATURE:
<223> OTHER INFORMATION: PCR Primer

<400> SEQUENCE: 13
gcggccgctt tatcggcgcc tttcagctcc agcttggtcc cag              43

<210> SEQ ID NO 14
<211> LENGTH: 67
<212> TYPE: DNA
<213> ORGANISM: Artificial
<220> FEATURE:
<223> OTHER INFORMATION: PCR Primer

<400> SEQUENCE: 14
gcggccgctt cagcattaaa ctctttggga acgtatgttt catctttcag ctccagcttg    60
gtcccag                                                              67

<210> SEQ ID NO 15
<211> LENGTH: 24
<212> TYPE: DNA
<213> ORGANISM: Artificial
<220> FEATURE:
<223> OTHER INFORMATION: PCR Primer

<400> SEQUENCE: 15
agatctgccc aggtgcagct tcag                                  24

<210> SEQ ID NO 16
<211> LENGTH: 47
<212> TYPE: DNA
<213> ORGANISM: Artificial
<220> FEATURE:
<223> OTHER INFORMATION: PCR Primer

<400> SEQUENCE: 16
ccaccaccgc ccgagccacc gccacctgag gagacggtga ccagggt          47

<210> SEQ ID NO 17
<211> LENGTH: 64
<212> TYPE: DNA
<213> ORGANISM: Artificial
<220> FEATURE:
<223> OTHER INFORMATION: PCR Primer

<400> SEQUENCE: 17
tggctcgggc ggtggtgggt cgggtggcgg cggatctgat attgtgatga ctcagtctcc    60
actc                                                                 64

<210> SEQ ID NO 18
<211> LENGTH: 34
<212> TYPE: DNA
<213> ORGANISM: Artificial

<220> FEATURE:
<223> OTHER INFORMATION: PCR Primer

<400> SEQUENCE: 18
gcggccgctt tgatttccac cttggtccct tggc         34

<210> SEQ ID NO 19
<211> LENGTH: 46
<212> TYPE: DNA
<213> ORGANISM: Artificial
<220> FEATURE:
<223> OTHER INFORMATION: PCR Primer

<400> SEQUENCE: 19
gcggccgctt tatcggcgcc tttgatttcc accttggtcc cttggc    46

<210> SEQ ID NO 20
<211> LENGTH: 70
<212> TYPE: DNA
<213> ORGANISM: Artificial
<220> FEATURE:
<223> OTHER INFORMATION: PCR Primer

<400> SEQUENCE: 20
gcggccgctt cagcattaaa ctctttggga acgtatgttt catctttgat ttccaccttg    60
gtcccttggc    70

<210> SEQ ID NO 21
<211> LENGTH: 24
<212> TYPE: DNA
<213> ORGANISM: Artificial
<220> FEATURE:
<223> OTHER INFORMATION: PCR Primer

<400> SEQUENCE: 21
agatctgccc aggtgcagct tcag    24

<210> SEQ ID NO 22
<211> LENGTH: 34
<212> TYPE: DNA
<213> ORGANISM: Artificial
<220> FEATURE:
<223> OTHER INFORMATION: PCR Primer

<400> SEQUENCE: 22
gcggccgctt tgatttccac cttggtccct tggc    34

<210> SEQ ID NO 23
<211> LENGTH: 46
<212> TYPE: DNA
<213> ORGANISM: Artificial
<220> FEATURE:
<223> OTHER INFORMATION: PCR Primer

<400> SEQUENCE: 23
gcggccgctt tatcggcgcc tttgatttcc accttggtcc cttggc    46

<210> SEQ ID NO 24
<211> LENGTH: 70
<212> TYPE: DNA
<213> ORGANISM: Artificial
<220> FEATURE:
<223> OTHER INFORMATION: PCR Primer

<400> SEQUENCE: 24
gcggccgctt cagcattaaa ctctttggga acgtatgttt catctttgat ttccaccttg    60
gtcccttggc                                                           70

<210> SEQ ID NO 25
<211> LENGTH: 41
<212> TYPE: DNA
<213> ORGANISM: Artificial
<220> FEATURE:
<223> OTHER INFORMATION: PCR Primer

<400> SEQUENCE: 25
cgatcctccc acaagacatc ttgctgactc agtctccagt c                        41

<210> SEQ ID NO 26
<211> LENGTH: 43
<212> TYPE: DNA
<213> ORGANISM: Artificial
<220> FEATURE:
<223> OTHER INFORMATION: PCR Primer

<400> SEQUENCE: 26
gcgtgccact gcagtacttg tcaggtgcag ctgaagcagt cag                      43

<210> SEQ ID NO 27
<211> LENGTH: 49
<212> TYPE: DNA
<213> ORGANISM: Artificial
<220> FEATURE:
<223> OTHER INFORMATION: PCR Primer

<400> SEQUENCE: 27
ggttttagcg cttctccagc attcttccag gtgcagctga agcagtcag                49

<210> SEQ ID NO 28
<211> LENGTH: 42
<212> TYPE: DNA
<213> ORGANISM: Artificial
<220> FEATURE:
<223> OTHER INFORMATION: PCR Primer

<400> SEQUENCE: 28
acaccccgat cctcccacaa caggtgcagc tgaagcagtc ag                       42

<210> SEQ ID NO 29
<211> LENGTH: 43
<212> TYPE: DNA
<213> ORGANISM: Artificial
<220> FEATURE:
<223> OTHER INFORMATION: PCR Primer

<400> SEQUENCE: 29
ctgactgctt cagctgcacc tgacaagtac tgcagtggca cgc                      43

<210> SEQ ID NO 30
<211> LENGTH: 49
<212> TYPE: DNA
<213> ORGANISM: Artificial
<220> FEATURE:
<223> OTHER INFORMATION: PCR Primer

<400> SEQUENCE: 30
ctgactgctt cagctgcacc tggaagaatg ctggagaagc gctaaaacc                49

<210> SEQ ID NO 31
<211> LENGTH: 42

```
<212> TYPE: DNA
<213> ORGANISM: Artificial
<220> FEATURE:
<223> OTHER INFORMATION: PCR Primer

<400> SEQUENCE: 31
ctgagtcagc aagatgtctt gtgggaggat cggggtgtcc ga                    42

<210> SEQ ID NO 32
<211> LENGTH: 42
<212> TYPE: DNA
<213> ORGANISM: Artificial
<220> FEATURE:
<223> OTHER INFORMATION: PCR Primer

<400> SEQUENCE: 32
ctgactgctt cagctgcacc tgttgtggga ggatcggggt gt                    42

<210> SEQ ID NO 33
<211> LENGTH: 431
<212> TYPE: DNA
<213> ORGANISM: Artificial
<220> FEATURE:
<223> OTHER INFORMATION: EGFR variable region

<400> SEQUENCE: 33
agatctgcca tggctgtctt ggcgctgctc ttctgcctgg tgacattccc aagctgtgtc    60
ctatcccagg tgcagctgaa gcagtcagga cctggcctag tgcagccctc acagagcctg   120
tccatcacct gcacagtctc tggtttctca ttaactaact atggtgtaca ctgggttcgc   180
cagtctccag gaaagggtct ggagtggctg ggagtgatat ggagtggtgg aaacacagac   240
tataatacac ctttcacatc cagactgagc atcaacaagg acaattccaa gagccaagtt   300
ttctttaaaa tgaacagtct gcaatctaat gacacagcca tatattactg tgccagagcc   360
ctcacctact atgattacga gtttgcttac tggggccaag ggactctggt cactgtctct   420
gcagcggccg c                                                        431

<210> SEQ ID NO 34
<211> LENGTH: 388
<212> TYPE: DNA
<213> ORGANISM: Artificial
<220> FEATURE:
<223> OTHER INFORMATION: EGFR Variable region

<400> SEQUENCE: 34
tgagggcccc tgctcagttc cttgtatttt tgcttttctg gattccagcc tccagaagtg    60
acatcttgct gactcagtct ccagtcatcc tgtctgtgag tccaggagaa agagtcagtt   120
tctcctgcag ggccagtcag agtattggca aaacataca ctggtatcag caaagaacaa    180
atggttctcc aaggcttctc ataaagtatg cttctgagtc tatctctggg atcccttcca   240
ggtttagtgg cagtggatca gggacagatt ttactcttag catcaacagt gtggagtctg   300
aagatattgc agattattac tgtcaacaaa ataataactg gccaaccacg ttcggtgctg   360
ggaccaagct ggagctgaaa gcggccgc                                      388

<210> SEQ ID NO 35
<211> LENGTH: 401
<212> TYPE: DNA
<213> ORGANISM: Artificial
<220> FEATURE:
<223> OTHER INFORMATION: plasmid
```

<400> SEQUENCE: 35

```
ttaaaggaac caattcagtc gactggatct tgaaccacca tggctacagg ctcccggacg      60
tccctgctcc tggcttttgg cctgctctgc ctgccctggc ttcaagaggg atccgccgcg     120
gccgcgcccg atgtgcagga ttgcccagaa tgcacgctac aggaaaaccc attcttctcc     180
cagccgggtg ccccaatact tcagtgcatg ggctgctgct tctctagagc atatcccact     240
ccactaaggt ccaagaagac gatgttggtc aaaagaacg tcacctcaga gtccacttgc      300
tgtgtagcta aatcatataa cagggtcaca gtaatggggg gtttcaaagt ggagaaccac     360
acggcgtgcc actgcagtac ttgttagctc gagatatcta g                        401
```

<210> SEQ ID NO 36
<211> LENGTH: 578
<212> TYPE: DNA
<213> ORGANISM: Artificial
<220> FEATURE:
<223> OTHER INFORMATION: Plasmid construct

<400> SEQUENCE: 36

```
ttaaaggaac caattcagtc gactggatct tgaaccacca tggctacagg ctcccggacg      60
tccctgctcc tggcttttgg cctgctctgc ctgccctggc ttcaagaggg atccgccgcg     120
gccgcgtcca aggagccgct tcggccacgg tgccgcccca tcaatgccac cctggctgtg     180
gagaaggagg gctgccccgt gtgcatcacc gtcaacacca ccatctgtgc cggctactgc     240
cccaccatga cccgcgtgct gcaggggtc ctgccggccc tgcctcaggt ggtgtgcaac      300
taccgcgatg tgcgcttcga gtccatccgg ctccctggct gcccgcgcgg cgtgaacccc     360
gtggtctcct acgccgtggc tctcagctgt caatgtgcac tctgccgccg cagcaccact     420
gactgcgggg gtcccaagga ccacccttg acctgtgatg accccgctt ccaggactcc       480
tcttcctcaa aggcccctcc ccccagcctt ccaagcccat cccgactccc ggggccctcg     540
gacaccccga tcctcccaca atagctcgag atatctag                            578
```

<210> SEQ ID NO 37
<211> LENGTH: 882
<212> TYPE: DNA
<213> ORGANISM: Artificial
<220> FEATURE:
<223> OTHER INFORMATION: EGFR construct

<400> SEQUENCE: 37

```
atggctacag gctcccggac gtccctgctc tggcttttg gcctgctctg cctgccctgg       60
cttcaagagg gatctgccca ggtgcagctg aagcagtcag gacctggcct agtgcagccc    120
tcacagagcc tgtccatcac ctgcacagtc tctggtttct cattaactaa ctatggtgta    180
cactgggttc gccagtctcc aggaaagggt ctggagtggc tgggagtgat atggagtggt    240
ggaaacacag actataatac ccttttcaca tccagactga gcatcaacaa ggacaattcc    300
aagagccaag tttctcttaa atgaacagt ctgcaatcta atgacacagc catatattac     360
tgtgccagag ccctcaccta ctatgattac gagtttgctt actggggcca agggactctg    420
gtcactgtct ctgcagcggc cgcgtccaag agccgcttc ggccacggtg ccgccccatc     480
aatgccaccc tggctgtgga aggagggc tgccccgtgt gcatcaccgt caacaccacc      540
atctgtgccg gctactgccc caccatgacc cgcgtgctgc agggggtcct gccggccctg    600
cctcaggtgg tgtgcaacta ccgcgatgtg cgcttcgagt ccatccggct ccctggctgc    660
ccgcgcggcg tgaaccccgt ggtctcctac gccgtggctc tcagctgtca atgtgcactc    720
```

-continued

```
tgccgccgca gcaccactga ctgcgggggt cccaaggacc accccttgac ctgtgatgac      780
ccccgcttcc aggactcctc ttcctcaaag gcccctcccc cagccttcc aagcccatcc       840 cgactcccgg ggccctcgga caccccgatc ctcccacaat ag                        882
```

```
<210> SEQ ID NO 38
<211> LENGTH: 293
<212> TYPE: PRT
<213> ORGANISM: Artificial
<220> FEATURE:
<223> OTHER INFORMATION: EGFR construct

<400> SEQUENCE: 38
```

| Met | Ala | Thr | Gly | Ser | Arg | Thr | Ser | Leu | Leu | Leu | Ala | Phe | Gly | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Cys | Leu | Pro | Trp | Leu | Gln | Glu | Gly | Ser | Ala | Gln | Val | Gln | Leu | Lys | Gln |
|-----|-----|-----|-----|-----|-----|-----|-----|-----|-----|-----|-----|-----|-----|-----|-----|
|     |     |     | 20  |     |     |     | 25  |     |     |     | 30  |     |     |     |     |

| Ser | Gly | Pro | Gly | Leu | Val | Gln | Pro | Ser | Gln | Ser | Leu | Ser | Ile | Thr | Cys |
|-----|-----|-----|-----|-----|-----|-----|-----|-----|-----|-----|-----|-----|-----|-----|-----|
|     |     | 35  |     |     |     | 40  |     |     |     | 45  |     |     |     |     |     |

| Thr | Val | Ser | Gly | Phe | Ser | Leu | Thr | Asn | Tyr | Gly | Val | His | Trp | Val | Arg |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Gln | Ser | Pro | Gly | Lys | Gly | Leu | Glu | Trp | Leu | Gly | Val | Ile | Trp | Ser | Gly |
|-----|-----|-----|-----|-----|-----|-----|-----|-----|-----|-----|-----|-----|-----|-----|-----|
| 65  |     |     |     | 70  |     |     |     |     | 75  |     |     |     |     | 80  |     |

| Gly | Asn | Thr | Asp | Tyr | Asn | Thr | Pro | Phe | Thr | Ser | Arg | Leu | Ser | Ile | Asn |
|-----|-----|-----|-----|-----|-----|-----|-----|-----|-----|-----|-----|-----|-----|-----|-----|
|     |     |     | 85  |     |     |     |     | 90  |     |     |     | 95  |     |     |     |

| Lys | Asp | Asn | Ser | Lys | Ser | Gln | Val | Phe | Phe | Lys | Met | Asn | Ser | Leu | Gln |
|-----|-----|-----|-----|-----|-----|-----|-----|-----|-----|-----|-----|-----|-----|-----|-----|
|     |     |     | 100 |     |     |     |     | 105 |     |     |     | 110 |     |     |     |

| Ser | Asn | Asp | Thr | Ala | Ile | Tyr | Tyr | Cys | Ala | Arg | Ala | Leu | Thr | Tyr | Tyr |
|-----|-----|-----|-----|-----|-----|-----|-----|-----|-----|-----|-----|-----|-----|-----|-----|
|     |     |     | 115 |     |     |     |     | 120 |     |     |     | 125 |     |     |     |

| Asp | Tyr | Glu | Phe | Ala | Tyr | Trp | Gly | Gln | Gly | Thr | Leu | Val | Thr | Val | Ser |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Ala | Ala | Ala | Ala | Ser | Lys | Glu | Pro | Leu | Arg | Pro | Arg | Cys | Arg | Pro | Ile |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asn | Ala | Thr | Leu | Ala | Val | Glu | Lys | Glu | Gly | Cys | Pro | Val | Cys | Ile | Thr |
|-----|-----|-----|-----|-----|-----|-----|-----|-----|-----|-----|-----|-----|-----|-----|-----|
|     |     |     |     | 165 |     |     |     |     | 170 |     |     |     | 175 |     |     |

| Val | Asn | Thr | Thr | Ile | Cys | Ala | Gly | Tyr | Cys | Pro | Thr | Met | Thr | Arg | Val |
|-----|-----|-----|-----|-----|-----|-----|-----|-----|-----|-----|-----|-----|-----|-----|-----|
|     |     |     | 180 |     |     |     |     | 185 |     |     |     | 190 |     |     |     |

| Leu | Gln | Gly | Val | Leu | Pro | Ala | Leu | Pro | Gln | Val | Val | Cys | Asn | Tyr | Arg |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asp | Val | Arg | Phe | Glu | Ser | Ile | Arg | Leu | Pro | Gly | Cys | Pro | Arg | Gly | Val |
|-----|-----|-----|-----|-----|-----|-----|-----|-----|-----|-----|-----|-----|-----|-----|-----|
| 210 |     |     |     |     | 215 |     |     |     |     | 220 |     |     |     |     |     |

| Asn | Pro | Val | Val | Ser | Tyr | Ala | Val | Ala | Leu | Ser | Cys | Gln | Cys | Ala | Leu |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Cys | Arg | Arg | Ser | Thr | Thr | Asp | Cys | Gly | Gly | Pro | Lys | Asp | His | Pro | Leu |
|-----|-----|-----|-----|-----|-----|-----|-----|-----|-----|-----|-----|-----|-----|-----|-----|
|     |     |     |     | 245 |     |     |     |     | 250 |     |     |     | 255 |     |     |

| Thr | Cys | Asp | Asp | Pro | Arg | Phe | Gln | Asp | Ser | Ser | Ser | Lys | Ala | Pro |
|-----|-----|-----|-----|-----|-----|-----|-----|-----|-----|-----|-----|-----|-----|-----|
|     |     |     | 260 |     |     |     |     | 265 |     |     |     | 270 |     |     |

| Pro | Pro | Ser | Leu | Pro | Ser | Pro | Ser | Arg | Leu | Pro | Gly | Pro | Ser | Asp | Thr |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Pro | Ile | Leu | Pro | Gln |
|-----|-----|-----|-----|-----|
|     | 290 |     |     |     |

```
<210> SEQ ID NO 39
<211> LENGTH: 669
<212> TYPE: DNA
<213> ORGANISM: Artificial
```

<220> FEATURE:
<223> OTHER INFORMATION: EGFR construct

<400> SEQUENCE: 39

| | | | | | |
|---|---|---|---|---|---|
| atggctacag | gctcccggac | gtccctgctc | ctggcttttg | gcctgctctg | cctgccctgg | 60 |
| cttcaagagg | gatctgccga | catcttgctg | actcagtctc | cagtcatcct | gtctgtgagt | 120 |
| ccaggagaaa | gagtcagttt | ctcctgcagg | gccagtcaga | gtattggcac | aaacatacac | 180 |
| tggtatcagc | aaagaacaaa | tggttctcca | aggcttctca | taaagtatgc | ttctgagtct | 240 |
| atctctggga | tcccttccag | gtttagtggc | agtggatcag | ggacagattt | tactcttagc | 300 |
| atcaacagtg | tggagtctga | agatattgca | gattattact | gtcaacaaaa | taataactgg | 360 |
| ccaaccacgt | tcggtgctgg | gaccaagctg | gagctgaaag | cggccgcgcc | cgatgtgcag | 420 |
| gattgcccag | aatgcacgct | acaggaaaac | ccattcttct | cccagccggg | tgccccaata | 480 |
| cttcagtgca | tgggctgctg | cttctctaga | gcatatccca | ctccactaag | gtccaagaag | 540 |
| acgatgttgg | tccaaaagaa | cgtcacctca | gagtccactt | gctgtgtagc | taaatcatat | 600 |
| aacagggtca | cagtaatggg | gggtttcaaa | gtggagaacc | acacggcgtg | ccactgcagt | 660 |
| acttgttag | | | | | | 669 |

<210> SEQ ID NO 40
<211> LENGTH: 222
<212> TYPE: PRT
<213> ORGANISM: Artificial
<220> FEATURE:
<223> OTHER INFORMATION: EGFR construct

<400> SEQUENCE: 40

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Leu Leu Thr Gln
            20                  25                  30

Ser Pro Val Ile Leu Ser Val Ser Pro Gly Glu Arg Val Ser Phe Ser
        35                  40                  45

Cys Arg Ala Ser Gln Ser Ile Gly Thr Asn Ile His Trp Tyr Gln Gln
    50                  55                  60

Arg Thr Asn Gly Ser Pro Arg Leu Leu Ile Lys Tyr Ala Ser Glu Ser
65                  70                  75                  80

Ile Ser Gly Ile Pro Ser Arg Phe Ser Gly Ser Gly Ser Gly Thr Asp
                85                  90                  95

Phe Thr Leu Ser Ile Asn Ser Val Glu Ser Glu Asp Ile Ala Asp Tyr
            100                 105                 110

Tyr Cys Gln Gln Asn Asn Asn Trp Pro Thr Thr Phe Gly Ala Gly Thr
        115                 120                 125

Lys Leu Glu Leu Lys Ala Ala Ala Pro Asp Val Gln Asp Cys Pro Glu
    130                 135                 140

Cys Thr Leu Gln Glu Asn Pro Phe Phe Ser Gln Pro Gly Ala Pro Ile
145                 150                 155                 160

Leu Gln Cys Met Gly Cys Cys Phe Ser Arg Ala Tyr Pro Thr Pro Leu
                165                 170                 175

Arg Ser Lys Lys Thr Met Leu Val Gln Lys Asn Val Thr Ser Glu Ser
            180                 185                 190

Thr Cys Cys Val Ala Lys Ser Tyr Asn Arg Val Thr Val Met Gly Gly
        195                 200                 205

Phe Lys Val Glu Asn His Thr Ala Cys His Cys Ser Thr Cys

-continued

```
             210                215                220
```

<210> SEQ ID NO 41
<211> LENGTH: 1071
<212> TYPE: DNA
<213> ORGANISM: Artificial
<220> FEATURE:
<223> OTHER INFORMATION: EGFR single chain

<400> SEQUENCE: 41

```
atggctacag gctcccggac gtccctgctc ctggcttttg gcctgctctg cctgccctgg      60
cttcaagagg gatctgccca ggtgcagctg aagcagtcag gacctggcct agtgcagccc     120
tcacagagcc tgtccatcac ctgcacagtc tctggtttct cattaactaa ctatggtgta     180
cactgggttc gccagtctcc aggaaagggt ctggagtggc tgggagtgat atggagtggt     240
ggaaacacag actataatac cctttcaca tccagactga gcatcaacaa ggacaattcc     300
aagagccaag tttctcttaa atgaacagt ctgcaatcta atgacacagc catatattac      360
tgtgccagag ccctcaccta ctatgattac gagtttgctt actggggcca agggactctg     420
gtcactgtct ctgcaggtgg cggtggctcg ggcggtggtg gtcgggtgg cggcggatct      480
gacatcttgc tgactcagtc tccagtcatc ctgtctgtga gtccaggaga aagagtcagt     540
ttctcctgca gggccagtca gagtattggc acaaacatac actggtatca gcaagaaca     600
aatggttctc caaggcttct cataaagtat gcttctgagt ctatctctgg atcccttcc     660
aggtttagtg gcagtggatc agggacagat tttactctta gcatcaacag tgtggagtct     720
gaagatattg cagattatta ctgtcaacaa aataataact ggccaaccac gttcggtgct     780
gggaccaagc tggagctgaa agcggccgcg cccgatgtgc aggattgccc agaatgcacg     840
ctacaggaaa accattcttt ctcccagccg ggtgccccaa tacttcagtg catgggctgc     900
tgcttctcta gagcatatcc cactccacta aggtccaaga agacgatgtt ggtccaaaag     960
aacgtcacct cagagtccac ttgctgtgta gctaaatcat ataacagggt cacagtaatg    1020
gggggtttca agtggagaa ccacacggcg tgccactgca gtacttgtta g              1071
```

<210> SEQ ID NO 42
<211> LENGTH: 330
<212> TYPE: PRT
<213> ORGANISM: Artificial
<220> FEATURE:
<223> OTHER INFORMATION: EGFR single chain

<400> SEQUENCE: 42

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110
```

```
Thr Leu Val Thr Val Ser Ala Gly Gly Gly Ser Gly Gly Gly Gly
        115                 120                 125

Ser Gly Gly Gly Ser Asp Ile Leu Leu Thr Gln Ser Pro Val Ile
        130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
210                 215                 220

Asn Asn Asn Trp Pro Thr Thr Phe Gly Ala Gly Thr Lys Leu Glu Leu
225                 230                 235                 240

Lys Ala Ala Ala Pro Asp Val Gln Asp Cys Pro Glu Cys Thr Leu Gln
                245                 250                 255

Glu Asn Pro Phe Phe Ser Gln Pro Gly Ala Pro Ile Leu Gln Cys Met
            260                 265                 270

Gly Cys Cys Phe Ser Arg Ala Tyr Pro Thr Pro Leu Arg Ser Lys Lys
        275                 280                 285

Thr Met Leu Val Gln Lys Asn Val Thr Ser Glu Ser Thr Cys Cys Val
        290                 295                 300

Ala Lys Ser Tyr Asn Arg Val Thr Val Met Gly Gly Phe Lys Val Glu
305                 310                 315                 320

Asn His Thr Ala Cys His Cys Ser Thr Cys
                325                 330
```

<210> SEQ ID NO 43
<211> LENGTH: 1248
<212> TYPE: DNA
<213> ORGANISM: Artificial
<220> FEATURE:
<223> OTHER INFORMATION: EGFR construct

<400> SEQUENCE: 43

```
atggctacag gctcccggac gtccctgctc ctggcttttg gcctgctctg cctgccctgg      60
cttcaagagg gatctgccca ggtgcagctg aagcagtcag gacctggcct agtgcagccc     120
tcacagagcc tgtccatcac ctgcacagtc tctggtttct cattaactaa ctatggtgta     180
cactgggttc gccagtctcc aggaaagggt ctggagtggc tgggagtgat atggagtggt     240
ggaaacacag actataatac cctttcaca tccagactga gcatcaacaa ggacaattcc      300
aagagccaag ttttctttaa aatgaacagt ctgcaatcta tgacacagc catatattac      360 tgtgccagag ccctcaccta ctatgattac gagtttgctt actggggcca agggactctg     420
gtcactgtct ctgcaggtgg cggtggctcg ggcggtggtg gtcgggtgg cggcggatct      480 gacatcttgc tgactcagtc tccagtcatc ctgtctgtga gtccaggaga aagagtcagt     540
ttctcctgca gggccagtca gagtattggc acaaacatac actggtatca gcaagaaaca     600
aatggttctc caaggcttct cataaagtat gcttctgagt ctatctctgg gatcccttcc     660
aggtttagtg gcagtggatc aggaacagat tttactctta gcatcaacag tgtggagtct     720
gaagatattg cagattatta ctgtcaacaa aataataact ggccaaccac gttcggtgct     780
gggaccaagc tggagctgaa agcggccgcg tccaaggagc gcttcggcc acggtgccgc     840
```

-continued

```
cccatcaatg ccaccctggc tgtggagaag gagggctgcc ccgtgtgcat caccgtcaac      900
accaccatct gtgccggcta ctgccccacc atgacccgcg tgctgcaggg ggtcctgccg      960
gccctgcctc aggtggtgtg caactaccgc gatgtgcgct cgagtccat ccggctccct     1020 ggctgcccgc gcggcgtgaa ccccgtggtc tcctacgccg tggctctcag ctgtcaatgt    1080
gcactctgcc gccgcagcac cactgactgc gggggtccca aggaccaccc cttgacctgt    1140
gatgaccccc gcttccagga ctcctcttcc tcaaaggccc ctcccccag ccttccaagc     1200 ccatcccgac tcccggggcc ctcggacacc ccgatcctcc cacaatag                 1248
```

```
<210> SEQ ID NO 44
<211> LENGTH: 415
<212> TYPE: PRT
<213> ORGANISM: Artificial
<220> FEATURE:
<223> OTHER INFORMATION: EGFR construct

<400> SEQUENCE: 44
```

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Gln Val Gln Leu Lys Gln
             20                  25                  30

Ser Gly Pro Gly Leu Val Gln Pro Ser Gln Ser Leu Ser Ile Thr Cys
         35                  40                  45

Thr Val Ser Gly Phe Ser Leu Thr Asn Tyr Gly Val His Trp Val Arg
     50                  55                  60

Gln Ser Pro Gly Lys Gly Leu Glu Trp Leu Gly Val Ile Trp Ser Gly
 65                  70                  75                  80

Gly Asn Thr Asp Tyr Asn Thr Pro Phe Thr Ser Arg Leu Ser Ile Asn
                 85                  90                  95

Lys Asp Asn Ser Lys Ser Gln Val Phe Phe Lys Met Asn Ser Leu Gln
            100                 105                 110

Ser Asn Asp Thr Ala Ile Tyr Tyr Cys Ala Arg Ala Leu Thr Tyr Tyr
        115                 120                 125

Asp Tyr Glu Phe Ala Tyr Trp Gly Gln Gly Thr Leu Val Thr Val Ser
    130                 135                 140

Ala Gly Gly Gly Gly Ser Gly Gly Gly Gly Ser Gly Gly Gly Gly Ser
145                 150                 155                 160

Asp Ile Leu Leu Thr Gln Ser Pro Val Ile Leu Ser Val Ser Pro Gly
                165                 170                 175

Glu Arg Val Ser Phe Ser Cys Arg Ala Ser Gln Ser Ile Gly Thr Asn
            180                 185                 190

Ile His Trp Tyr Gln Gln Arg Thr Asn Gly Ser Pro Arg Leu Leu Ile
        195                 200                 205

Lys Tyr Ala Ser Glu Ser Ile Ser Gly Ile Pro Ser Arg Phe Ser Gly
    210                 215                 220

Ser Gly Ser Gly Thr Asp Phe Thr Leu Ser Ile Asn Ser Val Glu Ser
225                 230                 235                 240

Glu Asp Ile Ala Asp Tyr Tyr Cys Gln Gln Asn Asn Asn Trp Pro Thr
                245                 250                 255

Thr Phe Gly Ala Gly Thr Lys Leu Glu Leu Lys Ala Ala Ala Ser Lys
            260                 265                 270

Glu Pro Leu Arg Pro Arg Cys Arg Pro Ile Asn Ala Thr Leu Ala Val
        275                 280                 285
```

| Glu | Lys | Glu | Gly | Cys | Pro | Val | Cys | Ile | Thr | Val | Asn | Thr | Thr | Ile | Cys |
| | 290 | | | | 295 | | | | 300 | | | | | | |

| Ala | Gly | Tyr | Cys | Pro | Thr | Met | Thr | Arg | Val | Leu | Gln | Gly | Val | Leu | Pro |
| 305 | | | | | 310 | | | | 315 | | | | | 320 | |

| Ala | Leu | Pro | Gln | Val | Val | Cys | Asn | Tyr | Arg | Asp | Val | Arg | Phe | Glu | Ser |
| | | | 325 | | | | 330 | | | | | 335 | | | |

| Ile | Arg | Leu | Pro | Gly | Cys | Pro | Arg | Gly | Val | Asn | Pro | Val | Val | Ser | Tyr |
| | | | 340 | | | | | 345 | | | | | 350 | | |

| Ala | Val | Ala | Leu | Ser | Cys | Gln | Cys | Ala | Leu | Cys | Arg | Arg | Ser | Thr | Thr |
| | | | 355 | | | | 360 | | | | | 365 | | | |

| Asp | Cys | Gly | Gly | Pro | Lys | Asp | His | Pro | Leu | Thr | Cys | Asp | Asp | Pro | Arg |
| | 370 | | | | | 375 | | | | | 380 | | | | |

| Phe | Gln | Asp | Ser | Ser | Ser | Ser | Lys | Ala | Pro | Pro | Pro | Ser | Leu | Pro | Ser |
| 385 | | | | | 390 | | | | | 395 | | | | | 400 |

| Pro | Ser | Arg | Leu | Pro | Gly | Pro | Ser | Asp | Thr | Pro | Ile | Leu | Pro | Gln |
| | | | | 405 | | | | | 410 | | | | | 415 |

<210> SEQ ID NO 45
<211> LENGTH: 386
<212> TYPE: DNA
<213> ORGANISM: Artificial
<220> FEATURE:
<223> OTHER INFORMATION: codon optimized VEGF

<400> SEQUENCE: 45

```
agatctgccg aggtccagct ggtcgagtca ggaggcggac ttgtccagcc cggtggctcc    60
ttgagactga gctgtgccgc aagcggctat acatttacaa attatggaat gaattgggtg   120
cggcaggcac tgggaagggg actggagtgg gtgggctgga tcaatacata cactggcgag   180
cctacatacg ccgcggattt caagcggaga ttcacattct ctcttgacac aagtaagtcc   240
acagcttatt tgcaaatgaa ctcattgaga gccgaggaca cagctgtgta ctattgtgcc   300
aagtaccccc actattatgg atcaagccac tggtattttg atgtttgggg acagggtacg   360
ctggtgaccg tgtcatcagc ggccgc                                         386
```

<210> SEQ ID NO 46
<211> LENGTH: 341
<212> TYPE: DNA
<213> ORGANISM: Artificial
<220> FEATURE:
<223> OTHER INFORMATION: Codon optimized

<400> SEQUENCE: 46

```
agatctgccg atatccaaat gacccagtcc ccttcatcac tgtccgcatc tgtagggat    60
cgagttacaa tcacttgttc tgcctcccag gatatttcca attacctcaa ctggtatcag   120
caaaagcccg gaaggcccc aaaggtgctg atctacttta ccagttccct gcattctggc   180
gtgccaagta gattcagcgg tagtggttct ggtacagact ttactttgac catctcatct   240
ctgcagcctg aagatttcgc cacatattac tgtcagcagt actcaaccgt ccctggacg   300
tttggacagg gaaccaaggt ggaaatcaag cgcgcggccg c                       341
```

<210> SEQ ID NO 47
<211> LENGTH: 806
<212> TYPE: DNA
<213> ORGANISM: Artificial
<220> FEATURE:
<223> OTHER INFORMATION: VEGF single chain

<400> SEQUENCE: 47

```
agatctgccg aggtccagct ggtcgagtca ggaggcggac ttgtccagcc cggtggctcc     60
ttgagactga gctgtgccgc aagcggctat acatttacaa attatggaat gaattgggtg    120
cggcaggcac ctgggaaggg actggagtgg gtgggctgga tcaatacata cactggcgag    180
cctacatacg ccgcggattt caagcggaga ttcacattct ctcttgacac aagtaagtcc    240
acagcttatt tgcaaatgaa ctcattgaga gccgaggaca cagctgtgta ctattgtgcc    300
aagtaccccc actattatgg atcaagccac tggtattttg atgtttgggg acagggtacg    360
ctggtgaccg tgtcatcagg tggcggtggc tcgggcggtg gtgggtcggg tggcggcgga    420
tctgatatcc aaatgaccca gtccccttca tcactgtccg catctgtagg ggatcgagtt    480
acaatcactt gttctgcctc ccaggatatt ccaattacc tcaactggta tcagcaaaag    540
cccgggaagg ccccaaaggt gctgatctac tttaccagtt ccctgcattc tggcgtgcca    600
agtagattca gcggtagtgg ttctggtaca gactttactt tgaccatctc atctctgcag    660
cctgaagatt tcgccacata ttactgtcag cagtactcaa ccgtcccctg gacgtttgga    720
cagggaacca aggtggaaat caagcgcgac aaaactcaca catgcccacc gtgcccagca    780
cctgaactcc tgggggagc ggccgc                                          806

<210> SEQ ID NO 48
<211> LENGTH: 806
<212> TYPE: DNA
<213> ORGANISM: Artificial
<220> FEATURE:
<223> OTHER INFORMATION: VEGF single chain

<400> SEQUENCE: 48
agatctgccg atatccaaat gacccagtcc ccttcatcac tgtccgcatc tgtaggggat     60
cgagttacaa tcacttgttc tgcctcccag gatattccaa ttacctcaa ctggtatcag    120 caaaagcccg gaaggcccc aaaggtgctg atctacttta ccagttccct gcattctggc    180
gtgccaagta gattcagcgg tagtggttct ggtacagact ttactttgac catctcatct    240
ctgcagcctg aagatttcgc cacatattac tgtcagcagt actcaaccgt cccctggacg    300
tttggacagg gaaccaaggt ggaaatcaag cgcggtggcg gtggctcggg cggtggtggg    360
tcgggtggcg gcggatctga ggtccagctg gtcgagtcag gaggcggact tgtccagccc    420
ggtggctcct tgagactgag ctgtgccgca agcggctata catttacaaa ttatggaatg    480
aattgggtgc ggcaggcacc tgggaaggga ctggagtggg tgggctggat caatacatac    540
actggcgagc ctacatacgc cgcggatttc aagcggagat tcacattctc tcttgacaca    600
agtaagtcca cagcttattt gcaaatgaac tcattgagag ccgaggacac agctgtgtac    660
tattgtgcca agtaccccca ctattatgga tcaagccact ggtattttga tgtttgggga    720
cagggtacgc tggtgaccgt gtcatcagac aaaactcaca catgcccacc gtgcccagca    780
cctgaactcc tgggggagc ggccgc                                          806

<210> SEQ ID NO 49
<211> LENGTH: 368
<212> TYPE: DNA
<213> ORGANISM: Artificial
<220> FEATURE:
<223> OTHER INFORMATION: IGF-1R construct

<400> SEQUENCE: 49
agatctgccc aggtgcagct tcaggagtcg ggcccaggac tggtgaagcc ttcggagacc     60
```

```
ctgtccctca cctgcactgt ctctggttac tccatcaccg gtggttattt atggaactgg    120
atacggcagc ccccagggaa gggactggag tggatcgggt atatcagcta cgacggtacc    180
aataactaca accctccct  caaggatcga gtcaccatat cacgtgacac gtccaagaac    240
cagttctccc tgaagctgag ctctgtgacc gctgcggaca ctgcagtgta ttactgtgcg    300
agatacggta gggtcttctt tgactactgg ggccagggaa ccctggtcac cgtctcctca    360
gcggccgc                                                             368
```

<210> SEQ ID NO 50
<211> LENGTH: 353
<212> TYPE: DNA
<213> ORGANISM: Artificial
<220> FEATURE:
<223> OTHER INFORMATION: IGF-1R construct

<400> SEQUENCE: 50

```
agatctgccg atattgtgat gactcagtct ccactctccc tgcccgtcac ccctggagag    60
ccggcctcca tctcctgcag gtctagtcag agcattgtac atagtaatgg aaacacctat    120
ttgcaatggt acctgcagaa gccagggcag tctccacagc tcctgatcta taaagttttct   180 aatcggcttt atggggtccc tgacaggttc agtggcagtg gatcaggcac agattttaca    240
ctgaaaatca gcagagtgga ggctgaggat gttggggttt attactgctt tcaaggttca    300
catgttccgt ggacgttcgg ccaagggacc aaggtggaaa tcaaagcggc cgc           353
```

<210> SEQ ID NO 51
<211> LENGTH: 699
<212> TYPE: DNA
<213> ORGANISM: Artificial
<220> FEATURE:
<223> OTHER INFORMATION: IGF-1R construct

<400> SEQUENCE: 51

```
atggctacag gctcccggac gtccctgctc ctggcttttg gcctgctctg cctgccctgg    60
cttcaagagg gatctgccca ggtgcagctt caggagtcgg gcccaggact ggtgaagcct    120
tcggagaccc tgtccctcac ctgcactgtc tctggttact ccatcaccgg tggttattta    180
tggaactgga tacggcagcc cccagggaag ggactggagt ggatcgggta tatcagctac    240
gacggtacca ataactacaa ccctccctc aaggatcgag tcaccatatc acgtgacacg    300
tccaagaacc agttctccct gaagctgagc tctgtgaccg ctgcggacac tgcagtgtat    360
tactgtgcga gatacggtag ggtcttcttt gactactggg gccagggaac cctggtcacc    420
gtctcctcag cggccgcgcc cgatgtgcag gattgcccag aatgcacgct acaggaaaac    480
ccattcttct cccagccggg tgccccaata cttcagtgca tgggctgctg cttctctaga    540
gcatatccca ctccactaag gtccaagaag acgatgttgg tccaaaagaa cgtcacctca    600
gagtccactt gctgtgtagc taaatcatat aacagggtca cagtaatggg gggtttcaaa    660
gtggagaacc acacggcgtg ccactgcagt acttgttag                          699
```

<210> SEQ ID NO 52
<211> LENGTH: 232
<212> TYPE: PRT
<213> ORGANISM: Artificial
<220> FEATURE:
<223> OTHER INFORMATION: IGF-1R construct

<400> SEQUENCE: 52

Met Ala Thr Gly Ser Arg Thr Ser Leu Leu Leu Ala Phe Gly Leu Leu

```
                 1               5              10              15
Cys Leu Pro Trp Leu Gln Glu Gly Ser Ala Gln Val Gln Leu Gln Glu
                        20                  25                  30

Ser Gly Pro Gly Leu Val Lys Pro Ser Glu Thr Leu Ser Leu Thr Cys
                35                  40                  45

Thr Val Ser Gly Tyr Ser Ile Thr Gly Gly Tyr Leu Trp Asn Trp Ile
             50                  55                  60

Arg Gln Pro Pro Gly Lys Gly Leu Glu Trp Ile Gly Tyr Ile Ser Tyr
 65                  70                  75                  80

Asp Gly Thr Asn Asn Tyr Lys Pro Ser Leu Lys Asp Arg Val Thr Ile
                    85                  90                  95

Ser Arg Asp Thr Ser Lys Asn Gln Phe Ser Leu Lys Leu Ser Ser Val
                100                 105                 110

Thr Ala Ala Asp Thr Ala Val Tyr Tyr Cys Ala Arg Tyr Gly Arg Val
                115                 120                 125

Phe Phe Asp Tyr Trp Gly Gln Gly Thr Leu Val Thr Val Ser Ser Ala
130                 135                 140

Ala Ala Pro Asp Val Gln Asp Cys Pro Glu Cys Thr Leu Gln Glu Asn
145                 150                 155                 160

Pro Phe Phe Ser Gln Pro Gly Ala Pro Ile Leu Gln Cys Met Gly Cys
                165                 170                 175

Cys Phe Ser Arg Ala Tyr Pro Thr Pro Leu Arg Ser Lys Lys Thr Met
                180                 185                 190

Leu Val Gln Lys Asn Val Thr Ser Glu Ser Thr Cys Cys Val Ala Lys
                195                 200                 205

Ser Tyr Asn Arg Val Thr Val Met Gly Gly Phe Lys Val Glu Asn His
            210                 215                 220

Thr Ala Cys His Cys Ser Thr Cys
225                 230

<210> SEQ ID NO 53
<211> LENGTH: 876
<212> TYPE: DNA
<213> ORGANISM: Artificial
<220> FEATURE:
<223> OTHER INFORMATION: IGF-1R construct

<400> SEQUENCE: 53
atggctacag gctcccggac gtccctgctc ctggcttttg gcctgctctg cctgccctgg     60
cttcaagagg gatctgccca ggtgcagctt caggagtcgg gcccaggact ggtgaagcct    120
tcggagaccc tgtccctcac ctgcactgtc tctggttact ccatcaccgg tggttattta    180
tggaactgga tacggcagcc cccagggaag ggactgagt ggatcgggta tatcagctac     240
gacggtacca ataactacaa accctccctc aaggatcgag tcaccatatc acgtgacacg    300
tccaagaacc agttctccct gaagctgagc tctgtgaccg ctgcggacac tgcagtgtat    360
tactgtgcga gatacggtag gtcttctttt gactactggg gccagggaac cctggtcacc    420
gtctcctcag cggccgcgtc caaggagccg cttcggccac ggtgccgccc catcaatgcc    480
accctggctg tggagaagga gggctgcccc gtgtgcatca ccgtcaacac caccatctgt    540
gccggctact gccccaccat gacccgcgtg ctgcagggg tcctgccggc cctgcctcag    600
gtggtgtgca actaccgcga tgtgcgcttc gagtccatcc ggctccctgg ctgccgcgc    660 ggcgtgaacc ccgtggtctc ctacgccgtg gctctcagct gtcaatgtgc actctgccgc    720
cgcagcacca ctgactgcgg gggtcccaag gaccacccct tgacctgtga tgaccccgc    780
```

-continued

```
ttccaggact cctcttcctc aaaggcccct ccccccagcc ttccaagccc atcccgactc        840
ccggggccct cggacacccc gatcctccca caatag                                 876
```

<210> SEQ ID NO 54
<211> LENGTH: 291
<212> TYPE: PRT
<213> ORGANISM: Artificial
<220> FEATURE:
<223> OTHER INFORMATION: IGF-1R construct

<400> SEQUENCE: 54

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Val Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Tyr Ser Ile Thr Gly Gly Tyr Leu Trp Asn Trp Ile
    50                  55                  60

Arg Gln Pro Pro Gly Lys Gly Leu Glu Trp Ile Gly Tyr Ile Ser Tyr
65                  70                  75                  80

Asp Gly Thr Asn Asn Tyr Lys Pro Ser Leu Lys Asp Arg Val Thr Ile
                85                  90                  95

Ser Arg Asp Thr Ser Lys Asn Gln Phe Ser Leu Lys Leu Ser Ser Val
            100                 105                 110

Thr Ala Ala Asp Thr Ala Val Tyr Tyr Cys Ala Arg Tyr Gly Arg Val
        115                 120                 125

Phe Phe Asp Tyr Trp Gly Gln Gly Thr Leu Val Thr Val Ser Ser Ala
    130                 135                 140

Ala Ser Lys Glu Pro Leu Arg Pro Arg Cys Arg Pro Ile Asn Ala
145                 150                 155                 160

Thr Leu Ala Val Glu Lys Glu Gly Cys Pro Val Cys Ile Thr Val Asn
                165                 170                 175

Thr Thr Ile Cys Ala Gly Tyr Cys Pro Thr Met Thr Arg Val Leu Gln
            180                 185                 190

Gly Val Leu Pro Ala Leu Pro Gln Val Val Cys Asn Tyr Arg Asp Val
        195                 200                 205

Arg Phe Glu Ser Ile Arg Leu Pro Gly Cys Pro Arg Gly Val Asn Pro
    210                 215                 220

Val Val Ser Tyr Ala Val Ala Leu Ser Cys Gln Cys Ala Leu Cys Arg
225                 230                 235                 240

Arg Ser Thr Thr Asp Cys Gly Gly Pro Lys Asp His Pro Leu Thr Cys
                245                 250                 255

Asp Asp Pro Arg Phe Gln Asp Ser Ser Ser Lys Ala Pro Pro Pro
            260                 265                 270

Ser Leu Pro Ser Pro Ser Arg Leu Pro Gly Pro Ser Asp Thr Pro Ile
        275                 280                 285

Leu Pro Gln
    290
```

<210> SEQ ID NO 55
<211> LENGTH: 684
<212> TYPE: DNA
<213> ORGANISM: Artificial
<220> FEATURE:
<223> OTHER INFORMATION: IGF-1R construct

<400> SEQUENCE: 55

```
atggctacag gctcccggac gtccctgctc ctggcttttg gcctgctctg cctgccctgg      60
cttcaagagg gatctgccga tattgtgatg actcagtctc cactctccct gcccgtcacc     120
cctggagagc cggcctccat ctcctgcagg tctagtcaga gcattgtaca tagtaatgga     180
aacacctatt tgcaatggta cctgcagaag ccagggcagt ctccacagct cctgatctat     240
aaagtttcta atcggcttta tggggtccct gacaggttca gtggcagtgg atcaggcaca     300
gattttacac tgaaaatcag cagagtggag gctgaggatg ttggggttta ttactgcttt     360
caaggttcac atgttccgtg gacgttcggc caagggacca aggtggaaat caaagcggcc     420
gcgcccgatg tgcaggattg cccagaatgc acgctacagg aaaacccatt cttctcccag     480
ccgggtgccc caatacttca gtgcatgggc tgctgcttct ctagagcata tcccactcca     540
ctaaggtcca agaagacgat gttggtccaa aagaacgtca cctcagagtc cacttgctgt     600
gtagctaaat catataacag ggtcacagta atgggggtt tcaaagtgga gaaccacacg     660
gcgtgccact gcagtacttg ttag                                           684
```

<210> SEQ ID NO 56
<211> LENGTH: 227
<212> TYPE: PRT
<213> ORGANISM: Artificial
<220> FEATURE:
<223> OTHER INFORMATION: IGF-1R construct

<400> SEQUENCE: 56

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Val Met Thr Gln
            20                  25                  30

Ser Pro Leu Ser Leu Pro Val Thr Pro Gly Glu Pro Ala Ser Ile Ser
        35                  40                  45

Cys Arg Ser Ser Gln Ser Ile Val His Ser Asn Gly Asn Thr Tyr Leu
    50                  55                  60

Gln Trp Tyr Leu Gln Lys Pro Gly Gln Ser Pro Gln Leu Leu Ile Tyr
65                  70                  75                  80

Lys Val Ser Asn Arg Leu Tyr Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Val Gly Val Tyr Tyr Cys Phe Gln Gly Ser His Val Pro Trp Thr
        115                 120                 125

Phe Gly Gln Gly Thr Lys Val Glu Ile Lys Ala Ala Pro Asp Val
    130                 135                 140

Gln Asp Cys Pro Glu Cys Thr Leu Gln Glu Asn Pro Phe Phe Ser Gln
145                 150                 155                 160

Pro Gly Ala Pro Ile Leu Gln Cys Met Gly Cys Cys Phe Ser Arg Ala
                165                 170                 175

Tyr Pro Thr Pro Leu Arg Ser Lys Lys Thr Met Leu Val Gln Lys Asn
            180                 185                 190

Val Thr Ser Glu Ser Thr Cys Cys Val Ala Lys Ser Tyr Asn Arg Val
        195                 200                 205

Thr Val Met Gly Gly Phe Lys Val Glu Asn His Thr Ala Cys His Cys
    210                 215                 220
```

Ser Thr Cys
225

<210> SEQ ID NO 57
<211> LENGTH: 861
<212> TYPE: DNA
<213> ORGANISM: Artificial
<220> FEATURE:
<223> OTHER INFORMATION: IGF-1R cnstruct

<400> SEQUENCE: 57

```
atggctacag gctcccggac gtccctgctc ctggcttttg gcctgctctg cctgccctgg       60
cttcaagagg gatctgccga tattgtgatg actcagtctc cactctccct gcccgtcacc      120
cctggagagc cggcctccat ctcctgcagg tctagtcaga gcattgtaca tagtaatgga      180
aacacctatt tgcaatggta cctgcagaag ccagggcagt ctccacagct cctgatctat      240
aaagtttcta atcggcttta tggggtccct gacaggttca gtggcagtgg atcaggcaca      300
gattttacac tgaaaatcag cagagtggag gctgaggatg ttggggttta ttactgcttt      360
caaggttcac atgttccgtg gacgttcggc caagggacca aggtggaaat caaagcggcc      420
gcgtccaagg agccgcttcg gccacggtgc cgccccatca atgccaccct ggctgtggag      480
aaggagggct gccccgtgtg catcaccgtc aacaccacca tctgtgccgg ctactgcccc      540
accatgaccc gcgtgctgca gggggtcctg ccggccctgc ctcaggtggt gtgcaactac      600
cgcgatgtgc gcttcgagtc catccggctc cctggctgcc cgcgcggcgt gaaccccgtg      660
gtctcctacg ccgtggctct cagctgtcaa tgtgcactct gccgccgcag caccactgac      720
tgcgggggtc ccaaggacca ccccttgacc tgtgatgacc ccgcttcca ggactcctct      780
tcctcaaagg cccctccccc cagccttcca agcccatccc gactcccggg gccctcggac      840
accccgatcc tcccacaata g                                               861
```

<210> SEQ ID NO 58
<211> LENGTH: 286
<212> TYPE: PRT
<213> ORGANISM: Artificial
<220> FEATURE:
<223> OTHER INFORMATION: IGF-1R construct

<400> SEQUENCE: 58

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Val Met Thr Gln
            20                  25                  30

Ser Pro Leu Ser Leu Pro Val Thr Pro Gly Glu Pro Ala Ser Ile Ser
        35                  40                  45

Cys Arg Ser Ser Gln Ser Ile Val His Ser Asn Gly Asn Thr Tyr Leu
    50                  55                  60

Gln Trp Tyr Leu Gln Lys Pro Gly Gln Ser Pro Gln Leu Leu Ile Tyr
65                  70                  75                  80

Lys Val Ser Asn Arg Leu Tyr Gly Val Pro Asp Arg Phe Ser Gly Ser
                85                  90                  95

Gly Ser Gly Thr Asp Phe Thr Leu Lys Ile Ser Arg Val Glu Ala Glu
            100                 105                 110

Asp Val Gly Val Tyr Tyr Cys Phe Gln Gly Ser His Val Pro Trp Thr
        115                 120                 125

Phe Gly Gln Gly Thr Lys Val Glu Ile Lys Ala Ala Ala Ser Lys Glu
    130                 135                 140
```

Pro Leu Arg Pro Arg Cys Arg Pro Ile Asn Ala Thr Leu Ala Val Glu
145                 150                 155                 160

Lys Glu Gly Cys Pro Val Cys Ile Thr Val Asn Thr Thr Ile Cys Ala
            165                 170                 175

Gly Tyr Cys Pro Thr Met Thr Arg Val Leu Gln Gly Val Leu Pro Ala
        180                 185                 190

Leu Pro Gln Val Val Cys Asn Tyr Arg Asp Val Arg Phe Glu Ser Ile
        195                 200                 205

Arg Leu Pro Gly Cys Pro Arg Gly Val Asn Pro Val Val Ser Tyr Ala
        210                 215                 220

Val Ala Leu Ser Cys Gln Cys Ala Leu Cys Arg Arg Ser Thr Thr Asp
225                 230                 235                 240

Cys Gly Gly Pro Lys Asp His Pro Leu Thr Cys Asp Asp Pro Arg Phe
                245                 250                 255

Gln Asp Ser Ser Ser Ser Lys Ala Pro Pro Ser Leu Pro Ser Pro
            260                 265                 270

Ser Arg Leu Pro Gly Pro Ser Asp Thr Pro Ile Leu Pro Gln
        275                 280                 285

<210> SEQ ID NO 59
<211> LENGTH: 1080
<212> TYPE: DNA
<213> ORGANISM: Artificial
<220> FEATURE:
<223> OTHER INFORMATION: IGF-1R single chain

<400> SEQUENCE: 59
atggctacag ctcccggac gtccctgctc ctggcttttg gcctgctctg cctgccctgg    60
cttcaagagg atctgcccca ggtgcagctt caggagtcgg gcccaggact ggtgaagcct   120
tcggagaccc tgtccctcac ctgcactgtc tctggttact ccatcaccgg tggttattta   180
tggaactgga tacggcagcc cccagggaag ggactggagt ggatcgggta tatcagctac   240
gacggtacca taactacaa accctccctc aaggatcgag tcaccatatc acgtgacacg   300
tccaagaacc agttctccct gaagctgagc tctgtgaccg ctgcggacac tgcagtgtat   360
tactgtgcga atacggtag gtcttctttt gactactggg gccagggaac cctggtcacc   420
gtctcctcag gtggcggtgg ctcgggcggt ggtgggtcgg gtggcggcgg atctgatatt   480
gtgatgactc agtctccact ctccctgccc gtcaccctg gagagccggc ctccatctcc    540
tgcaggtcta gtcagagcat tgtacatagt aatggaaaca cctatttgca atggtacctg   600
cagaagccag gcagtctcc acagctcctg atctataaag tttctaatcg gctttatggg   660
gtccctgaca ggttcagtgg cagtggatca ggcacagatt ttacactgaa aatcagcaga    720
gtggaggctg aggatgttgg ggtttattac tgctttcaag gttcacatgt tccgtggacg    780
ttcggccaag ggaccaaggt ggaaatcaaa gcggccgcgc cgatgtgca ggattgccca    840 gaatgcacgc tacaggaaaa ccccattcttc tcccagccgg tgccccaat acttcagtgc    900 atgggctgct gcttctctag agcatatccc actccactaa ggtccaagaa gacgatgttg   960
gtccaaaaga acgtcacctc agagtccact tgctgtgtag ctaaatcata acagggtc    1020 acagtaatgg ggggtttcaa agtggagaac cacacggcgt gccactgcag tacttgttag  1080

<210> SEQ ID NO 60
<211> LENGTH: 359
<212> TYPE: PRT
<213> ORGANISM: Artificial

<220> FEATURE:
<223> OTHER INFORMATION: IGF-1R single chain

<400> SEQUENCE: 60

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Val Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Tyr Ser Ile Thr Gly Gly Tyr Leu Trp Asn Trp Ile
    50                  55                  60

Arg Gln Pro Pro Gly Lys Gly Leu Glu Trp Ile Gly Tyr Ile Ser Tyr
65                  70                  75                  80

Asp Gly Thr Asn Asn Tyr Lys Pro Ser Leu Lys Asp Arg Val Thr Ile
                85                  90                  95

Ser Arg Asp Thr Ser Lys Asn Gln Phe Ser Leu Lys Leu Ser Ser Val
            100                 105                 110

Thr Ala Ala Asp Thr Ala Val Tyr Tyr Cys Ala Arg Tyr Gly Arg Val
        115                 120                 125

Phe Phe Asp Tyr Trp Gly Gln Gly Thr Leu Val Thr Val Ser Ser Gly
130                 135                 140

Gly Gly Gly Ser Gly Gly Gly Gly Ser Gly Gly Gly Gly Ser Asp Ile
145                 150                 155                 160

Val Met Thr Gln Ser Pro Leu Ser Leu Pro Val Thr Pro Gly Glu Pro
                165                 170                 175

Ala Ser Ile Ser Cys Arg Ser Ser Gln Ser Ile Val His Ser Asn Gly
            180                 185                 190

Asn Thr Tyr Leu Gln Trp Tyr Leu Gln Lys Pro Gly Gln Ser Pro Gln
        195                 200                 205

Leu Leu Ile Tyr Lys Val Ser Asn Arg Leu Tyr Gly Val Pro Asp Arg
    210                 215                 220

Phe Ser Gly Ser Gly Ser Gly Thr Asp Phe Thr Leu Lys Ile Ser Arg
225                 230                 235                 240

Val Glu Ala Glu Asp Val Gly Val Tyr Tyr Cys Phe Gln Gly Ser His
                245                 250                 255

Val Pro Trp Thr Phe Gly Gln Gly Thr Lys Val Glu Ile Lys Ala Ala
            260                 265                 270

Ala Pro Asp Val Gln Asp Cys Pro Glu Cys Thr Leu Gln Glu Asn Pro
        275                 280                 285

Phe Phe Ser Gln Pro Gly Ala Pro Ile Leu Gln Cys Met Gly Cys Cys
    290                 295                 300

Phe Ser Arg Ala Tyr Pro Thr Pro Leu Arg Ser Lys Lys Thr Met Leu
305                 310                 315                 320

Val Gln Lys Asn Val Thr Ser Glu Ser Thr Cys Cys Val Ala Lys Ser
                325                 330                 335

Tyr Asn Arg Val Thr Val Met Gly Gly Phe Lys Val Glu Asn His Thr
            340                 345                 350

Ala Cys His Cys Ser Thr Cys
        355
```

<210> SEQ ID NO 61
<211> LENGTH: 1257
<212> TYPE: DNA
<213> ORGANISM: Artificial
<220> FEATURE:
<223> OTHER INFORMATION: IGF-1R single chain

<400> SEQUENCE: 61

```
atggctacag gctcccggac gtccctgctc ctggcttttg gcctgctctg cctgccctgg      60
cttcaagagg gatctgccca ggtgcagctt caggagtcgg gcccaggact ggtgaagcct     120
tcggagaccc tgtccctcac ctgcactgtc tctggttact ccatcaccgg tggttattta     180
tggaactgga tacggcagcc cccagggaag ggactggagt ggatcgggta tatcagctac     240
gacggtacca taactacaa accctccctc aaggatcgag tcaccatatc acgtgacacg     300
tccaagaacc agttctccct gaagctgagc tctgtgaccg ctgcggacac tgcagtgtat     360
tactgtgcga gatacggtag ggtcttcttt gactactggg gccagggaac cctggtcacc     420
gtctcctcag gtggcggtgg ctcgggcggt ggtgggtcgg gtggcggcgg atctgatatt     480
gtgatgactc agtctccact ctccctgccc gtcacccctg gagagccggc ctccatctcc     540
tgcaggtcta gtcagagcat tgtacatagt aatggaaaca cctatttgca atggtacctg     600
cagaagccag gcagtctcc acagctcctg atctataaag tttctaatcg gctttatggg     660
gtccctgaca ggttcagtgg cagtggatca ggcacagatt ttacactgaa aatcagcaga     720
gtggaggctg aggatgttgg ggtttattac tgctttcaag gttcacatgt tccgtggacg     780
ttcggccaag ggaccaaggt ggaaatcaaa gcggccgcgt ccaaggagcc gcttcggcca     840
cggtgccgcc ccatcaatgc caccctggct gtggagaagg agggctgccc cgtgtgcatc     900
accgtcaaca ccaccatctg tgccggctac tgccccacca tgacccgcgt gctgcagggg     960
gtcctgccgg ccctgcctca ggtggtgtgc aactaccgcg atgtgcgctt cgagtccatc    1020
cggctccctg gctgccgcg cggcgtgaac cccgtggtct cctacgccgt ggctctcagc    1080
tgtcaatgtg cactctgccg ccgcagcacc actgactgcg ggggtcccaa ggaccacccc    1140
ttgacctgtg atgaccccgc gcttccaggac tcctcttcct caaaggcccc tcccccagc    1200
cttccaagcc catcccgact cccggggccc tcggacaccc cgatcctccc acaatag       1257
```

<210> SEQ ID NO 62
<211> LENGTH: 418
<212> TYPE: PRT
<213> ORGANISM: Artificial
<220> FEATURE:
<223> OTHER INFORMATION: IGF-1R single chain

<400> SEQUENCE: 62

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Val Gln Leu Gln Glu
            20                  25                  30

Ser Gly Pro Gly Leu Val Lys Pro Ser Glu Thr Leu Ser Leu Thr Cys
        35                  40                  45

Thr Val Ser Gly Tyr Ser Ile Thr Gly Gly Tyr Leu Trp Asn Trp Ile
    50                  55                  60

Arg Gln Pro Pro Gly Lys Gly Leu Glu Trp Ile Gly Tyr Ile Ser Tyr
65                  70                  75                  80

Asp Gly Thr Asn Asn Tyr Lys Pro Ser Leu Lys Asp Arg Val Thr Ile
                85                  90                  95

Ser Arg Asp Thr Ser Lys Asn Gln Phe Ser Leu Lys Leu Ser Ser Val
            100                 105                 110

Thr Ala Ala Asp Thr Ala Val Tyr Tyr Cys Ala Arg Tyr Gly Arg Val
```

```
            115                 120                 125
Phe Phe Asp Tyr Trp Gly Gln Gly Thr Leu Val Thr Val Ser Ser Gly
130                 135                 140

Gly Gly Gly Ser Gly Gly Gly Ser Gly Gly Gly Ser Asp Ile
145                 150                 155                 160

Val Met Thr Gln Ser Pro Leu Ser Leu Pro Val Thr Pro Gly Glu Pro
                165                 170                 175

Ala Ser Ile Ser Cys Arg Ser Ser Gln Ser Ile Val His Ser Asn Gly
            180                 185                 190

Asn Thr Tyr Leu Gln Trp Tyr Leu Gln Lys Pro Gly Gln Ser Pro Gln
        195                 200                 205

Leu Leu Ile Tyr Lys Val Ser Asn Arg Leu Tyr Gly Val Pro Asp Arg
210                 215                 220

Phe Ser Gly Ser Gly Ser Gly Thr Asp Phe Thr Leu Lys Ile Ser Arg
225                 230                 235                 240

Val Glu Ala Glu Asp Val Gly Val Tyr Tyr Cys Phe Gln Gly Ser His
                245                 250                 255

Val Pro Trp Thr Phe Gly Gln Gly Thr Lys Val Glu Ile Lys Ala Ala
            260                 265                 270

Ala Ser Lys Glu Pro Leu Arg Pro Arg Cys Arg Pro Ile Asn Ala Thr
        275                 280                 285

Leu Ala Val Glu Lys Glu Gly Cys Pro Val Cys Ile Thr Val Asn Thr
290                 295                 300

Thr Ile Cys Ala Gly Tyr Cys Pro Thr Met Thr Arg Val Leu Gln Gly
305                 310                 315                 320

Val Leu Pro Ala Leu Pro Gln Val Val Cys Asn Tyr Arg Asp Val Arg
                325                 330                 335

Phe Glu Ser Ile Arg Leu Pro Gly Cys Pro Arg Gly Val Asn Pro Val
            340                 345                 350

Val Ser Tyr Ala Val Ala Leu Ser Cys Gln Cys Ala Leu Cys Arg Arg
        355                 360                 365

Ser Thr Thr Asp Cys Gly Gly Pro Lys Asp His Pro Leu Thr Cys Asp
370                 375                 380

Asp Pro Arg Phe Gln Asp Ser Ser Ser Lys Ala Pro Pro Pro Ser
385                 390                 395                 400

Leu Pro Ser Pro Ser Arg Leu Pro Gly Pro Ser Asp Thr Pro Ile Leu
                405                 410                 415

Pro Gln

<210> SEQ ID NO 63
<211> LENGTH: 1071
<212> TYPE: DNA
<213> ORGANISM: Artificial
<220> FEATURE:
<223> OTHER INFORMATION: EGFR construct

<400> SEQUENCE: 63
atggctacag gctcccggac gtccctgctc ctggcttttg gcctgctctg cctgccctgg      60
cttcaagagg gcagtgccgc tcctgatgtg caggattgcc agaatgcac gctacaggaa     120 aacccattct ctcccagcc gggtgcccca atacttcagt gcatgggctg ctgcttctct     180
agagcatatc ccactccact aaggtccaag aagacgatgt tggtccaaaa gaacgtcacc    240
tcagagtcca cttgctgtgt agctaaatca tataacaggg tcacagtaat ggggggtttc    300
aaagtggaga accacacggc gtgccactgc agtacttgtc aggtgcagct gaagcagtca    360
```

```
ggacctggcc tagtgcagcc ctcacagagc ctgtccatca cctgcacagt ctctggtttc    420
tcattaacta actatggtgt acactgggtt cgccagtctc caggaaaggg tctggagtgg    480
ctgggagtga tatggagtgg tggaaacaca gactataata cacctttcac atccagactg    540
agcatcaaca aggacaattc caagagccaa gttttcttta aaatgaacag tctgcaatct    600
aatgacacag ccatatatta ctgtgccaga gccctcacct actatgatta cgagtttgct    660
tactggggcc aagggactct ggtcactgtc tctgcaggtg gcggtggctc gggcggtggt    720
gggtcgggtg gcggcggatc tgacatcttg ctgactcagt ctccagtcat cctgtctgtg    780
agtccaggag aaagagtcag tttctcctgc agggccagtc agagtattgg cacaaacata    840
cactggtatc agcaaagaac aaatggttct ccaaggcttc tcataaagta tgcttctgag    900
tctatctctg ggatcccttc caggtttagt ggcagtggat cagggacaga ttttactctt    960
agcatcaaca gtgtggagtc tgaagatatt gcagattatt actgtcaaca aaataataac   1020
tggccaacca cgttcggtgc tgggaccaag ctggagctga atgactcga g             1071
```

<210> SEQ ID NO 64
<211> LENGTH: 353
<212> TYPE: PRT
<213> ORGANISM: Artificial
<220> FEATURE:
<223> OTHER INFORMATION: EGFR single chain

<400> SEQUENCE: 64

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Pro Asp Val Gln Asp
            20                  25                  30

Cys Pro Glu Cys Thr Leu Gln Glu Asn Pro Phe Phe Ser Gln Pro Gly
        35                  40                  45

Ala Pro Ile Leu Gln Cys Met Gly Cys Cys Phe Ser Arg Ala Tyr Pro
    50                  55                  60

Thr Pro Leu Arg Ser Lys Lys Thr Met Leu Val Gln Lys Asn Val Thr
65                  70                  75                  80

Ser Glu Ser Thr Cys Cys Val Ala Lys Ser Tyr Asn Arg Val Thr Val
                85                  90                  95

Met Gly Gly Phe Lys Val Glu Asn His Thr Ala Cys His Cys Ser Thr
            100                 105                 110

Cys Gln Val Gln Leu Lys Gln Ser Gly Pro Gly Leu Val Gln Pro Ser
        115                 120                 125

Gln Ser Leu Ser Ile Thr Cys Thr Val Ser Gly Phe Ser Leu Thr Asn
    130                 135                 140

Tyr Gly Val His Trp Val Arg Gln Ser Pro Gly Lys Gly Leu Glu Trp
145                 150                 155                 160

Leu Gly Val Ile Trp Ser Gly Gly Asn Thr Asp Tyr Asn Thr Pro Phe
                165                 170                 175

Thr Ser Arg Leu Ser Ile Asn Lys Asp Asn Ser Lys Ser Gln Val Phe
            180                 185                 190

Phe Lys Met Asn Ser Leu Gln Ser Asn Asp Thr Ala Ile Tyr Tyr Cys
        195                 200                 205

Ala Arg Ala Leu Thr Tyr Tyr Asp Tyr Glu Phe Ala Tyr Trp Gly Gln
    210                 215                 220

Gly Thr Leu Val Thr Val Ser Ala Gly Gly Gly Ser Gly Gly Gly
225                 230                 235                 240
```

Gly Ser Gly Gly Gly Ser Asp Ile Leu Leu Thr Gln Ser Pro Val
            245                 250                 255

Ile Leu Ser Ser Pro Gly Glu Arg Val Ser Phe Ser Cys Arg Ala Ser
                260                 265                 270

Gln Ser Ile Gly Thr Asn Ile His Trp Tyr Gln Arg Thr Asn Gly
        275                 280                 285

Ser Pro Arg Leu Leu Ile Lys Tyr Ala Ser Glu Ser Ile Ser Gly Ile
        290                 295                 300

Pro Ser Arg Phe Ser Gly Ser Gly Ser Gly Thr Asp Phe Thr Leu Ser
305                 310                 315                 320

Ile Asn Ser Val Glu Ser Glu Asp Ile Ala Asp Tyr Tyr Cys Gln Gln
                325                 330                 335

Asn Asn Asn Trp Pro Thr Thr Phe Gly Ala Gly Thr Lys Leu Glu Leu
                340                 345                 350

Lys

<210> SEQ ID NO 65
<211> LENGTH: 1098
<212> TYPE: DNA
<213> ORGANISM: Artificial
<220> FEATURE:
<223> OTHER INFORMATION: EGFR construct

<400> SEQUENCE: 65
atggctacag gctcccggac gtccctgctc ctggcttttg gcctgctctg cctgcctgg      60 cttcaagagg gcagtgccgc tcctgatgtg caggattgcc agaatgcac gctacaggaa    120 aacccattct ctcccagcc gggtgcccca atacttcagt gcatgggctg ctgcttctct    180
agagcatatc ccactccact aaggtccaag aagacgatgt tggtccaaaa gaacgtcacc   240
tcagagtcca cttgctgtgt agctaaatca tataacaggg tcacagtaat ggggggtttc   300
aaagtggaga accacacggc gtgccactgc agtacttgtg gttttagcgc ttctccagca   360
ttcttccagg tgcagctgaa gcagtcagga cctggcctag tgcagccctc acagagcctg   420
tccatcacct gcacagtctc tggtttctca ttaactaact atggtgtaca ctgggttcgc   480
cagtctccag gaaagggtct ggagtggctg ggagtgatat ggagtggtgg aaacacagac   540
tataatacac ctttcacatc cagactgagc atcaacaagg acaattccaa gagccaagtt   600
ttctttaaaa tgaacagtct gcaatctaat gacacagcca tatattactg tgccagagcc   660
ctcacctact atgattacga gtttgcttac tggggccaag gactctggt cactgtctct   720 gcaggtggcg gtggctcggg cggtggtggg tcgggtggcg gcggatctga catcttgctg   780
actcagtctc cagtcatcct gtctgtgagt ccaggagaaa gagtcagttt ctcctgcagg   840
gccagtcaga gtattggcac aaacatacac tggtatcagc aaagaacaaa tggttctcca   900
aggcttctca taaagtatgc ttctgagtct atctctggga tcccttccag gtttagtggc   960
agtggatcag ggacagattt tactcttagc atcaacagtg tggagtctga agatattgca  1020
gattattact gtcaacaaaa taataactgg ccaaccacgt tcggtgctgg gaccaagctg  1080
gagctgaaat gagtcgac                                                1098

<210> SEQ ID NO 66
<211> LENGTH: 363
<212> TYPE: PRT
<213> ORGANISM: Artificial
<220> FEATURE:
<223> OTHER INFORMATION: EGFR sinble chain

<400> SEQUENCE: 66

```
Met Ala Thr Gly Ser Arg Thr Ser Leu Leu Leu Ala Phe Gly Leu Leu
1               5                   10                  15
Cys Leu Pro Trp Leu Gln Glu Gly Ser Ala Ala Pro Asp Val Gln Asp
            20                  25                  30
Cys Pro Glu Cys Thr Leu Gln Glu Asn Pro Phe Phe Ser Gln Pro Gly
        35                  40                  45
Ala Pro Ile Leu Gln Cys Met Gly Cys Cys Phe Ser Arg Ala Tyr Pro
    50                  55                  60
Thr Pro Leu Arg Ser Lys Lys Thr Met Leu Val Gln Lys Asn Val Thr
65                  70                  75                  80
Ser Glu Ser Thr Cys Cys Val Ala Lys Ser Tyr Asn Arg Val Thr Val
                85                  90                  95
Met Gly Gly Phe Lys Val Glu Asn His Thr Ala Cys His Cys Ser Thr
            100                 105                 110
Cys Gly Phe Ser Ala Ser Pro Ala Phe Phe Gln Val Gln Leu Lys Gln
        115                 120                 125
Ser Gly Pro Gly Leu Val Gln Pro Ser Gln Ser Leu Ser Ile Thr Cys
    130                 135                 140
Thr Val Ser Gly Phe Ser Leu Thr Asn Tyr Gly Val His Trp Val Arg
145                 150                 155                 160
Gln Ser Pro Gly Lys Gly Leu Glu Trp Leu Gly Val Ile Trp Ser Gly
                165                 170                 175
Gly Asn Thr Asp Tyr Asn Thr Pro Phe Thr Ser Arg Leu Ser Ile Asn
            180                 185                 190
Lys Asp Asn Ser Lys Ser Gln Val Phe Phe Lys Met Asn Ser Leu Gln
        195                 200                 205
Ser Asn Asp Thr Ala Ile Tyr Tyr Cys Ala Arg Ala Leu Thr Tyr Tyr
    210                 215                 220
Asp Tyr Glu Phe Ala Tyr Trp Gly Gln Gly Thr Leu Val Thr Val Ser
225                 230                 235                 240
Ala Gly Gly Gly Gly Ser Gly Gly Gly Ser Gly Gly Gly Gly Ser
                245                 250                 255
Asp Ile Leu Leu Thr Gln Ser Pro Val Ile Leu Ser Val Ser Pro Gly
            260                 265                 270
Glu Arg Val Ser Phe Ser Cys Arg Ala Ser Gln Ser Ile Gly Thr Asn
        275                 280                 285
Ile His Trp Tyr Gln Gln Arg Thr Asn Gly Ser Pro Arg Leu Leu Ile
    290                 295                 300
Lys Tyr Ala Ser Glu Ser Ile Ser Gly Ile Pro Ser Arg Phe Ser Gly
305                 310                 315                 320
Ser Gly Ser Gly Thr Asp Phe Thr Leu Ser Ile Asn Ser Val Glu Ser
                325                 330                 335
Glu Asp Ile Ala Asp Tyr Tyr Cys Gln Gln Asn Asn Asn Trp Pro Thr
            340                 345                 350
Thr Phe Gly Ala Gly Thr Lys Leu Glu Leu Lys
        355                 360
```

<210> SEQ ID NO 67
<211> LENGTH: 705
<212> TYPE: DNA
<213> ORGANISM: Artificial
<220> FEATURE:
<223> OTHER INFORMATION: EGFR construct

<400> SEQUENCE: 67

```
atggctacag gctcccggac gtccctgctc ctggcttttg gcctgctctg cctgccctgg      60
cttcaagagg gcagtgccgc tcctgatgtg caggattgcc cagaatgcac gctacaggaa     120
aacccattct ctcccagcc gggtgcccca atacttcagt gcatgggctg ctgcttctct      180
agagcatatc ccactccact aaggtccaag aagacgatgt tggtccaaaa gaacgtcacc     240
tcagagtcca cttgctgtgt agctaaatca tataacaggg tcacagtaat ggggggtttc     300
aaagtggaga accacacggc gtgccactgc agtacttgtc aggtgcagct gaagcagtca     360
ggacctggcc tagtgcagcc ctcacagagc ctgtccatca cctgcacagt tctctggtttc    420
tcattaacta actatggtgt acactgggtt cgccagtctc caggaaaggg tctggagtgg     480
ctgggagtga tatggagtgg tggaaacaca gactataata cccttttcac atccagactg     540
agcatcaaca aggacaattc caagagccaa gttttctta aaatgaacag tctgcaatct     600
aatgacacag ccatatatta ctgtgccaga gccctcacct actatgatta cgagtttgct     660
tactggggcc aagggactct ggtcactgtc tctgcatgag tcgac                      705
```

<210> SEQ ID NO 68
<211> LENGTH: 232
<212> TYPE: PRT
<213> ORGANISM: Artificial
<220> FEATURE:
<223> OTHER INFORMATION: EGFR construct

<400> SEQUENCE: 68

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Pro Asp Val Gln Asp
            20                  25                  30

Cys Pro Glu Cys Thr Leu Gln Glu Asn Pro Phe Phe Ser Gln Pro Gly
        35                  40                  45

Ala Pro Ile Leu Gln Cys Met Gly Cys Cys Phe Ser Arg Ala Tyr Pro
    50                  55                  60

Thr Pro Leu Arg Ser Lys Lys Thr Met Leu Val Gln Lys Asn Val Thr
65                  70                  75                  80

Ser Glu Ser Thr Cys Cys Val Ala Lys Ser Tyr Asn Arg Val Thr Val
                85                  90                  95

Met Gly Gly Phe Lys Val Glu Asn His Thr Ala Cys His Cys Ser Thr
            100                 105                 110

Cys Gln Val Gln Leu Lys Gln Ser Gly Pro Gly Leu Val Gln Pro Ser
        115                 120                 125

Gln Ser Leu Ser Ile Thr Cys Thr Val Ser Gly Phe Ser Leu Thr Asn
    130                 135                 140

Tyr Gly Val His Trp Val Arg Gln Ser Pro Gly Lys Gly Leu Glu Trp
145                 150                 155                 160

Leu Gly Val Ile Trp Ser Gly Gly Asn Thr Asp Tyr Asn Thr Pro Phe
                165                 170                 175

Thr Ser Arg Leu Ser Ile Asn Lys Asp Asn Ser Lys Ser Gln Val Phe
            180                 185                 190

Phe Lys Met Asn Ser Leu Gln Ser Asn Asp Thr Ala Ile Tyr Tyr Cys
        195                 200                 205

Ala Arg Ala Leu Thr Tyr Tyr Asp Tyr Glu Phe Ala Tyr Trp Gly Gln
    210                 215                 220
```

Gly Thr Leu Val Thr Val Ser Ala
225                 230

<210> SEQ ID NO 69
<211> LENGTH: 1239
<212> TYPE: DNA
<213> ORGANISM: Artificial
<220> FEATURE:
<223> OTHER INFORMATION: EGFR single chain

<400> SEQUENCE: 69

| | | | | | |
|---|---|---|---|---|---|
| atggctacag | gctcccggac | gtccctgctc | ctggcttttg | gcctgctctg | cctgccctgg | 60 |
| cttcaagagg | gatccgcctc | caaggagccg | cttcggccac | ggtgccgccc | catcaatgcc | 120 |
| accctggctg | tggagaagga | gggctgcccc | gtgtgcatca | ccgtcaacac | caccatctgt | 180 |
| gccggctact | gccccaccat | gacccgcgtg | ctgcaggggg | tcctgccggc | cctgcctcag | 240 |
| gtggtgtgca | actaccgcga | tgtgcgcttc | gagtccatcc | ggctccctgg | ctgcccgcgc | 300 |
| ggcgtgaacc | ccgtggtctc | ctacgccgtg | gctctcagct | gtcaatgtgc | actctgccgc | 360 |
| cgcagcacca | ctgactgcgg | gggtcccaag | gaccacccct | tgacctgtga | tgaccccgc | 420 |
| ttccaggact | cctcttcctc | aaaggcccct | cccccagcc | ttccaagccc | atcccgactc | 480 |
| ccggggccct | cggacacccc | gatcctccca | aacaggtgc | agctgaagca | gtcaggacct | 540 |
| ggcctagtgc | agccctcaca | gagcctgtcc | atcacctgca | cagtctctgg | tttctcatta | 600 |
| actaactatg | gtgtacactg | ggttcgccag | tctccaggaa | agggtctgga | gtggctggga | 660 |
| gtgatatgga | gtggtggaaa | cacagactat | aatacacctt | tcacatccag | actgagcatc | 720 |
| aacaaggaca | attccaagag | ccaagttttc | tttaaaatga | acagtctgca | atctaatgac | 780 |
| acagccatat | attactgtgc | cagagccctc | acctactatg | attacgagtt | tgcttactgg | 840 |
| ggccaaggga | ctctggtcac | tgtctctgca | ggtggcggtg | gctcgggcgg | tggtgggtcg | 900 |
| ggtggcggcg | gatctgacat | cttgctgact | cagtctccag | tcatcctgtc | tgtgagtcca | 960 |
| ggagaaagag | tcagtttctc | ctgcagggcc | agtcagagta | ttggcacaaa | catacactgg | 1020 |
| tatcagcaaa | gaacaaatgg | ttctccaagg | cttctcataa | agtatgcttc | tgagtctatc | 1080 |
| tctgggatcc | cttccaggtt | tagtggcagt | ggatcaggga | cagatttac | tcttagcatc | 1140 |
| aacagtgtgg | agtctgaaga | tattgcagat | tattactgtc | aacaaaataa | taactggcca | 1200 |
| accacgttcg | gtgctgggac | caagctggag | ctgaaatga | | | 1239 |

<210> SEQ ID NO 70
<211> LENGTH: 412
<212> TYPE: PRT
<213> ORGANISM: Artificial
<220> FEATURE:
<223> OTHER INFORMATION: EGFR single chain

<400> SEQUENCE: 70

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Lys Glu Pro Leu Arg
            20                  25                  30

Pro Arg Cys Arg Pro Ile Asn Ala Thr Leu Ala Val Glu Lys Glu Gly
        35                  40                  45

Cys Pro Val Cys Ile Thr Val Asn Thr Thr Ile Cys Ala Gly Tyr Cys
    50                  55                  60

Pro Thr Met Thr Arg Val Leu Gln Gly Val Leu Pro Ala Leu Pro Gln
65                  70                  75                  80

Val Val Cys Asn Tyr Arg Asp Val Arg Phe Glu Ser Ile Arg Leu Pro
            85                  90                  95

Gly Cys Pro Arg Gly Val Asn Pro Val Val Ser Tyr Ala Val Ala Leu
        100                 105                 110

Ser Cys Gln Cys Ala Leu Cys Arg Arg Ser Thr Thr Asp Cys Gly Gly
    115                 120                 125

Pro Lys Asp His Pro Leu Thr Cys Asp Asp Pro Arg Phe Gln Asp Ser
130                 135                 140

Ser Ser Ser Lys Ala Pro Pro Ser Leu Pro Ser Pro Ser Arg Leu
145                 150                 155                 160

Pro Gly Pro Ser Asp Thr Pro Ile Leu Pro Gln Gln Val Gln Leu Lys
                165                 170                 175

Gln Ser Gly Pro Gly Leu Val Gln Pro Ser Gln Ser Leu Ser Ile Thr
            180                 185                 190

Cys Thr Val Ser Gly Phe Ser Leu Thr Asn Tyr Gly Val His Trp Val
        195                 200                 205

Arg Gln Ser Pro Gly Lys Gly Leu Glu Trp Leu Gly Val Ile Trp Ser
    210                 215                 220

Gly Gly Asn Thr Asp Tyr Asn Thr Pro Phe Thr Ser Arg Leu Ser Ile
225                 230                 235                 240

Asn Lys Asp Asn Ser Lys Ser Gln Val Phe Phe Lys Met Asn Ser Leu
                245                 250                 255

Gln Ser Asn Asp Thr Ala Ile Tyr Tyr Cys Ala Arg Ala Leu Thr Tyr
            260                 265                 270

Tyr Asp Tyr Glu Phe Ala Tyr Trp Gly Gln Gly Thr Leu Val Thr Val
        275                 280                 285

Ser Ala Gly Gly Gly Gly Ser Gly Gly Gly Gly Ser Gly Gly Gly Gly
    290                 295                 300

Ser Asp Ile Leu Leu Thr Gln Ser Pro Val Ile Leu Ser Val Ser Pro
305                 310                 315                 320

Gly Glu Arg Val Ser Phe Ser Cys Arg Ala Ser Gln Ser Ile Gly Thr
                325                 330                 335

Asn Ile His Trp Tyr Gln Gln Arg Thr Asn Gly Ser Pro Arg Leu Leu
            340                 345                 350

Ile Lys Tyr Ala Ser Glu Ser Ile Ser Gly Ile Pro Ser Arg Phe Ser
        355                 360                 365

Gly Ser Gly Ser Gly Thr Asp Phe Thr Leu Ser Ile Asn Ser Val Glu
    370                 375                 380

Ser Glu Asp Ile Ala Asp Tyr Tyr Cys Gln Gln Asn Asn Asn Trp Pro
385                 390                 395                 400

Thr Thr Phe Gly Ala Gly Thr Lys Leu Glu Leu Lys
                405                 410

```
<210> SEQ ID NO 71
<211> LENGTH: 837
<212> TYPE: DNA
<213> ORGANISM: Artificial
<220> FEATURE:
<223> OTHER INFORMATION: EGFR construct

<400> SEQUENCE: 71
atggctacag gctcccggac gtccctgctc ctggcttttg gcctgctctg cctgccctgg      60
cttcaagagg gatccgcctc caaggagccg cttcggccac ggtgccgccc catcaatgcc     120
accctggctg tggagaagga gggctgcccc gtgtgcatca ccgtcaacac caccatctgt     180
```

-continued

```
gccggctact gccccaccat gacccgcgtg ctgcagggggg tcctgccggc cctgcctcag    240
gtggtgtgca actaccgcga tgtgcgcttc gagtccatcc ggctccctgg ctgccgcgc     300 ggcgtgaacc ccgtggtctc ctacgccgtg gctctcagct gtcaatgtgc actctgccgc    360
cgcagcacca ctgactgcgg gggtcccaag gaccacccct tgacctgtga tgaccccgc     420 ttccaggact cctcttcctc aaaggcccct ccccccagcc ttccaagccc atcccgactc    480 ccgggggccct cggacacccc gatcctccca caagacatct tgctgactca gtctccagtc   540
atcctgtctg tgagtccagg agaaagagtc agtttctcct gcagggccag tcagagtatt    600
ggcacaaaca tacactggta tcagcaaaga acaaatggtt ctccaaggct tctcataaag    660
tatgcttctg agtctatctc tgggatccct tccaggttta gtggcagtgg atcagggaca    720 gatttttactc ttagcatcaa cagtgtggag tctgaagata ttgcagatta ttactgtcaa   780
caaaataata actggccaac cacgttcggt gctgggacca agctggagct gaaatga       837
```

<210> SEQ ID NO 72
<211> LENGTH: 278
<212> TYPE: PRT
<213> ORGANISM: Artificial
<220> FEATURE:
<223> OTHER INFORMATION: EGFR construct

<400> SEQUENCE: 72

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Ser Lys Glu Pro Leu Arg
                20                  25                  30

Pro Arg Cys Arg Pro Ile Asn Ala Thr Leu Ala Val Glu Lys Glu Gly
            35                  40                  45

Cys Pro Val Cys Ile Thr Val Asn Thr Thr Ile Cys Ala Gly Tyr Cys
        50                  55                  60

Pro Thr Met Thr Arg Val Leu Gln Gly Val Leu Pro Ala Leu Pro Gln
 65                  70                  75                  80

Val Val Cys Asn Tyr Arg Asp Val Arg Phe Glu Ser Ile Arg Leu Pro
                 85                  90                  95

Gly Cys Pro Arg Gly Val Asn Pro Val Val Ser Tyr Ala Val Ala Leu
            100                 105                 110

Ser Cys Gln Cys Ala Leu Cys Arg Arg Ser Thr Thr Asp Cys Gly Gly
        115                 120                 125

Pro Lys Asp His Pro Leu Thr Cys Asp Asp Pro Arg Phe Gln Asp Ser
    130                 135                 140

Ser Ser Lys Ala Pro Pro Ser Leu Pro Ser Pro Ser Arg Leu
145                 150                 155                 160

Pro Gly Pro Ser Asp Thr Pro Ile Leu Pro Gln Asp Ile Leu Leu Thr
                165                 170                 175

Gln Ser Pro Val Ile Leu Ser Val Ser Pro Gly Glu Arg Val Ser Phe
            180                 185                 190

Ser Cys Arg Ala Ser Gln Ser Ile Gly Thr Asn Ile His Trp Tyr Gln
        195                 200                 205

Gln Arg Thr Asn Gly Ser Pro Arg Leu Leu Ile Lys Tyr Ala Ser Glu
    210                 215                 220

Ser Ile Ser Gly Ile Pro Ser Arg Phe Ser Gly Ser Gly Ser Gly Thr
225                 230                 235                 240

Asp Phe Thr Leu Ser Ile Asn Ser Val Glu Ser Glu Asp Ile Ala Asp
```

```
                        245                 250                 255
Tyr Tyr Cys Gln Gln Asn Asn Asn Trp Pro Thr Thr Phe Gly Ala Gly
            260                 265                 270

Thr Lys Leu Glu Leu Lys
        275

<210> SEQ ID NO 73
<211> LENGTH: 620
<212> TYPE: PRT
<213> ORGANISM: Artificial
<220> FEATURE:
<223> OTHER INFORMATION: Fab12 scFvHL

<400> SEQUENCE: 73

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Val Gln Leu Val Glu
            20                  25                  30

Ser Gly Gly Gly Leu Val Gln Pro Gly Gly Ser Leu Arg Leu Ser Cys
        35                  40                  45

Ala Ala Ser Gly Tyr Thr Phe Thr Asn Tyr Gly Met Asn Trp Val Arg
    50                  55                  60

Gln Ala Pro Gly Lys Gly Leu Glu Trp Val Gly Trp Ile Asn Thr Tyr
65                  70                  75                  80

Thr Gly Glu Pro Thr Tyr Ala Ala Asp Phe Lys Arg Arg Phe Thr Phe
                85                  90                  95

Ser Leu Asp Thr Ser Lys Ser Thr Ala Tyr Leu Gln Met Asn Ser Leu
            100                 105                 110

Arg Ala Glu Asp Thr Ala Val Tyr Tyr Cys Ala Lys Tyr Pro His Tyr
        115                 120                 125

Tyr Gly Ser Ser His Trp Tyr Phe Asp Val Trp Gly Gln Gly Thr Leu
    130                 135                 140

Val Thr Val Ser Ser Gly Gly Gly Ser Gly Gly Gly Gly Ser Gly
145                 150                 155                 160

Gly Gly Gly Ser Asp Ile Gln Met Thr Gln Ser Pro Ser Ser Leu Ser
                165                 170                 175

Ala Ser Val Gly Asp Arg Val Thr Ile Thr Cys Ser Ala Ser Gln Asp
            180                 185                 190

Ile Ser Asn Tyr Leu Asn Trp Tyr Gln Gln Lys Pro Gly Lys Ala Pro
        195                 200                 205

Lys Val Leu Ile Tyr Phe Thr Ser Ser Leu His Ser Gly Val Pro Ser
    210                 215                 220

Arg Phe Ser Gly Ser Gly Ser Gly Thr Asp Phe Thr Leu Thr Ile Ser
225                 230                 235                 240

Ser Leu Gln Pro Glu Asp Phe Ala Thr Tyr Tyr Cys Gln Gln Tyr Ser
                245                 250                 255

Thr Val Pro Trp Thr Phe Gly Gln Gly Thr Lys Val Glu Ile Lys Arg
            260                 265                 270

Ala Pro Asp Val Gln Asp Cys Pro Glu Cys Thr Leu Gln Glu Asn Pro
        275                 280                 285

Phe Phe Ser Gln Pro Gly Ala Pro Ile Leu Gln Cys Met Gly Cys Cys
    290                 295                 300

Phe Ser Arg Ala Tyr Pro Thr Pro Leu Arg Ser Lys Lys Thr Met Leu
305                 310                 315                 320

Val Gln Lys Asn Val Thr Ser Glu Ser Thr Cys Cys Val Ala Lys Ser
```

-continued

```
                325                 330                 335
Tyr Asn Arg Val Thr Val Met Gly Gly Phe Lys Val Glu Asn His Thr
                340                 345                 350
Ala Cys His Cys Ser Thr Cys Gly Gly Gly Ser Gly Gly Gly Gly
                355                 360                 365
Ser Gly Gly Gly Ser Gly Gly Gly Ser Gln Val Gln Leu Lys
        370                 375                 380
Gln Ser Gly Pro Gly Leu Val Gln Pro Ser Gln Ser Leu Ser Ile Thr
385                 390                 395                 400
Cys Thr Val Ser Gly Phe Ser Leu Thr Asn Tyr Gly Val His Trp Val
                405                 410                 415
Arg Gln Ser Pro Gly Lys Gly Leu Glu Trp Leu Gly Val Ile Trp Ser
                420                 425                 430
Gly Gly Asn Thr Asp Tyr Asn Thr Pro Phe Thr Ser Arg Leu Ser Ile
                435                 440                 445
Asn Lys Asp Asn Ser Lys Ser Gln Val Phe Phe Lys Met Asn Ser Leu
        450                 455                 460
Gln Ser Asn Asp Thr Ala Ile Tyr Tyr Cys Ala Arg Ala Leu Thr Tyr
465                 470                 475                 480
Tyr Asp Tyr Glu Phe Ala Tyr Trp Gly Gln Gly Thr Leu Val Thr Val
                485                 490                 495
Ser Ala Gly Gly Gly Ser Gly Gly Gly Ser Gly Gly Gly Gly
                500                 505                 510
Ser Asp Ile Leu Leu Thr Gln Ser Pro Val Ile Leu Ser Val Ser Pro
        515                 520                 525
Gly Glu Arg Val Ser Phe Ser Cys Arg Ala Ser Gln Ser Ile Gly Thr
        530                 535                 540
Asn Ile His Trp Tyr Gln Gln Arg Thr Asn Gly Ser Pro Arg Leu Leu
545                 550                 555                 560
Ile Lys Tyr Ala Ser Glu Ser Ile Ser Gly Ile Pro Ser Arg Phe Ser
                565                 570                 575
Gly Ser Gly Ser Gly Thr Asp Phe Thr Leu Ser Ile Asn Ser Val Glu
                580                 585                 590
Ser Glu Asp Ile Ala Asp Tyr Tyr Cys Gln Gln Asn Asn Asn Trp Pro
                595                 600                 605
Thr Thr Phe Gly Ala Gly Thr Lys Leu Glu Leu Lys
        610                 615                 620

<210> SEQ ID NO 74
<211> LENGTH: 658
<212> TYPE: PRT
<213> ORGANISM: Artificial
<220> FEATURE:
<223> OTHER INFORMATION: Fab12 scFvHL

<400> SEQUENCE: 74

Met Ala Thr Gly Ser Arg Thr Ser Leu Leu Leu Ala Phe Gly Leu Leu
1               5                   10                  15
Cys Leu Pro Trp Leu Gln Glu Gly Ser Ala Glu Val Gln Leu Val Glu
                20                  25                  30
Ser Gly Gly Gly Leu Val Gln Pro Gly Gly Ser Leu Arg Leu Ser Cys
            35                  40                  45
Ala Ala Ser Gly Tyr Thr Phe Thr Asn Tyr Gly Met Asn Trp Val Arg
        50                  55                  60
Gln Ala Pro Gly Lys Gly Leu Glu Trp Val Gly Trp Ile Asn Thr Tyr
```

-continued

```
                65                  70                  75                  80
Thr Gly Glu Pro Thr Tyr Ala Ala Asp Phe Lys Arg Arg Phe Thr Phe
                    85                  90                  95
Ser Leu Asp Thr Ser Lys Ser Thr Ala Tyr Leu Gln Met Asn Ser Leu
                100                 105                 110
Arg Ala Glu Asp Thr Ala Val Tyr Tyr Cys Ala Lys Tyr Pro His Tyr
                115                 120                 125
Tyr Gly Ser Ser His Trp Tyr Phe Asp Val Trp Gly Gln Gly Thr Leu
            130                 135                 140
Val Thr Val Ser Ser Gly Gly Gly Gly Ser Gly Gly Gly Gly Ser Gly
145                 150                 155                 160
Gly Gly Gly Ser Asp Ile Gln Met Thr Gln Ser Pro Ser Ser Leu Ser
                165                 170                 175
Ala Ser Val Gly Asp Arg Val Thr Ile Thr Cys Ser Ala Ser Gln Asp
                180                 185                 190
Ile Ser Asn Tyr Leu Asn Trp Tyr Gln Gln Lys Pro Gly Lys Ala Pro
            195                 200                 205
Lys Val Leu Ile Tyr Phe Thr Ser Ser Leu His Ser Gly Val Pro Ser
            210                 215                 220
Arg Phe Ser Gly Ser Gly Ser Gly Thr Asp Phe Thr Leu Thr Ile Ser
225                 230                 235                 240
Ser Leu Gln Pro Glu Asp Phe Ala Thr Tyr Tyr Cys Gln Gln Tyr Ser
                245                 250                 255
Thr Val Pro Trp Thr Phe Gly Gln Gly Thr Lys Val Glu Ile Lys Arg
                260                 265                 270
Ser Lys Glu Pro Leu Arg Pro Arg Cys Arg Pro Ile Asn Ala Thr Leu
                275                 280                 285
Ala Val Glu Lys Glu Gly Cys Pro Val Cys Ile Thr Val Asn Thr Thr
                290                 295                 300
Ile Cys Ala Gly Tyr Cys Pro Thr Met Thr Arg Val Leu Gln Gly Val
305                 310                 315                 320
Leu Pro Ala Leu Pro Gln Val Val Cys Asn Tyr Arg Asp Val Arg Phe
                325                 330                 335
Glu Ser Ile Arg Leu Pro Gly Cys Pro Arg Gly Val Asn Pro Val Val
                340                 345                 350
Ser Tyr Ala Val Ala Leu Ser Cys Gln Cys Ala Leu Cys Arg Arg Ser
            355                 360                 365
Thr Thr Asp Cys Gly Gly Pro Lys Asp His Pro Leu Thr Cys Asp Asp
            370                 375                 380
Pro Arg Phe Gln Asp Ser Ser Ser Ser Lys Ala Pro Pro Pro Ser Leu
385                 390                 395                 400
Pro Ser Pro Ser Arg Leu Pro Gly Pro Ser Asp Thr Pro Ile Leu Pro
                405                 410                 415
Gln Gln Val Gln Leu Lys Gln Ser Gly Pro Gly Leu Val Gln Pro Ser
                420                 425                 430
Gln Ser Leu Ser Ile Thr Cys Thr Val Ser Gly Phe Ser Leu Thr Asn
            435                 440                 445
Tyr Gly Val His Trp Val Arg Gln Ser Pro Gly Lys Gly Leu Glu Trp
            450                 455                 460
Leu Gly Val Ile Trp Ser Gly Gly Asn Thr Asp Tyr Asn Thr Pro Phe
465                 470                 475                 480
Thr Ser Arg Leu Ser Ile Asn Lys Asp Asn Ser Lys Ser Gln Val Phe
                485                 490                 495
```

```
Phe Lys Met Asn Ser Leu Gln Ser Asn Asp Thr Ala Ile Tyr Tyr Cys
            500                 505                 510

Ala Arg Ala Leu Thr Tyr Tyr Asp Tyr Glu Phe Ala Tyr Trp Gly Gln
            515                 520                 525

Gly Thr Leu Val Thr Val Ser Ala Gly Gly Gly Gly Ser Gly Gly Gly
            530                 535                 540

Gly Ser Gly Gly Gly Ser Asp Ile Leu Leu Thr Gln Ser Pro Val
545                 550                 555                 560

Ile Leu Ser Val Ser Pro Gly Glu Arg Val Ser Phe Ser Cys Arg Ala
                565                 570                 575

Ser Gln Ser Ile Gly Thr Asn Ile His Trp Tyr Gln Gln Arg Thr Asn
            580                 585                 590

Gly Ser Pro Arg Leu Leu Ile Lys Tyr Ala Ser Glu Ser Ile Ser Gly
            595                 600                 605

Ile Pro Ser Arg Phe Ser Gly Ser Gly Ser Gly Thr Asp Phe Thr Leu
            610                 615                 620

Ser Ile Asn Ser Val Glu Ser Glu Asp Ile Ala Asp Tyr Tyr Cys Gln
625                 630                 635                 640

Gln Asn Asn Asn Trp Pro Thr Thr Phe Gly Ala Gly Thr Lys Leu Glu
                645                 650                 655

Leu Lys

<210> SEQ ID NO 75
<211> LENGTH: 616
<212> TYPE: PRT
<213> ORGANISM: Artificial
<220> FEATURE:
<223> OTHER INFORMATION: VEGF FvHL

<400> SEQUENCE: 75

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Val Gln Leu Val Gln
            20                  25                  30

Ser Gly Ala Glu Val Lys Lys Pro Gly Ala Ser Val Lys Val Ser Cys
        35                  40                  45

Lys Ala Ser Gly Asp Thr Phe Thr Thr Tyr Val Ile His Trp Met Arg
    50                  55                  60

Gln Ala Pro Gly Gln Gly Leu Glu Trp Ile Gly Tyr Ile Asn Pro Tyr
65                  70                  75                  80

Asn Asp Gly Thr Lys Tyr Asn Glu Lys Phe Lys Gly Arg Val Thr Ile
                85                  90                  95

Thr Ser Asp Lys Ser Thr Ser Thr Ala Tyr Met Glu Leu Ser Ser Leu
            100                 105                 110

Arg Ser Glu Asp Thr Ala Val Tyr Tyr Cys Ala Arg Ile Tyr Tyr Asp
            115                 120                 125

Tyr Asp Gly Asp Tyr Trp Gly Gln Gly Thr Leu Val Thr Val Ser Ser
            130                 135                 140

Gly Gly Gly Gly Ser Gly Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Ile Thr Ser Asn Asp Ile Asp Asp Asp Met
            180                 185                 190
```

-continued

```
Asn Trp Tyr Gln Gln Lys Pro Gly Lys Ala Pro Lys Leu Leu Ile Ser
        195                 200                 205

Glu Gly Asn Thr Leu Arg Pro Gly Val Pro Ser Arg Phe Ser Gly Ser
210                 215                 220

Gly Tyr Gly Thr Asp Phe Thr Leu Thr Ile Ser Ser Leu Gln Pro Glu
225                 230                 235                 240

Asp Val Ala Thr Tyr Tyr Cys Phe Gln Ser Asp Asn Leu Pro Tyr Thr
                245                 250                 255

Phe Gly Gln Gly Thr Lys Val Glu Ile Lys Ala Ala Pro Asp Val
                260                 265                 270

Gln Asp Cys Pro Glu Cys Thr Leu Gln Glu Asn Pro Phe Phe Ser Gln
        275                 280                 285

Pro Gly Ala Pro Ile Leu Gln Cys Met Gly Cys Cys Phe Ser Arg Ala
290                 295                 300

Tyr Pro Thr Pro Leu Arg Ser Lys Lys Thr Met Leu Val Gln Lys Asn
305                 310                 315                 320

Val Thr Ser Glu Ser Thr Cys Cys Val Ala Lys Ser Tyr Asn Arg Val
                325                 330                 335

Thr Val Met Gly Gly Phe Lys Val Glu Asn His Thr Ala Cys His Cys
                340                 345                 350

Ser Thr Cys Gly Gly Gly Ser Gly Gly Gly Ser Gly Gly Gly
        355                 360                 365

Gly Ser Gly Gly Gly Ser Gln Val Gln Leu Lys Gln Ser Gly Pro
        370                 375                 380

Gly Leu Val Gln Pro Ser Gln Ser Leu Ser Ile Thr Cys Thr Val Ser
385                 390                 395                 400

Gly Phe Ser Leu Thr Asn Tyr Gly Val His Trp Val Arg Gln Ser Pro
                405                 410                 415

Gly Lys Gly Leu Glu Trp Leu Gly Val Ile Trp Ser Gly Gly Asn Thr
                420                 425                 430

Asp Tyr Asn Thr Pro Phe Thr Ser Arg Leu Ser Ile Asn Lys Asp Asn
        435                 440                 445

Ser Lys Ser Gln Val Phe Phe Lys Met Asn Ser Leu Gln Ser Asn Asp
        450                 455                 460

Thr Ala Ile Tyr Tyr Cys Ala Arg Ala Leu Thr Tyr Tyr Asp Tyr Glu
465                 470                 475                 480

Phe Ala Tyr Trp Gly Gln Gly Thr Leu Val Thr Val Ser Ala Gly Gly
                485                 490                 495

Gly Gly Ser Gly Gly Gly Gly Ser Gly Gly Gly Gly Ser Asp Ile Leu
                500                 505                 510

Leu Thr Gln Ser Pro Val Ile Leu Ser Val Ser Pro Gly Glu Arg Val
        515                 520                 525

Ser Phe Ser Cys Arg Ala Ser Gln Ser Ile Gly Thr Asn Ile His Trp
        530                 535                 540

Tyr Gln Gln Arg Thr Asn Gly Ser Pro Arg Leu Leu Ile Lys Tyr Ala
545                 550                 555                 560

Ser Glu Ser Ile Ser Gly Ile Pro Ser Arg Phe Ser Gly Ser Gly Ser
                565                 570                 575

Gly Thr Asp Phe Thr Leu Ser Ile Asn Ser Val Glu Ser Glu Asp Ile
                580                 585                 590

Ala Asp Tyr Tyr Cys Gln Gln Asn Asn Asn Trp Pro Thr Thr Phe Gly
                595                 600                 605

Ala Gly Thr Lys Leu Glu Leu Lys
```

610             615

<210> SEQ ID NO 76
<211> LENGTH: 655
<212> TYPE: PRT
<213> ORGANISM: Artificial
<220> FEATURE:
<223> OTHER INFORMATION: VEGF beta

<400> SEQUENCE: 76

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Val Gln Leu Val Gln
            20                  25                  30

Ser Gly Ala Glu Val Lys Lys Pro Gly Ala Ser Val Lys Val Ser Cys
        35                  40                  45

Lys Ala Ser Gly Asp Thr Phe Thr Thr Tyr Val Ile His Trp Met Arg
    50                  55                  60

Gln Ala Pro Gly Gln Gly Leu Glu Trp Ile Gly Tyr Ile Asn Pro Tyr
65                  70                  75                  80

Asn Asp Gly Thr Lys Tyr Asn Glu Lys Phe Lys Gly Arg Val Thr Ile
                85                  90                  95

Thr Ser Asp Lys Ser Thr Ser Thr Ala Tyr Met Glu Leu Ser Ser Leu
            100                 105                 110

Arg Ser Glu Asp Thr Ala Val Tyr Tyr Cys Ala Arg Ile Tyr Tyr Asp
        115                 120                 125

Tyr Asp Gly Asp Tyr Trp Gly Gln Gly Thr Leu Val Thr Val Ser Ser
    130                 135                 140

Gly Gly Gly Gly Ser Gly Gly Gly Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Ile Thr Ser Asn Asp Ile Asp Asp Asp Met
            180                 185                 190

Asn Trp Tyr Gln Gln Lys Pro Gly Lys Ala Pro Lys Leu Leu Ile Ser
        195                 200                 205

Glu Gly Asn Thr Leu Arg Pro Gly Val Pro Ser Arg Phe Ser Gly Ser
    210                 215                 220

Gly Tyr Gly Thr Asp Phe Thr Leu Thr Ile Ser Ser Leu Gln Pro Glu
225                 230                 235                 240

Asp Val Ala Thr Tyr Tyr Cys Phe Gln Ser Asp Asn Leu Pro Tyr Thr
                245                 250                 255

Phe Gly Gln Gly Thr Lys Val Glu Ile Lys Ala Ala Ala Ser Lys Glu
            260                 265                 270

Pro Leu Arg Pro Arg Cys Arg Pro Ile Asn Ala Thr Leu Ala Val Glu
        275                 280                 285

Lys Glu Gly Cys Pro Val Cys Ile Thr Val Asn Thr Thr Ile Cys Ala
    290                 295                 300

Gly Tyr Cys Pro Thr Met Thr Arg Val Leu Gln Gly Val Leu Pro Ala
305                 310                 315                 320

Leu Pro Gln Val Val Cys Asn Tyr Arg Asp Val Arg Phe Glu Ser Ile
                325                 330                 335

Arg Leu Pro Gly Cys Pro Arg Gly Val Asn Pro Val Val Ser Tyr Ala
            340                 345                 350

Val Ala Leu Ser Cys Gln Cys Ala Leu Cys Arg Arg Ser Thr Thr Asp

-continued

```
                355                 360                 365
Cys Gly Gly Pro Lys Asp His Pro Leu Thr Cys Asp Asp Pro Arg Phe
        370                 375                 380

Gln Asp Ser Ser Ser Lys Ala Pro Pro Ser Leu Pro Ser Pro
385                 390                 395                 400

Ser Arg Leu Pro Gly Pro Ser Asp Thr Pro Ile Leu Pro Gln Gln Val
                405                 410                 415

Gln Leu Lys Gln Ser Gly Pro Gly Leu Val Gln Pro Ser Gln Ser Leu
            420                 425                 430

Ser Ile Thr Cys Thr Val Ser Gly Phe Ser Leu Thr Asn Tyr Gly Val
            435                 440                 445

His Trp Val Arg Gln Ser Pro Gly Lys Gly Leu Glu Trp Leu Gly Val
        450                 455                 460

Ile Trp Ser Gly Gly Asn Thr Asp Tyr Asn Thr Pro Phe Thr Ser Arg
465                 470                 475                 480

Leu Ser Ile Asn Lys Asp Asn Ser Lys Ser Gln Val Phe Phe Lys Met
                485                 490                 495

Asn Ser Leu Gln Ser Asn Asp Thr Ala Ile Tyr Tyr Cys Ala Arg Ala
            500                 505                 510

Leu Thr Tyr Tyr Asp Tyr Glu Phe Ala Tyr Trp Gly Gln Gly Thr Leu
            515                 520                 525

Val Thr Val Ser Ala Gly Gly Gly Gly Ser Gly Gly Gly Gly Ser Gly
        530                 535                 540

Gly Gly Gly Ser Asp Ile Leu Leu Thr Gln Ser Pro Val Ile Leu Ser
545                 550                 555                 560

Val Ser Pro Gly Glu Arg Val Ser Phe Ser Cys Arg Ala Ser Gln Ser
                565                 570                 575

Ile Gly Thr Asn Ile His Trp Tyr Gln Gln Arg Thr Asn Gly Ser Pro
            580                 585                 590

Arg Leu Leu Ile Lys Tyr Ala Ser Glu Ser Ile Ser Gly Ile Pro Ser
            595                 600                 605

Arg Phe Ser Gly Ser Gly Ser Gly Thr Asp Phe Thr Leu Ser Ile Asn
        610                 615                 620

Ser Val Glu Ser Glu Asp Ile Ala Asp Tyr Tyr Cys Gln Gln Asn Asn
625                 630                 635                 640

Asn Trp Pro Thr Thr Phe Gly Ala Gly Thr Lys Leu Glu Leu Lys
                645                 650                 655

<210> SEQ ID NO 77
<211> LENGTH: 616
<212> TYPE: PRT
<213> ORGANISM: Artificial
<220> FEATURE:
<223> OTHER INFORMATION: VEGF scFvLH

<400> SEQUENCE: 77

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Gln Met Thr Gln
                20                  25                  30

Ser Pro Ser Ser Leu Ser Ala Ser Val Gly Asp Arg Val Thr Ile Thr
            35                  40                  45

Cys Ile Thr Ser Asn Asp Ile Asp Asp Asp Met Asn Trp Tyr Gln Gln
        50                  55                  60

Lys Pro Gly Lys Ala Pro Lys Leu Leu Ile Ser Glu Gly Asn Thr Leu
```

```
            65                  70                  75                  80
Arg Pro Gly Val Pro Ser Arg Phe Ser Gly Gly Tyr Gly Thr Asp
                    85                  90                  95

Phe Thr Leu Thr Ile Ser Ser Leu Gln Pro Glu Asp Val Ala Thr Tyr
                100                 105                 110

Tyr Cys Phe Gln Ser Asp Asn Leu Pro Tyr Thr Phe Gly Gln Gly Thr
            115                 120                 125

Lys Val Glu Ile Lys Gly Gly Gly Ser Gly Gly Gly Ser Gly
        130                 135                 140

Gly Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Asp Thr
                165                 170                 175

Phe Thr Thr Tyr Val Ile His Trp Met Arg Gln Ala Pro Gly Gln Gly
                180                 185                 190

Leu Glu Trp Ile Gly Tyr Ile Asn Pro Tyr Asn Asp Gly Thr Lys Tyr
            195                 200                 205

Asn Glu Lys Phe Lys Gly Arg Val Thr Ile Thr Ser Asp Lys Ser Thr
        210                 215                 220

Ser Thr Ala Tyr Met Glu Leu Ser Ser Leu Arg Ser Glu Asp Thr Ala
225                 230                 235                 240

Val Tyr Tyr Cys Ala Arg Ile Tyr Tyr Asp Tyr Asp Gly Asp Tyr Trp
                245                 250                 255

Gly Gln Gly Thr Leu Val Thr Val Ser Ser Ala Ala Pro Asp Val
            260                 265                 270

Gln Asp Cys Pro Glu Cys Thr Leu Gln Glu Asn Pro Phe Phe Ser Gln
        275                 280                 285

Pro Gly Ala Pro Ile Leu Gln Cys Met Gly Cys Cys Phe Ser Arg Ala
290                 295                 300

Tyr Pro Thr Pro Leu Arg Ser Lys Lys Thr Met Leu Val Gln Lys Asn
305                 310                 315                 320

Val Thr Ser Glu Ser Thr Cys Cys Val Ala Lys Ser Tyr Asn Arg Val
                325                 330                 335

Thr Val Met Gly Gly Phe Lys Val Glu Asn His Thr Ala Cys His Cys
            340                 345                 350

Ser Thr Cys Gly Gly Gly Gly Ser Gly Gly Gly Gly Ser Gly Gly
        355                 360                 365

Gly Ser Gly Gly Gly Ser Gln Val Gln Leu Lys Gln Ser Gly Pro
    370                 375                 380

Gly Leu Val Gln Pro Ser Gln Ser Leu Ser Ile Thr Cys Thr Val Ser
385                 390                 395                 400

Gly Phe Ser Leu Thr Asn Tyr Gly Val His Trp Val Arg Gln Ser Pro
                405                 410                 415

Gly Lys Gly Leu Glu Trp Leu Gly Val Ile Trp Ser Gly Gly Asn Thr
            420                 425                 430

Asp Tyr Asn Thr Pro Phe Thr Ser Arg Leu Ser Ile Asn Lys Asp Asn
        435                 440                 445

Ser Lys Ser Gln Val Phe Phe Lys Met Asn Ser Leu Gln Ser Asn Asp
        450                 455                 460

Thr Ala Ile Tyr Tyr Cys Ala Arg Ala Leu Thr Tyr Tyr Asp Tyr Glu
465                 470                 475                 480

Phe Ala Tyr Trp Gly Gln Gly Thr Leu Val Thr Val Ser Ala Gly Gly
                485                 490                 495
```

-continued

Gly Gly Ser Gly Gly Gly Ser Gly Gly Gly Ser Asp Ile Leu
            500                 505                 510

Leu Thr Gln Ser Pro Val Ile Leu Ser Val Ser Pro Gly Glu Arg Val
            515                 520                 525

Ser Phe Ser Cys Arg Ala Ser Gln Ser Ile Gly Thr Asn Ile His Trp
            530                 535                 540

Tyr Gln Gln Arg Thr Asn Gly Ser Pro Arg Leu Leu Ile Lys Tyr Ala
545                 550                 555                 560

Ser Glu Ser Ile Ser Gly Ile Pro Ser Arg Phe Ser Gly Ser Gly Ser
                565                 570                 575

Gly Thr Asp Phe Thr Leu Ser Ile Asn Ser Val Glu Ser Glu Asp Ile
            580                 585                 590

Ala Asp Tyr Tyr Cys Gln Gln Asn Asn Asn Trp Pro Thr Thr Phe Gly
            595                 600                 605

Ala Gly Thr Lys Leu Glu Leu Lys
            610                 615

<210> SEQ ID NO 78
<211> LENGTH: 655
<212> TYPE: PRT
<213> ORGANISM: Artificial
<220> FEATURE:
<223> OTHER INFORMATION: VEGF LH beta

<400> SEQUENCE: 78

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Gln Met Thr Gln
                20                  25                  30

Ser Pro Ser Ser Leu Ser Ala Ser Val Gly Asp Arg Val Thr Ile Thr
            35                  40                  45

Cys Ile Thr Ser Asn Asp Ile Asp Asp Asp Met Asn Trp Tyr Gln Gln
        50                  55                  60

Lys Pro Gly Lys Ala Pro Lys Leu Leu Ile Ser Glu Gly Asn Thr Leu
65                  70                  75                  80

Arg Pro Gly Val Pro Ser Arg Phe Ser Gly Ser Gly Tyr Gly Thr Asp
                85                  90                  95

Phe Thr Leu Thr Ile Ser Ser Leu Gln Pro Glu Asp Val Ala Thr Tyr
            100                 105                 110

Tyr Cys Phe Gln Ser Asp Asn Leu Pro Tyr Thr Phe Gly Gln Gly Thr
        115                 120                 125

Lys Val Glu Ile Lys Gly Gly Gly Ser Gly Gly Gly Ser Gly
    130                 135                 140

Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Asp Thr
                165                 170                 175

Phe Thr Thr Tyr Val Ile His Trp Met Arg Gln Ala Pro Gly Gln Gly
            180                 185                 190

Leu Glu Trp Ile Gly Tyr Ile Asn Pro Tyr Asn Asp Gly Thr Lys Tyr
        195                 200                 205

Asn Glu Lys Phe Lys Gly Arg Val Thr Ile Thr Ser Asp Lys Ser Thr
    210                 215                 220

Ser Thr Ala Tyr Met Glu Leu Ser Ser Leu Arg Ser Glu Asp Thr Ala
225                 230                 235                 240

-continued

```
Val Tyr Tyr Cys Ala Arg Ile Tyr Tyr Asp Tyr Asp Gly Asp Tyr Trp
            245                 250                 255

Gly Gln Gly Thr Leu Val Thr Val Ser Ser Ala Ala Ser Lys Glu
        260                 265                 270

Pro Leu Arg Pro Arg Cys Arg Pro Ile Asn Ala Thr Leu Ala Val Glu
        275                 280                 285

Lys Glu Gly Cys Pro Val Cys Ile Thr Val Asn Thr Thr Ile Cys Ala
    290                 295                 300

Gly Tyr Cys Pro Thr Met Thr Arg Val Leu Gln Gly Val Leu Pro Ala
305                 310                 315                 320

Leu Pro Gln Val Val Cys Asn Tyr Arg Asp Val Arg Phe Glu Ser Ile
            325                 330                 335

Arg Leu Pro Gly Cys Pro Arg Gly Val Asn Pro Val Val Ser Tyr Ala
            340                 345                 350

Val Ala Leu Ser Cys Gln Cys Ala Leu Cys Arg Arg Ser Thr Thr Asp
        355                 360                 365

Cys Gly Gly Pro Lys Asp His Pro Leu Thr Cys Asp Asp Pro Arg Phe
    370                 375                 380

Gln Asp Ser Ser Ser Lys Ala Pro Pro Ser Leu Pro Ser Pro
385                 390                 395                 400

Ser Arg Leu Pro Gly Pro Ser Asp Thr Pro Ile Leu Pro Gln Gln Val
            405                 410                 415

Gln Leu Lys Gln Ser Gly Pro Gly Leu Val Gln Pro Ser Gln Ser Leu
        420                 425                 430

Ser Ile Thr Cys Thr Val Ser Gly Phe Ser Leu Thr Asn Tyr Gly Val
        435                 440                 445

His Trp Val Arg Gln Ser Pro Gly Lys Gly Leu Glu Trp Leu Gly Val
    450                 455                 460

Ile Trp Ser Gly Gly Asn Thr Asp Tyr Asn Thr Pro Phe Thr Ser Arg
465                 470                 475                 480

Leu Ser Ile Asn Lys Asp Asn Ser Lys Ser Gln Val Phe Phe Lys Met
            485                 490                 495

Asn Ser Leu Gln Ser Asn Asp Thr Ala Ile Tyr Tyr Cys Ala Arg Ala
        500                 505                 510

Leu Thr Tyr Tyr Asp Tyr Glu Phe Ala Tyr Trp Gly Gln Gly Thr Leu
        515                 520                 525

Val Thr Val Ser Ala Gly Gly Gly Ser Gly Gly Gly Ser Gly
    530                 535                 540

Gly Gly Gly Ser Asp Ile Leu Leu Thr Gln Ser Pro Val Ile Leu Ser
545                 550                 555                 560

Val Ser Pro Gly Glu Arg Val Ser Phe Ser Cys Arg Ala Ser Gln Ser
            565                 570                 575

Ile Gly Thr Asn Ile His Trp Tyr Gln Gln Arg Thr Asn Gly Ser Pro
        580                 585                 590

Arg Leu Leu Ile Lys Tyr Ala Ser Glu Ser Ile Ser Gly Ile Pro Ser
        595                 600                 605

Arg Phe Ser Gly Ser Gly Ser Gly Thr Asp Phe Thr Leu Ser Ile Asn
    610                 615                 620

Ser Val Glu Ser Glu Asp Ile Ala Asp Tyr Tyr Cys Gln Gln Asn Asn
625                 630                 635                 640

Asn Trp Pro Thr Thr Phe Gly Ala Gly Thr Lys Leu Glu Leu Lys
            645                 650                 655
```

<210> SEQ ID NO 79
<211> LENGTH: 617
<212> TYPE: PRT
<213> ORGANISM: Artificial
<220> FEATURE:
<223> OTHER INFORMATION: V2 LH alpha

<400> SEQUENCE: 79

```
Met Ala Thr Gly Ser Arg Thr Ser Leu Leu Ala Phe Gly Leu Leu
1               5                   10                  15

Cys Leu Pro Trp Leu Gln Glu Gly Ser Ala Asp Ile Gln Met Thr Gln
                20                  25                  30

Ser Pro Ser Ser Leu Ser Ala Ser Val Gly Asp Arg Val Thr Ile Thr
                35                  40                  45

Cys Ile Thr Ser Asn Asp Ile Asp Asp Asp Met Asn Trp Tyr Gln Gln
        50                  55                  60

Lys Pro Gly Lys Ala Pro Lys Leu Leu Ile Ser Glu Gly Asn Thr Leu
65                  70                  75                  80

Arg Pro Gly Val Pro Ser Arg Phe Ser Gly Ser Gly Tyr Gly Thr Asp
                85                  90                  95

Phe Thr Leu Thr Ile Ser Ser Leu Gln Pro Glu Asp Val Ala Thr Tyr
                100                 105                 110

Tyr Cys Phe Gln Ser Asp Asn Leu Pro Tyr Thr Phe Gly Gln Gly Thr
        115                 120                 125

Lys Val Glu Ile Lys Gly Gly Gly Ser Gly Gly Gly Gly Ser Gly
130                 135                 140

Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Asp Thr
                165                 170                 175

Phe Thr Thr Tyr Val Ile His Trp Met Arg Gln Ala Pro Gly Gln Gly
                180                 185                 190

Leu Glu Trp Ile Gly Tyr Ile Asn Pro Tyr Asn Asp Gly Thr Lys Tyr
                195                 200                 205

Asn Glu Lys Phe Lys Gly Arg Val Thr Ile Thr Ser Asp Lys Ser Thr
        210                 215                 220

Ser Thr Ala Tyr Met Glu Leu Ser Ser Leu Arg Ser Glu Asp Thr Ala
225                 230                 235                 240

Val Tyr Tyr Cys Ala Arg Ile Tyr Tyr Asp Tyr Asp Gly Asp Tyr Trp
                245                 250                 255

Gly Gln Gly Thr Leu Val Thr Val Ser Ser Ala Ala Ala Pro Asp Val
                260                 265                 270

Gln Asp Cys Pro Glu Cys Thr Leu Gln Glu Asn Pro Phe Phe Ser Gln
        275                 280                 285

Pro Gly Ala Pro Ile Leu Gln Cys Met Gly Cys Cys Phe Ser Arg Ala
        290                 295                 300

Tyr Pro Thr Pro Leu Arg Ser Lys Lys Thr Met Leu Val Gln Lys Asn
305                 310                 315                 320

Val Thr Ser Glu Ser Thr Cys Cys Val Ala Lys Ser Tyr Asn Arg Val
                325                 330                 335

Thr Val Met Gly Gly Phe Lys Val Glu Asn His Thr Ala Cys His Cys
                340                 345                 350

Ser Thr Cys Gly Gly Gly Ser Gly Gly Gly Gly Ser Gly Gly Gly
        355                 360                 365
```

Gly Ser Gly Gly Gly Ser Leu Glu Ala Asp Ile Leu Met Thr Gln
        370             375                 380

Ser Pro Ser Ser Met Ser Val Ser Leu Gly Asp Thr Val Ser Ile Thr
385                 390                 395                 400

Cys His Ser Ser Gln Asp Ile Asn Ser Asn Ile Gly Trp Leu Gln Gln
                405                 410                 415

Arg Pro Gly Lys Ser Phe Lys Gly Leu Ile Tyr His Gly Thr Asn Leu
            420                 425                 430

Asp Asp Glu Val Pro Ser Arg Phe Ser Gly Ser Gly Ser Gly Ala Asp
            435                 440                 445

Tyr Ser Leu Thr Ile Ser Ser Leu Glu Ser Glu Asp Phe Ala Asp Tyr
        450                 455                 460

Tyr Cys Val Gln Tyr Ala Gln Phe Pro Trp Thr Phe Gly Gly Gly Thr
465                 470                 475                 480

Lys Leu Glu Ile Lys Arg Gly Gly Gly Ser Gly Gly Gly Gly Ser
                485                 490                 495

Gly Gly Gly Gly Ser Asp Val Gln Leu Gln Glu Ser Gly Pro Ser Leu
            500                 505                 510

Val Lys Pro Ser Gln Ser Leu Ser Leu Thr Cys Thr Val Thr Gly Tyr
        515                 520                 525

Ser Ile Thr Ser Asp Phe Ala Trp Asn Trp Ile Arg Gln Phe Pro Gly
        530                 535                 540

Asn Lys Leu Glu Trp Met Gly Tyr Ile Ser Tyr Ser Gly Asn Thr Arg
545                 550                 555                 560

Tyr Asn Pro Ser Leu Lys Ser Arg Ile Ser Ile Thr Arg Asp Thr Ser
                565                 570                 575

Lys Asn Gln Phe Phe Leu Gln Leu Asn Ser Val Thr Ile Glu Asp Thr
            580                 585                 590

Ala Thr Tyr Tyr Cys Val Thr Ala Gly Arg Gly Phe Pro Tyr Trp Gly
        595                 600                 605

Gln Gly Thr Leu Val Thr Val Ser Ala
    610                 615

<210> SEQ ID NO 80
<211> LENGTH: 656
<212> TYPE: PRT
<213> ORGANISM: Artificial
<220> FEATURE:
<223> OTHER INFORMATION: V2 LH beta

<400> SEQUENCE: 80

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Gln Met Thr Gln
                20                  25                  30

Ser Pro Ser Ser Leu Ser Ala Ser Val Gly Asp Arg Val Thr Ile Thr
            35                  40                  45

Cys Ile Thr Ser Asn Asp Ile Asp Asp Asp Met Asn Trp Tyr Gln Gln
        50                  55                  60

Lys Pro Gly Lys Ala Pro Lys Leu Leu Ile Ser Glu Gly Asn Thr Leu
65                  70                  75                  80

Arg Pro Gly Val Pro Ser Arg Phe Ser Gly Ser Gly Tyr Gly Thr Asp
                85                  90                  95

Phe Thr Leu Thr Ile Ser Ser Leu Gln Pro Glu Asp Val Ala Thr Tyr
            100                 105                 110

-continued

```
Tyr Cys Phe Gln Ser Asp Asn Leu Pro Tyr Thr Phe Gly Gln Gly Thr
        115                 120                 125
Lys Val Glu Ile Lys Gly Gly Gly Ser Gly Gly Gly Ser Gly
130                 135                 140
Gly Gly Gly Ser Glu Val Gln Leu Val Gln Ser Gly Ala Glu Val Lys
145                 150                 155                 160
Lys Pro Gly Ala Ser Val Lys Val Ser Cys Lys Ala Ser Gly Asp Thr
                    165                 170                 175
Phe Thr Thr Tyr Val Ile His Trp Met Arg Gln Ala Pro Gly Gln Gly
                180                 185                 190
Leu Glu Trp Ile Gly Tyr Ile Asn Pro Tyr Asn Asp Gly Thr Lys Tyr
            195                 200                 205
Asn Glu Lys Phe Lys Gly Arg Val Thr Ile Thr Ser Asp Lys Ser Thr
210                 215                 220
Ser Thr Ala Tyr Met Glu Leu Ser Ser Leu Arg Ser Glu Asp Thr Ala
225                 230                 235                 240
Val Tyr Tyr Cys Ala Arg Ile Tyr Tyr Asp Tyr Asp Gly Asp Tyr Trp
                245                 250                 255
Gly Gln Gly Thr Leu Val Thr Val Ser Ser Ala Ala Ser Lys Glu
                260                 265                 270
Pro Leu Arg Pro Arg Cys Arg Pro Ile Asn Ala Thr Leu Ala Val Glu
            275                 280                 285
Lys Glu Gly Cys Pro Val Cys Ile Thr Val Asn Thr Thr Ile Cys Ala
290                 295                 300
Gly Tyr Cys Pro Thr Met Thr Arg Val Leu Gln Gly Val Leu Pro Ala
305                 310                 315                 320
Leu Pro Gln Val Val Cys Asn Tyr Arg Asp Val Arg Phe Glu Ser Ile
                325                 330                 335
Arg Leu Pro Gly Cys Pro Arg Gly Val Asn Pro Val Val Ser Tyr Ala
                340                 345                 350
Val Ala Leu Ser Cys Gln Cys Ala Leu Cys Arg Arg Ser Thr Thr Asp
            355                 360                 365
Cys Gly Gly Pro Lys Asp His Pro Leu Thr Cys Asp Asp Pro Arg Phe
370                 375                 380
Gln Asp Ser Ser Ser Lys Ala Pro Pro Pro Ser Leu Pro Ser Pro
385                 390                 395                 400
Ser Arg Leu Pro Gly Pro Ser Asp Thr Pro Ile Leu Pro Gln Leu Glu
                405                 410                 415
Ala Asp Ile Leu Met Thr Gln Ser Pro Ser Ser Met Ser Val Ser Leu
                420                 425                 430
Gly Asp Thr Val Ser Ile Thr Cys His Ser Ser Gln Asp Ile Asn Ser
            435                 440                 445
Asn Ile Gly Trp Leu Gln Gln Arg Pro Gly Lys Ser Phe Lys Gly Leu
450                 455                 460
Ile Tyr His Gly Thr Asn Leu Asp Asp Glu Val Pro Ser Arg Phe Ser
465                 470                 475                 480
Gly Ser Gly Ser Gly Ala Asp Tyr Ser Leu Thr Ile Ser Ser Leu Glu
                485                 490                 495
Ser Glu Asp Phe Ala Asp Tyr Tyr Cys Val Gln Tyr Ala Gln Phe Pro
                500                 505                 510
Trp Thr Phe Gly Gly Gly Thr Lys Leu Glu Ile Lys Arg Gly Gly Gly
            515                 520                 525
Gly Ser Gly Gly Gly Gly Ser Gly Gly Gly Gly Ser Asp Val Gln Leu
```

```
                530                 535                 540
Gln Glu Ser Gly Pro Ser Leu Val Lys Pro Ser Gln Ser Leu Ser Leu
545                 550                 555                 560

Thr Cys Thr Val Thr Gly Tyr Ser Ile Thr Ser Asp Phe Ala Trp Asn
                565                 570                 575

Trp Ile Arg Gln Phe Pro Gly Asn Lys Leu Glu Trp Met Gly Tyr Ile
            580                 585                 590

Ser Tyr Ser Gly Asn Thr Arg Tyr Asn Pro Ser Leu Lys Ser Arg Ile
        595                 600                 605

Ser Ile Thr Arg Asp Thr Ser Lys Asn Gln Phe Phe Leu Gln Leu Asn
    610                 615                 620

Ser Val Thr Ile Glu Asp Thr Ala Thr Tyr Tyr Cys Val Thr Ala Gly
625                 630                 635                 640

Arg Gly Phe Pro Tyr Trp Gly Gln Gly Thr Leu Val Thr Val Ser Ala
                645                 650                 655

<210> SEQ ID NO 81
<211> LENGTH: 616
<212> TYPE: PRT
<213> ORGANISM: Artificial
<220> FEATURE:
<223> OTHER INFORMATION: Tom alpha

<400> SEQUENCE: 81

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Ile Leu Met Thr Gln
                20                  25                  30

Ser Pro Ser Ser Met Ser Val Ser Leu Gly Asp Thr Val Ser Ile Thr
            35                  40                  45

Cys His Ser Ser Gln Asp Ile Asn Ser Asn Ile Gly Trp Leu Gln Gln
        50                  55                  60

Arg Pro Gly Lys Ser Phe Lys Gly Leu Ile Tyr His Gly Thr Asn Leu
65                  70                  75                  80

Asp Asp Glu Val Pro Ser Arg Phe Ser Gly Ser Gly Ser Gly Ala Asp
                85                  90                  95

Tyr Ser Leu Thr Ile Ser Ser Leu Glu Ser Glu Asp Phe Ala Asp Tyr
            100                 105                 110

Tyr Cys Val Gln Tyr Ala Gln Phe Pro Trp Thr Phe Gly Gly Gly Thr
        115                 120                 125

Lys Leu Glu Ile Lys Arg Gly Gly Gly Gly Ser Gly Gly Gly Gly Ser
    130                 135                 140

Gly Gly Gly Gly Ser Asp Val Gln Leu Gln Glu Ser Gly Pro Ser Leu
145                 150                 155                 160

Val Lys Pro Ser Gln Ser Leu Ser Leu Thr Cys Thr Val Thr Gly Tyr
                165                 170                 175

Ser Ile Thr Ser Asp Phe Ala Trp Asn Trp Ile Arg Gln Phe Pro Gly
            180                 185                 190

Asn Lys Leu Glu Trp Met Gly Tyr Ile Ser Tyr Ser Gly Asn Thr Arg
        195                 200                 205

Tyr Asn Pro Ser Leu Lys Ser Arg Ile Ser Ile Thr Arg Asp Thr Ser
    210                 215                 220

Lys Asn Gln Phe Phe Leu Gln Leu Asn Ser Val Thr Ile Glu Asp Thr
225                 230                 235                 240

Ala Thr Tyr Tyr Cys Val Thr Ala Gly Arg Gly Phe Pro Tyr Trp Gly
```

-continued

```
                245                 250                 255
Gln Gly Thr Leu Val Thr Val Ser Ala Ala Ala Pro Asp Val Gln
            260                 265                 270

Asp Cys Pro Glu Cys Thr Leu Gln Glu Asn Pro Phe Phe Ser Gln Pro
        275                 280                 285

Gly Ala Pro Ile Leu Gln Cys Met Gly Cys Cys Phe Ser Arg Ala Tyr
    290                 295                 300

Pro Thr Pro Leu Arg Ser Lys Lys Thr Met Leu Val Gln Lys Asn Val
305                 310                 315                 320

Thr Ser Glu Ser Thr Cys Cys Val Ala Lys Ser Tyr Asn Arg Val Thr
                325                 330                 335

Val Met Gly Gly Phe Lys Val Glu Asn His Thr Ala Cys His Cys Ser
            340                 345                 350

Thr Cys Gly Gly Gly Ser Gly Gly Gly Ser Gly Gly Gly Gly
        355                 360                 365

Ser Gly Gly Gly Ser Leu Asp Asp Ile Gln Met Thr Gln Ser Pro
    370                 375                 380

Ser Ser Leu Ser Ala Ser Val Gly Asp Arg Val Thr Ile Thr Cys Ile
385                 390                 395                 400

Thr Ser Asn Asp Ile Asp Asp Met Asn Trp Tyr Gln Gln Lys Pro
                405                 410                 415

Gly Lys Ala Pro Lys Leu Leu Ile Ser Glu Gly Asn Thr Leu Arg Pro
            420                 425                 430

Gly Val Pro Ser Arg Phe Ser Gly Ser Gly Tyr Gly Thr Asp Phe Thr
        435                 440                 445

Leu Thr Ile Ser Ser Leu Gln Pro Glu Asp Val Ala Thr Tyr Tyr Cys
    450                 455                 460

Phe Gln Ser Asp Asn Leu Pro Tyr Thr Phe Gly Gln Gly Thr Lys Val
465                 470                 475                 480

Glu Ile Lys Gly Gly Gly Gly Ser Gly Gly Gly Gly Ser Gly Gly Gly
                485                 490                 495

Gly Ser Glu Val Gln Leu Val Gln Ser Gly Ala Glu Val Lys Lys Pro
            500                 505                 510

Gly Ala Ser Val Lys Val Ser Cys Lys Ala Ser Gly Asp Thr Phe Thr
        515                 520                 525

Thr Tyr Val Ile His Trp Met Arg Gln Ala Pro Gly Gln Gly Leu Glu
    530                 535                 540

Trp Ile Gly Tyr Ile Asn Pro Tyr Asn Asp Gly Thr Lys Tyr Asn Glu
545                 550                 555                 560

Lys Phe Lys Gly Arg Val Thr Ile Thr Ser Asp Lys Ser Thr Ser Thr
                565                 570                 575

Ala Tyr Met Glu Leu Ser Ser Leu Arg Ser Glu Asp Thr Ala Val Tyr
            580                 585                 590

Tyr Cys Ala Arg Ile Tyr Tyr Asp Tyr Asp Gly Asp Tyr Trp Gly Gln
        595                 600                 605

Gly Thr Leu Val Thr Val Ser Ser
    610                 615
```

<210> SEQ ID NO 82
<211> LENGTH: 658
<212> TYPE: PRT
<213> ORGANISM: Artificial
<220> FEATURE:
<223> OTHER INFORMATION: Tom V2 LH

```
<400> SEQUENCE: 82

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gly Ser Ala Asp Ile Leu
            20                  25                  30

Met Thr Gln Ser Pro Ser Ser Met Ser Val Ser Leu Gly Asp Thr Val
        35                  40                  45

Ser Ile Thr Cys His Ser Ser Gln Asp Ile Asn Ser Asn Ile Gly Trp
    50                  55                  60

Leu Gln Gln Arg Pro Gly Lys Ser Phe Lys Gly Leu Ile Tyr His Gly
65                  70                  75                  80

Thr Asn Leu Asp Asp Glu Val Pro Ser Arg Phe Ser Gly Ser Gly Ser
                85                  90                  95

Gly Ala Asp Tyr Ser Leu Thr Ile Ser Ser Leu Glu Ser Glu Asp Phe
            100                 105                 110

Ala Asp Tyr Tyr Cys Val Gln Tyr Ala Gln Phe Pro Trp Thr Phe Gly
        115                 120                 125

Gly Gly Thr Lys Leu Glu Ile Lys Arg Gly Gly Gly Ser Gly Gly
    130                 135                 140

Gly Gly Ser Gly Gly Gly Ser Asp Val Gln Leu Gln Glu Ser Gly
145                 150                 155                 160

Pro Ser Leu Val Lys Pro Ser Gln Ser Leu Ser Leu Thr Cys Thr Val
                165                 170                 175

Thr Gly Tyr Ser Ile Thr Ser Asp Phe Ala Trp Asn Trp Ile Arg Gln
            180                 185                 190

Phe Pro Gly Asn Lys Leu Glu Trp Met Gly Tyr Ile Ser Tyr Ser Gly
        195                 200                 205

Asn Thr Arg Tyr Asn Pro Ser Leu Lys Ser Arg Ile Ser Ile Thr Arg
    210                 215                 220

Asp Thr Ser Lys Asn Gln Phe Phe Leu Gln Leu Asn Ser Val Thr Ile
225                 230                 235                 240

Glu Asp Thr Ala Thr Tyr Tyr Cys Val Thr Ala Gly Arg Gly Phe Pro
                245                 250                 255

Tyr Trp Gly Gln Gly Thr Leu Val Thr Val Ser Ala Ala Ala Ser
            260                 265                 270

Lys Glu Pro Leu Arg Pro Arg Cys Arg Pro Ile Asn Ala Thr Leu Ala
        275                 280                 285

Val Glu Lys Glu Gly Cys Pro Val Cys Ile Thr Val Asn Thr Thr Ile
    290                 295                 300

Cys Ala Gly Tyr Cys Pro Thr Met Thr Arg Val Leu Gln Gly Val Leu
305                 310                 315                 320

Pro Ala Leu Pro Gln Val Val Cys Asn Tyr Arg Asp Val Arg Phe Glu
                325                 330                 335

Ser Ile Arg Leu Pro Gly Cys Pro Arg Gly Val Asn Pro Val Val Ser
            340                 345                 350

Tyr Ala Val Ala Leu Ser Cys Gln Cys Ala Leu Cys Arg Arg Ser Thr
        355                 360                 365

Thr Asp Cys Gly Gly Pro Lys Asp His Pro Leu Thr Cys Asp Asp Pro
    370                 375                 380

Arg Phe Gln Asp Ser Ser Ser Lys Ala Pro Pro Pro Ser Leu Pro
385                 390                 395                 400

Ser Pro Ser Arg Leu Pro Gly Pro Ser Asp Thr Pro Ile Leu Pro Gln
                405                 410                 415
```

-continued

Leu Asp Asp Ile Gln Met Thr Gln Ser Pro Ser Ser Leu Ser Ala Ser
                420                 425                 430

Val Gly Asp Arg Val Thr Ile Thr Cys Ile Thr Ser Asn Asp Ile Asp
            435                 440                 445

Asp Asp Met Asn Trp Tyr Gln Gln Lys Pro Gly Lys Ala Pro Lys Leu
        450                 455                 460

Leu Ile Ser Glu Gly Asn Thr Leu Arg Pro Gly Val Pro Ser Arg Phe
465                 470                 475                 480

Ser Gly Ser Gly Tyr Gly Thr Asp Phe Thr Leu Thr Ile Ser Ser Leu
                485                 490                 495

Gln Pro Glu Asp Val Ala Thr Tyr Tyr Cys Phe Gln Ser Asp Asn Leu
            500                 505                 510

Pro Tyr Thr Phe Gly Gln Gly Thr Lys Val Glu Ile Lys Gly Gly Gly
        515                 520                 525

Gly Ser Gly Gly Gly Gly Ser Gly Gly Gly Gly Ser Glu Val Gln Leu
    530                 535                 540

Val Gln Ser Gly Ala Glu Val Lys Lys Pro Gly Ala Ser Val Lys Val
545                 550                 555                 560

Ser Cys Lys Ala Ser Gly Asp Thr Phe Thr Thr Tyr Val Ile His Trp
                565                 570                 575

Met Arg Gln Ala Pro Gly Gln Gly Leu Glu Trp Ile Gly Tyr Ile Asn
            580                 585                 590

Pro Tyr Asn Asp Gly Thr Lys Tyr Asn Glu Lys Phe Lys Gly Arg Val
        595                 600                 605

Thr Ile Thr Ser Asp Lys Ser Thr Ser Thr Ala Tyr Met Glu Leu Ser
    610                 615                 620

Ser Leu Arg Ser Glu Asp Thr Ala Val Tyr Tyr Cys Ala Arg Ile Tyr
625                 630                 635                 640

Tyr Asp Tyr Asp Gly Asp Tyr Trp Gly Gln Gly Thr Leu Val Thr Val
                645                 650                 655

Ser Ser

<210> SEQ ID NO 83
<211> LENGTH: 356
<212> TYPE: PRT
<213> ORGANISM: Artificial
<220> FEATURE:
<223> OTHER INFORMATION: EGFR alpha

<400> SEQUENCE: 83

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Val Gln Leu Val Gln
            20                  25                  30

Ser Gly Ala Glu Val Lys Lys Pro Gly Ala Ser Val Lys Val Ser Cys
        35                  40                  45

Lys Ala Ser Gly Phe Ser Leu Thr Asn Tyr Gly Val His Trp Met Arg
    50                  55                  60

Gln Ala Pro Gly Gln Gly Leu Glu Trp Ile Gly Val Ile Trp Ser Gly
65                  70                  75                  80

Gly Asn Thr Asp Tyr Asn Thr Pro Phe Thr Ser Arg Val Thr Ile Thr
                85                  90                  95

Ser Asp Lys Ser Thr Ser Thr Ala Tyr Met Glu Leu Ser Ser Leu Arg
            100                 105                 110

```
Ser Glu Asp Thr Ala Val Tyr Tyr Cys Ala Arg Ala Leu Thr Tyr Tyr
        115                 120                 125

Asp Tyr Glu Phe Ala Tyr Trp Gly Gln Gly Thr Leu Val Thr Val Ser
        130                 135                 140

Ser Gly Gly Gly Gly Ser Gly Gly Gly Ser Gly Gly Gly Gly Ser
145                 150                 155                 160

Asp Ile Gln Met Thr Gln Ser Pro Ser Ser Leu Ser Ala Ser Val Gly
                    165                 170                 175

Asp Arg Val Thr Ile Thr Cys Arg Ala Ser Gln Ser Ile Gly Thr Asn
            180                 185                 190

Ile His Trp Tyr Gln Gln Lys Pro Gly Lys Ala Pro Lys Leu Leu Ile
        195                 200                 205

Lys Tyr Ala Ser Glu Ser Ile Ser Gly Val Pro Ser Arg Phe Ser Gly
210                 215                 220

Ser Gly Tyr Gly Thr Asp Phe Thr Leu Thr Ile Ser Ser Leu Gln Pro
225                 230                 235                 240

Glu Asp Val Ala Thr Tyr Tyr Cys Gln Gln Asn Asn Asn Trp Pro Thr
                    245                 250                 255

Thr Phe Gly Gln Gly Thr Lys Val Glu Ile Lys Ala Ala Ala Pro Asp
            260                 265                 270

Val Gln Asp Cys Pro Glu Cys Thr Leu Gln Glu Asn Pro Phe Phe Ser
        275                 280                 285

Gln Pro Gly Ala Pro Ile Leu Gln Cys Met Gly Cys Cys Phe Ser Arg
290                 295                 300

Ala Tyr Pro Thr Pro Leu Arg Ser Lys Lys Thr Met Leu Val Gln Lys
305                 310                 315                 320

Asn Val Thr Ser Glu Ser Thr Cys Cys Val Ala Lys Ser Tyr Asn Arg
                    325                 330                 335

Val Thr Val Met Gly Gly Phe Lys Val Glu Asn His Thr Ala Cys His
            340                 345                 350

Cys Ser Thr Cys
        355

<210> SEQ ID NO 84
<211> LENGTH: 415
<212> TYPE: PRT
<213> ORGANISM: Artificial
<220> FEATURE:
<223> OTHER INFORMATION: EGFR beta

<400> SEQUENCE: 84

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Val Gln Leu Val Gln
            20                  25                  30

Ser Gly Ala Glu Val Lys Lys Pro Gly Ala Ser Val Lys Val Ser Cys
        35                  40                  45

Lys Ala Ser Gly Phe Ser Leu Thr Asn Tyr Gly Val His Trp Met Arg
    50                  55                  60

Gln Ala Pro Gly Gln Gly Leu Glu Trp Ile Gly Val Ile Trp Ser Gly
65                  70                  75                  80

Gly Asn Thr Asp Tyr Asn Thr Pro Phe Thr Ser Arg Val Thr Ile Thr
                85                  90                  95

Ser Asp Lys Ser Thr Ser Thr Ala Tyr Met Glu Leu Ser Ser Leu Arg
            100                 105                 110
```

```
Ser Glu Asp Thr Ala Val Tyr Tyr Cys Ala Arg Ala Leu Thr Tyr Tyr
        115                 120                 125

Asp Tyr Glu Phe Ala Tyr Trp Gly Gln Gly Thr Leu Val Thr Val Ser
        130                 135                 140

Ser Gly Gly Gly Gly Ser Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Thr Cys Arg Ala Ser Gln Ser Ile Gly Thr Asn
            180                 185                 190

Ile His Trp Tyr Gln Gln Lys Pro Gly Lys Ala Pro Lys Leu Leu Ile
        195                 200                 205

Lys Tyr Ala Ser Glu Ser Ile Ser Gly Val Pro Ser Arg Phe Ser Gly
    210                 215                 220

Ser Gly Tyr Gly Thr Asp Phe Thr Leu Thr Ile Ser Ser Leu Gln Pro
225                 230                 235                 240

Glu Asp Val Ala Thr Tyr Tyr Cys Gln Gln Asn Asn Asn Trp Pro Thr
                245                 250                 255

Thr Phe Gly Gln Gly Thr Lys Val Glu Ile Lys Ala Ala Ala Ser Lys
            260                 265                 270

Glu Pro Leu Arg Pro Arg Cys Arg Pro Ile Asn Ala Thr Leu Ala Val
        275                 280                 285

Glu Lys Glu Gly Cys Pro Val Cys Ile Thr Val Asn Thr Thr Ile Cys
    290                 295                 300

Ala Gly Tyr Cys Pro Thr Met Thr Arg Val Leu Gln Gly Val Leu Pro
305                 310                 315                 320

Ala Leu Pro Gln Val Val Cys Asn Tyr Arg Asp Val Arg Phe Glu Ser
                325                 330                 335

Ile Arg Leu Pro Gly Cys Pro Arg Gly Val Asn Pro Val Val Ser Tyr
            340                 345                 350

Ala Val Ala Leu Ser Cys Gln Cys Ala Leu Cys Arg Arg Ser Thr Thr
        355                 360                 365

Asp Cys Gly Gly Pro Lys Asp His Pro Leu Thr Cys Asp Asp Pro Arg
    370                 375                 380

Phe Gln Asp Ser Ser Ser Lys Ala Pro Pro Pro Ser Leu Pro Ser
385                 390                 395                 400

Pro Ser Arg Leu Pro Gly Pro Ser Asp Thr Pro Ile Leu Pro Gln
                405                 410                 415

<210> SEQ ID NO 85
<211> LENGTH: 618
<212> TYPE: PRT
<213> ORGANISM: Artificial
<220> FEATURE:
<223> OTHER INFORMATION: EGFR alpha V

<400> SEQUENCE: 85

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Val Gln Leu Val Gln
                20                  25                  30

Ser Gly Ala Glu Val Lys Lys Pro Gly Ala Ser Val Lys Val Ser Cys
            35                  40                  45

Lys Ala Ser Gly Phe Ser Leu Thr Asn Tyr Gly Val His Trp Met Arg
        50                  55                  60
```

-continued

```
Gln Ala Pro Gly Gln Gly Leu Glu Trp Ile Gly Val Ile Trp Ser Gly
 65                  70                  75                  80

Gly Asn Thr Asp Tyr Asn Thr Pro Phe Thr Ser Arg Val Thr Ile Thr
                 85                  90                  95

Ser Asp Lys Ser Thr Ser Thr Ala Tyr Met Glu Leu Ser Ser Leu Arg
            100                 105                 110

Ser Glu Asp Thr Ala Val Tyr Tyr Cys Ala Arg Ala Leu Thr Tyr Tyr
            115                 120                 125

Asp Tyr Glu Phe Ala Tyr Trp Gly Gln Gly Thr Leu Val Thr Val Ser
130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Ser Leu Ser Ala Ser Val Gly
                165                 170                 175

Asp Arg Val Thr Ile Thr Cys Arg Ala Ser Gln Ser Ile Gly Thr Asn
            180                 185                 190

Ile His Trp Tyr Gln Gln Lys Pro Gly Lys Ala Pro Lys Leu Leu Ile
            195                 200                 205

Lys Tyr Ala Ser Glu Ser Ile Ser Gly Val Pro Ser Arg Phe Ser Gly
210                 215                 220

Ser Gly Tyr Gly Thr Asp Phe Thr Leu Thr Ile Ser Ser Leu Gln Pro
225                 230                 235                 240

Glu Asp Val Ala Thr Tyr Tyr Cys Gln Gln Asn Asn Asn Trp Pro Thr
                245                 250                 255

Thr Phe Gly Gln Gly Thr Lys Val Glu Ile Lys Ala Ala Ala Pro Asp
            260                 265                 270

Val Gln Asp Cys Pro Glu Cys Thr Leu Gln Glu Asn Pro Phe Phe Ser
            275                 280                 285

Gln Pro Gly Ala Pro Ile Leu Gln Cys Met Gly Cys Cys Phe Ser Arg
290                 295                 300

Ala Tyr Pro Thr Pro Leu Arg Ser Lys Lys Thr Met Leu Val Gln Lys
305                 310                 315                 320

Asn Val Thr Ser Glu Ser Thr Cys Cys Val Ala Lys Ser Tyr Asn Arg
                325                 330                 335

Val Thr Val Met Gly Gly Phe Lys Val Glu Asn His Thr Ala Cys His
            340                 345                 350

Cys Ser Thr Cys Gly Gly Gly Ser Gly Gly Gly Ser Gly Gly
            355                 360                 365

Gly Gly Ser Gly Gly Gly Ser Leu Asp Asp Ile Gln Met Thr Gln
            370                 375                 380

Ser Pro Ser Ser Leu Ser Ala Ser Val Gly Asp Arg Val Thr Ile Thr
385                 390                 395                 400

Cys Ile Thr Ser Asn Asp Ile Asp Asp Met Asn Trp Tyr Gln Gln
            405                 410                 415

Lys Pro Gly Lys Ala Pro Lys Leu Leu Ile Ser Glu Gly Asn Thr Leu
            420                 425                 430

Arg Pro Gly Val Pro Ser Arg Phe Ser Gly Ser Gly Tyr Gly Thr Asp
            435                 440                 445

Phe Thr Leu Thr Ile Ser Ser Leu Gln Pro Glu Asp Val Ala Thr Tyr
            450                 455                 460

Tyr Cys Phe Gln Ser Asp Asn Leu Pro Tyr Thr Phe Gly Gln Gly Thr
465                 470                 475                 480

Lys Val Glu Ile Lys Gly Gly Gly Gly Ser Gly Gly Gly Gly Ser Gly
```

```
                     485                 490                 495
Gly Gly Gly Ser Glu Val Gln Leu Val Gln Ser Gly Ala Glu Val Lys
            500                 505                 510
Lys Pro Gly Ala Ser Val Lys Val Ser Cys Lys Ala Ser Gly Asp Thr
            515                 520                 525
Phe Thr Thr Tyr Val Ile His Trp Met Arg Gln Ala Pro Gly Gln Gly
            530                 535                 540
Leu Glu Trp Ile Gly Tyr Ile Asn Pro Tyr Asn Asp Gly Thr Lys Tyr
545                 550                 555                 560
Asn Glu Lys Phe Lys Gly Arg Val Thr Ile Thr Ser Asp Lys Ser Thr
                565                 570                 575
Ser Thr Ala Tyr Met Glu Leu Ser Ser Leu Arg Ser Glu Asp Thr Ala
            580                 585                 590
Val Tyr Tyr Cys Ala Arg Ile Tyr Tyr Asp Tyr Asp Gly Asp Tyr Trp
            595                 600                 605
Gly Gln Gly Thr Leu Val Thr Val Ser Ser
            610                 615

<210> SEQ ID NO 86
<211> LENGTH: 657
<212> TYPE: PRT
<213> ORGANISM: Artificial
<220> FEATURE:
<223> OTHER INFORMATION: EGFR beta V2

<400> SEQUENCE: 86

Met Ala Thr Gly Ser Arg Thr Ser Leu Leu Leu Ala Phe Gly Leu Leu
1               5                   10                  15
Cys Leu Pro Trp Leu Gln Glu Gly Ser Ala Glu Val Gln Leu Val Gln
            20                  25                  30
Ser Gly Ala Glu Val Lys Lys Pro Gly Ala Ser Val Lys Val Ser Cys
        35                  40                  45
Lys Ala Ser Gly Phe Ser Leu Thr Asn Tyr Gly Val His Trp Met Arg
    50                  55                  60
Gln Ala Pro Gly Gln Gly Leu Glu Trp Ile Gly Val Ile Trp Ser Gly
65                  70                  75                  80
Gly Asn Thr Asp Tyr Asn Thr Pro Phe Thr Ser Arg Val Thr Ile Thr
                85                  90                  95
Ser Asp Lys Ser Thr Ser Thr Ala Tyr Met Glu Leu Ser Ser Leu Arg
            100                 105                 110
Ser Glu Asp Thr Ala Val Tyr Tyr Cys Ala Arg Ala Leu Thr Tyr Tyr
        115                 120                 125
Asp Tyr Glu Phe Ala Tyr Trp Gly Gln Gly Thr Leu Val Thr Val Ser
    130                 135                 140
Ser Gly Gly Gly Ser Gly Gly Gly Ser Gly Gly Gly Ser
145                 150                 155                 160
Asp Ile Gln Met Thr Gln Ser Pro Ser Ser Leu Ser Ala Ser Val Gly
                165                 170                 175
Asp Arg Val Thr Ile Thr Cys Arg Ala Ser Gln Ser Ile Gly Thr Asn
            180                 185                 190
Ile His Trp Tyr Gln Gln Lys Pro Gly Lys Ala Pro Lys Leu Leu Ile
        195                 200                 205
Lys Tyr Ala Ser Glu Ser Ile Ser Gly Val Pro Ser Arg Phe Ser Gly
    210                 215                 220
Ser Gly Tyr Gly Thr Asp Phe Thr Leu Thr Ile Ser Ser Leu Gln Pro
```

-continued

```
           225                 230                 235                 240

Glu Asp Val Ala Thr Tyr Tyr Cys Gln Gln Asn Asn Asn Trp Pro Thr
                245                 250                 255

Thr Phe Gly Gln Gly Thr Lys Val Glu Ile Lys Ala Ala Ala Ser Lys
                260                 265                 270

Glu Pro Leu Arg Pro Arg Cys Arg Pro Ile Asn Ala Thr Leu Ala Val
                275                 280                 285

Glu Lys Glu Gly Cys Pro Val Cys Ile Thr Val Asn Thr Thr Ile Cys
                290                 295                 300

Ala Gly Tyr Cys Pro Thr Met Thr Arg Val Leu Gln Gly Val Leu Pro
305                 310                 315                 320

Ala Leu Pro Gln Val Val Cys Asn Tyr Arg Asp Val Arg Phe Glu Ser
                325                 330                 335

Ile Arg Leu Pro Gly Cys Pro Arg Gly Val Asn Pro Val Val Ser Tyr
                340                 345                 350

Ala Val Ala Leu Ser Cys Gln Cys Ala Leu Cys Arg Arg Ser Thr Thr
                355                 360                 365

Asp Cys Gly Gly Pro Lys Asp His Pro Leu Thr Cys Asp Asp Pro Arg
370                 375                 380

Phe Gln Asp Ser Ser Ser Lys Ala Pro Pro Ser Leu Pro Ser
385                 390                 395                 400

Pro Ser Arg Leu Pro Gly Pro Ser Asp Thr Pro Ile Leu Pro Gln Leu
                405                 410                 415

Asp Asp Ile Gln Met Thr Gln Ser Pro Ser Ser Leu Ser Ala Ser Val
                420                 425                 430

Gly Asp Arg Val Thr Ile Thr Cys Ile Thr Ser Asn Asp Ile Asp Asp
                435                 440                 445

Asp Met Asn Trp Tyr Gln Gln Lys Pro Gly Lys Ala Pro Lys Leu Leu
                450                 455                 460

Ile Ser Glu Gly Asn Thr Leu Arg Pro Gly Val Pro Ser Arg Phe Ser
465                 470                 475                 480

Gly Ser Gly Tyr Gly Thr Asp Phe Thr Leu Thr Ile Ser Ser Leu Gln
                485                 490                 495

Pro Glu Asp Val Ala Thr Tyr Tyr Cys Phe Gln Ser Asp Asn Leu Pro
                500                 505                 510

Tyr Thr Phe Gly Gln Gly Thr Lys Val Glu Ile Lys Gly Gly Gly Gly
                515                 520                 525

Ser Gly Gly Gly Gly Ser Gly Gly Gly Gly Ser Glu Val Gln Leu Val
                530                 535                 540

Gln Ser Gly Ala Glu Val Lys Lys Pro Gly Ala Ser Val Lys Val Ser
545                 550                 555                 560

Cys Lys Ala Ser Gly Asp Thr Phe Thr Thr Tyr Val Ile His Trp Met
                565                 570                 575

Arg Gln Ala Pro Gly Gln Gly Leu Glu Trp Ile Gly Tyr Ile Asn Pro
                580                 585                 590

Tyr Asn Asp Gly Thr Lys Tyr Asn Glu Lys Phe Lys Gly Arg Val Thr
                595                 600                 605

Ile Thr Ser Asp Lys Ser Thr Ser Thr Ala Tyr Met Glu Leu Ser Ser
                610                 615                 620

Leu Arg Ser Glu Asp Thr Ala Val Tyr Tyr Cys Ala Arg Ile Tyr Tyr
625                 630                 635                 640

Asp Tyr Asp Gly Asp Tyr Trp Gly Gln Gly Thr Leu Val Thr Val Ser
                645                 650                 655
```

Ser

<210> SEQ ID NO 87
<211> LENGTH: 369
<212> TYPE: PRT
<213> ORGANISM: Artificial
<220> FEATURE:
<223> OTHER INFORMATION: A12 alpha

<400> SEQUENCE: 87

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Glu Leu Thr Gln
            20                  25                  30

Asp Pro Ala Val Ser Val Ala Leu Gly Gln Thr Val Arg Ile Thr Cys
        35                  40                  45

Gln Gly Asp Ser Leu Arg Ser Tyr Tyr Ala Thr Trp Tyr Gln Gln Lys
    50                  55                  60

Pro Gly Gln Ala Pro Ile Leu Val Ile Tyr Gly Glu Asn Lys Arg Pro
65                  70                  75                  80

Ser Gly Ile Pro Asp Arg Phe Ser Gly Ser Ser Ser Gly Asn Thr Ala
                85                  90                  95

Ser Leu Thr Ile Thr Gly Ala Gln Ala Glu Asp Glu Ala Asp Tyr Tyr
            100                 105                 110

Cys Lys Ser Arg Asp Gly Ser Gly Gln His Leu Val Phe Gly Gly Gly
        115                 120                 125

Thr Lys Leu Thr Val Leu Gly Gly Gly Gly Ser Gly Gly Gly Gly
    130                 135                 140

Ser Gly Gly Gly Gly Ser Glu Val Gln Leu Val Gln Ser Gly Ala Glu
145                 150                 155                 160

Val Lys Lys Pro Gly Ser Ser Val Lys Val Ser Cys Lys Ala Ser Gly
                165                 170                 175

Gly Thr Phe Ser Ser Tyr Ala Ile Ser Trp Val Arg Gln Ala Pro Gly
            180                 185                 190

Gln Gly Leu Glu Trp Met Gly Gly Ile Ile Pro Ile Phe Gly Thr Ala
        195                 200                 205

Asn Tyr Ala Gln Lys Phe Gln Gly Arg Val Thr Ile Thr Ala Asp Lys
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Ala Pro Leu Arg Phe Leu Glu Trp
                245                 250                 255

Ser Thr Gln Asp His Tyr Tyr Tyr Tyr Met Asp Val Trp Gly Lys
            260                 265                 270

Gly Thr Thr Val Thr Val Ser Ser Ala Ala Pro Asp Val Gln Asp
        275                 280                 285

Cys Pro Glu Cys Thr Leu Gln Glu Asn Pro Phe Phe Ser Gln Pro Gly
    290                 295                 300

Ala Pro Ile Leu Gln Cys Met Gly Cys Cys Phe Ser Arg Ala Tyr Pro
305                 310                 315                 320

Thr Pro Leu Arg Ser Lys Lys Thr Met Leu Val Gln Lys Asn Val Thr
                325                 330                 335

Ser Glu Ser Thr Cys Cys Val Ala Lys Ser Tyr Asn Arg Val Thr Val
            340                 345                 350
```

```
Met Gly Gly Phe Lys Val Glu Asn His Thr Ala Cys His Cys Ser Thr
        355                 360                 365
Cys

<210> SEQ ID NO 88
<211> LENGTH: 428
<212> TYPE: PRT
<213> ORGANISM: Artificial
<220> FEATURE:
<223> OTHER INFORMATION: A12 LH beta

<400> SEQUENCE: 88

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Glu Leu Thr Gln
            20                  25                  30

Asp Pro Ala Val Ser Val Ala Leu Gly Gln Thr Val Arg Ile Thr Cys
        35                  40                  45

Gln Gly Asp Ser Leu Arg Ser Tyr Tyr Ala Thr Trp Tyr Gln Gln Lys
    50                  55                  60

Pro Gly Gln Ala Pro Ile Leu Val Ile Tyr Gly Glu Asn Lys Arg Pro
65                  70                  75                  80

Ser Gly Ile Pro Asp Arg Phe Ser Gly Ser Ser Ser Gly Asn Thr Ala
                85                  90                  95

Ser Leu Thr Ile Thr Gly Ala Gln Ala Glu Asp Glu Ala Asp Tyr Tyr
            100                 105                 110

Cys Lys Ser Arg Asp Gly Ser Gly Gln His Leu Val Phe Gly Gly Gly
        115                 120                 125

Thr Lys Leu Thr Val Leu Gly Gly Gly Gly Ser Gly Gly Gly Gly
    130                 135                 140

Ser Gly Gly Gly Gly Ser Glu Val Gln Leu Val Gln Ser Gly Ala Glu
145                 150                 155                 160

Val Lys Lys Pro Gly Ser Ser Val Lys Val Ser Cys Lys Ala Ser Gly
                165                 170                 175

Gly Thr Phe Ser Ser Tyr Ala Ile Ser Trp Val Arg Gln Ala Pro Gly
            180                 185                 190

Gln Gly Leu Glu Trp Met Gly Gly Ile Ile Pro Ile Phe Gly Thr Ala
        195                 200                 205

Asn Tyr Ala Gln Lys Phe Gln Gly Arg Val Thr Ile Thr Ala Asp Lys
    210                 215                 220

Ser Thr Ser Thr Ala Tyr Met Glu Leu Ser Ser Leu Arg Ser Glu Asp
225                 230                 235                 240

Thr Ala Val Tyr Tyr Cys Ala Arg Ala Pro Leu Arg Phe Leu Glu Trp
                245                 250                 255

Ser Thr Gln Asp His Tyr Tyr Tyr Tyr Met Asp Val Trp Gly Lys
            260                 265                 270

Gly Thr Thr Val Thr Val Ser Ser Ala Ala Ala Ser Lys Glu Pro Leu
        275                 280                 285

Arg Pro Arg Cys Arg Pro Ile Asn Ala Thr Leu Ala Val Glu Lys Glu
    290                 295                 300

Gly Cys Pro Val Cys Ile Thr Val Asn Thr Thr Ile Cys Ala Gly Tyr
305                 310                 315                 320

Cys Pro Thr Met Thr Arg Val Leu Gln Gly Val Leu Pro Ala Leu Pro
                325                 330                 335

Gln Val Val Cys Asn Tyr Arg Asp Val Arg Phe Glu Ser Ile Arg Leu
```

```
                    340                 345                 350
Pro Gly Cys Pro Arg Gly Val Asn Pro Val Ser Tyr Ala Val Ala
            355                 360                 365

Leu Ser Cys Gln Cys Ala Leu Cys Arg Arg Ser Thr Thr Asp Cys Gly
    370                 375                 380

Gly Pro Lys Asp His Pro Leu Thr Cys Asp Asp Pro Arg Phe Gln Asp
385                 390                 395                 400

Ser Ser Ser Ser Lys Ala Pro Pro Ser Leu Pro Ser Pro Ser Arg
                405                 410                 415

Leu Pro Gly Pro Ser Asp Thr Pro Ile Leu Pro Gln
            420                 425

<210> SEQ ID NO 89
<211> LENGTH: 367
<212> TYPE: PRT
<213> ORGANISM: Artificial
<220> FEATURE:
<223> OTHER INFORMATION: EM164 alpha

<400> SEQUENCE: 89

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Val Val Met Thr Gln
            20                  25                  30

Thr Pro Leu Ser Leu Pro Val Ser Leu Gly Asp Pro Ala Ser Ile Ser
        35                  40                  45

Cys Arg Ser Ser Gln Ser Ile Val His Ser Asn Val Asn Thr Tyr Leu
    50                  55                  60

Glu Trp Tyr Leu Gln Lys Pro Gly Gln Ser Pro Arg Leu Leu Ile Tyr
65                  70                  75                  80

Lys Val Ser Asn Arg Phe Ser Gly Val Pro Asp Arg Phe Ser Gly Ser
                85                  90                  95

Gly Ala Gly Thr Asp Phe Thr Leu Arg Ile Ser Arg Val Glu Ala Glu
            100                 105                 110

Asp Leu Gly Ile Tyr Tyr Cys Phe Gln Gly Ser His Val Pro Pro Thr
        115                 120                 125

Phe Gly Gly Gly Thr Lys Leu Glu Ile Lys Arg Gly Gly Gly Gly Ser
    130                 135                 140

Gly Gly Gly Gly Ser Gly Gly Gly Ser Gln Val Gln Leu Val Gln
145                 150                 155                 160

Ser Gly Ala Glu Val Val Lys Pro Gly Ala Ser Val Lys Leu Ser Cys
                165                 170                 175

Lys Ala Ser Gly Tyr Thr Phe Thr Ser Tyr Trp Met His Trp Val Lys
            180                 185                 190

Gln Arg Pro Gly Gln Gly Leu Glu Trp Ile Gly Glu Ile Asn Pro Ser
        195                 200                 205

Asn Gly Arg Thr Asn Tyr Asn Gln Lys Phe Gln Gly Lys Ala Thr Leu
    210                 215                 220

Thr Val Asp Lys Ser Ser Ser Thr Ala Tyr Met Gln Leu Ser Ser Leu
225                 230                 235                 240

Thr Ser Glu Asp Ser Ala Val Tyr Tyr Phe Ala Arg Gly Arg Pro Asp
                245                 250                 255

Tyr Tyr Gly Ser Ser Lys Trp Tyr Phe Asp Val Trp Gly Gln Gly Thr
            260                 265                 270

Thr Val Thr Val Ser Ser Ala Ala Ala Pro Asp Val Gln Asp Cys Pro
```

```
                275                 280                 285
Glu Cys Thr Leu Gln Glu Asn Pro Phe Phe Ser Gln Pro Gly Ala Pro
290                 295                 300

Ile Leu Gln Cys Met Gly Cys Cys Phe Ser Arg Ala Tyr Pro Thr Pro
305                 310                 315                 320

Leu Arg Ser Lys Lys Thr Met Leu Val Gln Lys Asn Val Thr Ser Glu
                325                 330                 335

Ser Thr Cys Cys Val Ala Lys Ser Tyr Asn Arg Val Thr Val Met Gly
                340                 345                 350

Gly Phe Lys Val Glu Asn His Thr Ala Cys His Cys Ser Thr Cys
                355                 360                 365

<210> SEQ ID NO 90
<211> LENGTH: 426
<212> TYPE: PRT
<213> ORGANISM: Artificial
<220> FEATURE:
<223> OTHER INFORMATION: EM164 beta

<400> SEQUENCE: 90

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Val Val Met Thr Gln
                20                  25                  30

Thr Pro Leu Ser Leu Pro Val Ser Leu Gly Asp Pro Ala Ser Ile Ser
            35                  40                  45

Cys Arg Ser Ser Gln Ser Ile Val His Ser Asn Val Asn Thr Tyr Leu
50                  55                  60

Glu Trp Tyr Leu Gln Lys Pro Gly Gln Ser Pro Arg Leu Leu Ile Tyr
65                  70                  75                  80

Lys Val Ser Asn Arg Phe Ser Gly Val Pro Asp Arg Phe Ser Gly Ser
                85                  90                  95

Gly Ala Gly Thr Asp Phe Thr Leu Arg Ile Ser Arg Val Glu Ala Glu
            100                 105                 110

Asp Leu Gly Ile Tyr Tyr Cys Phe Gln Gly Ser His Val Pro Pro Thr
        115                 120                 125

Phe Gly Gly Gly Thr Lys Leu Glu Ile Lys Arg Gly Gly Gly Gly Ser
130                 135                 140

Gly Gly Gly Gly Ser Gly Gly Gly Ser Gln Val Gln Leu Val Gln
145                 150                 155                 160

Ser Gly Ala Glu Val Val Lys Pro Gly Ala Ser Val Lys Leu Ser Cys
                165                 170                 175

Lys Ala Ser Gly Tyr Thr Phe Thr Ser Tyr Trp Met His Trp Val Lys
            180                 185                 190

Gln Arg Pro Gly Gln Gly Leu Glu Trp Ile Gly Glu Ile Asn Pro Ser
        195                 200                 205

Asn Gly Arg Thr Asn Tyr Asn Gln Lys Phe Gln Gly Lys Ala Thr Leu
    210                 215                 220

Thr Val Asp Lys Ser Ser Ser Thr Ala Tyr Met Gln Leu Ser Ser Leu
225                 230                 235                 240

Thr Ser Glu Asp Ser Ala Val Tyr Tyr Phe Ala Arg Gly Arg Pro Asp
                245                 250                 255

Tyr Tyr Gly Ser Ser Lys Trp Tyr Phe Asp Val Trp Gly Gln Gly Thr
            260                 265                 270

Thr Val Thr Val Ser Ser Ala Ala Ala Ser Lys Glu Pro Leu Arg Pro
```

```
                275                 280                 285
Arg Cys Arg Pro Ile Asn Ala Thr Leu Ala Val Glu Lys Glu Gly Cys
    290                 295                 300

Pro Val Cys Ile Thr Val Asn Thr Thr Ile Cys Ala Gly Tyr Cys Pro
305                 310                 315                 320

Thr Met Thr Arg Val Leu Gln Gly Val Leu Pro Ala Leu Pro Gln Val
                325                 330                 335

Val Cys Asn Tyr Arg Asp Val Arg Phe Glu Ser Ile Arg Leu Pro Gly
                340                 345                 350

Cys Pro Arg Gly Val Asn Pro Val Val Ser Tyr Ala Val Ala Leu Ser
            355                 360                 365

Cys Gln Cys Ala Leu Cys Arg Arg Ser Thr Thr Asp Cys Gly Gly Pro
        370                 375                 380

Lys Asp His Pro Leu Thr Cys Asp Asp Pro Arg Phe Gln Asp Ser Ser
385                 390                 395                 400

Ser Ser Lys Ala Pro Pro Ser Leu Pro Ser Pro Ser Arg Leu Pro
                405                 410                 415

Gly Pro Ser Asp Thr Pro Ile Leu Pro Gln
                420                 425

<210> SEQ ID NO 91
<211> LENGTH: 357
<212> TYPE: PRT
<213> ORGANISM: Artificial
<220> FEATURE:
<223> OTHER INFORMATION: 19D12 aplha

<400> SEQUENCE: 91

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Ile Val Leu Thr Gln
                20                  25                  30

Val Pro Asp Phe Gln Ser Val Thr Pro Lys Glu Lys Val Thr Ile Thr
            35                  40                  45

Cys Arg Ala Ser Gln Ser Ile Gly Ser Ser Leu His Trp Tyr Gln Gln
        50                  55                  60

Lys Pro Asp Gln Ser Pro Lys Leu Leu Ile Lys Tyr Ala Ser Gln Ser
65                  70                  75                  80

Leu Ser Gly Val Pro Ser Arg Phe Ser Gly Ser Gly Ser Gly Thr Asp
                85                  90                  95

Phe Thr Leu Thr Ile Asn Ser Leu Glu Ala Glu Asp Ala Ala Ala Tyr
                100                 105                 110

Tyr Cys His Gln Ser Ser Arg Leu Pro His Thr Phe Gly Gly Gly Thr
            115                 120                 125

Lys Val Glu Ile Lys Arg Thr Gly Gly Gly Ser Gly Gly Gly Gly
130                 135                 140

Ser Gly Gly Gly Gly Ser Glu Val Gln Leu Val Gln Ser Gly Gly Gly
145                 150                 155                 160

Leu Val His Pro Gly Gly Ser Leu Arg Leu Ser Cys Ala Ala Ser Gly
                165                 170                 175

Phe Thr Phe Ser Ser Phe Ala Met His Trp Val Arg Gln Ala Pro Gly
                180                 185                 190

Lys Gly Leu Glu Trp Ile Ser Val Ile Asp Thr Arg Gly Ala Thr Tyr
            195                 200                 205

Tyr Ala Asp Ser Val Lys Gly Arg Phe Thr Ile Ser Arg Asp Asn Ala
```

-continued

```
                210                 215                 220
Lys Asn Ser Leu Tyr Leu Gln Met Asn Ser Leu Arg Ala Glu Asp Met
225                 230                 235                 240

Ala Val Tyr Tyr Cys Ala Arg Leu Gly Asn Phe Tyr Tyr Gly Met Asp
                245                 250                 255

Val Trp Gly Gln Gly Thr Thr Val Thr Val Ser Ser Ala Ala Ala Pro
            260                 265                 270

Asp Val Gln Asp Cys Pro Glu Cys Thr Leu Gln Glu Asn Pro Phe Phe
        275                 280                 285

Ser Gln Pro Gly Ala Pro Ile Leu Gln Cys Met Gly Cys Cys Phe Ser
    290                 295                 300

Arg Ala Tyr Pro Thr Pro Leu Arg Ser Lys Lys Thr Met Leu Val Gln
305                 310                 315                 320

Lys Asn Val Thr Ser Glu Ser Thr Cys Cys Val Ala Lys Ser Tyr Asn
                325                 330                 335

Arg Val Thr Val Met Gly Gly Phe Lys Val Glu Asn His Thr Ala Cys
            340                 345                 350

His Cys Ser Thr Cys
        355

<210> SEQ ID NO 92
<211> LENGTH: 416
<212> TYPE: PRT
<213> ORGANISM: Artificial
<220> FEATURE:
<223> OTHER INFORMATION: 19D12 beta

<400> SEQUENCE: 92

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Ile Val Leu Thr Gln
                20                  25                  30

Val Pro Asp Phe Gln Ser Val Thr Pro Lys Glu Lys Val Thr Ile Thr
            35                  40                  45

Cys Arg Ala Ser Gln Ser Ile Gly Ser Ser Leu His Trp Tyr Gln Gln
50                  55                  60

Lys Pro Asp Gln Ser Pro Lys Leu Leu Ile Lys Tyr Ala Ser Gln Ser
65                  70                  75                  80

Leu Ser Gly Val Pro Ser Arg Phe Ser Gly Ser Gly Ser Gly Thr Asp
                85                  90                  95

Phe Thr Leu Thr Ile Asn Ser Leu Glu Ala Glu Asp Ala Ala Ala Tyr
            100                 105                 110

Tyr Cys His Gln Ser Ser Arg Leu Pro His Thr Phe Gly Gly Gly Thr
        115                 120                 125

Lys Val Glu Ile Lys Arg Thr Gly Gly Gly Ser Gly Gly Gly Gly
    130                 135                 140

Ser Gly Gly Gly Gly Ser Glu Val Gln Leu Val Gln Ser Gly Gly Gly
145                 150                 155                 160

Leu Val His Pro Gly Gly Ser Leu Arg Leu Ser Cys Ala Ala Ser Gly
                165                 170                 175

Phe Thr Phe Ser Ser Phe Ala Met His Trp Val Arg Gln Ala Pro Gly
            180                 185                 190

Lys Gly Leu Glu Trp Ile Ser Val Ile Asp Thr Arg Gly Ala Thr Tyr
        195                 200                 205

Tyr Ala Asp Ser Val Lys Gly Arg Phe Thr Ile Ser Arg Asp Asn Ala
```

-continued

```
                  210                 215                 220
Lys Asn Ser Leu Tyr Leu Gln Met Asn Ser Leu Arg Ala Glu Asp Met
225                 230                 235                 240

Ala Val Tyr Tyr Cys Ala Arg Leu Gly Asn Phe Tyr Tyr Gly Met Asp
                245                 250                 255

Val Trp Gly Gln Gly Thr Thr Val Thr Val Ser Ser Ala Ala Ala Ser
                260                 265                 270

Lys Glu Pro Leu Arg Pro Arg Cys Arg Pro Ile Asn Ala Thr Leu Ala
                275                 280                 285

Val Glu Lys Glu Gly Cys Pro Val Cys Ile Thr Val Asn Thr Thr Ile
290                 295                 300

Cys Ala Gly Tyr Cys Pro Thr Met Thr Arg Val Leu Gln Gly Val Leu
305                 310                 315                 320

Pro Ala Leu Pro Gln Val Val Cys Asn Tyr Arg Asp Val Arg Phe Glu
                325                 330                 335

Ser Ile Arg Leu Pro Gly Cys Pro Arg Gly Val Asn Pro Val Val Ser
                340                 345                 350

Tyr Ala Val Ala Leu Ser Cys Gln Cys Ala Leu Cys Arg Arg Ser Thr
                355                 360                 365

Thr Asp Cys Gly Gly Pro Lys Asp His Pro Leu Thr Cys Asp Asp Pro
370                 375                 380

Arg Phe Gln Asp Ser Ser Ser Lys Ala Pro Pro Pro Ser Leu Pro
385                 390                 395                 400

Ser Pro Ser Arg Leu Pro Gly Pro Ser Asp Thr Pro Ile Leu Pro Gln
                405                 410                 415
```

<210> SEQ ID NO 93
<211> LENGTH: 241
<212> TYPE: PRT
<213> ORGANISM: Artificial
<220> FEATURE:
<223> OTHER INFORMATION: EGFR VH E105

<400> SEQUENCE: 93

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
                35                  40                  45

Gly Val Ile Trp Ser Gly Gly Asn Thr Asp Tyr Asn Thr Pro Phe Thr
                50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Cys Phe Ala Tyr Trp Gly Gln Gly
                100                 105                 110

Thr Leu Val Thr Val Ser Ala Gly Gly Gly Ser Gly Gly Gly
                115                 120                 125

Ser Gly Gly Gly Ser Asp Ile Leu Leu Thr Gln Ser Pro Val Ile
                130                 135                 140

Leu Ser Val Ser Pro Gly Glu Arg Val Ser Phe Ser Cys Arg Ala Ser
145                 150                 155                 160

Gln Ser Ile Gly Thr Asn Ile Cys Trp Tyr Gln Gln Arg Thr Asn Gly
```

```
                     165                 170                 175
Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
            195                 200                 205

Ile Asn Ser Val Glu Ser Glu Asp Ile Ala Asp Tyr Tyr Cys Gln Gln
            210                 215                 220

Asn Asn Asn Trp Pro Thr Thr Phe Gly Ala Gly Thr Lys Leu Glu Leu
225                 230                 235                 240

Lys

<210> SEQ ID NO 94
<211> LENGTH: 241
<212> TYPE: PRT
<213> ORGANISM: Artificial
<220> FEATURE:
<223> OTHER INFORMATION: EGFR scFv VH

<400> SEQUENCE: 94

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Cys Gly Gln Gly
            100                 105                 110

Thr Leu Val Thr Val Ser Ala Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Cys Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
            195                 200                 205

Ile Asn Ser Val Glu Ser Glu Asp Ile Ala Asp Tyr Tyr Cys Gln Gln
            210                 215                 220

Asn Asn Asn Trp Pro Thr Thr Phe Gly Ala Gly Thr Lys Leu Glu Leu
225                 230                 235                 240

Lys

<210> SEQ ID NO 95
<211> LENGTH: 241
<212> TYPE: PRT
<213> ORGANISM: Artificial
<220> FEATURE:
```

<223> OTHER INFORMATION: EGFR L46C

<400> SEQUENCE: 95

| | | | | | | | | | | | | | | |
|---|---|---|---|---|---|---|---|---|---|---|---|---|---|---|
| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 | |
| Ser | Leu | Ser | Ile | Thr | Cys | Thr | Val | Ser | Gly | Phe | Ser | Leu | Thr | Asn | Tyr |
| | | | | 20 | | | | | 25 | | | | | 30 | |
| Gly | Val | His | Trp | Val | Arg | Gln | Ser | Pro | Gly | Lys | Gly | Leu | Glu | Trp | Leu |
| | | | 35 | | | | | 40 | | | | | 45 | | |
| Gly | Val | Ile | Trp | Ser | Gly | Gly | Asn | Thr | Asp | Tyr | Asn | Thr | Pro | Phe | Thr |
| | | | 50 | | | | 55 | | | | | 60 | | | |
| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |
| Lys | Met | Asn | Ser | Leu | Gln | Ser | Asn | Asp | Thr | Ala | Ile | Tyr | Tyr | Cys | Ala |
| | | | | 85 | | | | | 90 | | | | | 95 | |
| Arg | Ala | Leu | Thr | Tyr | Tyr | Asp | Tyr | Glu | Phe | Cys | Tyr | Trp | Gly | Gln | Gly |
| | | | 100 | | | | | 105 | | | | | 110 | | |
| Thr | Leu | Val | Thr | Val | Ser | Ala | Gly | Gly | Gly | Ser | Gly | Gly | Gly | Gly |
| | | | 115 | | | | | 120 | | | | | 125 | |
| Ser | Gly | Gly | Gly | Gly | Ser | Asp | Ile | Leu | Leu | Thr | Gln | Ser | Pro | Val | Ile |
| | 130 | | | | | 135 | | | | | 140 | | | | |
| Leu | Ser | Val | Ser | Pro | Gly | Glu | Arg | Val | Ser | Phe | Ser | Cys | Arg | Ala | Ser |
| 145 | | | | | 150 | | | | | 155 | | | | | 160 |
| Gln | Ser | Ile | Gly | Thr | Asn | Ile | His | Trp | Tyr | Gln | Gln | Arg | Thr | Asn | Gly |
| | | | | 165 | | | | | 170 | | | | | 175 | |
| Ser | Pro | Arg | Cys | Leu | Ile | Lys | Tyr | Ala | Ser | Glu | Ser | Ile | Ser | Gly | Ile |
| | | | 180 | | | | | 185 | | | | | 190 | | |
| Pro | Ser | Arg | Phe | Ser | Gly | Ser | Gly | Ser | Gly | Thr | Asp | Phe | Thr | Leu | Ser |
| | | | 195 | | | | | 200 | | | | | 205 | | |
| Ile | Asn | Ser | Val | Glu | Ser | Glu | Asp | Ile | Ala | Asp | Tyr | Tyr | Cys | Gln | Gln |
| | | | 210 | | | | | 215 | | | | | 220 | | |
| Asn | Asn | Asn | Trp | Pro | Thr | Thr | Phe | Gly | Ala | Gly | Thr | Lys | Leu | Glu | Leu |
| 225 | | | | | 230 | | | | | 235 | | | | | 240 |
| Lys | | | | | | | | | | | | | | | |

<210> SEQ ID NO 96
<211> LENGTH: 241
<212> TYPE: PRT
<213> ORGANISM: Artificial
<220> FEATURE:
<223> OTHER INFORMATION: EGFR VH L45C

<400> SEQUENCE: 96

| | | | | | | | | | | | | | | | |
|---|---|---|---|---|---|---|---|---|---|---|---|---|---|---|---|
| Gln | Val | Gln | Leu | Lys | Gln | Ser | Gly | Pro | Gly | Leu | Val | Gln | Pro | Ser | Gln |
| 1 | | | | 5 | | | | | 10 | | | | | 15 | |
| Ser | Leu | Ser | Ile | Thr | Cys | Thr | Val | Ser | Gly | Phe | Ser | Leu | Thr | Asn | Tyr |
| | | | | 20 | | | | | 25 | | | | | 30 | |
| Gly | Val | His | Trp | Val | Arg | Gln | Ser | Pro | Gly | Lys | Gly | Cys | Glu | Trp | Leu |
| | | | 35 | | | | | 40 | | | | | 45 | | |
| Gly | Val | Ile | Trp | Ser | Gly | Gly | Asn | Thr | Asp | Tyr | Asn | Thr | Pro | Phe | Thr |
| | | | 50 | | | | 55 | | | | | 60 | | | |
| Ser | Arg | Leu | Ser | Ile | Asn | Lys | Asp | Asn | Ser | Lys | Ser | Gln | Val | Phe | Phe |
| 65 | | | | | 70 | | | | | 75 | | | | | 80 |
| Lys | Met | Asn | Ser | Leu | Gln | Ser | Asn | Asp | Thr | Ala | Ile | Tyr | Tyr | Cys | Ala |
| | | | | 85 | | | | | 90 | | | | | 95 | |

-continued

Arg Ala Leu Thr Tyr Tyr Asp Tyr Glu Phe Ala Tyr Trp Gly Gln Gly
                100                 105                 110

Thr Leu Val Thr Val Ser Ala Gly Gly Gly Ser Gly Gly Gly Gly
        115                 120                 125

Ser Gly Gly Gly Gly Ser Asp Ile Leu Leu Thr Gln Ser Pro Val Ile
        130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
                180                 185                 190

Pro Ser Arg Phe Ser Gly Ser Gly Ser Gly Thr Asp Phe Thr Leu Ser
                195                 200                 205

Ile Asn Ser Val Glu Ser Glu Asp Ile Ala Asp Tyr Tyr Cys Gln Gln
                210                 215                 220

Asn Asn Asn Trp Pro Thr Thr Cys Gly Ala Gly Thr Lys Leu Glu Leu
225                 230                 235                 240

Lys

<210> SEQ ID NO 97
<211> LENGTH: 241
<212> TYPE: PRT
<213> ORGANISM: Artificial
<220> FEATURE:
<223> OTHER INFORMATION: EGFR VH S34C

<400> SEQUENCE: 97

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
                35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Cys
                100                 105                 110

Thr Leu Val Thr Val Ser Ala Gly Gly Gly Ser Gly Gly Gly Gly
        115                 120                 125

Ser Gly Gly Gly Gly Ser Asp Ile Leu Leu Thr Gln Ser Pro Val Ile
        130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Cys Pro Arg Leu Leu Ile Lys Tyr Ala Ser Glu Ser Ile Ser Gly Ile
                180                 185                 190

Pro Ser Arg Phe Ser Gly Ser Gly Ser Gly Thr Asp Phe Thr Leu Ser
                195                 200                 205

Ile Asn Ser Val Glu Ser Glu Asp Ile Ala Asp Tyr Tyr Cys Gln Gln

```
                210                 215                 220
Asn Asn Asn Trp Pro Thr Thr Phe Gly Ala Gly Thr Lys Leu Glu Leu
225                 230                 235                 240

Lys

<210> SEQ ID NO 98
<211> LENGTH: 8
<212> TYPE: PRT
<213> ORGANISM: Artificial Sequence
<220> FEATURE:
<223> OTHER INFORMATION: Peptide Linker

<400> SEQUENCE: 98

Gly Phe Ala Ser Pro Ala Phe Phe
1               5

<210> SEQ ID NO 99
<211> LENGTH: 19
<212> TYPE: PRT
<213> ORGANISM: Artificial Sequence
<220> FEATURE:
<223> OTHER INFORMATION: Peptide Linker

<400> SEQUENCE: 99

Asp Lys Thr His Thr Cys Pro Pro Cys Pro Ala Pro Glu Leu Leu Gly
1               5                   10                  15

Gly Ala Ala

<210> SEQ ID NO 100
<211> LENGTH: 20
<212> TYPE: PRT
<213> ORGANISM: Artificial Sequence
<220> FEATURE:
<223> OTHER INFORMATION: Peptide Linker

<400> SEQUENCE: 100

Asp Lys Thr His Thr Cys Pro Pro Cys Pro Ala Pro Glu Leu Leu Gly
1               5                   10                  15

Gly Ala Ala Ala
            20

<210> SEQ ID NO 101
<211> LENGTH: 19
<212> TYPE: PRT
<213> ORGANISM: Artificial Sequence
<220> FEATURE:
<223> OTHER INFORMATION: Peptide Linker

<400> SEQUENCE: 101

Asp Lys Thr His Thr Ser Pro Pro Ser Pro Ala Pro Glu Leu Leu Gly
1               5                   10                  15

Gly Ala Ala

<210> SEQ ID NO 102
<211> LENGTH: 20
<212> TYPE: PRT
<213> ORGANISM: Artificial Sequence
<220> FEATURE:
<223> OTHER INFORMATION: Peptide Linker

<400> SEQUENCE: 102

Asp Lys Thr His Thr Ser Pro Pro Ser Pro Ala Pro Glu Leu Leu Gly
1               5                   10                  15
```

Gly Ala Ala Ala
        20

<210> SEQ ID NO 103
<211> LENGTH: 4
<212> TYPE: PRT
<213> ORGANISM: Artificial Sequence
<220> FEATURE:
<223> OTHER INFORMATION: Peptide Linker

<400> SEQUENCE: 103

Gly Gly Gly Ser
1

<210> SEQ ID NO 104
<211> LENGTH: 8
<212> TYPE: PRT
<213> ORGANISM: Artificial Sequence
<220> FEATURE:
<223> OTHER INFORMATION: Peptide Linker

<400> SEQUENCE: 104

Gly Gly Gly Ser Gly Gly Gly Ser
1               5

<210> SEQ ID NO 105
<211> LENGTH: 5
<212> TYPE: PRT
<213> ORGANISM: Artificial Sequence
<220> FEATURE:
<223> OTHER INFORMATION: Peptide Linker

<400> SEQUENCE: 105

Gly Gly Gly Gly Ser
1               5

<210> SEQ ID NO 106
<211> LENGTH: 10
<212> TYPE: PRT
<213> ORGANISM: Artificial Sequence
<220> FEATURE:
<223> OTHER INFORMATION: Peptide Linker

<400> SEQUENCE: 106

Gly Gly Gly Gly Ser Gly Gly Gly Gly Ser
1               5                   10

<210> SEQ ID NO 107
<211> LENGTH: 20
<212> TYPE: PRT
<213> ORGANISM: Artificial Sequence
<220> FEATURE:
<223> OTHER INFORMATION: Peptide Linker

<400> SEQUENCE: 107

Gly Gly Gly Gly Ser Gly Gly Gly Gly Ser Gly Gly Gly Gly Ser Gly
1               5                   10                  15

Gly Gly Gly Ser
        20

<210> SEQ ID NO 108
<211> LENGTH: 5
<212> TYPE: PRT
<213> ORGANISM: Artificial Sequence
<220> FEATURE:
<223> OTHER INFORMATION: Peptide Linker

```
<400> SEQUENCE: 108

Gly Gly Gly Gly Cys
1               5

<210> SEQ ID NO 109
<211> LENGTH: 6
<212> TYPE: PRT
<213> ORGANISM: Artificial Sequence
<220> FEATURE:
<223> OTHER INFORMATION: Peptide Linker

<400> SEQUENCE: 109

Ser Cys Ala Gly Ala Gly
1               5

<210> SEQ ID NO 110
<211> LENGTH: 10
<212> TYPE: PRT
<213> ORGANISM: Artificial Sequence
<220> FEATURE:
<223> OTHER INFORMATION: Peptide Linker

<400> SEQUENCE: 110

Gly Gly Gly Ser Ser Gly Gly Gly Ser Gly
1               5                   10

<210> SEQ ID NO 111
<211> LENGTH: 6
<212> TYPE: PRT
<213> ORGANISM: Artificial Sequence
<220> FEATURE:
<223> OTHER INFORMATION: Peptide Linker

<400> SEQUENCE: 111

Gly Ala Asp Lys Ala Ala
1               5

<210> SEQ ID NO 112
<211> LENGTH: 7
<212> TYPE: PRT
<213> ORGANISM: Artificial Sequence
<220> FEATURE:
<223> OTHER INFORMATION: Peptide Linker

<400> SEQUENCE: 112

Gly Ala Asp Lys Ala Ala Ala
1               5
```